(12) United States Patent
Mudge et al.

(10) Patent No.: US 11,638,758 B2
(45) Date of Patent: *May 2, 2023

(54) ITRACONAZOLE COMPOSITIONS AND DOSAGE FORMS, AND METHODS OF USING THE SAME

(71) Applicant: Mayne Pharma International Pty Ltd., Salisbury South (AU)

(72) Inventors: Stuart James Mudge, Northcote (AU); David Hayes, Rostrevor (AU); Stefan Lukas, Manningham (AU)

(73) Assignee: MAYNE PHARMA INTERNATIONAL PTY. LTD, Salisbury South (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/074,497

(22) Filed: Oct. 19, 2020

(65) Prior Publication Data

US 2021/0038728 A1 Feb. 11, 2021

Related U.S. Application Data

(63) Continuation of application No. 16/671,606, filed on Nov. 1, 2019, now Pat. No. 10,806,792, which is a (Continued)

(30) Foreign Application Priority Data

Jun. 21, 2012 (AU) .................................. 2012902624

(51) Int. Cl.
*A61K 31/496* (2006.01)
*A61K 47/38* (2006.01)
(Continued)

(52) U.S. Cl.
CPC ............ *A61K 47/38* (2013.01); *A61K 9/0053* (2013.01); *A61K 9/4866* (2013.01); *A61K 31/496* (2013.01)

(58) Field of Classification Search
CPC ..................................................... A61K 31/496
See application file for complete search history.

(56) References Cited

U.S. PATENT DOCUMENTS 5,340,591 A   8/1994   Nakano et al.
5,633,015 A   5/1997   Gillis et al.
(Continued)

FOREIGN PATENT DOCUMENTS

EP   0 521 310 B1   1/1999
EP   0 784 974 B1   5/2003
(Continued)

OTHER PUBLICATIONS

Koks, C.H.W., et al., "Itraconazole Solution: Summary of Pharmacokinetic Features and Review of Activity in the Treatment of Fluconazole-Resistant Oral candidosis in HIV-Infected Persons," Pharmacological Research 46(2):195-201, Aug. 2002.
(Continued)

*Primary Examiner* — Benjamin J Packard
(74) *Attorney, Agent, or Firm* — Christensen O'Connor Johnson Kindness PLLC

(57) ABSTRACT

The disclosure relates to, among other things, pharmaceutical compositions, such as solid oral dosage forms, comprising itraconazole, methods of making the compositions, and methods of using the same for treating disorders including, but not limited to, fungal infections.

15 Claims, 64 Drawing Sheets

Related U.S. Application Data continuation of application No. 16/198,645, filed on Nov. 21, 2018, now Pat. No. 10,463,740, which is a continuation of application No. 15/623,742, filed on Jun. 15, 2017, now abandoned, which is a continuation of application No. 14/882,662, filed on Oct. 14, 2015, now Pat. No. 9,713,642, which is a continuation of application No. 14/511,420, filed on Oct. 10, 2014, now Pat. No. 9,272,046, which is a continuation of application No. 13/924,222, filed on Jun. 21, 2013, now Pat. No. 8,921,374.

(51) Int. Cl.
*A61K 9/48* (2006.01)
*A61K 9/00* (2006.01)

(56) References Cited

U.S. PATENT DOCUMENTS

| | | | |
|---|---|---|---|
| 8,921,374 | B2 | 12/2014 | Mudge et al. |
| 9,272,046 | B2 | 3/2016 | Mudge et al. |
| 2003/0086976 | A1 | 5/2003 | Hayes et al. |
| 2008/0260835 | A1 | 10/2008 | Hayes et al. |
| 2015/0099763 | A1 | 4/2015 | Mudge et al. |
| 2016/0030582 | A1 | 2/2016 | Mudge et al. |

FOREIGN PATENT DOCUMENTS

| | | |
|---|---|---|
| EP | 1 027 886 B1 | 7/2008 |
| JP | 4-360833 A | 12/1992 |
| JP | 11-509238 A | 8/1999 |
| JP | 2006-143683 A | 6/2006 |
| KR | 10-2005-026169 A | 3/2005 |
| WO | 1997/004782 A1 | 2/1997 |
| WO | 1997/044014 A1 | 11/1997 |
| WO | 1998/000113 A1 | 1/1998 |
| WO | 1999/033467 A1 | 7/1999 |
| WO | 2000/000179 A1 | 1/2000 |
| WO | 2000/040220 A1 | 7/2000 |
| WO | 2005/023262 A1 | 3/2005 |
| WO | 2013/192566 A1 | 12/2013 |

OTHER PUBLICATIONS

Korashy, H.M., et al., "Induction of Cytochrome P450 1A1 by Ketoconazole and Itraconazole but not Fluconazole in Murine and Human Hepatoma Cell Lines," Toxicological Sciences 97(1):32-43, May 2007.

Kurowski, R., and M. Ostapchuk, "Overview of Histoplasmosis," American Family Physician 66(12):2247-2252, Dec. 2002.

Lange, D., et al., "Effect of a Cola Beverage on the Bioavailability of Itraconazole in the Presence of H2 Blockers," Journal of Clinical Pharmacology 37(6):535-540, Jun. 1997.

Martinez, J.E., "Microbial Bioburden on Oral Solid Dosage Forms," Pharmaceutical Technology 26(2):58-70, 2002.

Masiero, G., et al., "Socioeconomic Determinants of Outpatient Antibiotic Use in Europe," International Journal of Public Health 55(5):55:469-478, Oct. 2010.

Material Safety Data Sheet: Itraconazole, Revision 4, Jul. 3, 2007, 12 pages.

Matthieu, L., et al., "Itraconazole Penetrates the Nail Via the Nail Matrix and the Nail Bed—An Investigation in Onchomycosis," Clinical and Experimental Dermatology 16(5):374-376, Sep. 1991.

Meis, J.F.G.M., and P.E. Verweij, "Current Management of Fungal Infections," Drugs 61(Suppl. 1):13-25, Dec. 2001.

Mikamo, H., et al., "Comparative Study on the Effectiveness of Antifungal Agents in Different Regimens Against Vaginal Candidiasis," Chemotherapy 44(5):364 368, Sep.-Oct. 1998.

Miranda, K.C., et al., "Antifungal Activities of Azole Agents Against the Malassezia Species," International Journal of Antimicrobial Agents 29(3):281-284, Mar. 2007.

Mishra, N.N., et al., "Pathogenicity and Drug Resistance in *Candida albicans* and Other Yeast Species," Acta Microbiologica et Immunologica Hungarica 54(3):201-235, Sep. 2007.

Mocherla, S., and L.J. Wheat, "Treatment of Histoplasmosis," Seminars in Respiratory Infections 16(2):141-148, Jun. 2001.

Morgan, J., et al., "Incidence of Invasive Aspergillosis Following Hematopoietic Stem Cell and Solid Organ Transplantation: Interim Results of a Prospective Multicenter Surveillance Program," Medical Mycology 43(Supp. 1):S49-S58, May 2005.

Mouton, J.W., et al., "Standardization of Pharmacokinetic/ Pharmacodynamic (PK/PD) Terminology for Anti-Infective Drugs: An Update," Journal of Antimicrobial Chemotherapy 55(5):601-607, May 2005.

Myoken, Y., et al., "Itraconazole Prophylaxis for Invasive Gingival Aspergillosis in Neutropenic Patients With Acute Leukemia," Journal of Periodontology 73(1):33-38, Jan. 2002.

Nakamura, Y., et al., "Susceptibility Testing of Malassezia Species Using the Urea Broth Microdilution Method," Antimicrobial Agents and Chemotherapy 44(8):2185-2186, Aug. 2000.

Nucci, M., et al., "A Double-Blind, Randomized, Placebo-Controlled Trial of Itraconazole Capsules as Antifungal Prophylaxis for Neutropenic Patients," Clinical Infectious Diseases 30(2):300-305, Feb. 2000.

Odom, R., et al., "A Double-Blind, Randomized Comparison of Itraconazole Capsules and Placebo in the Treatment of Onychomycosis of the Toenail," Journal of the American Academy of Dermatology 35(1):110-111, Jul. 1996.

Odom, R.B., et al., "A Multicenter, Placebo-Controlled, Double-Blind Study of Intermittent Therapy With Itraconazole for the Treatment of Onychomycosis of the Fingernail," Journal of the American Academy of Dermatology 36(2):231-235, Feb. 1997.

OECD, "Health at a Glance: Europe 2010," OECD Publishing, <http://dx.doi.org/10.1787/health_glance-2010-en>, 130 pages.

Partap, R., et al., "Single-Dose Fluconazole Versus Itraconazole in Pityriasis versicolor," Dermatology 208(1):55-59, 2004.

Patterson, T.F., "Advances and Challenges in Management of Invasive Mycoses," The Lancet 366(9490):1013-1025, Sep. 2005.

Pfaller, M.A., and D.J. Diekema, "Epidemiology of Invasive Candidiasis: A Persistent Public Health Problem," Clinical Microbiology Reviews 20(1):133-163, Jan. 2007.

Pfaller, M.A., and D.J. Diekema, "Epidemiology of Invasive Mycoses in North America," Critical Reviews in Microbiology 36(1):1-53, 2010.

Pfaller, M.A., et al., "In Vitro Activities of Ravuconazole and Voriconazole Compared With Those of Four Approved Systemic Antifungal Agents Against 6,970 Clinical Isolates of *Candida* spp.," Antimicrobial Agents and Chemotherapy 46(6):1723-1727, Jun. 2002.

Pfaller, M., et al., "Use of Epidemiological Cutoff Values To Examine 9-Year Trends in Susceptibility of *Aspergillus* Species to the Triazoles," Journal of Clinical Microbiology 49(2):586-590, Feb. 2011.

Pfaller, M.A., et al., Antifungal Activities of Posaconazole, Ravuconazole, and Voriconazole Compared to Those of Itraconazole and Amphotericin B Against 239 Clinical Isolates of *Aspergillus* spp. and Other Filamentous Fungi: Report From SENTRY Antimicrobial Surveillance Program, 2000, Antimicrobial Agents and Chemotherapy 46(4):1032-1037, Apr. 2002.

Piérard, G.E., et al., "Itraconazole," Expert Opinion on Pharmacotherapy 1(2):287-304, Jan. 2000.

Piérard, G.E., et al., "The Boosted Oral Antifungal Treatment for Onychomycosis Beyond the Regular Itraconazole Pulse Dosing Regimen," Dermatology 200(2):185-187, 2000.

Poirier, J.M., and G. Cheymol, "Optimisation of Itraconazole Therapy Using Target Drug Concentrations," Clinical Pharmacokinetics 35(6):461-473, Dec. 1998.

Poirier, J.M., et al., "Marked Intra- and Inter-Patient Variability of Itraconazole Steady State Plasma Concentrations," Therapie 51(2):163-167, Mar.-Apr. 1996.

Prentice, A.G., and A. Glasmacher, "Making Sense of Itraconazole Pharmacokinetics," Journal of Antimicrobial Chemotherapy 56(Suppl. S1):i17-i22, Sep. 2005.

(56) References Cited

OTHER PUBLICATIONS

Public Assessment Report: Itraconazole 100mg Capsules, Doc. No. UK/H/1317/01/DC, Pharmakal Limited, Mar. 13, 2009, 28 pages.
Rex, J.H., et al., "Development of Interpretive Breakpoints for Antifungal Susceptibility Testing: Conceptual Framework and Analysis of In Vitro-In Vivo Correlation Data for Fluconazole, Itraconazole, and Candida Infections," Clinical Infectious Diseases 24(2):235-247, Feb. 1997.
Reynes, J., et al., "Itraconazole Oral Solution for Treatment of Fluconazole Resistant Oral/Esophageal Candidosis in HIV-Infected Patients: Results of a Prospective Multicenter Study. I. Clinical Assessment," Journal of Medical Mycology 9(2):83-87, Jul. 1999.
Richter, S.S., et al., "Antifungal Susceptibilities of *Candida* Species Causing Vulvovaginitis and Epidemiology of Recurrent Cases," Journal of Clinical Microbiology 43(5):2155-2162, May 2005.
Ringshausen, I., et al., "Antifungal Therapy With Itraconazole Impairs the Anti-Lymphoma Effects of Rituximab by nhibiting Recruitment of CD20 to Cell Surface Lipid Rafts," Cancer Research 70(11):4292-4296, Jun. 2010.
Roongpisuthipong, A., et al., "Itraconazole in the Treatment of Acute Vaginal Candidosis," Journal of the Medical Association of Thailand 75(1):30-34, Jan. 1992.
Rydén, L., et al., "Guidelines on Diabetes, Pre-Diabetes, and Cardiovascular Diseases: Full Text," European Heart Journal Supplements 9(Suppl. C):C3-C74, 2007.
Sabatelli, F., et al., "In Vitro Activities of Posaconazole, Fluconazole, Itraconazole, Voriconazole, and Amphotericin B Against a Large Collection of Clinically Important Molds and Yeasts," Antimicrobial Agents and Chemotherapy 50(6):2009-2015, Jun. 2006.
Santos, D.A., and J.S. Hamdan, "In vitro Antifungal Oral Drug and Drug-Combination Activity Against Onychomycosis Causative Dermatophytes," Medical Mycology 44(4):357-362, Jun. 2006.
Scher, R.K., "Onychomycosis: Therapeutic Update," Journal of the American Academy of Dermatology 40(6, Suppl.):S21-S26, Jun. 1999.
Sharkey, P.K., et al., "High-Dose Itraconazole in the Treatment of Severe Mycoses," Antimicrobial Agents and Chemotherapy 35(4):707-713, Apr. 1991.
Shegokar, R., and R.H. Müller, "Nanocrystals: Industrially Feasible Multifunctional Formulation Technology for Poorly Soluble Actives," International Journal of Pharmacology 399(1-2):129-139, Oct. 2010.
Shin, J.H., et al., "Dose-Dependent Pharmacokinetics of Itraconazole After Intravenous or Oral Administration to Rats Intestinal First-Pass Effect," Antimicrobial Agents and Chemotherapy 48(5):1756-1762, May 2004.
Sigurgeirsson, B., et al., "Long-Term Effectiveness of Treatment With Terbinafine vs Itraconazole in Onychomycosis: A 5-Year Blinded Prospective Follow-Up Study," Archives of Dermatology 138(3):353-357, Mar. 2002.
Singson-Alday, A.P., and A.R. Ortega, "A Single Blind Comparative Study Between Itraconazole and Fluconazole in the One-Day Treatment of Vulva-Vaginal Candidiasis," Philippine Journal of Obstetrics and Gynecology 22(4):119-121, Oct.-Dec. 1998.
Sinnollareddy, M., et al., "Using Pharmacokinetics and Pharmacodynamics to Optimise Dosing of Antifungal Agents in Critically Ill Patients: A Systematic Review," International Journal of Antimicrobial Agents 39(1):1-10, Jan. 2012.
Smith, D.E., et al., "A Randomized, Double-Blind, Placebo-Controlled Study of Itraconazole Capsules for the Prevention of Deep Fungal Infections in Immunodeficient Patients With HIV Infection," HIV Medicine 2(2):78-83, Apr. 2001.
European Centre for Disease Prevention and Control/WHO Regional Office for Europe, "HIV/AIDS Surveillance in Europe 2009," Stockholm: European Centre for Disease Prevention and Control, 2010, 104 pages.
European Office Action dated Oct. 12, 2012, for European Application No. 11187961.5, filed Dec. 22, 2000, 12 pages.
Evans, E.G., and B. Sigurgeirsson, "Double Blind, Randomised Study of Continuous Terbinafine Compared With Intermittent Itraconazole in Treatment of Toenail Onvchomvcosis," BMJ 318(7190):1031-1035, Apr. 1999.
Evans, E.G., "The Rationale for Combination Therapy," British Journal of Dermatology 145(Suppl. 60):9-13, Oct. 2001.
Faergemann, J., "Management of Seborrheic Dermatitis and Pityriasis Versicolor" American Journal of Clinical Dermatology 1(2):75-80, Mar.-Apr. 2000.
Faergemann, J., et al., "Efficacy of Itraconazole in the Prophylactic Treatment of Pityriasis (Tinea) Versicolor," Archives of Dermatology 138(1):69-73, Jan. 2002.
Fernández-Torres, B., et al., "In Vitro Activities of 10 Antifungal Drugs Against 508 Dermatophyte Strains," Antimicrobial Agents and Chemotherapy 45(9):2524-2528, Sep. 2001.
Firooz, A., et al., "Itraconazole Pulse Therapy Improves the Quality of Life of Patients With Toenail Onychomycosis," Journal of Dermatological Treatment 14(2):95-98, Jun. 2003.
Galimberti, R.L., et al., "Itraconazole in Pityriasis Versicolor: Ultrastructural Changes in Malassezia furfur Produced During Treatment," Reviews of Infectious Diseases 9(Suppl 1):S134-S138, Jan.-Feb. 1987.
Gallin, J.I., et al., "Itraconazole to Prevent Fungal Infections in Chronic Granulomatous Disease," New England Journal of Medicine 348(24):2416-2422, Jun. 2003.
Glasmacher, A., and A.G. Prentice, "Evidence-Based Review of Antifungal Prophylaxis in Neutropenic Patients With Haematological Malignancies," Journal of Antimicrobial Chemotherapy 56(Suppl 1):i23-i32, Sep. 2005.
Glasmacher, A., et al., "An Open-Label Randomized Trial Comparing Itraconazole Oral Solution With Fluconazole Oral Solution for Primary Prophylaxis of Fungal Infections in Patients With Haematological Malignancy and Profound Neutropenia," Journal of Antimicrobial Chemotherapy 57(2):317-325, Feb. 2006.
Glasmacher, A., et al., "Itraconazole Prevents Invasive Fungal Infections in Neutropenic Patients Treated for Hematologic Malignancies: Evidence From a Meta-Analysis of 3,597 Patients," Journal of Clinical Oncology 21(24):4615-4626, Dec. 2003.
González, G.M., et al., "In Vitro Activities of New and Established Triazoles Against Opportunistic Filamentous and Dimorphic Fungi," Medical Mycology 43(3):281-284, May 2005.
Grant, S.M., and S.P. Clissold, "Itraconazole: A Review of Its Pharmacodynamic and Pharmacokinetic Properties and Therapeutic Use in Superficial and Systemic Mycoses," Drugs 37(3):310-344, Mar. 1989.
Guého, E., et al., "The Genus Malassezia With Description of Four New Species," Antonie van Leeuwenhoek 69(4):337-355, May 1996.
Gupta, A.K., et al., "Hepatic Safety of Itraconazole," Journal of Cutaneous Medical Surgery 6(3):210-213, May-Jun. 2002.
Gupta, A.K., et al., "In Vitro Susceptibility of the Seven Malassezia Species to Ketoconazole, Voriconazole, Itraconazole and Terbinafine," British Journal of Dermatology 142(4):758-765, 2000.
Gupta, A.K., et al., "Onychomycosis: Predisposed Populations and Some Predictors of Suboptimal Response to Oral Antifungal Agents," European Journal of Dermatology 9(8):633-638, Dec. 1999.
Gupta, A.K., et al., "Single-Blind, Randomized, Prospective Study of Sequential Itraconazole and Terbinafine Pulse Compared With Terbinafine Pulse for the Treatment of Toenail Onychomycosis," Journal of the American Academy of Dermatology 44(3):485-491, Mar. 2001.
Gupta, A.K., et al., "Single-Blind, Randomized, Prospective Study on Terbinafine and Itraconazole for Treatment of Dermatophyte Toenail Onychomycosis in the Elderly," Journal of the American Academy of Dermatology 44(3):479-484, Mar. 2001.
Gupta, A.K., et al., "Tinea Capitis: An Overview With Emphasis on Management," Pediatric Dermatology 16(3):171-189, May-Jun. 1999.
Gupta, A., et al., "Update on the Safety of Itraconazole Pulse Therapy in Onychomycosis and Dermatomycoses," European Journal of Dermatology 11(1):6-10, Jan.-Feb. 2001.
Hainer, B.L., "Dermatophyte Infections," American Family Physician 67(1):101-108, Jan. 2003.
Hajjeh, R.A., et al., "Incidence of Bloodstream Infections Due to *Candida* Species and In Vitro Susceptibilities of Isolates Collected

(56) References Cited

OTHER PUBLICATIONS

From 1998 to 2000 in a Population-Based Active Surveillance Program," Journal of Clinical Microbiology 42(4):1519-1527, Apr. 2004.
Hardin, T.C., et al., "Pharmacokinetics of Itraconazole Following Oral Administration to Normal Volunteers," Antimicrobial Agents and Chemotherapy 32(9): 1310-1313, Sep. 1988.
Haria, M., et al., "Itraconazole: A Reappraisal of its Pharmacological Properties and Therapeutic Use in the Management of Superficial Fungal Infections," Drugs 51(4):585-620, Apr. 1996.
Harousseau, J.L., et al., "Itraconazole Oral Solution for Primary Prophylaxis of Fungal Infections in Patients with Hematological Malignancy and Profound Neutropenia: A Randomized, Double-Blind, Double-Placebo, Multicenter Trial Comparing Itraconazole and Amphotericin B," Antimicrobial Agents and Chemotherapy 44(7): 1887-1893, Jul. 2000.
Havu, V., et al., "A Double-Blind, Randomized Study Comparing Itraconazole Pulse Therapy With Continuous Dosing tor the Treatment of Toe-Nail Onychomycosis," British Journal of Dermatology 136(2):230-234, Feb. 1997.
Havu, V., et al., "Continuous and Intermittent Itraconazole Dosing Schedules for the Treatment of Onychomycosis: A Pharmacokinetic Comparison," British Journal of Dermatology 140(1):96-101, Jan. 1999.
Hay, R.J., "The Future of Onychomycosis Therapy May Involve a Combination of Approaches," British Journal of Dermatology 145(Suppl. 60):3-8, Oct. 2001.
Hay, R.J., "The Management of Superficial Candidiasis," Journal of the American Academy of Dermatology 40(6, Suppl.):S35-S42, Jun. 1999.
Heykants, J., et al., "The Clinical Pharmacokinetics of Itraconazole: An Overview," Mycoses 32(Supp. 1):67-87, Nov. 1989.
Holland, J., et al., "Vulvovaginal Carriage of Yeasts Other Than Candido albicons," Sexually Transmitted Infections 79(3):249-250, Jun. 2003.
Hope, W.W., et al., "Therapeutic Drug Monitoring for Triazoles," Current Opinion in Infectious Diseases 21(6):580-586, Dec. 2008.
Hostetler, U.S., et al., "US Experience With Itraconazole in Aspergillus, Cryptococcus and Histoplasma Infections in the Immunocompromised Host,"Chemotherapy 38(Suppl. 1):12-22, 1992.
Inman, W., et al., "PEM Report No. 7. Itraconazole," Pharmacoepidemiology and Drug Safety 2(4-5):423-443, Jul.-Oct. 1993.
International Preliminary Report on Patentability for International Application No. PCT/US2013/047135, dated Dec. 23, 2014, 13 pages.
International Search Report and Written Opinion for International Application No. PCT/US2013/047135, dated Sep. 16, 2013, 20 pages.
Itraconazole: British Pharmacopoeia Online, 2008, 5 pages.
Jain, S., and V.N. Sehgal, "Itraconazole Versus Terbinafine in the Management of Onychomycosis: An Overview," Journal of Dermatological Treatment 14(1):30-42, Jan. 2003.
Jaruratanasirikul, S., and A. Kleepkaew, "Influence of an Acidic Beverage (Coca-Cola) on the Absorption of Itraconazole," European Journal of Clinical Pharmacology 52(3):235-237, May 1997.
Kageyama, S., et al., "Plasma Concentration of Itraconazole and Its Antifungal Prophylactic Efficacy in Patients With Neutropenia After Chemotherapy for Acute Leukemia," Journal of Infection and Chemotherapy 5(4):213-216, 1999.
Kai, T., et al., "Oral Absorption Improvement of Poorly Soluble Drug Using Solid Dispersion Technique," Chemical & Pharmaceutical Bulletin (Tokyo) 44(3):568-571, Mar. 1996.
Kakourou, T., and U. Uksal, "Guidelines for the Management of Tinea capitis in Children," Pediatric Dermatology 27(3):226-228, May-Jun. 2010.
Katz, H.I., "Drug Interactions of the Newer Oral Antifungal Agents," British Journal of Dermatology 141 (Suppl. 56):26-32, Nov. 1999.
Kauffman, C.A., "Management of Histoplasmosis," Expert Opinion on Pharmacotherapy 3(8): 1067-1072, Aug. 2002.
Kejda, J., "Itraconazole Pulse Therapy vs Continuous Terbinafine Dosing for Toenail Onychomycosis," Postgraduate Medicine Spec No. 12-15, Jul. 1999.
Kidd, S., et al., "Australian Antifungal Susceptibility Data 2008-2011: Part 2—The Moulds Aspergillus, Scedosporium and Fusarium," ASA Newsletter No. 38, pp. 6-10, Aug. 2011.
Kiraz, N., et al., "The Prevalence of Tinea pedis and Tinea manuum in Adults in Rural Areas in Turkey," International Journal of Environmental Health Research 20(5):379-386, Oct. 2010.
Ahmad, S R., et al., "Congestive Heart Failure Associated With Itraconazole," The Lancet 357(9270):1766-1767, Jun. 2001.
Alcantara, R., and J.M. Garibay, "Itraconazole Therapy in Dermatomycosis and Vaginal Candidiasis: Efficacy and Adverse Effects Profile in a Large Multi-Center Study," Advances In Therapy 5:326-334, 1988.
Andes, D., "In Vivo Pharmacodynamics of Antifungal Drugs in Treatment of Candidiasis," Antimicrobial Agents and Chemotherapy 47(4):1179-1186, Apr. 2003.
Arca, E., et al., "An Open, Randomized, Comparative Study of Oral Fluconazole, Itraconazole and Terbinafine Therapy in Onychomycosis," Journal of Dermatological Treatment 13(1):3-9, Mar. 2002.V.
Bae, S.K., et al., "Increased Oral Bioavailability of Itraconazole and Its Active Metabolite, 7-Hydroxyitraconazole, When Coadministered With a Vitamin C Beverage in Healthy Participants," Journal of Clinical Pharmacology 51(3):444-451, Mar. 2011.
Bailey, E.M., et al., "The Triazole Antifungal Agents: A Review of Itraconazole and Fluconazole," Pharmacotherapy 10(2):146-153, 1990.
Barone, J.A., et al., "Enhanced Bioavailability of Itraconazole in Hydroxypropyl-$\beta$-Cyclodextrin Solution Versus Capsules in Healthy Volunteers," Antimicrobial Agents and Chemotherapy 42(7):1862-1865, Jul. 1998.
Barone, J.A., et al., "Food Interaction and Steady-State Pharmacokinetics of Itraconazole Capsules in Healthy Male Volunteers," Antimicrobial Agents and Chemotherapy 37(4):778-784, Apr. 1993.
Barone, J.A., et al., "Food Interaction and Steady-State Pharmacokinetics of Itraconazole Oral Solution in Healthy Volunteers," Pharmacotherapy 18(2):295-301, Mar. 1998.
Bauters, T.G.M., et al., "Prevalence of Vulvovaginal candidiasis and Susceptibility to Fluconazole in Women," American Journal of Obstetrics and Gynecology 187(3):569-574, Sep. 2002.
Benko, I., et al., "Comparison of the Toxicity of Fluconazole and Other Azole Antifungal Drugs to Murine and Human Granulocyte-Macrophage Progenitor Cells In Vitro," Journal of Antimicrobial Chemotherapy 43(5):675-681, May 1999.
Bennet, J.E., "Antifungal Agents," in Hardman and Limbird (eds.), "Goodman & Gilman's: The Pharmacological Basis of Therapeutics," 10th ed., McGraw-Hill, 2001; Chapter 49, pp. 1295-1312.
Bonifaz, A., and A. Saúl, "Treatment of tinea pedis With a Single Pulse of Itraconazole," European Journal of Dermatology 12(2):157-159, Mar.-Apr. 2002.
Boogaerts, M.A., et al., "Pharmacokinetics and Safety of a 7-Day Administration of Intravenous Itraconazole Followed by a 14-Day Administration of Itraconazole Oral Solution in Patients With Hematologic Malignancy," Antimicrobial Agents and Chemotherapy 45(3):981-985, Mar. 2001.
Bräutigam, M., "Terbinafine Versus Itraconazole: A Controlled Clinical Comparison in Onychomycosis of the Toenails," Journal of the American Academy of Dermatology 38(5, Suppl. 2):S53-S56, May 1998.
Brautigam, M., et al., "Randomised Double Blind Comparison of Terbinafine and Itraconazole for Treatment of Toenail Tinea Infection," BMJ 311(7010):919-922, Oct. 1995.
Bremm, K.D., and M. Plempel, "Modulation of Leukotriene Metabolism From Human Polymorphonuclear Granulocytes by Bifonazole," Mycoses 34(1-2):41-45, Jan.-Feb. 1991.
Bundkirchen, A., and R.H.G. Schwinger, "Epidemiology and Economic Burden of Chronic Heart Failure," European Heart Journal Supplements 6(Suppl. D):D57-D60, Aug. 2004.
Caillot, D., "Intravenous Itraconazole Followed by Oral Itraconazole for the Treatment of Amphotericin-B-Refractory Invasive Pulmonary Aspergillosis," Acta Haematologica 109(3):111-118, 2003.

(56) References Cited

OTHER PUBLICATIONS

Caillot, D., et al., "Intravenous Itraconazole Followed by Oral Itraconazole in the Treatment of Invasive Pulmonary Aspergillosis in Patients With Hematologic Malignancies, Chronic Granulomatous Disease, or AIDS," Clinical Infectious Diseases 33(8):e83-90, Oct. 2001.

Caputo, R., "Itraconazole (Sporanox®) in Superficial and Systemic Fungal Infections," Expert Reviews of Anti-Infective Therapy 1(4):531-542, Dec. 2003.

Cartledge, J.D., et al., "Itraconazole Solution: Higher Serum Drug Concentrations and Better Clinical Response Rates Than the Capsule Formulation in Acquired Immunodeficiency Syndrome Patients With Candidosis," Journal of Clinical Pathology 50(6):477-480, Jun. 1997.

Cauwenbergh, G., and P. Stoffels, "Focus on Itraconazole," Indian Journal of Dermatology, Venereology and Leprology 57(1):4-16, 1991.

Cervera, R., et al., "Systemic Lupus Erythematosus: Pathogenesis, Clinical Manifestations, and Diagnosis," Eular On-Line Course on Rheumatic Diseases, Module No. 17, 2007, 31 pages.

Chen, S., et al., "Active Surveillance for candidemia, Australia," Emerging Infectious Diseases 12(10):1508-1516, Oct. 2006.

Chow, K.W., et al., "Short Treatment Schedules of Itraconazole in Dermatophytosis," International Journal of Dermatology 37(6):446-448, Jun. 1998.

Committee For Medicinal Products For Human Use (CHMP), "Guideline on Clinical Investigation of Immunosuppressants for Solid Organ Transplantation," Doc. Ref. CHMP/EWP/263148/06, 15 pages, Jul. 24, 2008.

Cross, L.J., et al., "Serum Itraconazole Concentrations and Clinical Responses in Candida-Associated Denture Stomatitis Patients Treated With Itraconazole Solution and Itraconazole Capsules," Journal of Antimicrobial Chemotherapy 45(1):95-99, Jan. 2000.

Cuenca-Estrella, M., et al., "Head-to-Head Comparison of the Activities of Currently Available Antifungal Agents Against 3,378 Spanish Clinical Isolates of Yeasts and Filamentous Fungi," Antimicrobial Agents and Chemotherapy 50(3):917-921, Mar. 2006.

De Backer, M., et al., "A 12-Week Treatment for Dermatophyte Toe Onychomycosis Terbinafine 250mg/Day vs. Itraconazole 200mg/Day—A Double-Blind Comparative Trial," British Journal of Dermatology 134((Suppl. 46):16-17, Jun. 1996.

De Beule, K., and J. Van Gestel, "Pharmacology of Itraconazole," Drugs 61(Supp 1):27-37, Dec. 2001.

De Doncker, P.R.G., et al., "Itraconazole Therapy is Effective for Pedal Onychomycosis Caused by Some Nondermatophyte Molds and in Mixed Infection With Dermatophytes and Molds: A Multicenter Study With 36 Patients," Journal of the American Academy of Dermatology 36(2):173-177, Feb. 1996.

Del Rosso, J.Q., et al., "Itraconazole in the Treatment of Superficial Cutaneous and Mucosal Candida Infections," Journal of the American Osteopathic Association 98(9):497-502, Sep. 1998.

Denning, D.W., et al., "Correlation Between In-Vitro Susceptibility Testing to Itraconazole and In-Vivo Outcome of Aspergillus fumigatus Infection," Journal of Antimicrobial Chemotherapy 40(3):401-414, Sep. 1997.

Denning, D.W., et al., "Itraconazole Therapy for Cryptococcal Meningitis and Cryptococcosis," Archives of Internal Medicine 149(10):2301-2308, Oct. 1989.

DiNunzio, J.C., et al., "Amorphous Compositions Using Concentration Enhancing Polymers for Improved Bioavailability of Itraconazole," Molecular Pharmaceutics 5(6):968-980, Nov.-Dec. 2008.

Drake, L., et al., "Once-Weekly Fluconazole (150, 300, or 450 mg) in the Treatment of Distal Subungual Onychomycosis of the Fingernail," Journal of the American Academy of Dermatology 38(6 Pt 2):S87-S94, Jun. 1998.

Drake, L.A., et al., "Oral Terbinafine in the Treatment of Toenail Onychomycosis: North American Multicenter Trial," Journal of the American Academy of Dermatology 37(5 Pt 1):740-745, Nov. 1997.

Drakensjö, I.T., and E. Chryssanthou, "Epidemiology of Dermatophyte Infections in Stockholm, Sweden: A Retrospective Study From 2005-2009," Medical Mycology 49(5):484-488, Jul. 2011.

Easl, "Facts and Figures-The Liver: Vital for Life," <www.easl.eu/assets/application/files/19d80b59a26a03c_file.pdf>, 2011, 2 pages.

Eichel, M., et al., "Itraconazole Suspension in the Treatment of HIV-Infected Patients Suffering From Fluconazole-Resistant Oropharyngeal Candidiasis and Esophagitis," Mycoses 39(Supp. 1):102-106, 1996.

Electronic Medicines Compendium (eMC), Sporanox Capsules, 16 pages, Sep. 16, 2010.

Elewski, B., and A. Tavakkol, "Safety and Tolerability of Oral Antifungal Agents in the Treatment of Fungal Nail Disease: A Proven Reality," Therapeutics and Clinical Risk Management 1(4):299-306, Dec. 2005.

Elewski, B.E., et al., "Onychomycosis: Treatment, Quality of Life, and Economic Issues," American Journal of Clinical Dermatology 1(1):19-26, Jan.-Feb. 2000.

Ellis, D., and R. Handke, "Australian Antifungal Susceptibility Data 2008-2011," ASA Newsletter No. 35, Aug. 2010, pp. 3-7.

Enoch, D.A., et al., "Invasive Fungal Infections: A Review of Epidemiology and Management Options," Journal of Medical Microbiology 55(Pt 7):809-818, Jul. 2006.

Espinel-Ingroff, A., "In Vitro Fungicidal Activities of Voriconazole, Itraconazole, and Amphotericin B Against Dpportunistic Moniliaceous and Dematiaceous Fungi," Journal of Clinical Microbiology 39(3):954-958, Mar. 2001.

Espinel-Ingroff, A., et al., "In Vitro Antifungal Activities of Voriconazole and Reference Agents as Determined by NCCLS Methods: Review of the Literature," Mycopathologia 150(3):101-115, 2001.

Eugloreh, "Chronic Kidney Disease and End Stage Renal Disease," <www.era-edta.org/.../EUGLOREH-final-report-AR-edit-090414.pdf>, 26 pages, 2007.

European Association for the Study of the Liver (EASL), "EASL Clinical Practice Guidelines on the Management of Ascites, Spontaneous Bacterial Peritonitis and Hepatorenal Syndrome in Cirrhosis," Journal of Hepatology 53(3):397-417, Sep. 2010.

Sobel, J.D., "Genital candidiasis," in G.P. Bodey (ed.), "Candidiasis: Pathogenesis, Diagnosis and Treatment," Raven Press, New York, NY, 1993, pp. 225-247.

Spacek, J., and V. Buchta, "Itraconazole in the Treatment of Acute and Recurrent Vulvovaginal Candidosisi Comparison of a 1-Day and a 3-Day Regimen," Mycoses 48(3):165-171, May 2005.

SPORANOX® (itraconazole) Capsules Label, Nov. 2009, 34 pages.

Steinhilber, D., et al., "Effects of Novel Antifungal Azole Derivatives on the 5-Lipoxygenase and Cyclooxygenase Pathway," Arzneimittel-Fforschung 40(11):1260-1263, Nov. 1990.

Stengel, B., and C. Couchoud, "Chronic Kidney Disease Prevalence and Treated End-Stage Renal Disease ncidencei A Complex Relationship," Journal of the American Society of Nephrology 17(8):2094-2096, Aug. 2006.

Tendera, M., et al., "Epidemiology, Treatment, and Guidelines for the Treatment of Heart Failure in Europe," European Heart Journal Supplements 7:J5-J9, 2005.

Tiboni, G.M., et al., "Defining Critical Periods for Itraconazole-Induced Cleft Palate, Limb Defects and Axial Skeletal Malformations in the Mouse," Toxicology Letters 167(1):8-18, Nov. 2006.

Tucker, R.M., et al., "Adverse Events Associated With Itraconazole in 189 Patients on Chronic Therapy," Journal of Antimicrobial Chemotherapy 26(4):561-566, Oct. 1990.

Urünsak, M., et al., "Clinical and Mycological Efficacy of Single-Day Oral Treatment With Itraconazole (400 mg) in Acute Vulvovaginal Candidosis," Mycoses 47(9-10):422-427, Oct. 2004.

United States Pharmacopeia and National Formulary (USP 23), "Ordinary Impurities/Chemical Tests," Jan. 1, 1995, 2 pages.

United States Pharmacopeia and National Formulary (USP 34), "General Information/Application of Water Activity," Aug. 1, 2011, 3 pages.

Van Cauteren, H., et al., "Itraconazole: Pharmacologic Studies in Animals and Humans," Reviews of Infectious Diseases 9(Supp. 1):S43-S46, Jan.-Feb. 1987.

(56) References Cited

OTHER PUBLICATIONS

Van Cauteren, H., et al., "Safety Aspects of Oral Antifungal Agents," British Journal of Clinical Practice. Supplement 71:47-49, Sep. 1990.

Van Cauteren, H., et al., "Toxicological Profile and Safety Evaluation of Antifungal Azole Derivatives," Mycoses 32 (Suppl. 1):60-66, 1989.

Van Cutsem, J., et al., "Activity of Orally, Topically, and Parenterally Administered Itraconazole in the Treatment of Superficial and Deep Mycoses: Animal Models," Revs. Infect. Dis., 9(Supp. 1):S15-S32 (1987).

Van Cutsem, J., et al., "The In Vitro and In Vivo Antifungal Activity of Itraconazole," in R.A. Fromtling (ed.), "Recent Trends in the Discovery, Development, and Evolution of Antifungal Agents," J.R. Prous Science Publishers, 1987, pp. 177-192.

Van Peer, A., et al., "The Effects of Food and Dose on the Oral Systemic Availability of Itraconazole in Healthy Subjects," European Journal of Clinical Pharmacology 36(4):423-426, 1989.

Vanden Bossche, H., et al., "Cytochrome p-450: Target for Itraconazole," Drug Development Research 8(1-4):287-298, 1986.

Vanden Bossche, H., et al., "Effects of Itraconazole on Cytochrome P-450-Dependent Sterol 14a-Demethylation and Reduction of 3-Ketosteroids in Cryptococcus neoformans," Antimicrobial Agents and Chemotherapy 37(10):2101-2105, Oct. 1993.

Vanden Bossche, H., et al., "Interaction of Azole Derivatives With Cytochrome P-450 Isozymes in Yeast, Fungi, Plants and Mammalian Cells," Pesticide Science 21(4):289-306, 1987.

Vanden Bossche, H., et al., "Molecular Mechanisms of Drug Resistance in Fungi," Trends in Microbiology 2(10)2:393-400, Oct. 1994.

Vanden Bossche, H., et al., "P450 Inhibitors of Use in Medical Treatment: Focus on Mechanisms of Action," Pharmacology & Therapeutics 67(1):79-100, 1995.

Vazquez, J.A., "Therapeutic Options for the Management of Oropharyngeal and Esophageal Candidiasis in HIV/AIDS Patients," HIV Clinical Trials 1(1):47-59, Jul.-Aug. 2000.

Velegraki, A., et al., "Use of Fatty Acid RPMI 1640 Media for Testing Susceptibilities of Eight Malassezia Species to the New Triazole Posaconazole and to Six Established Antifungal Agents by a Modified NCCLS M27-A2 Microdilution Method and Etest," Journal of Clinical Microbiology 42(8):3589-3593, Aug. 2004.

Verweij, P.E., et al., "Multiple-Triazole-Resistant Aspergillosis," New England Journal of Medicine 356(14):1481-1483, Apr. 2007.

Wang, E.-J., et al., "Interaction of Common Azole Antifungals with P Glycoprotein," Antimicrobial Agents and Chemotherapy 46(1):160-165, Jan. 2002.

Wesel, S., "Itraconazole: A Single-Day Oral Treatment for Acute Vulvovaginal Candidosis," British Journal of Clinical Practice, Supplement 71:77-80, Sep. 1990.

Wheat, L.J., et al., "Clearance of Fungal Burden During Treatment of Disseminated Histoplasmosis With Liposomal Amphotericin B Versus Itraconazole," Antimicrobial Agents and Chemotherapy 45(8):2354-2357, Aug. 2001.

Wheat, L.J., et al., "Clinical Practice Guidelines for the Management of Patients With Histoplasmosis: 2007 Update by the Infectious Diseases Society of America," Clinical Infectious Diseases 45(7):807-825, Oct. 2007.

Wheat, J., et al., "Prevention of Relapse of Histoplasmosis With Itraconazole in Patients With the Acquired Immunodeficiency Syndrome," Annals of Internal Medicine 118(8):610-616, Apr. 1993.

World Health Organization (WHO), "HIV/AIDS Treatment and Care: Clinical Protocols for the WHO European Region,". I. Eramova et al. (eds ), Copenhagen WHO Regional Office for Europe, 2007, 501 pages.

Willacy, H., "Acute Kidney Injury," http://www.patient.co.uk/printer.asp?doc=40000679, 2010, 7 pages.

Winston, D.J., and R.W. Busuttil, "Randomized Controlled Trial of Oral Itraconazole Solution Versus Intravenous/Oral Fluconazole for Prevention of Fungal Infections in Liver Transplant Recipients," Transplant 74(5):688-695, Sep. 2002.

Winston, D.J., et al., "Intravenous and Oral Itraconazole Versus Intravenous and Oral Fluconazole for Long-Term Antifungal Prophylaxis in Allogeneic Hematopoietic Stem-Cell Transplant Recipients," Annals of Internal Medicine 138(9):705-713, May 2003.

Witt, A., et al., "Monthly Itraconazole Versus Classic Homeopathy for the Treatment of Recurrent Vulvovaginal Candidiasis: A Randomised Trial," BJOG: An International Journal of Obstetrics & Gynaecology 116(11):1499-1505, Oct. 2009.

Woo, J.S., et al., "Reduced Food-Effect and Enhanced Bioavailability of a Self-Microemulsifying Formulation of Itraconazole in Healthy Volunteers," European Journal of Pharmaceutical Science 33(2):159-165, Feb. 2008.

Wooley, P.D., and S.P. Higgins, "Comparison of Clotrimazole, Fluconazole and Intraconazole in Vaginal Candidiasis," British Journal of Clinical Practice 49(2):65-66, Mar.-Apr. 1995.

Yeates, R.A., et al., "Comparative Pharmacokinetics of Fluconazole and of Itraconazole in Japanese and in German Subjects," International Journal of Clinical Pharmacology and Therapeutics 32(3):131-135, Mar. 1995.

Yun, H.Y., et al., "Comparative Analysis of the Effects of Rice and Bread Meals on Bioavailability of Itraconazole Jsing NONMEM in Healthy Volunteers," European Journal of Clinical Pharmacology 62(12):1033-1039, Dec. 2006.

Zimmermann, T., et al., "Influence of Concomitant Food Intake on the Oral Absorption of Two Triazole Antifungal Agents, Itraconazole and Fluconazole," European Journal of Clinical Pharmacology 46(2):147-150, Mar. 1994.

Zimmermann, T., et al., "Influence of Concomitant Food Intake on the Gastrointestinal Absorption of Fluconazole and Itraconazole in Japanese Subjects," International Journal of Clinical Pharmacology Research 14(3):87-93, 1994.

Zonios, D.I., and J.E. Bennett, "Update on Azole Antifungals," Seminars in Respiratory and Critcal Care Medicine 29(2): 198-210, Apr. 2008.

Backer et al., "A 12-week treatment for dermatophyte toe onychomycosis terbinafine 250mg/day vs. itraconazole 200mg/day-a double-blind comparative trial", British J. of Dermatology 134 (Suppl. 46), 16-17 (1996).

Brandt et al. "A double-blind, randomized study comparing itraconazole pulse therapy with continuious dosing for the treatment of toe-nail onychomycosis", Br. J. Dermatol., 136:230-234 (1997).

Brandt et al. "Continuous and intermittent itraconazole dosing schedules for the treatment of onychomycosis: a pharmacokinetic comparison", Br. J. Dermatol., 140:96-101 (1999).

EASL, "EASL clinical practice guidelines on the management of ascites, spontanious bacterial peritonitis and hepatorenal syndrome in cirrhosis", Journal of Hepatology, 53:367-417 (2010).

Figure 7  Mean Concentration - Time Profiles (linear) for Hydroxyitraconazole

Geometric Mean Plasma Concentrations of Itraconazole Following Single Oral Doses of 50 mg SUBA®-itraconazole and 100 mg SPORANOX® (Itraconazole) Capsules in the Fed Condition (Semi-log Scale)

Figure 43. Geometric Mean Plasma Concentrations of Hydroxyitraconazole Following Single Oral Doses of 50 mg LOZANOC and 100 mg SPORANOX® (Itraconazole) Capsules in the Fed Condition (Linear Scale)

Geometric Mean Plasma Concentrations of Hydroxyitraconazole Following Single Oral Doses of 50 mg LOZANOC and 100 mg SPORANOX® (Itraconazole) Capsules in the Fed Condition (Semi-log Scale)

Lozanoc 50 mg hard capsules (fed) vs Sporanox® 100 mg Capsules (fed); AUC/MIC ratio = 25

Example 12 second administration - Lozanoc 50 mg hard capsules (fed) vs Sporanox® 100 mg Capsules; AUC/MIC ratio = 25

ITRACONAZOLE COMPOSITIONS AND DOSAGE FORMS, AND METHODS OF USING THE SAME

CROSS-REFERENCE TO RELATED APPLICATIONS

This application is a continuation of U.S. patent application Ser. No. 16/671,606, filed Nov. 1, 2019, which is a continuation of U.S. patent application Ser. No. 16/198,645, filed Nov. 21, 2018, now U.S. Pat. No. 10,463,740, which is a continuation of U.S. patent application Ser. No. 15/623,742, filed Jun. 15, 2017, now abandoned, which is a continuation of U.S. patent application Ser. No. 14/882,662, filed Oct. 14, 2015, now U.S. Pat. No. 9,713,642, which is a continuation of U.S. patent application Ser. No. 14/511,420, filed Oct. 10, 2014, now U.S. Pat. No. 9,272,046, which is a continuation of U.S. patent application Ser. No. 13/924,222, filed Jun. 21, 2013, now U.S. Pat. No. 8,921,374, which claims the benefit of priority to Australian Provisional Patent Application No. 2012902624, filed on Jun. 21, 2012 and entitled "Itraconazole Formulations and Uses", the contents of each of which are hereby incorporated by reference in its entirety for all purposes.

BACKGROUND

Itraconazole is a triazole antifungal compound that can be used for the treatment of fungal infections, including superficial infections, such as onychomycosis, as well as systemic fungal infections, for example, pulmonary or extrapulmonary blastomycosis, histoplasmosis, and aspergillosis. Solid oral dosage forms of itraconazole are commercially available under the tradename SPORANOX®. SPORANOX® must be taken with food because bioavailability of the itraconazole in the SPORANOX® formulation is enhanced when ingested in the fasted state. Further, the bioavailability of itraconazole in SPORANOX® varies greatly both between subjects (inter-subject), and from dose to dose in a single subject (intra-subject).

This variability is particularly problematic because itraconazole is known to have harmful side effects, especially upon overdosing. Known side effects include gastrointestinal discomfort, dyspepsia, nausea, abdominal pain, constipation, vomiting, diarrhea, headache, increased hepatic enzyme levels, menstrual disorders, dizziness, pruritus, rash, angioedema, and urticaria. Conversely, when insufficient itraconazole is administered, efficacy of the itraconazole is minimal and can contribute to the evolution of multi-drug resistant microbes. Because of the variability in bioavailability of SPORANOX® itraconazole, consistent delivery of a therapeutically effective dose can be a challenge. Thus, improved itraconazole compositions, dosage forms, formulations, and methods of using the same are needed.

SUMMARY OF THE INVENTION

In one embodiment, the present invention provides an oral pharmaceutical composition comprising about 50 mg of itraconazole, wherein the composition exhibits an AUC0-t which is 80% to 125% of about 440 h*ng/ml to about 740 h*ng/ml following administration of the composition to a subject under fed conditions. In one embodiment, the composition exhibits a Cmax which is 80% to 125% of about 60 ng/ml to about 75 ng/ml following administration of the composition to a subject under fed conditions.

In one embodiment, the present composition under fed conditions is therapeutically similar to the reference composition under fed conditions. In another embodiment, the present composition exhibits an absorption profile under fed conditions which is therapeutically similar to the absorption profile of the reference composition under fed conditions. In one embodiment, the present composition under fed conditions is bioequivalent to the reference composition under fed conditions. In another embodiment, the present composition exhibits an absorption profile under fed conditions which is bioequivalent to the absorption profile of the reference composition under fed conditions. In one embodiment, the present composition under fasting conditions is therapeutically similar to the reference composition under fed conditions. In another embodiment, the present composition exhibits an absorption profile under fasting conditions which is therapeutically similar to the absorption profile of the reference composition under fed conditions. In one embodiment, the present composition under fasting conditions is bioequivalent to the reference composition under fed conditions. In another embodiment, the present composition exhibits an absorption profile under fasting conditions which is bioequivalent to the absorption profile of the reference composition under fed conditions. In one embodiment, the present composition under fed conditions is substantially similar to the same composition under fasting conditions. In another embodiment, the present composition exhibits an absorption profile under fed conditions which is substantially similar to the absorption profile of the same composition under fasting conditions.

In one embodiment, the present invention provides an oral pharmaceutical composition comprising about 50 mg of itraconazole, wherein the composition exhibits an $AUC_{0-t}$ which is 80% to 125% of about 350 h*ng/ml to about 620 h*ng/ml following administration of the composition to a subject under fasting conditions. In one embodiment, the composition exhibits a $C_{max}$ which is 80% to 125% of about 30 ng/ml to about 60 ng/ml following administration of the composition to a subject under fasting conditions.

In one embodiment, the present invention provides an oral pharmaceutical composition comprising about 65 mg of itraconazole, wherein the composition exhibits an $AUC_{0-t}$ which is 80% to 125% of about 650 h*ng/ml to about 1200 h*ng/ml following administration of the composition to a subject under fed conditions. In one embodiment, the composition exhibits a $C_{max}$ which is 80% to 125% of about 65 ng/ml to about 100 ng/ml following administration of the composition to a subject under fed conditions.

In one embodiment, the present invention provides an oral pharmaceutical composition comprising about 65 mg of itraconazole, wherein the composition exhibits an $AUC_{0-t}$ which is 80% to 125% of about 450 h*ng/ml to about 900 h*ng/ml following administration of the composition to a subject under fasting conditions. In one embodiment, the composition exhibits a $C_{max}$ which is 80% to 125% of about 36 ng/ml to about 70 ng/ml following administration of the composition to a subject under fasting conditions.

In one embodiment, the present invention provides an oral pharmaceutical composition comprising itraconazole, wherein the composition exhibits an $AUC_{0-t}$ which is 80% to 125% of about 8.8 h*ng/ml to about 14.8 h*ng/ml per milligram of itraconazole following administration of the composition to a subject under fed conditions.

In one embodiment, the present invention provides an oral pharmaceutical composition comprising itraconazole, wherein the composition exhibits an $AUC_{0-t}$ which is 80% to 125% of about 7.0 h*ng/ml to about 12.4 h*ng/ml per milligram of itraconazole following administration of the composition to a subject under fasting conditions.

In one embodiment, the present composition exhibits a reduced variability in the $AUC_{0-t}$ as compared to the reference composition. In another embodiment, the present composition exhibits a variability in the C and/or T as not worse than the reference composition. In another embodiment, the present composition exhibits a reduced variability in the $C_{max}$ and/or T as compared to the reference composition.

In one embodiment, the present invention provides an oral pharmaceutical composition comprising itraconazole, which exhibits an intra-subject coefficient of variation under fed conditions for the $AUC_{0-t}$ of less than about 35%. In one embodiment, the amount of itraconazole in the composition is about 50% to about 65% by weight of the amount of itraconazole in a reference composition.

In one embodiment, the present invention provides an oral pharmaceutical composition comprising itraconazole, which exhibits an inter-subject coefficient of variation under fed conditions for the $AUC_{0-t}$ of less than about 35%. In one embodiment, the amount of itraconazole in the composition is about 50% to about 65% by weight of the amount of itraconazole in a reference composition.

In one embodiment, the present invention provides oral pharmaceutical composition comprising itraconazole, wherein the composition under fed conditions is substantially similar to the same composition under fasting conditions. In another embodiment, the present invention provides oral pharmaceutical composition comprising itraconazole, wherein the composition exhibits an absorption profile under fed conditions which is substantially similar to the absorption profile of the same composition under fasting conditions. In one embodiment, the amount of itraconazole in the composition is about 50% to about 65% by weight of the amount of itraconazole in a reference composition.

In one embodiment, the present invention provides a method of reducing food effect of itraconazole in a subject comprising administering to the subject an oral pharmaceutical composition comprising about 50 mg of itraconazole, and the composition provides an $AUC_{0-t}$ which is 80% to 125% of about 440 h*ng/ml to about 740 h*ng/ml following administration of the composition to a subject under fed conditions. In one embodiment, the composition exhibits an $AUC_{0-t}$ which is 80% to 125% of about 350 h*ng/ml to about 620 h*ng/ml following administration of the composition to a subject under fasting conditions.

In one embodiment, the present invention provides a method of reducing food effect of itraconazole in a subject comprising administering to the subject an oral pharmaceutical composition comprising about 65 mg of itraconazole, and the composition provides an $AUC_{0-t}$ which is 80% to 125% of about 650 h*ng/ml to about 1200 h*ng/ml following administration of the composition to a subject under fed conditions. In one embodiment, the composition exhibits an $AUC_{0-t}$ which is 80% to 125% of about 450 h*ng/ml to about 900 h*ng/ml following administration of the composition to a subject under fasting conditions.

In one embodiment, the present invention provides a method of reducing food effect of itraconazole in a subject comprising administering to the subject an oral pharmaceutical composition comprising of itraconazole, and the composition provides an $AUC_{0-t}$ which is 80% to 125% of about 8.8 h*ng/ml to about 14.8 h*ng/ml per milligram of itraconazole following administration of the composition to a subject under fed conditions. In one embodiment, the composition provides an $AUC_{0-t}$ which is 80% to 125% of about 7.0 h*ng/ml to about 12.4 h*ng/ml per milligram of itraconazole following administration of the composition to a subject under fasting conditions.

In one embodiment, the present invention provides a method of reducing intra-subject variability of itraconazole comprising administering to a subject an oral pharmaceutical composition comprising itraconazole, and the composition exhibits an intra-subject coefficient of variation under fed conditions for the $AUC_{0-t}$ of less than about 35%.

In one embodiment, the present invention provides a method of reducing inter-subject variability of itraconazole comprising administering to subjects an oral pharmaceutical composition comprising itraconazole, and the composition exhibits an inter-subject coefficient of variation under fed conditions for the $AUC_{0-t}$ of less than about 35%.

In one embodiment, the present invention provides a method of treating onychomycosis comprising administering to a subject an oral pharmaceutical composition comprising itraconazole, wherein the amount of itraconazole in the composition is about 50% to about 65% by weight of the amount of itraconazole in a reference composition and the composition is therapeutically equivalent to the reference composition.

In one embodiment, the present invention provides a method of treating onychomycosis comprising administering to a subject an oral pharmaceutical composition comprising itraconazole, wherein the amount of itraconazole in the composition is about 50% to about 65% by weight of the amount of itraconazole in a reference composition and the method provides an effective cure with faster onset efficacy as compared to the reference composition. In one embodiment, the method exhibits efficacy end points at a time when the reference composition does not exhibits efficacy end points. In one embodiment, the efficacy end points is at week five, six, seven, eight, or nine.

In one embodiment, the present invention provides a method of treating a disease or condition comprising co-administering to a subject an oral pharmaceutical composition comprising itraconazole; and a gastric acid suppressor or neutralizer.

In one embodiment, the present invention provides a method of treating cancer comprising administering to a subject an oral pharmaceutical composition of the present invention.

DETAILED DESCRIPTION

Figure 1:
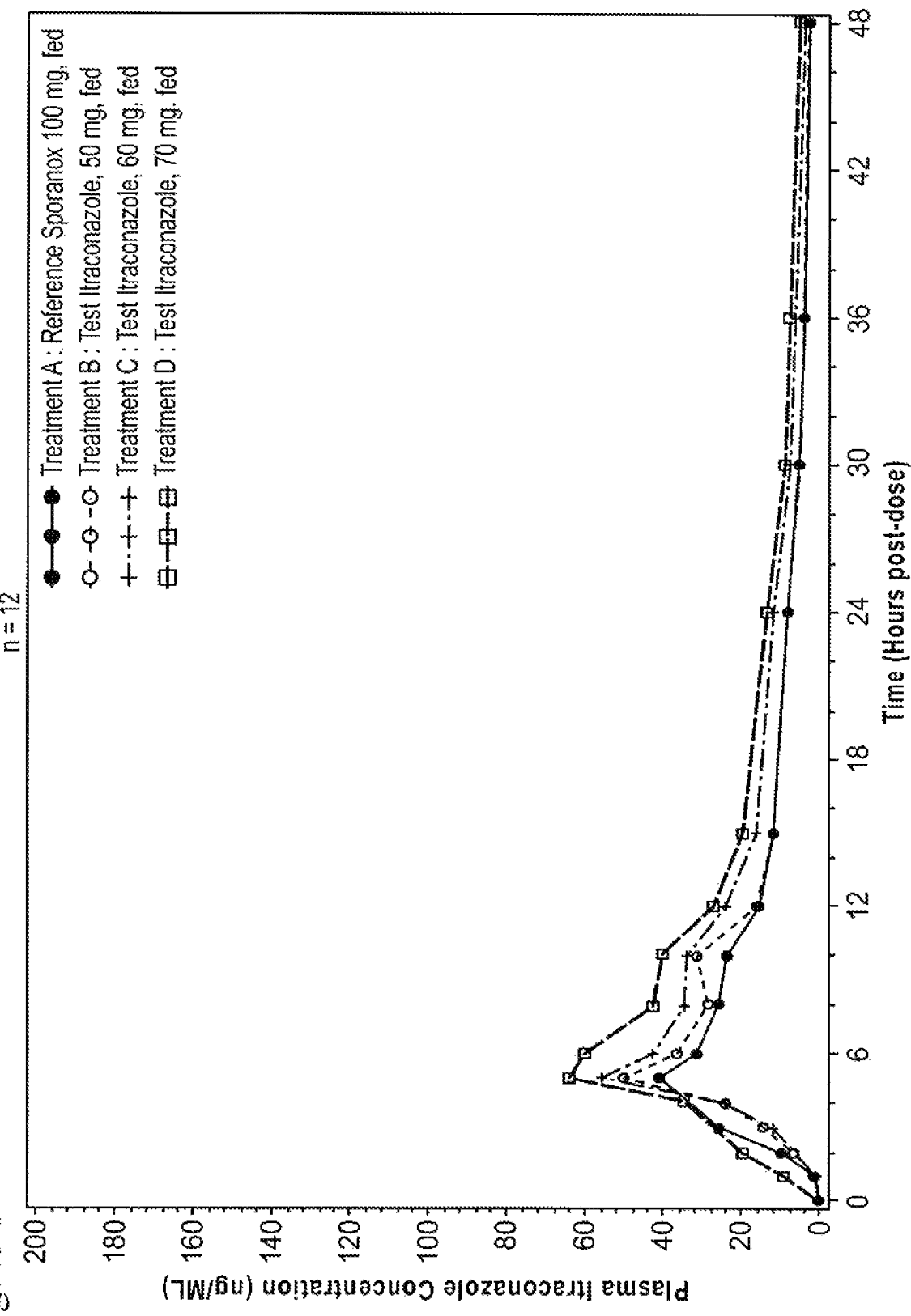
FIG. 1 shows the linear scale graph of the plasma itraconazole concentration against time in a study assessing the relative bioavailability of various LOZANOC doses with a 100 mg dose SPORANOX® under fed conditions. Circles represent the reference SPORANOX® 100 mg dose; diamonds represent the 50 mg LOZANOC dose; stars represent the 60 mg LOZANOC dose; and squares represent the 70 mg LOZANOC dose. All doses were administered under fed conditions.
Figure 2:
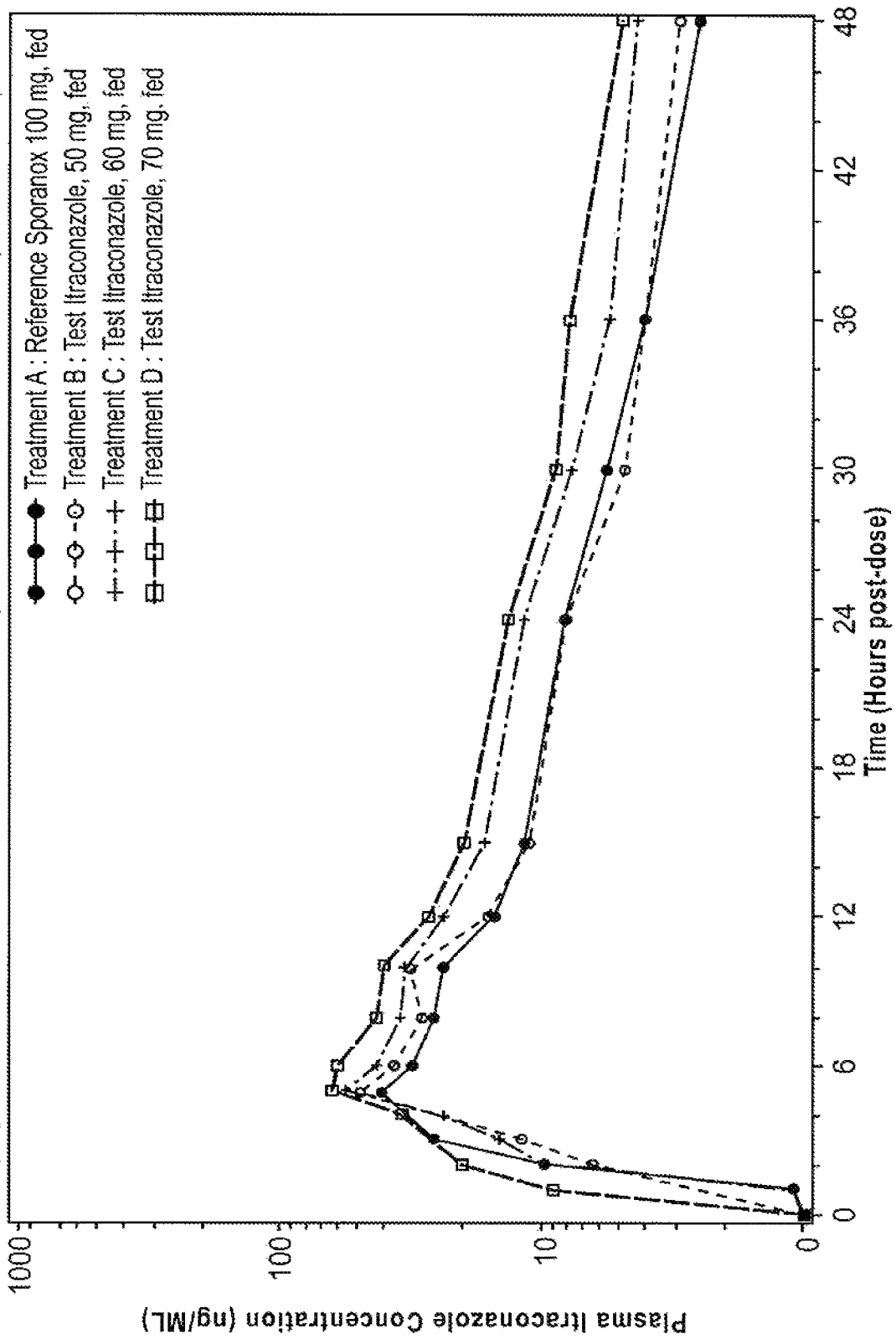
FIG. 2 shows the log-transformed scale graph of the plasma itraconazole concentration against time in a study assessing the relative bioavailability of various LOZANOC doses with a 100 mg dose SPORANOX® under fed conditions. Circles represent the reference SPORANOX® 100 mg dose; diamonds represent the 50 mg LOZANOC dose; stars represent the 60 mg LOZANOC dose; and squares represent the 70 mg LOZANOC dose. All doses were administered under fed conditions.

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

Definitions

Except for the terms discussed below, all of the terms used in this Application are intended to have the meanings that one of skill in the art at the time of the invention would ascribe to them.

"About" includes all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±15%, ±10%, ±5%, ±4%, ±3%, ±2%, ±1%, or ±less than 1%. Importantly, all recitations of a reference value preceded by the term "about" are intended to also be a recitation of the reference value alone. Notwithstanding the preceding, in this application the term "about" has a special meaning with regard to pharmacokinetic parameters, such as area under the curve (including AUC, $AUC_t$, and $AUC_\infty$) $C_{max}$, $T_{max}$, and the like. When used in relationship to a value for a pharmacokinetic parameter, the term "about" means from 80% to 125% of the reference parameter.

"Absorption profile" refers to the rate and extent of exposure of a drug, e.g., itraconazole, by data analysis of the AUC and/or Cmax including the curves thereof.

"Administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, and transdermal. "Administering" can also include prescribing or filling a prescription for a dosage form comprising a particular compound, such as itraconazole, as well as providing directions to carry out a method involving a particular compound or a dosage form comprising the compound. In particular, the administration method can be oral administration.

"Bioequivalence" means the absence of a significant difference in the rate and extent to which the active agent or surrogate marker for the active agent in pharmaceutical equivalents or pharmaceutical alternatives becomes available at the site of action when administered in an appropriately designed study. For example, bioequivalence can be defined by the definition promulgated by the U.S. Food and Drug Administration or any successor agency thereof, such as the Federal Drug Administration's guidelines and criteria, including "GUIDANCE FOR INDUSTRY BIOAVAILABILITY AND BIOEQUVALENCE STUDIES FOR ORALLY ADMINISTERED DRUG PRODUCTS—GENERAL CONSIDERATIONS" available from the U.S. Department of Health and Human Services (DHHS), Food and Drug Administration (FDA), Center for Drug Evaluation and Research (CDER) March 2003 Revision 1; and "GUIDANCE FOR INDUSTRY STATISTICAL APPROACHES TO ESTABLISHING BIOEQUIVALENCE" DHHS, FDA, CDER, January 2001, both of which are incorporated by reference herein in their entirety. Alternatively bioequivalence can be shown by Europe's EMEA guidelines, wherein the 90% CI limits for a ratio of the geometric mean of logarithmic transformed AUC0-∞ and AUC0-t for the two products or methods are about 0.80 to about 1.25. The 90% CI limits for a ratio of the geometric mean of logarithmic transformed Cmax for the two products or methods can have a wider acceptance range when justified by safety and efficacy considerations. For example the acceptance range can be about 0.70 to about 1.43, specifically about 0.75 to about 1.33, and more specifically about 0.80 to about 1.25.

"Co-administration" refers to administration of two or more different active agents together in a coordinated manner. Co-administration includes administration of two or more different active agents simultaneously, sequentially, or separately. Thus, "co-administration" includes administration in the same or different dosage forms, concurrent administration, as well as administration that is not concurrent, such as administration of a first active agent followed or alternated with administration of a second active agent as part of a coordinated plan for treatment.

A "composition" is a collection of materials containing the specified components. One or more dosage forms may constitute a composition, so long as those dosage forms are associated and designed for use together. For example, a composition comprising about 50 mg of itraconazole includes two unit dosage forms having about 25 mg of itraconazole each if the two dosage forms are designed to be administered together or at approximately the same time to the same subject.

"Enteric polymer" refers to a polymer that is poorly soluble in aqueous medium at a pH of about 4.5 or less, but becomes soluble in aqueous medium at a pH of greater than about 5. For example, an enteric polymer is poorly soluble in gastric juice, but is soluble in the lower GI tract environment.

"Itraconazole" is a common name for a triazole antifungal compound, the specific chemical structure and IUPAC name of which are well known in the art. It is available commercially (see Merck Index Reg. No. 5262 (12th ed. 1996) and U.S. Pat. No. 4,267,179). As used herein, "itraconazole" includes not only the chemical compound (free base form, also referred to as "free itraconazole"), but also all optical isomers, such as enantiomers, diastereomers, meso compounds, and the like, as well as pharmaceutically acceptable salts, solvates, and prodrugs (such as esters) thereof.

"Pharmaceutical composition" refers to a formulation of a compound of the disclosure, such as itraconazole, and a medium generally accepted in the art for the delivery of the biologically active compound to mammals, e.g., humans. Such a medium includes all pharmaceutically acceptable carriers, diluents or excipients therefor. The pharmaceutical composition may be in various dosage forms or contain one or more unit dose formulations.

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

A "reference composition of itraconazole" (reference composition) is a composition comprising itraconazole that exhibits one or more of (1) has a $AUC_t$ in the fasted state that is about 35% or more lower than the $AUC_t$ in the fed state; (2) has an intra-subject variability of about 30% or greater; and (3) about 100 mg of itraconazole or more. Particular reference compositions include those with about 100 mg of itraconazole or more. Other particular reference compositions include those that do not include a solid solution or solid dispersion of itraconazole in an acid resistant polymeric carrier. One exemplary particular reference composition contains a blend of itraconazole, and one or more excipients, such as diluents, carriers, fillers, disintegrants, and the like. Another exemplary particular reference composition contains 100 mg of itraconazole, sugar spheres, hydroxypropyl methyl cellulose, and polyethylene glycol, such as polyethylene glycol 20000, in a gelatin capsule shell.

For example, and most particularly, the reference dosage form can be a capsule commercially available under the name SPORANOX®.

"Salts" include derivatives of an active agent, wherein the active agent is modified by making acid or base addition salts thereof. Examples of pharmaceutically acceptable salts include, but are not limited to, mineral or organic acid addition salts of basic residues such as amines; alkali or organic addition salts of acidic residues; and the like, or a combination comprising one or more of the foregoing salts. The pharmaceutically acceptable salts include salts and the quaternary ammonium salts of the active agent. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; or a combination comprising one or more of the foregoing salts.

"Solvate" means a complex formed by solvation (the combination of solvent molecules with molecules or ions of the active agent of the present invention), or an aggregate that consists of a solute ion or molecule (the active agent of the present invention) with one or more solvent molecules. For example, a solvate where the solvent molecule or molecules are water is called a hydrate. Hydrates are particularly contemplated as solvates of the materials described herein.

"Solid dispersion" relates to a solid system comprising a nearly homogeneous or homogeneous dispersion of an active ingredient, such as itraconazole, in an inert carrier or matrix.

"Substantially similar to" means having a great extent or degree of likeness to the reference item, term, quantity, etc.

"Prodrug" refers to a precursor of the active agent wherein the precursor itself may or may not be pharmaceutically active but, upon administration, will be converted, either metabolically or otherwise, into the active agent or drug of interest. For example, prodrug includes an ester or an ether form of an active agent.

"Therapeutically effective amount" or "effective amount" refers the amount of a pharmaceutically active agent, such as itraconazole, that, when administered to a patient for treating a disease according to the dosing regimen as described herein, is sufficient to effect such treatment for the disease. The "therapeutically effective amount" will vary depending on the disease and its severity, and the age, weight, and other conditions of the patient to be treated.

A composition or dosage form is "therapeutically equivalent" to a reference composition or dosage form if it has a therapeutic effect that is substantially similar to the therapeutic effect of the reference composition or dosage form, for example, therapeutically equivalent dosage forms can have substantially similar efficacy towards a particular disease or condition when administered over a substantially similar time period.

"Treating" includes ameliorating, mitigating, and reducing the instances of a disease or condition, or the symptoms of a disease or condition, in addition to providing directions or prescribing a drug for such purpose.

"Patient" or "subject" refers to a mammal, e.g., a human, in need of medical treatment. Particular pharmacokinetic parameters are defined in Table 1.

TABLE 1

| Parameter | Definition |
|---|---|
| $AUC_{0-tlast}$ | Area under the plasma concentration-time curve from time zero up to the last quantifiable concentration |
| $AUC_{0-\infty}$ | Area under the plasma concentration-time curve from time zero to infinity |
| $\%AUC_{extrap}$ | Percentage of AUC that is due to extrapolation from $t_{last}$ to infinity |
| $C_{max}$ | Maximum observed plasma concentration |
| $t_{max}$ | Time of the maximum observed plasma concentration |
| $t_{lag}$ | Time before the start of absorption |
| $t_{last}$ | Time of the last quantifiable plasma concentration |
| $t_{1/2}$ | Apparent plasma terminal elimination half-life |
| CL/F | Apparent total plasma clearance (itraconazole only) |
| $V_z/F$ | Apparent volume of distribution during the terminal phase (itraconazole only) |
| $MR_{AUC}$ | Metabolic ratio based on AUC (hydoxyitraconazole only) |
| $MR_{Cmax}$ | Metabolic ration based on $C_{max}$ (hydroxyitraconazole only) |

It is noted that $AUC_{0-t}$ and $AUC_{0-tlast}$ are used interchangeably herein. Also, $AUC_{inf}$ and $AUC_{t-inf}$ are used interchangeably with $AUC_{0-\infty}$. It should also be understood that, unless otherwise specified, all pharmacokinetic parameters are measured after a single administration of the specified amount of itraconazole followed by a washout period in which no additional itraconazole is administered.

Pharmaceutical Composition Comprising Itraconazole

A composition comprising itraconazole can comprise a therapeutically amount of itraconazole and less than 75 mg of itraconazole, such as about 50 mg to about 65 mg of itraconazole. Particular compositions can comprise about 50 mg of itraconazole. Other particular compositions can comprise about 65 mg of itraconazole.

When administered to a subject in the fed state, a composition, such as any described herein, and particular a composition comprising about 50 mg of itraconazole, can exhibit certain pharmacokinetic parameters. For example, when administered to a subject in the fed state, the composition can exhibit an $AUC_{0-t}$ of about 440 ng hr/mL or higher, such as from about 440 ng hr/mL to about 740 ng hr/mL, about 440 ng hr/mL to about 700 ng hr/mL, or about 448 ng hr/mL to about 676 ng hr/mL. In particular, when administered to a subject in the fed state, the composition can exhibit an $AUC_{0-t}$ from about 475 to about 625 ng hr/mL. Even more particularly, when administered to a subject in the fed state, the composition can exhibit an $AUC_{0-t}$ from about 500 to about 600 ng hr/mL. Thus, the ratio of $AUC_{0-t}$ (in ng hr/mL) administered in a fed state to itraconazole mass (in mg) can be about 8.8 or higher, such as from about 8.8 to about 14.8, about 8.8 to about 14.0, about 9.0 to about 13.6, about 9.5 to about 12.5, or about 10.0 to about 12.0.

A composition, including any dosage form described herein, and particularly a composition comprising about 50 mg of itraconazole, can also have a particular $AUC_{0-t}$ when administered to a subject in the fasted state. For example, when administered to a subject in the fasted state, the $AUC_{0-t}$ can be about 350 ng hr/mL or higher, such as from about 350 to about 620 ng hr/mL, about 355 to about 550 ng hr/mL, or about 359 to about 534 ng hr/mL. In particular, when administered to a subject in the fasted state, the $AUC_{0-t}$ can be from about 375 to about 515 ng hr/mL. Even more particularly, when administered to a subject in the fasted state, the $AUC_{0-t}$ can be from about 400 to about 500 ng hr/mL. Thus, the ratio of $AUC_{0-t}$ (in ng hr/mL) when administered to a subject in the fasted state to mass of itraconazole (in mg) can be about 7.0 or higher, such as from about 7.0 to about 12.4, about 7.1 to about 11.0, about 7.0 to about 10.7, about 7.5 to about 10.3, or about 8.0 to about 10.0.

A composition, including any described herein, and particularly a composition comprising about 50 mg of itraconazole, can have a particular $AUC_{inf}$ when administered to a subject in the fed state. For example, the $AUC_{inf}$, when administered to a subject in the fed state, can be about 575 ng hr/mL or higher, such as about 590 to about 750 ng hr/mL. Particularly, the $AUC_{inf}$, when administered to a subject in the fed state, can be about 591 to about 736 ng hr/mL, such as about 600 to about 725 ng hr/m. Even more particularly, the AUCinf, when administered to a subject in the fed state, can be about 625 to about 700 ng hr/mL. Thus, the ratio of $AUC_{inf}$ when administered to a subject in the fed state (in ng hr/mL) to mass of itraconazole (in mg) can be about 11.5 or higher, such as about 11.8 to about 15, about 12 to about 14.5, or about 12.5 to about 14.

A composition, including any described herein, and particularly a composition comprising about 50 mg of itraconazole, can have a particular $AUC_{inf}$ when administered to a subject in the fasted state. For example, the $AUC_{inf}$, when administered to a subject in the fasted state, can be about 500 ng hr/mL or higher, such as about 521 ng hr/mL to about 611 ng hr/mL. Particularly, the $AUC_{inf}$ when administered to a subject in the fasted state, can be about 550 ng hr/mL to about 600 ng hr/mL. Thus, the ratio of $AUC_{inf}$ when administered to a subject in the fasted state (in ng hr/mL) to mass of itraconazole (in mg) can be about 10 or higher, such as about 10.4 to about 12.22, or about 11.0 to about 12.0.

A composition, including any described herein, and particularly a dosage form comprising about 50 mg of itraconazole, can have a particular C when administered to a subject in the fed state. For example, when administered to a subject in the fed state, the Cmax can be about 60 ng/mL or higher, such as from about 60 to about 75 ng/mL or about 63 to about 75 ng/mL. In particular, when administered to a subject in the fed state, the $C_{max}$ can be from about 65 to about 70 ng/mL.

A composition, including any described herein, and particularly a dosage form comprising about 50 mg of itraconazole, can have a particular $C_{max}$ when administered to a subject in the fasted state. For example, when administered to a subject in the fasted state, the $C_{max}$ can be about 30 ng/mL or higher, such as about 30 ng/mL to about 60 ng/mL or about 32 ng/mL to about 55 ng/mL. In particular, when administered to a subject in the fasted state, the $C_{max}$ can be from about 37 ng/mL to about 52 ng/mL or about 35 ng/mL to about 50 ng/mL. More particularly, when administered to a subject in the fasted state, the $C_{max}$ can be from about 40 ng/mL to about 50 ng/mL or about 42 ng/mL to about 50 ng/mL.

A composition, including any described herein, and particularly a dosage form comprising about 65 mg of itraconazole can have a particular $AUC_{0-t}$ when administered to a subject in the fed state. For example, the $AUC_{0-t}$, when administered to a subject in the fed state, can be about 650 ng hr/mL or greater, such as about 650 to about 1200 ng hr/mL or about 671 to about 1172 ng hr/mL. Particularly, the $AUC_{0-t}$, when administered to a subject in the fed state, can be about 700 to about 950 ng hr/mL. Even more particularly, the $AUC_{0-t}$, when administered to a subject in the fed state, can be about 750 to about 850 ng hr/mL. Thus, the ratio of $AUC_{0-t}$ (in ng hr/mL) when administered to a subject in the fed state to mass of itraconazole (in mg) can be about 10.0 or higher, such as about 10.3 to about 18.0, about 10.8 to about 14.6, or about 11.5 to about 13.0.

A composition, including any described herein, and particularly a dosage form comprising about 65 mg of itraconazole, can have a particular $AUC_{0-t}$ when administered to a subject in the fasted state. For example, the $AUC_{0-t}$, when administered to a subject in the fasted state, can be about 450 ng hr/mL or greater, such as about 450 to about 900 ng hr/mL, about 485 to about 900 ng hr/mL, or about 500 to about 885 ng hr/mL. Particularly, the $AUC_{0-t}$, when administered to a subject in the fasted state, can be about 525 to about 725 ng hr/mL. Even more particularly, the $AUC_{0-t}$, when administered to a subject in the fasted state, can be about 600 to about 700 ng hr/mL. Thus, the ratio of $AUC_{0-t}$ (in ng hr/mL) when administered to a subject in the fasted state to the mass of itraconazole (in mg) can be about 7.5 or greater, such as about 7.5 to about 13.6, about 7.7 to about 13.6, about 801 to about 11.2, or about 9.2 to about 10.8.

A composition, including any described herein, and particularly a dosage form comprising about 65 mg of itraconazole, can have a particular $AUC_{inf}$ when administered to a subject in the fed state. For example, the $AUC_{inf}$, when administered to a subject in the fed state, can be about 800 ng hr/mL or greater, such as about 811 ng hr/mL to about 1,400 ng hr/mL. In particular, the $AUC_{inf}$ when administered to a subject in the fed state, can be about 850 ng hr/mL to about 1,200 ng hr/mL. Even more particularly, the $AUC_{inf}$ when administered to a subject in the fed state, can be about 900 ng hr/mL to about 1,000 ng hr/mL, or about 850 to about 950 ng hr/mL. Thus, the ratio of the $AUC_{inf}$ (in ng hr/mL) when administered to a subject in the fed state to the mass of itraconazole (in mg) can be about 12.3 or greater, such as, about 12.3 to about 21.5, about 12.5 to about 21.5, about 13.1 to about 18.5, about 13.9 to about 15.4, or about 13.1 to about 14.6.

A composition, including any described herein, and particularly a dosage form comprising about 65 mg of itraconazole, can have a particular $AUC_{inf}$ when administered to a subject in the fasted state. For example, the $AUC_{inf}$, when administered to a subject in the fasted state, can be about 600 ng hr/mL or greater, such as about 610 ng hr/mL to about 1,050 ng hr/mL. In particular, the $AUC_{inf}$ when administered to a subject in the fasted state, can be about 640 ng hr/mL to about 900 ng hr/mL. Even more particularly, the $AUC_{inf}$ when administered to a subject in the fasted state, can be about 675 ng hr/mL to about 750 ng hr/mL, or about 625 to about 800 ng hr/mL. Thus, the ratio of $AUC_{inf}$ (in ng hr/mL when administered to a subject in the fasted state to the mass of itraconazole (in mg) can be about 9.2 or greater, such as about 9.2 to about 16.2, about 9.4 to about 16.2, about 9.8 to about 13.8, about 10.4 to about 12.3, or about 9.6 to about 11.5.

A composition, including any described herein, and particularly a dosage form comprising about 65 mg of itraconazole, when administered to a subject in the fed state, can have a $C_{max}$ of about 65 ng/mL or higher, such as about 85 ng/mL to about 100 ng/mL. Particularly, when administered to a subject in the fed state, the $C_{max}$ can be about 70 ng/mL to about 80 ng/mL. Thus the ratio of C (in ng/mL) when administered to a subject in the fed state to the mass of itraconazole (in mg) can be about 1.00 or greater, such as about 1.00 to about 1.54 about 1.31 to about 1.54, or about 1.08 to about 1.23.

A composition, including any described herein, and particularly a dosage form comprising about 65 mg of itraconazole, when administered to a subject in the fasted state, can have a C of about 35 ng/mL or higher, such as about 35 ng/mL to about 70 ng/mL. Particularly, when administered to a subject in the fasted state, the Cmax can be about 40 ng/mL to about 65 ng/mL. Thus the ratio of $C_{max}$ (in ng/mL) when administered to a subject in the fasted state to the mass of itraconazole (in mg) can be about 0.54 or greater, such as about 0.54 to about 1.08, or about 0.62 to about 1.00.

The present composition comprising itraconazole can also comprise one or more excipients. The excipients can include one or more of waxes, polymers, binders, fillers, disintegrants, glidants, and the like. The polymers can include any pharmaceutically acceptable polymer, such as one or more hydrophilic polymers; one or more non-gelling polymers; one or more acid-resistant polymers and enteric polymers; one or more osmopolymers; one or more film-forming, water insoluble polymers; one or more film-forming, water soluble polymers; or combinations thereof. The waxes can include one or more of beeswax, spermaceti, lanolin, carnauba wax, candelilla wax, ouricury wax, sugercane wax, retamo wax, jojoba oil, epicuticula waxes, paraffin, montan wax, waxes produced from cracking polyethylene, microcrystalline wax, petroleum jelly, and the like.

Binders can include any one or more of saccharides, such as sucrose, lactose, mannose, trehaolse, fructose, starches, cellulose, microcrystalline cellulose, methyl cellulose, ethyl cellulose, hydroxypropyl cellulose, hydroxypropyl methylcellulose, and the like, gelatin, polyvinylpyrrolidone, polyethylene glycol, and the like.

Disintegrants can include one or more of crospovidone, croscarmellose, such as crosscarmellose sodium, polyvinylpyrrolidone, methyl cellulose, microcrystalline cellulose, lower alkyl-substituted hydroxypropyl cellulose, such as hydroxypropyl methyl cellulose and hydroxypropyl ethyl cellulose, starch, pregelatinised starch, sodium alginate, and sodium starch glycolate, for example, sodium starch glycolate.

Fillers can include one or more of cellulose, microcrystalline cellulose, dibasic calcium phosphate, monobasic calcium phosphate, lactose, sucrose, glucose, mannitol, sorbitol, calcium carbonate, and the like.

Polymers can include any pharmaceutically acceptable polymer. The polymer can be formulated with the active compound (e.g., itraconazole) and one or more additional excipients in various forms. For example, the present composition may be formulated to a matrix system, an osmotic delivery system, or a multiparticulate system. As used herein, the term "matrix" denotes a homogeneous solid mixture composed of evenly dispersed ingredients throughout. In one embodiment, the matrix system is a solid solution or solid dispersion as described herein.

In one embodiment of the osmotic delivery system, the composition comprises a release rate controlling membrane disposed over a pull layer and an osmotic push layer, wherein the pull layer comprises itraconazole, and the release rate controlling membrane has an orifice immediately adjacent to the pull layer. The pull layer further optionally comprises a release rate controlling polymer and/or a pharmaceutically acceptable excipient. The release rate controlling membrane is a semipermeable wall that surrounds the pull layer and the osmotic push layer. The wall is permeable to the passage of fluid and has an orifice which allows passage of itraconazole, from inside of the wall to outside. Upon being exposed to biological or other fluids, the semipermeable wall allows permeation of the fluids through the wall causing expansion of the osmotic push layer, and consequently the osmotic push layer pushes the pull layer through the orifice. The release rate of itraconazole, is determined by the permeability of the wall and the osmotic pressure gradient across the wall. In one embodiment, the osmotic push layer comprises an osmopolymer. In one embodiment, the pull layer further comprises an osmagent, also known as osmotically effective solutes. The osmagent can be any compound, inorganic or organic, that exhibit an osmotic pressure gradient across an external fluid across the semipermeable wall.

Certain examples of the multiparticulate delivery system and the manufacturing thereof are described in detail in Lu, Int. J. Pharm., 1994, 112, pages 117-124, the content of which is herein incorporated by reference in its entirety. In one embodiment, the composition comprises one or more particles and each of the particles comprises an active core comprising itraconazole; and a release rate controlling polymer disposed over the core. In another embodiment, the composition comprises one or more particles and each of the particles comprises an inert core, an active layer comprising itraconazole disposed over the inert core, and a release rate controlling polymer disposed over the active layer. In another embodiment, the composition comprises an inert core, and a coating disposed over the inert core, wherein the coating comprises itraconazole. Any of the active core, the inert core, the active layer, the coating, or the coating formed by the release rate controlling polymer disposed over the active layer may optionally further comprise a pharmaceutically acceptable excipient. In one embodiment of the multiparticulate delivery system, the release rate controlling polymer comprises a film-forming, water insoluble polymer in combination with a film-forming, water soluble polymer. The ratio between the water insoluble polymer and the water soluble polymer can be adjusted depending on the intended drug release profile.

"Hydrophilic polymer" refers to a polymer having a strong affinity for water and tending to dissolve in, mix with, or be wetted by water. Examples of the hydrophilic polymer include, but are not limited to polyethylene oxide, hydroxypropyl cellulose, hydroxypropyl methyl cellulose, hydroxyethyl cellulose, sodium carboxymethylcellulose, calcium carboxymethyl cellulose, methyl cellulose, polyacrylic acid, maltodextrin, pre-gelatinized starch, guar gum, sodium alginate, polyvinyl alcohol, chitosan, locust bean gum, amylase, any other water-swelling polymer, and a combination thereof.

By "non-gelling polymer", it is meant a polymer that only swells slightly or does not swell to form a gel when exposed to an aqueous medium. Exemplary non-gelling polymers include cellulose acetate phthalate (e.g., powder: pH 6.2, available from Eastman Chemical Co. as C-A-P; Dispersion: pH: 6.0, available from FMC BioPolymer as AquaCoat® CPD), cellulose acetate succinate (e.g., LF: pH 5.5; MF: pH 6.0; HF: pH 6.8; LG; pH 5.5; MG: pH 6.0; HG: 6.8, F grades are an aqueous dispersion and G grades are from solvent available from Shin-Etsu under the trade name AQOAT®), hypromellose phthalate (HPMCP) (e.g., Grade HP-50: pH 5.0; Grade HP-55: pH 5.5 available from Shin-Etsu), hypromellose acetate succinate (HPMCAS), polyvinylacetate phthalate (e.g., aqueous dispersion: pH 5.0; Powder: pH 5.0 available from Colorcon, the aqueous dispersion under the trade name Sureteric® and the powder under the trade name Opadry® Enteric), hydroxyethyl cellulose phthalate, cellulose acetate maleate, cellulose acetate trimellitate, cellulose acetate butyrate, cellulose acetate propionate, methacrylic acid-methyl methacylate co-polymers (e.g., Type A: pH 6.0; Type B: pH 7.0 both available from Degussa/Evonik with the trade names EUDRAGIT® L 100 for Type A and EUDRAGIT® S 100 for Type B), methacrylic acid-ethylacrylate co-polymers (available under the trade name EUDRAGIT® L, e.g., L100-55), methacrylic acid-methyl acrylate-methyl methacrylate co-polymers (available under the trade name EUDRAGIT® FS-30D for delivery above pH 7.0), and the like or combinations comprising at least one of the foregoing. Methacrylic acid-methyl methacylate co-polymers, methacrylic acid-ethylacrylate co-polymers, and/or methacrylic acid-methyl acrylate-methyl methacrylate co-polymers are also known as polymethacrylates as described in the Handbook of Pharmaceutical Excipients, 2006, the Fifth Edition, edited by Raymond C Rowe, Paul J. Sheskey, and Sian C Owen, pages 553 to 560, the content of which is incorporated by references in its entirety. EUDRAGIT® is a trademark of Evonik Industries. The specifications for various EUDRAGIT® products including the above-mentioned ones can be found in the manufacture's product manual or on the website for the corresponding EUDRAGIT® product, the content of which is incorporated by references in its entirety.

The osmopolymers are typically hydrophilic polymers and interact with water and aqueous biological fluids and swell or expand to push a drug composition through the orifice. The osmopolymers exhibit the ability to swell in water and retain a significant portion of the imbibed water within the polymer structure. The osmopolymers may swell or expand to a very high degree. The osmopolymers can be noncross-linked or cross-linked. The swellable, hydrophilic polymers may be lightly cross-linked, such as cross-links being formed by covalent or ionic bonds. The osmopolymers can be of plant, animal or synthetic origin. Hydrophilic polymers suitable for the present purpose include, but are not limited to poly(hydroxyalkylmethacrylate) having a molecular weight of from 30,000 to 5,000,000; poly(vinylpyrrolidone) having molecular weight of from 10,000 to 360,000; anionic and cationic hydrogels; polyelectrolyte complexes, poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer reduced by forming a dispersion of finely divided copolymer of maleic anhydride with styrene, ethylene, propylene, butylene or isobutylene cross-linked with from 0.00001 to about 0.5 moles of polyunsaturated cross-linking agent per mole of maleic anhydride in the copolymer; water swellable polymers of N-vinyl lactams, and the like. Other osmopolymers include hydrogel polymers, such as Carbopol (acrylic acid-based polymers cross-linked with polyalkylene polyethers) and the sodium salt thereof; acidic carboxy polymers generally having a molecular weight of 450,000 to 4,000,000 and their metal salts; Polyox; polyethylene oxide polymers having a molecular weight of 100,000 to 7,500,000.

Examples of the film-forming, water insoluble polymer include, but are not limited to ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane, or any other water insoluble polymer, or mixtures thereof.

Examples of the film-forming, water soluble polymer include, but are not limited to polyvinyl alcohol, polyvinylpyrrolidone, methyl cellulose, hydroxypropyl cellulose, hydroxypropylmethyl cellulose and polyethylene glycol, Pluronic F108, Pluronic F127, Pluronic F68 or mixtures thereof.

The present composition may be formulated to a matrix system. The composition comprising itraconazole can comprise a solid solution or solid dispersion, for example, a solid dispersion, of itraconazole in a pharmaceutically acceptable carrier. The pharmaceutically acceptable carrier can be a polymer. Exemplary polymers include acid-resistant polymers and enteric polymers, although other polymers can also be used. Acid-resistant polymers can include polymers that are insoluble in water at any pH and polymers that are insoluble in water at an acidic pH, such as enteric polymers. Exemplary acid-resistant polymers include hydroxypropyl methylcellulose phthalate, polyvinyl acetate phthalate, hydroxypropyl methylcellulose acetate, such as hydroxypropyl methylcellulose acetate succinate, alginate, poly(meth)acrylic acid homopolymers and copolymers, carbomers, carboxymethyl cellulose, carboxymethyl cellulose, methacrylic acid copolymers, shellac, cellulose acetate phthalate, hydroxypropyl cellulose acetate phthalate, cellulose acetate terephthalate, methyl cellulose acetate phthalate, cellulose acetate isophthalate, cellulose acetate trimellitate, EUDRAGIT® polymers (copolymers of one or more of poly(meth)acrylates, poly(meth)acrylic esters, and poly (meth)acrylamides), and the like. A particular exemplary acid-resistant polymer is hydroxypropyl methylcellulose phthalate.

Exemplary enteric polymers include one or more of hydroxypropyl methylcellulose phthalate; polyvinyl acetate phthalate; hydroxypropylmethylcellulose acetate succinate; alginate; carbomer; carboxymethyl cellulose; methacrylic acid copolymer; shellac; cellulose acetate phthalate; starch glycolate; polacrylin; cellulose acetate phthalate; methyl cellulose acetate phthalate; hydroxypropylcellulose acetate phthalate; cellulose acetate terephthalate; cellulose acetate isophthalate; and cellulose acetate trimellitate. A particular enteric polymer is hydroxypropyl methylcellulose phthalate, which is commercially available from Shin-Etsu Chemical Industry Co Ltd under the trade names HP-50, HP-55, and HP-55S.

A composition comprising itraconazole can comprise a solid solution or solid dispersion, for example, a solid dispersion, of itraconazole in a pharmaceutically acceptable carrier. The pharmaceutically acceptable carrier can be a polymer, such as an acid-resistant polymer or an enteric polymer, particularly the acid-resistant polymers discussed herein, or the enteric polymers discussed herein, and, for example, more particularly hydroxypropyl methylcellulose phthalate, which is commercially available from Shin-Etsu Chemical Industry Co Ltd under the trade names HP-50, HP-55, and HP-55S.

The solid solution or solid dispersion can be made by methods known in the art, for example, by methods disclosed in U.S. Pat. No. 6,881,745, which is hereby incorporated by reference in its entirety and for all purposes. For example, a solid solution or solid dispersion can be made by dissolving or dispersing the pharmaceutically acceptable carrier and the itraconazole in a suitable solvent and then removing the solvent. The suitable solvent can be, for example, one or more of methylene chloride, chloroform, ethanol, methanol, propan-2-ol, ethyl acetate, acetone, water, and mixtures thereof. A particular solvent is methylene chloride.

Removing the solvent can be accomplished by evaporation, spray drying, lyophilizing, and the like. Removing the solvent can also be accomplished by allowing the itraconazole and pharmaceutically acceptable carrier to co-precipitate or co-crystallize out of solution, followed by one or more of filtration, decanting, centrifuging, and the like.

Other methods of forming solid solutions or solid dispersions include co-grinding, melt extrusion, freeze drying, rotary evaporation, and other solvent removal processes.

The composition comprising itraconazole can comprise a therapeutically effective amount of free itraconazole. When the itraconazole is in the form of a solid dispersion, the solid dispersion can be present in sufficient amounts to provide a therapeutically effective amount of itraconazole. The therapeutically effective amount of itraconazole, which in the case of a salt, solvate, ester, or the like is measured by the amount of free itraconazole, can be less than about 100 mg, for example, less than about 70 mg. Exemplary amounts of free itraconazole for a single dosage form include about 48 mg to about 68 mg, such as about 50 mg to about 65 mg, for instance about 50 mg to about 65 mg, for example, about 50 mg or about 65 mg.

The weight ratio of the free itraconazole in the solid solution or solid dispersion to the pharmaceutically acceptable carrier, such as hydroxypropyl methylcellulose phthalate, can be from about 3:1 to about 1:20, such as about 3:1 to about 1:5, about 1:1 to about 1:3, or about 1:1.5, based on the weight of free itraconazole. Thus, the pharmaceutically acceptable carrier, such as hydroxypropyl methylcellulose phthalate, can be present from about 15 mg to about 1,360 mg, for example, from about 15 mg to about 340 mg, about 48 to about 204 mg, or particularly about 72 to about 102 mg, for example, about 75 mg or about 97.5 mg.

The composition comprising a solid dispersion of itraconazole can further comprise one or more additional pharmaceutically acceptable excipients. When present, the one or more additional pharmaceutically acceptable excipients can be in the solid solution or dispersion, or outside of the solid solution or dispersion, such as admixed or blended with the solid solution or dispersion. The one or more additional pharmaceutically acceptable excipients can include one or more disintegrants, one or more diluents, one or more fillers, one or more colorants, one or more flavorants, one or more binders, one or more glidants, one or more lubricants, one or more surface active agents, and mixtures thereof.

Exemplary disintegrants include one or more of crospovidone, croscarmellose, such as crosscarmellose sodium, polyvinylpyrrolidone, methyl cellulose, microcrystalline cellulose, lower alkyl-substituted hydroxypropyl cellulose, such as hydroxypropyl methyl cellulose and hydroxypropyl ethyl cellulose, starch, pregelatinised starch, sodium alginate, and sodium starch glycolate, for example, sodium starch glycolate. The disintegrant is often present outside of solid solution or solid dispersion, and the weight ratio of the solid solution to solid dispersion can be from about 1:1 to about 1:10, such as about 2:1 to about 6:1, about 4:1 to about 5:1, for example, from about 4.2:1, although this is not required unless otherwise specified. For example, when the dosage form is a tablet, the dosage form can comprise from about1 % to about 25% of disintegrant by weight.

Exemplary colorants include one or more of titanium dioxide and food dyes.

Exemplary flavors include one or more of cinnamon oil, wintergreen oil, peppermint oil, bay oil, anise oil, eucalyptus oil, thyme oil, vanilla, such as tincture of vanilla, citrus oil, such as one or more of lemon, orange, lime, and grapefruit oil, and essences of fruits, such as essence of one or more of apple, banana, pear, peach, strawberry, raspberry, cherry, plum, pineapple, and apricot.

Exemplary lubricants include one or more of hydrogenated vegetable oil, magnesium stearate, sodium lauryl sulfate, magnesium lauryl sulfate, colloidal silica, and talc. In some examples, the lubricant is magnesium stearate. In other examples, the lubricant is colloidal silica. In yet other examples, the lubricant is a mixture of magnesium stearate and colloidal silica.

Exemplary glidants include one or more of silicon dioxide and talc.

Exemplary binders include one or more of microcrystalline cellulose, gelatin, sugars, such as one or more of mannitol, lactose, and cellulose, polyethylene glycol, gums, such as one or more of xanthan gum and guar gum, polyvinylpyrrolidone, pregelatinised starch, hydroxypropyl cellulose, and hydroxypropylmethylcellulose.

Exemplary diluants include one or more of lactose, such as one or more of lactose monohydrate, spray-dried lactose monohydrate, and anhydrous lactose, mannitol, xylitol, dextrose, sucrose, sorbitol, microcrystalline cellulose, starch, and calcium phosphate, such as dibasic calcium phosphate dihydrate.

Exemplary surface active agents include one or more of sodium lauryl sulfate, polyethylene glycol, and polysorbate 80.

The composition can be, for example, in the form of one or more dosage forms, such as one or more of a powder, sachet, tablet, capsule, pill, suppository, implant, wafer, cream, ointment, syrup, gel, suspension, and the like. When the dosage form is a capsule, the capsule shell can be a hard capsule shell, such as a gelatin shell, comprising the solid solution or solid dispersion of itraconazole and the pharmaceutically acceptable carrier. The capsule shell can also comprise one or more of the additional pharmaceutically acceptable excipients discussed above, although that is not required unless otherwise specified. The capsule shell can be a sufficient size to accommodate the contents of the capsule.

An exemplary capsule can be filled with a solid dispersion that comprises about 50 mg itraconazole (based on the weight of free itraconazole) and about 75 mg hydroxypropyl methylcellulose phthalate, and, as additional pharmaceutical excipients not part of the dispersion, about 30 mg sodium starch glycolate, about 1 mg to about 2 mg colloidal silica, and about 1 mg to about 2 mg magnesium stearate. Another exemplary capsule can comprise about 65 mg itraconazole (based on the weight of free itraconazole), about 97.5 mg hydroxypropyl methylcellulose phthalate, and, as additional pharmaceutical excipients not part of the dispersion, about 39 mg sodium starch glycolate, about 1.3 mg to about 2.6 mg colloidal silica, and about 1.3 mg to about 2.6 mg magnesium stearate.

When the dosage form is a tablet, the tablet can comprise the solid solution or solid dispersion of itraconazole and pharmaceutically acceptable carrier such that the itraconazole is from about 1% to about 80%, such as about 5% to about 60%, by weight, of the tablet.

The tablet can also comprise one or more lubricant, such as the one or more lubricants discussed above. The one or more lubricant can be present from about 0.25% to about 10% by weight of the tablet.

The tablet can further comprise one or more disintegrants, such as one of more of the disintegrants discussed above. The one or more disintegrant can be present from about 1% to about 25% by weight of the tablet.

The tablet can further comprise one or more glidants, such as one or more of the glidants discussed above. The one or more glidants can be present from about 0.2% to about 1% by weight of the tablet.

The tablet can further comprise one or more surface active agents, such as one or more of the surface active agents discussed above. The one or more surface active agents can be present from about 0.2% to about 5% by weight of the tablet.

When the dosage form is a capsule, the capsule can comprise a therapeutically effective amount of itraconazole, such as the amounts discussed above. The remainder of the capsule can be filled with additional pharmaceutical excipients, such as those discussed above.

The composition can be specially adapted to be administered in the fasted state. The terms "in the fasted state" and "under fasting conditions" are herein used interchangeably. Similarly, the terms "in the fed state" and "under fed conditions" are herein used interchangeably. The composition can also be administered in either the fed or fasted state. For example, the dosage form can have a reduced food effect. The reduced food effect can be a difference of less than about 35% between a $AUC_{0-t}$ under fasting conditions and a $AUC_{0-t}$ under fed conditions, for example a difference of less than about 33%, about 30%, about 27%, about 25%, about 23%, or about 20% between a AUC0-t under fasting conditions and a $AUC_{0-t}$ under fed conditions. In another example, the composition exhibits an absorption profile under fasting conditions which is substantially similar to the absorption profile of a reference dosage form of itraconazole under the proprietary name Sporanox® (the reference dosage form) under fed conditions. In particular, the substantial similarity is bioequivalence.

Without wishing to be bound by theory, it is believed that the use of a solid dispersion of itraconazole in an acid resistant pharmaceutically acceptable carrier can prevent the itraconazole from dissolving too fast in the gastric juice and subsequently precipitating out in the higher pH environment of the lower GI tract thereby increasing the consistency of the bioavailability of itraconazole.

The composition can be specially adapted to have an AUC with a reduced dose-to-dose intra-subject variability in the same subject. The reduced intra-subject variability can be with respect to the SPORANOX® dosage form. For example, the dosage form can have a reduced variability in the $AUC_{0-t}$, $C_{max}$, and/or $T_{max}$ as compared to the reference dosage form, such as an intra-subject coefficient of variability under fed conditions for the $AUC_{0-t}$ can be about 35% or less. As another example an intra-subject coefficient of variability under fed conditions for the $AUC_{0-\infty}$ can be about 35% or less.

The composition can also comprise one or more additional antifungal agents. The one or more additional antifungal agents can comprise, for example, amphotericin B, candicidin, filipin, hamycin, natamycin, mystatin, rimocidin, bifunazole, butoconazole, clotrimazole, fenticonazole, isoconazole, ketoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafingin, casporofungin, micafungin, benzoic acid in combination with a keratolytic agent, ciclopirox, flucytosine, griseofulvin, haloprogin, polygodial, tolnaftate, undecylenic acid, zinc pyrithione, selenium sulfide, piroctone olamine, tar, tea oil, and crystal violet.

Particular parameters of the composition can be defined with respect to the commercially available SPORANOX® itraconazole composition (the "reference composition.") For example, when the present composition is administered in the fed state, it can have one or more pharmacokinetic parameters that are therapeutically similar to those of reference composition when administered in the fed state. Such therapeutic similarity can be determined by an in vivo pharmacokinetic study to compare one or more pharmacokinetic parameters the two compositions. A pharmacokinetic parameter for the compositions can be measured in a single or multiple dose study using a replicate or a nonreplicate design. For example, the pharmacokinetic parameters for the present oral solid composition and for the reference composition can be measured in a single dose pharmacokinetic study using a two-period, two-sequence crossover design. Alternately, a four-period, replicate design crossover study may also be used. Single doses of the present composition and the reference composition are administered and blood or plasma levels of itraconazole are measured over time. Pharmacokinetic parameters characterizing rate and extent of itraconazole absorption are evaluated statistically. The area under the plasma concentration-time curve from time zero to the time of measurement of the last quantifiable concentration ($AUC_{0-t}$) and to infinity ($AUC_{0-\infty}$), Cmax, and Tmax can be determined according to standard techniques. Statistical analysis of pharmacokinetic data is performed on logarithmic transformed data (e.g., $AUC_{0-t}$, $AUC_{0-\infty}$, or $C_{max}$ data) using analysis of variance (ANOVA). In one embodiment, two compositions (e.g. the present composition and the reference composition) or methods (e.g., dosing under fed versus fasted conditions) are therapeutically similar if the Confidence Interval (CI) range of 80% to 95% (e.g., including 90%) limits for a ratio of the geometric mean of logarithmic transformed $AUC_{0-\infty}$, $AUC_{0-t}$, and/or C for the two compositions or two methods are about 0.70 to about 1.43; or about 0.75 to about 1.33; or about 0.80 to about 1.25.

In addition or in the alternative, the composition can be therapeutically equivalent to the reference composition. For example, administration of the composition over about the same time period as the reference composition can produce a substantially similar therapeutic outcome.

The composition can be bioequivalent to the reference composition. For example, the composition can have 90% Confidence Interval (CI) limits for a ratio of the geometric mean of logarithmic transformed $AUC_{0-\infty}$, $AUC_{0-t}$, and $C_{max}$ for the composition is about 0.80 to about 1.25 of the reference composition. As another example, the composition can have 90% CI limits for a ratio of the geometric mean of logarithmic transformed $AUC_{0-\infty}$, and $AUC_{0-t}$ of about 0.80 to about 1.25 of the reference composition.

The amount of itraconazole in the composition can be from about 50% to about 65% by weight of the amount of itraconazole in the reference composition.

The composition can have an $AUC_{0-t}$ that is about 0.70 to about 1.43 of that of the reference composition. The composition can have an $AUC_{0-t}$ that is about 0.75 to about 1.33 of that of the reference composition. The composition can have a relative bioavailability (Frel) of greater than about 150% relative to the reference composition under fed conditions, such as a relative bioavailability (Frel) of greater than about 160%, about 165%, about 170%, about 175%, or about 180%, such as about 180%, relative to the reference composition under fed conditions.

Methods of Using Itraconazole Compositions and Dosage Forms

A method of treating a fungal infection can comprise administering one or more dosage forms comprising itraconazole, such as one or more of the dosage forms described herein, to a subject. The subject is typically a human.

The fungal infection can be any infection treatable by a triazole antifungal agent, such as itraconazole. The fungal infection can be a systemic infection or a local infection, particularly a systemic infection. Exemplary fungal infections that can be treated include one or more of onychomycosis, pulmonary or extrapulmonary blastomycosis, histoplasmosis, and aspergillosis. In particular, the dosage form is used to treat onychomycosis.

The dosage form can be any acceptable dosage form, such as a powder, sachet, tablet, capsule, pill, suppository, implant, wafer, cream, ointment, syrup, gel, suspension, and the like. The dosage form is particularly an orally deliverable dosage form, such as a tablet or capsule, and typically a capsule.

A dosage form as described herein, such as a capsule, can be administered at appropriate intervals. For example, once per day, twice per day, three times per day, and the like. In particular, the dosage form is administered once or twice per day. Even more particularly, the dosage form is administered once per day.

The dosage form can be administered for a duration of time sufficient to treat the fungal infection. In order to treat a fungal infection, the dosage form is typically administered for about four weeks to about forty weeks, particularly about eight weeks to about thirty six weeks. For example, the dosage form can be administered for about twelve weeks to about twenty four weeks. In a particular example, the dosage form is administered for about twelve weeks, at which point the therapeutic effect on the fungal infection is determined, for example, by determining the amount or degree of improvement in the patient conditions or the amount or degree of severity of the fungal infection after about twelve weeks of administration of the dosage form with respect to the amount or degree of severity before administration of the dosage form. If desired, administration of the dosage form can then be continued for about six to about thirty additional weeks, for example, about eight to about twenty eight additional weeks, such as about twelve additional weeks. For example, the dosage form can be administered for about twenty four weeks, which in studies was sufficient to treat most onychomycosis infections.

One or more additional antifungal agents can be coadministered with the dosage form described herein. The one or more additional antifungal agents can comprise, for example, amphotericin B, candicidin, filipin, hamycin, natamycin, mystatin, rimocidin, bifunazole, butoconazole, clotrimazole, fenticonazole, isoconazole, ketoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafingin, casporofungin, micafungin, benzoic acid in combination with a keratolytic agent, ciclopirox, flucytosine, griseofulvin, haloprogin, polygodial, tolnaftate, undecylenic acid, zinc pyrithione, selenium sulfide, piroctone olamine, tar, tea oil, and crystal violet. When administered concurrently, the one or more additional antifungal agents can be administered in the same dosage form or in a different dosage form as the itraconazole dosage forms described herein. The one or more additional antifungal agents can be administered at about the same time of the day as the itraconazole dosage form described herein, or at different times of the day, or even on different days. The one or more additional antifungal agents can also be administered by the same or different route of administration as the itraconazole dosage forms described herein. For example, an itraconazole dosage form described herein can be administered orally in a capsule and an additional antifungal agent can be administered topically as a cream.

A dosage form as described herein can be used in a method of reducing the food effect of itraconazole. The method can comprise administering a dosage form, such as a dosage form described herein, to a subject. The method can result in a bioavailability, as measured by AUC, in the fasted state that bears greater similarity to the bioavailability, as measured by AUC, in the fed state. For example, the bioavailability, as measured by AUC, in the fasted state can differ from that in the fed state by about 35% or less, about 30% or less, about 25% or less, or about 20% or less.

The dosage form used for a method of reducing food effect is typically an oral dosage form, such as a tablet, capsule, powder, sachet, lozenge, and the like, and particularly a capsule.

A dosage form as described herein can also be used in a method of administering itraconazole to a fasted subject, for example, a subject who has not eaten a meal about 30 minutes or more, about 1 hour or more, about 2 hours or more, about 3 hours or more, about 4 hours or more, about 5 hours or more, about 6 hours or more, about 7 hours or more, about 8 hours or more, about 9 hours or more, or about 10 hours or more before ingesting the dosage form.

The dosage form used for a method of administering itraconazole to a fasted subject is typically an oral dosage form, such as a tablet, capsule, powder, sachet, lozenge, and the like, and particularly a capsule.

A dosage form as described herein can also be used in a method of administering itraconazole to a subject, wherein the subject is in either a fed or fasted state. The dosage form used for such a method is typically an oral dosage form, such as a tablet, capsule, powder, sachet, lozenge, and the like, and particularly a capsule.

A dosage form as described herein can also be used in a method comprising coadministering an itraconazole dosage form with one or more second pharmaceutically active agents that alters the gastric pH, and particularly drugs that increase gastric pH. The second pharmaceutically active agent can be a gastric acid suppressor or neutralizer. Examples of second pharmaceutically active agents that alter the gastric pH include antacids, proton pump inhibitors, and H2-receptor antagonists. Exemplary antacids include alkali or alkali earth salts of carbonate or bicarbonate, such as sodium bicarbonate, potassium bicarbonate, calcium carbonate, magnesium carbonate, sodium carbonate, and potassium carbonate, hydroxides such as aluminum hydroxide and magnesium hydroxide, and, bismuth subsalicylate.

Exemplary proton pump inhibitors include omeprazole, lansoprazole, dexlansoprazole, esomeprazole, pantoprazole, rabeprazole, and ilaprazole. Exemplary H2-receptor antagonists include cimetidine, ranitidine, famotidine, and nizatidine.

Without wishing to be bound by theory, it is believed that altering, and particularly raising, the gastric pH substantially lowers the bioavailability of itraconazole in the SPORANOX® formulation. Thus, coadministration of antiacids, proton pump inhibitors, and H2-receptor antagonists is counterindicated for SPORANOX®. However, many of the dosage forms disclose herein feature a solid dispersion of itraconazole and an acid-resistant carrier. The acid resistant carrier is believed to protect the itraconazole from the effect of the less acidic environment.

A method of treating cancer can comprise administering a dosage form described herein to a patient. The cancers that can be treated include one or more of acute lymphoblastic leukemia, acute myeloid leukemia, adrenocortical carcinoma, kaposi sarcome, lymphoma, anal cancer, appendix cancer, central nervous system cancer, basel cell carcinoma, bile duct cancer, bladder cancer, ewing sarcoma, osteosarcoma, malignant fibrous histiocytoma, brain stel glioma, cancerous brain tumors, such as brain stem glioma, craniopharygnioma, and ependymoma, breast cancer, broncial tumors, Burkitt lymphoma, carcinoid tumors, including gastrointestinal carcinoid tumors, cancerous cardiac tumors, embryonal tumors, germ cell tumors, primary lymphoma, cervical cancer, chronic lymphocytic leukemia, chronic myelogenous leukemia, chronic myeloproliferative disorders, colon cancer, colorectal cancer, cutaneous T-cell lymphoma, bile duct cancer, ductal carcinoma, endometrial cancer, ependymoma, esophageal cancer, esthesioneuroblasoma, Ewing sarcoma, extracranial germ cell tumor, extraganodal germ cell tumor, extrahepatic bile duct cancer, cancers of the eye, such as intraocular melanoma and retinoblastoma, fibrous histiocytoma of bone, gallbladder cancer, gastric cancer, gastrointestinal carcinoid tumor, gastrointestinal stroma tumors (GIST), germ cell tumors, including central nervous system, extracranial, extragonadal, ovarian, and testicular, gestational trophoblastic disease, glioma, hairy cell leukemia, head and neck cancer, heart cancer, heatocellular (liver) cancer, histiocytosis of Langerhans cell, Hodgkin's lymphoma, hyopharyngeal cancer, islet cell tumors, pancreatic neuroendocrine tumors, kidney cancers, such as renal cell cancers and Wilms tumors, Langerhans cell histiocytosis, laryngeal cancer, leukemia, such as acute lymphoblasitc leukemia, acute myeloid leukemia, chronic lymphocytic leukemia, chronic myelogenous leukemia, and hairy cell leukemia, lip and oral cavity cancers, liver cancers, lobular carcinoma in situ, lung cancers, such as non-small cell and small cell lung cancers, lymphomas, including AIDS-related, Burkitt, non-Hodgin, cutaneous T-cell, Hodgin, and primary central nervous system, Waldenstrom macroglobulinemia, male breast cancer, melanoma, Merkel cell carcinoma, malignang mesothelioma, metastatic squamous neck cancer, midline tract carcinoma, such as those involving the NUT gene, mouth cancer, multiple endocrine neoplasa syndromes, multiple myeloma/plasma cell neoplasm, mycosis fungoides, myelodyplastic syndromes, myelodyplasitc/myeloproliferative neoplasms, myelogenous leukemia, either chronic or acute, myeloma, myeloproliferative disorders, nasal cavity and paranasal sinus cancer, nasopharyngeal cancer, neurolastoma, oral cancer, oral cavity cancer, such as lip and oraopharyngeal cancer, ovarian cancer, such as epithelial, germ cell tumor, and low malignant potential tumors of the ovaries, pancreatic cancer, such as pancreatic neuroendocrine tumors (Islet cell tumors), papillomatisis, paragangioma, paranasal sinus and nasal cavity cancer, parathyroid cancer, penile cancer, pharyngeal cancer, pheochromocytoma, pituitary tumors, plasma cell neoplasms, multiple myeloma, pleuropulmonary blastoma, pregnancy and breast cancer, primary central nervous system (CNS) lmphoma, prostate cancer, rectal cancer, renal cell (kidney) cancer, renal pelvis and ureter cancers, retinoblastoma, rhabdomysarcoma, salivary gland cancer, sarcomas, such as Ewing, Kaposi, osteosarcoma, rhabdomysarcoma, soft tissue, and uterine, Seazary syndrome, skin cancers, such as melanoma, Merkel cell carcinoma, and nonmelanoma, small cell lung cancer, small intestine cancer, soft tissue sarcoma, sqaumous cell carcinoma, stomach (gastric) cancers, cutaneous T-cell lymphoma, testicular cancer, throat cancer, thymoma and thymic carcinomas, thyroid cancer, transitional cell cancer of the renal pelvis and ureter, carcinomas of unknown primary origin, unusual cancers of childhood, urethral cancer, uterine cancer, uterine sarcoma, vaginal cancer, vulvar cancer Waldenstrom macroglobuloma, and Wilms tumors. Particular cancers include prostate cancers, skin cancers, and lung cancers. Of the prostate cancers, non-metastatic castration resistant prostate cancer is particularly contemplated. Of the skin cancers, advance basal cell carcinoma (NBCCS) is particularly contemplated. Of the lung cancers, non-small cell lung cancer (NSCLC) and squamous cell lung cancer are particularly contemplated.

Methods of treating any of the above-mentioned cancers can include administering an appropriate amount number of dosages of a form described herein, the dosage forms having a sufficient amount of itraconazole to treat the cancer of interest. The dosage form can be administered once a day, twice a day, three times a day, four times a day, or more. Administration can take place for as long as necessary for the cancer of interest to be treated, for example, until the cancer goes into remission.

The dosage for treating cancer can be the same or different from the amount of itraconazole per dose used to treat fungal infections. When different, the amount of itraconazole per dose for treating cancer can be, for example, about 100 mg or higher, such as about 200 mg or higher, about 300 mg or higher, about 400 mg or higher, about 600 mg or higher, about 700 mg or higher, about 800 mg or higher, about 900 mg or higher, or about 1,000 mg or higher. For example, the dosage can be about 100 mg to about 1,000 mg, about 200 mg to about 1,000 mg, about 200 mg to about 900 mg, about 300 mg to about 900 mg, about 300 mg to about 700 mg, and the like, such as any therapeutically effective amount of itraconazole.

EXAMPLES

Formulation Examples

Example 1—Formulation of 50, 60 and 70 mg LOZANOC Dosage Form

A solid dispersion was prepared by dispersing 0.6 kg of hydroxypropyl methylcellulose acetate phthalate (sold under the name HP-50) in 12.0 kg of methylene chloride and then adding 0.4 kg of itraconazole with stirring until a pale brown solution formed. The solution was spray-dried using a dual-fluid nozzle sprayer with 70° C. air inlet temperature and 15-20° C. air outlet temperature to form the solid dispersion as a spray dried powder.

870 g of the spray dried powder was blended with 209.0 g of sodium starch glycolate and 9.0 g of colloidal silicon dioxide. 13.0 g of magnesium stearate was added to the blend, and the mixture was further blended until uniform.

The powder was filled into size 0 gelatin capsules in an amount sufficient to provide 50 mg, 60 mg, or 70 mg of itraconazole per capsule, which corresponds to 158 mg, 190 mg, and 221 mg of powder per capsule, respectively. The content of the powder and the capsules is provided in Table 2.

TABLE 2

| | Weight percent | Mass in Powder (g) | Mass per Capsule (mg) | | |
|---|---|---|---|---|---|
| Dispersion Components | | | | | |
| Itraconazole | 31.61 | 348.0 | 50 | 60.0 | 70.0 |
| Hydroxypropyl methylcellulose phthalate | 47.41 | 522.0 | 75 | 90.0 | 105.0 |
| Other components | | | | | |
| Sodium starch glycolate | 18.98 | 209.0 | 30.0 | 36.0 | 42.0 |
| Silicon dioxide | 0.82 | 9.0 | 1.25 | 1.50 | 1.75 |
| Magnesium stearate | 1.18 | 13.0 | 1.85 | 2.22 | 2.59 |
| Total | 100 | 1101.0 | 158.1 | 189.7 | 221.3 |

Example 2—Formulation of 50 mg LOZANOC Dosage Form

A solid dispersion was prepared by dispersing 11.4 kg of hydroxypropyl methylcellulose acetate phthalate (sold under the name HP-50) in 228 kg of methylene chloride and then adding 7.6 kg of itraconazole with stirring until a pale brown solution formed. The solution was spray-dried using a dual-fluid nozzle sprayer with 70° C. air inlet temperature and 15-20° C. air outlet temperature to form the solid dispersion as a spray dried powder.

16.998 kg of the spray dried powder was blended with 4.081 kg of sodium starch glycolate and 0.17 kg of colloidal silicon dioxide. 0.252 kg of magnesium stearate was added to the blend, and the mixture was further blended until uniform.

The powder was filled into size 1 gelatin capsules in an amount sufficient to provide 50 mg of itraconazole per capsule. The content of the powder and the capsules is provided in Table 3.

TABLE 3

| | Weight percent | Mass in Powder (kg) | Mass per Capsule (mg) |
|---|---|---|---|
| Dispersion Components | | | |
| Itraconazole | 31.62 | 6.799 | 50 |
| Hydroxypropyl methylcellulose phthalate | 47.44 | 10.199 | 75 |
| Other components | | | |
| Sodium starch glycolate | 18.98 | 4.801 | 30.0 |
| Silicon dioxide | 0.79 | 0.170 | 1.25 |
| Magnesium stearate | 1.17 | 0.252 | 1.85 |
| Total | 100 | 21.501 | 158.1 |

Example 3—Formulation of 65 mg LOZANOC Dosage Form

A solid dispersion was prepared by dispersing 13.50 kg of hydroxypropyl methylcellulose acetate phthalate (sold under the name HP-50) in 270 kg of methylene chloride and then adding 9.0 kg of itraconazole with stirring until a pale brown solution formed. The solution was spray-dried using a dual-fluid nozzle sprayer with 70° C. air inlet temperature and 15-20° C. air outlet temperature to form the solid dispersion as a spray dried powder.

22.014 kg of the spray dried powder was blended with 5.284 kg of sodium starch glycolate and 0.219 kg of colloidal silicon dioxide. 0.326 kg of magnesium stearate was added to the blend, and the mixture was further blended until uniform.

The powder was filled into size 1 gelatin capsules in an amount sufficient to provide 65 mg of itraconazole per capsule. The content of the powder and the capsules is provided in Table 4.

TABLE 4

| | Weight percent | Mass in Powder (kg) | Mass per Capsule (mg) |
|---|---|---|---|
| Dispersion Components | | | |
| Itraconazole | 31.62 | 8.806 | 65 |
| Hydroxypropyl methylcellulose phthalate | 47.44 | 13.208 | 97.5 |
| Other components | | | |
| Sodium starch glycolate | 18.98 | 5.284 | 39.0 |
| Silicon dioxide | 0.79 | 0.219 | 1.63 |
| Magnesium stearate | 1.17 | 0.326 | 2.41 |
| Total | 100 | 27.843 | 205.5 |

Clinical Examples

Background and Introduction

Itraconazole is a poorly water-soluble drug and exhibits low bioavailability (Fz50%) from the current SPORANOX® 100 mg Capsules. Clinical use demonstrates relatively poor absorption associated with significant inter-patient variability and a highly variable effect of food on bioavailability of the drug. Formulation improvements could overcome the poor solubility of itraconazole in water and enhance its bioavailability.

The data below describes studies for the development of a new formulation of itraconazole (alternatively described in the studies as "itraconazole test formulation", SUBA-itraconazole, SUBACAP™-itraconazole, or LOZANOC).

The Applicant has developed a 50 mg itraconazole capsule formulation, LOZANOC 50 mg Hard Capsules, which with 1×50 mg capsule provides plasma levels comparable to those following administration of 1× SPORANOX® 100 mg Capsules. Applicants are also developing a 65 mg dosage of LOZANOC.

LOZANOC 50 mg Hard Capsules are powder-filled capsules consisting of a blend of itraconazole spray-dried powder and capsule blend excipients, encapsulated into hard gelatin Size #1, light blue, opaque gelatin capsules (Example 1). All inactive ingredients in LOZANOC 50 mg Hard Capsules formulation are present in concentrations at or below the levels that have been previously approved for orally administered products.

LOZANOC 50 mg Hard Capsules is a change in strength of the active substance vis-à-vis the reference medicinal product, SPORANOX® 100 mg Capsules, with no other changes, including in drug substance, pharmaceutical form, therapeutic indications, or route of administration.

Bioavailability Studies

Example 4—Comparison of the Relative Bioavailability of LOZANOC 50 mg Capsules with SPORANOX® (Itraconazole) 100 mg Capsules Under Fed Conditions Study Rationale One bioavailability study investigated the comparative bioavailability of the test itraconazole capsule (LOZANOC at doses of 50, 60 and 70 mg, with the reference formulation, SPORANOX® 100 mg capsule. In a previous study conducted at CMAX to investigate the bioequivalence of the test itraconazole formulation as a 100 mg capsule with the reference formulation, SPORANOX® 100 mg capsule, the test formulation was found to be superbioavailable, with least square mean ratio from analysis of logarithmically transformed data of 286% for itraconazole and 303% for hydroxyitraconazole. In a further study to compare test itraconazole formulation as a 100 mg capsule with the reference formulation, 2× SPORANOX® 100 mg capsule, the comparative bioavailability was 80% for itraconazole and 85% for hydroxyitraconazole. The current study was planned to investigate the pharmacokinetics of a range of dose levels for the test formulation to determine a dose level with comparative bioavailability similar to SPORANOX® 100 mg capsule.

Study Design

A single-dose, randomized, balanced, open-label, four treatment, four-way crossover study. Twelve subjects were studied. All subjects participated in the four treatment periods. Each subject received four single oral doses of itraconazole, at dose levels of 50 mg, 60 mg, and 70 mg of the test itraconazole formulation, and a dose level of 100 mg dose of SPORANOX®, Itraconazole reference formulation, according to the treatment randomization schedule. Each subject received the doses after consuming a standardized high fat breakfast. The interval between dosing occasions was at least 7 days, which was considered adequate to prevent carryover of itraconazole between treatment periods.

Study Population

Twelve healthy male subjects, aged between 18 to 50 years, who fulfilled the entry criteria, participated in this study.

Study Treatments

Study Drug: Itraconazole capsules, 50, 60 and 70 mg. Subjects were administered either Treatment B (1×50 mg LOZANOC itraconazole capsule), Treatment C (1×60 mg LOZANOC itraconazole capsule), or Treatment D (1×70 mg LOZANOC itraconazole capsule). The doses were administered within 30 minutes of consumption of a standardized high (50%) fat breakfast.

Reference Drug: SPORANOX®, Itraconazole capsules, 100 mg. Subjects were administered with Reference Formulation 1 (1×100 mg SPORANOX®, Itraconazole capsules) within 30 minutes of consumption of a standardized high (50%) fat breakfast.

A single oral dose was administered in each treatment period with 240 mL of room temperature water following a standardized high fat (50%) meal. Each subject received one of four possible treatments in each study period according to the treatment randomization schedule. A single dose was administered in each treatment period in the fed state, with a minimum of 7 days between doses.

Blood samples for pharmacokinetic analysis were collected at 1.0, 2.0, 3.0, 4.0, 5.0, 6.0, 8.0, 10, 12, 24, 36, and 48 hours after dosing. Pre-dose samples were collected up to 60 minutes prior to dosing. The blood samples were centrifuged at approximately 2500 rpm for 15 minutes, and the plasma collected for evaluation. Plasma samples were analyzed for itraconazole and 2-hydroxyitraconazole concentrations and agent pharmacokinetics.

The pharmacokinetic sampling schedule was based on results of previous studies and published results indicating an elimination half-life in the range of 13 to 24 hours, and peak plasma concentration at 5 to 10 hours post-dose for dose administration under fed conditions.

Pharmacokinetic Analysis

The concentration of itraconazole and hydroxyitraconazole (a metabolite of itraconazole) were measured in plasma samples from all subjects, using a validated assay method. Concentrations below quantization were assigned a value of zero. The concentration-time profiles for each subject and the mean concentration-time profiles were plotted with linear and logarithmic axes for concentration. The plasma concentrations at all time points were determined. The major pharmacokinetic parameters of itraconazole and hydroxyitraconazole calculated were:

1) maximal concentration (Cmax);
2) time to maximal concentration (Tmax);
3) area under the concentration-time curve from Time zero to the last measurable concentration after dosing (AUCt), calculated using the linear trapezoidal rule;
4) apparent terminal elimination rate, calculated as the slope of the regression line for the terminal log-linear plasma concentration-time values, using a minimum of 3 data points (using 4 or 5 data points where appropriate);
5) terminal elimination half-life (Thalf), calculated as $0.693/Kel$, where $0.693=\ln(2)$;
6) area under the concentration-time curve from 0 to infinity (AUCinf), calculated as AUCt+Clast/Kel where Clast is the last measurable concentration; and
7) percent extrapolated AUCt, calculated as (AUCinf−AUCt)/AUCinf.

Comparative Bioavailability Analysis

A parametric (normal-theory) general linear model was applied to each of the above variables using SAS® (Version 8.2). In addition, the logarithmic transformation of AUCt, AUCinf and Cmax, were analyzed with the same model. The analysis of variance (ANOVA) model included the following factors: sequences, subjects within sequence, period and formulation. Comparative bioavailability was assessed for the log-transformed parameters AUCt, AUCinf and Cmax by constructing 90% confidence intervals for the ratio of the test and reference means. The 90% confidence interval was obtained from the antilogs of the lower and upper bounds of the 90% confidence interval for the difference in the means of the log-transformed data. Mean ratio values, intrasubject CV % and intersubject CV % values, were provided for log-transformed values. Treatments being compared would be deemed to have comparable bioavailability if the 90% confidence interval of the ratios of the test and reference means for log transformed AUCt and Cmax fell within the acceptance interval of 80% to 125%, in accordance with the FDA Guidance for Industry: *Guidance for Industry: Bioavailability and Bioavailability Studies for Orally Administered Drug Products—General Considerations* (Revision 1, March 2003)

The pharmacokinetic parameters and observations were compared between treatments for all subjects who completed the study.

Statistical and Analytical Methods

Pharmacokinetic parameters were determined using calculation software developed specifically for CMAX (Area Under Curve, Version 3.0.1). Statistical analysis was performed using SAS® (Version 8.2). Logarithmically transformed AUCt, AUCinf and Cmax for itraconazole and hydroxyitraconazole were analyzed using an ANOVA model with terms including sequences, subjects within sequence, period and formulation. The residual mean squares were used to calculate the 90% confidence interval for the differences between formulation means. These were backtransformed to give the confidence intervals for the mean ratios. Observed values of Kel and Thalf were also analyzed using this ANOVA model.

Missing and Aberrant Values

There were no missing values for itraconazole and hydroxyitraconazole concentration. Values reported as below quantization were considered as zero in calculating summaries of concentrations by treatment over time. Concentrations for Subjects 011 and 012 at Hour 10 in Period 3 were aberrant compared with adjacent values. It was considered a possibility that these samples may have been mislabeled, swapped between these subjects. However, this could not be confirmed from the documentation. The pharmacokinetic analysis was performed with the values as reported.

Pharmacokinetic Results

Figure 3:
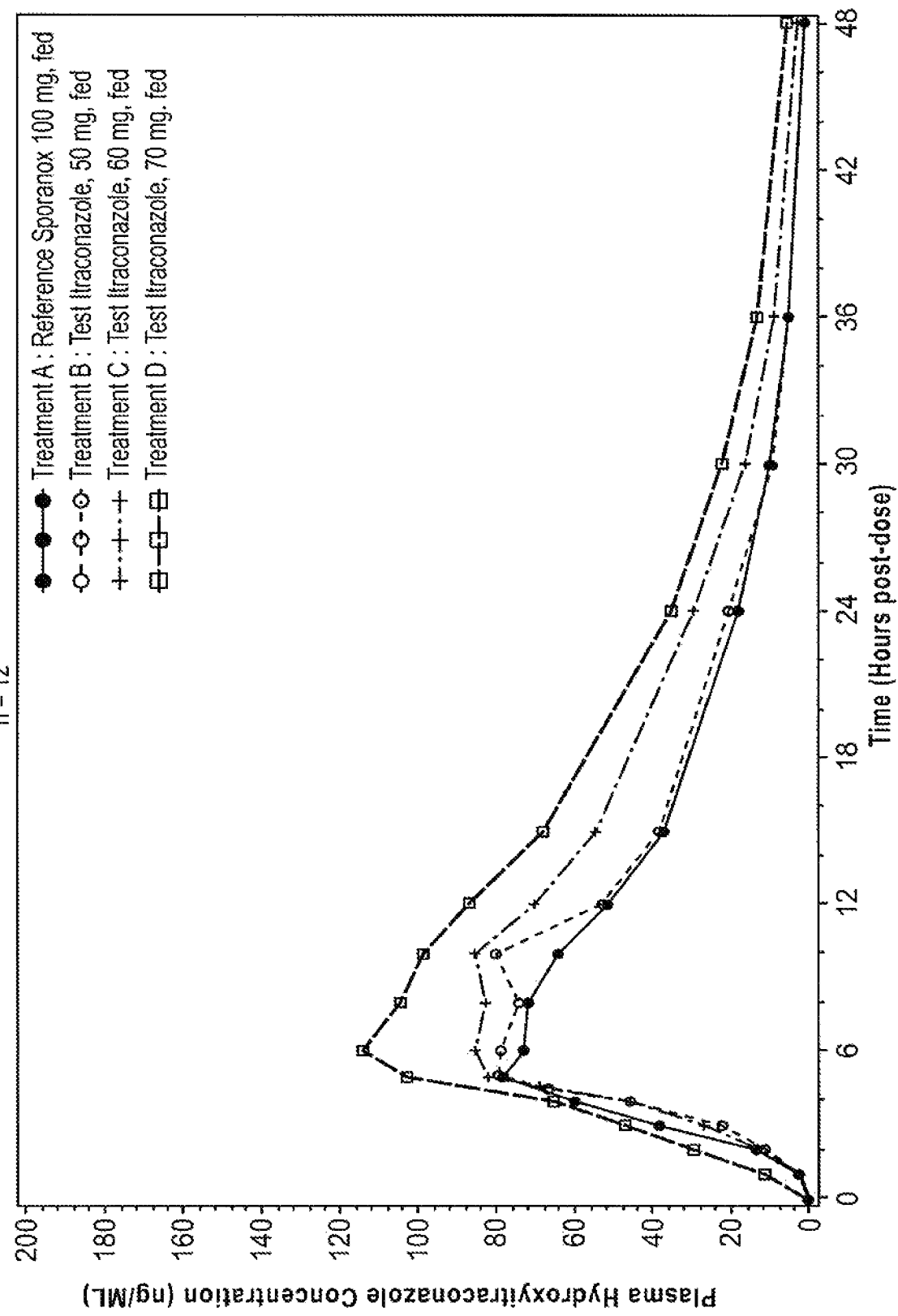
FIG. 3 shows the linear scale graph of the plasma hydroxyitraconazole concentration against time in a study assessing the relative bioavailability of various LOZANOC doses with a 100 mg dose SPORANOX® under fed conditions. Circles represent the reference SPORANOX® 100 mg dose; diamonds represent the 50 mg LOZANOC dose; stars represent the 60 mg LOZANOC dose; and squares represent the 70 mg LOZANOC dose. All doses were administered under fed conditions.
Figure 4:
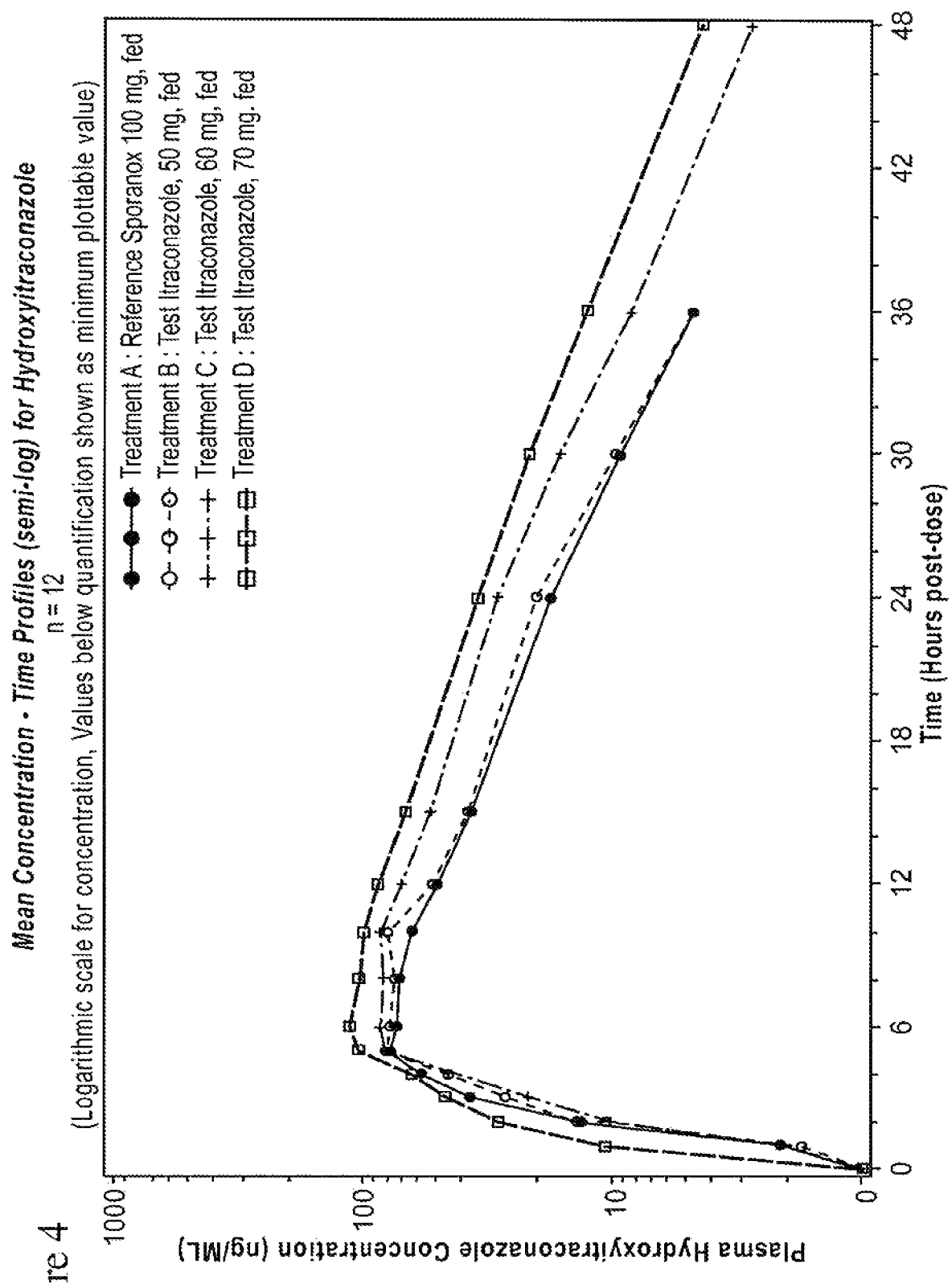
FIG. 4 shows the log-transformed scale graph of the plasma hydroxyitraconazole concentration against time in a study assessing the relative bioavailability of various LOZANOC doses with a 100 mg dose SPORANOX® under fed conditions. Circles represent the reference SPORANOX® 100 mg dose; diamonds represent the 50 mg LOZANOC dose; stars represent the 60 mg LOZANOC dose; and squares represent the 70 mg LOZANOC dose. All doses were administered under fed conditions.

FIGS. 1 (linear) and 2 (semi-logarithmic) show the plasma itraconazole concentration against time. FIGS. 3 (linear) and 4 (semi-logarithmic) show the plasma hydroxyitraconazole concentration against time.

Table 5 shows the summary of the pharmacokinetic parameters of itraconazole and hydroxyitraconazole for each treatment for the twelve subjects.

TABLE 5

Summary of pharmacokinetics of itraconazole and hydroxyitraconazole

| Mean (Standard Deviation) | | Reference Formulation A: 100 mg Sporanox® capsule | Test Formulation B: 50 mg itraconazole capsule | Test Formulation C: 60 mg itraconazole capsule | Test Formulation D: 70 mg itraconazole capsule |
|---|---|---|---|---|---|
| Itraconazole | Cmax (ng/mL) | 46.1 (27.2) | 54.4 (19.6) | 65.9 (30.1) | 77.9 (30.2) |
| | AUCt (ng * h/mL) | 505.5 (326.8) | 511.8 (206.8) | 671.8 (275.2) | 845.2 (327.0) |
| | AUCinf (ng * h/mL) | 658.4 (374.2) | 579.9 (197.0) | 811.8 (367.4) | 1044.9 (351.6) |
| Hydroxy-itraconazole | Cmax (ng/mL) | 89.4 (46.6) | 98.2 (28.6) | 106.1 (22.7) | 128.6 (27.1) |
| | AUCt (ng * h/mL) | 1118.4 (720.7) | 1169.1 (455.7) | 1522.6 (626.6) | 1973.3 (772.7) |
| | AUCinf (ng * h/mL) | 1196.7 (755.5) | 1286.1 (476.1) | 1598.0 (639.0) | 2047.4 (797.1) |

The comparative bioavailability of each strength of the test formulation compared with the reference treatment, was determined in the usual manner for bioequivalence assessment, as the 90% confidence interval of the ratio of least squares means from analysis of variance of log-transformed Cmax, AUCt and AUCinf. Table 6 shows the comparative bioavailability of each strength of the test formulation compared with the reference treatment, determined as the ratios of at least squares means from analysis of variance of log-transformed data.

TABLE 6

Comparative bioavailability of itraconazole and hydroxyitraconazole

| Least Squares Mean Ratio (90% Confidence Interval) | | Test Formulation B: 50 mg itraconazole capsule vs Reference Formula A: 100 mg Sporanox® capsule | Test Formulation C: 60 mg itraconazole capsule vs Reference Formula A: 100 mg Sporanox® capsule | Test Formulation D: 70 mg itraconazole capsule vs Reference Formula A: 100 mg Sporanox® capsule |
|---|---|---|---|---|
| Itraconazole | Cmax | 124.6% (98.9%-157.0%) | 146.5% (116.3%-184.6%) | 177.7% (141.1%-223.9%) |
| | AUCt | 113.2% (93.4%-137.1%) | 149.9% (123.7%-181.6%) | 189.6% (156.5%-229.8%) |
| | AUCinf | 107.1% (88.3%-130.0%) | 132.5% (110.4%-159.1%) | 176.9% (148.0%-211.5%) |
| Hydroxy-itraconazole | Cmax | 117.4% (99.1%-139.2%) | 129.3% (109.1%-153.3%) | 156.6% (132.2%-185.6%) |
| | AUCt | 119.3% (97.2%-146.3%) | 154.3% (125.8%-189.3%) | 200.2% (163.2%-245.6%) |
| | AUCinf | 117.1% (95.5%-143.7%) | 150.5% (123.2%-183.7%) | 192.5% (157.7%-235.1%) |

The mean ratios of Cmax, AUCt and AUCinf backtransformed following analysis on log-transformed parameters, for the test 50 mg, 60 mg and 70 mg itraconazole capsules compared with the reference 100 mg SPORANOX® were all greater than 100%. The 90% confidence interval for the least squares itraconazole and hydroxyitraconazole mean ratio of AUCt, Cmax and AUCinf, log-transformed data, extended above the standard bioequivalence acceptance interval of 80.0%-125.0% for the test 50 mg, 60 mg and 70 mg itraconazole capsules compared with the reference 100 mg SPORANOX®.

Safety and Tolerability

A total of 25 adverse events were reported by 9 of the 12 (75%) subjects during the conduct of the study. There were no deaths or other serious adverse events reported. Five of the adverse events, experienced for 5/12 subjects (42%), were deemed to be possibly related to the study treatments. Of these, 2 adverse events were experienced by 2 of 12 (17%) subjects after receiving the test formulation 50 mg itraconazole capsule, 1 adverse event was experienced by 1 of 12 (8%) subjects after receiving the test formulation 70 mg itraconazole capsule, and 2 adverse events were experienced by 2 of 12 (17%) subjects after receiving the reference formulation 100 mg SPORANOX® capsule. No adverse events experienced by subjects receiving the test formulation 60 mg itraconazole capsule were deemed to be possibly related to study treatment. There were no clinically significant changes in physical findings or clinical laboratory results throughout the study that were considered due to any study treatment, from Screening through to the Exit Evaluation.

In this single oral dose, open-label, randomized, balanced, four-period crossover study in 12 healthy adult male subjects, the mean ratios of Cmax, AUCt and AUCinf log-transformed data for itraconazole and hydroxyitraconazole for the test itraconazole 50 mg, 60 mg and 70 mg capsules compared with the reference SPORANOX® 100 mg were all greater than 100%. For test itraconazole 50 mg capsules compared with the reference SPORANOX® 100 mg, the mean ratios of Cmax, AUCt and AUCinf were 124.6%, 113.2% and 107.1% for itraconazole and 117.4%, 119.3%, and 117.1% for hydroxyitraconazole, respectively. The mean ratios of these parameters were all greater than 125% for test itraconazole 60 mg and 70 mg capsules compared with the reference SPORANOX® 100 mg. The 90% confidence intervals for the mean ratios of these parameters at all dose levels of the test formulation extended above the standard bioequivalence acceptance interval of 80.0%-125.0%.

The test 50 mg, 60 mg and 70 mg itraconazole capsules all demonstrated suprabioavailability for itraconazole and hydroxyitraconazole compared with the reference 100 mg SPORANOX® capsules, given under fed conditions.

Adverse events were experienced by 2/12 subjects (17%) following administration of the reference formulation, and by 4/12 (33%), 5/12 (42%), and 3/12 (25%) following administration of the test formulation at strengths of 50 mg, 60 mg, and 70 mg, respectively. There were no deaths or other serious adverse events during the study. No adverse events deemed to be possibly related were experienced by subjects receiving the test formulation 60 mg itraconazole. None of the subjects withdrew from the study due to adverse events deemed related to study treatments.

Example 5—Comparison of the Relative Bioavailability of 110 mg LOZANOC Itraconazole with 200 mg SPORANOX® (Itraconazole) Under Fed and Fasted Conditions Study Rationale This study investigated the comparative bioavailability of the test itraconazole capsule (LOZANOC) at a dose of 110 mg, with 200 mg of the reference formulation, SPORANOX®. An absolute oral bioavailability of approximately 55% has been reported for a 100 mg dose of itraconazole oral solution. A non-linear kinetic relationship has been found with increasing doses of itraconazole capsules and pharmacokinetic studies suggest that itraconazole may undergo saturation metabolism with multiple dosing. The major metabolite, hydroxyitraconazole, has antifungal activities similar to the parent compound. Approximately 3-18% of itraconazole is excreted unchanged in the feces, and no unchanged drug is found in the urine within 24 hours following the administration of an oral dose. The elimination half life after a single oral dose of 50 mg to 200 mg of itraconazole in healthy subjects is reported to range between 13 hours and 24 hours. The elimination half life of hydroxyitraconazole is reported to be 11.5 hours after a 200 mg dose of itraconazole. The oral bioavailability of itraconazole is maximized when taken with a light meal however, there is marked intersubject variability. If itraconazole is administered in the fasting state, peak plasma concentration (Cmax) and area under the curve (AUC) are reduced by 50-70% when compared to administration after a light meal.

In a previous study, the Cmax for SPORANOX® occurred at 3.6 hours. In a previous study conducted to investigate the bioequivalence of the test itraconazole formulation as a 100 mg capsule with the reference formulation, SPORANOX® 100 mg capsule, the test formulation was found to be superbioavailable, with least square mean ratio from analysis of logarithmically transformed data of 286% for itraconazole and 303% for hydroxyitraconazole. In a further study to compare test itraconazole formulation as a 100 mg capsule with the reference formulation, 2× Sporanox® 100 mg capsule, the comparative bioavailability was 80% for itraconazole and 85% for hydroxyitraconazole. The current study was planned to investigate the pharmacokinetics of the test formulation at a dose level of 110 mg (1×50 mg capsule plus 1×60 mg capsule) under both fed and fasted conditions to determine if a food effect is evident in comparison to SPORANOX® (2×100 mg capsules).

Study Design

A single-dose, randomized, balanced, open-label, four treatment, four-way crossover study. Twelve subjects were studied. All subjects participated in the four treatment periods. Overall each subject received four single oral doses of itraconazole, twice as the test formulation (110 mg as 50 mg and 60 mg capsules) under both fed and fasted conditions, and twice as the reference formulation SPORANOX® (2×100 mg capsules) under both fed and fasted conditions according to the treatment randomization schedule. Under the fed conditions, subjects received the dose after consuming a standardized high (50%) fat breakfast. The interval between dosing occasions was at least 7 days, which was considered adequate to prevent carryover of itraconazole between treatment periods.

Study Population

Twelve healthy male subjects, aged between 18 to 50 years, who fulfilled the entry criteria, participated in this study. Eleven subjects completed the study.

Study Treatments

Study Drug: Itraconazole capsules, 110 mg total dose administered as 1×50 mg capsule and 1×60 mg capsule. Subjects received either Treatment C (1×50 mg capsule plus 1×60 mg capsule of itraconazole test formulation administered within 30 minutes of consumption of a standardized high fat breakfast), or Treatment D (1×50 mg capsule plus 1×60 mg capsule of itraconazole test formulation administered following at least a 10-hour overnight fast).

Reference Drug: SPORANOX®, Itraconazole capsules, 2×100 mg capsules. Subjects received either Treatment A (2×100 mg SPORANOX®, Itraconazole capsules administered within 30 minutes of consumption of a standardized high fat breakfast), or Treatment B (2×100 mg SPORANOX®, Itraconazole capsules administered following at least a 10-hour overnight fast).

A single oral dose was administered in each treatment period with 240 mL of room temperature water following a standardized high fat (50%) meal or following a fast of at least 10 hours. Each subject received one of four possible treatments in each study period according to the treatment randomization schedule. A single dose was administered in each treatment period, with a minimum of 7 days between doses.

Blood samples for pharmacokinetic analysis were collected at 1.0, 2.0, 3.0, 4.0, 5.0, 6.0, 8.0, 10, 12, 24, 36, and 48 hours after dosing. Pre-dose samples were collected up to 60 minutes prior to dosing. The blood samples were centrifuged at approximately 2500 rpm for 15 minutes, and the plasma collected for evaluation. Plasma samples were analyzed for itraconazole and 2-hydroxyitraconazole concentrations and agent pharmacokinetics.

The pharmacokinetic sampling schedule was based on results of previous studies and published results indicating an elimination half-life in the range of 13 to 24 hours, and peak plasma concentration at 5 to 10 hours post-dose for dose administration under fed conditions and more rapid absorption for dose administration under fasted conditions.

Pharmacokinetic Analysis

The pharmacokinetic analysis was performed as described in Example 4. The concentration of itraconazole and hydroxyitraconazole (a metabolite of itraconazole) were measured in plasma samples from all subjects, using a validated assay method. Statistical and Analytical Methods were performed as described in Example 4.

Missing and Aberrant Values

There were no missing values for itraconazole and hydroxyitraconazole concentration. Values reported as below quantization were considered as zero in calculating summaries of concentrations by treatment over time.

Pharmacokinetic Results

Figure 5:
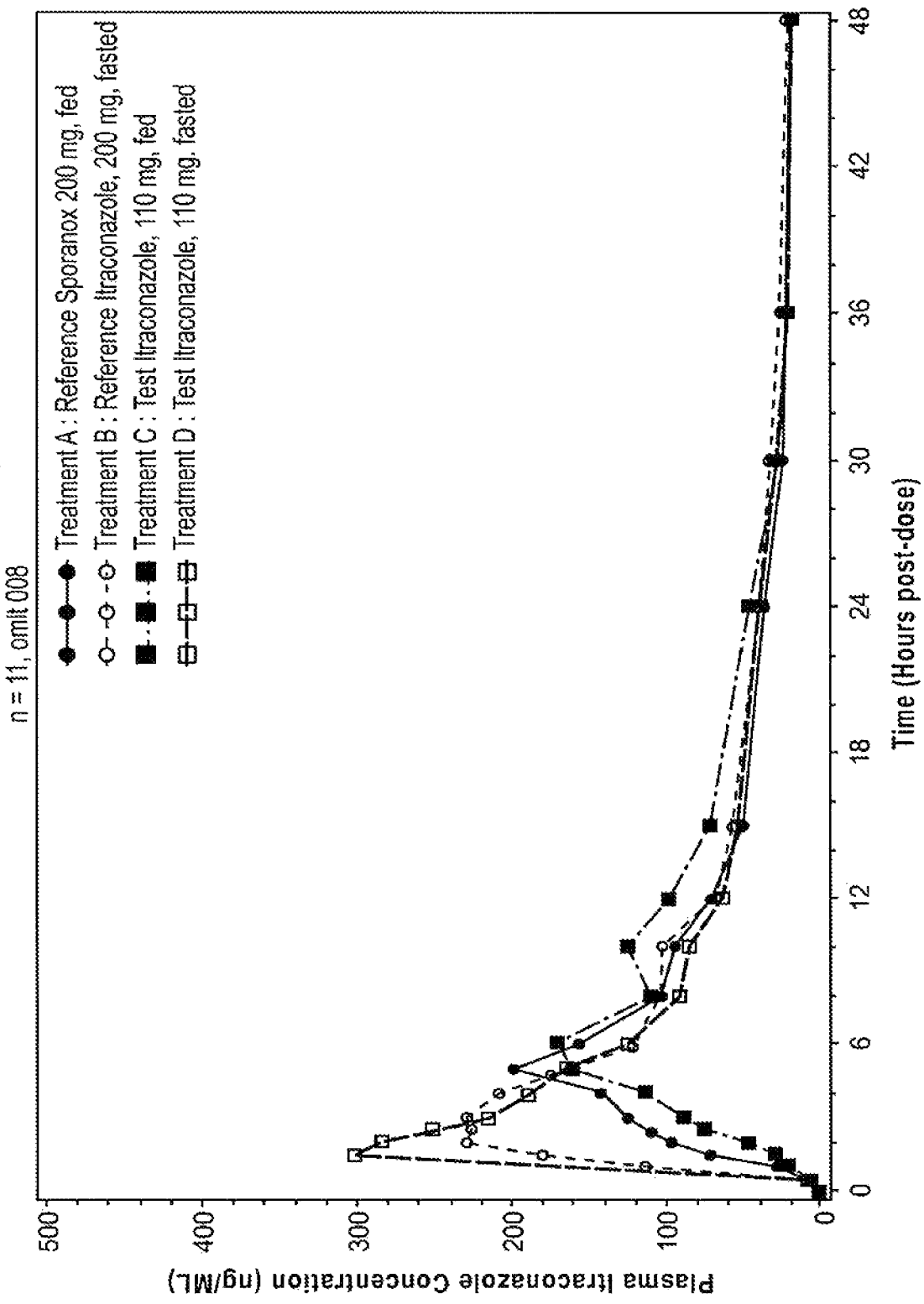
FIG. 5 shows the linear scale graph of the plasma itraconazole concentration against time in a study assessing the relative bioavailability of a 110 mg LOZANOC dose with a 200 mg dose of SPORANOX® (itraconazole) under fed and fasted conditions. Closed circles represent the reference SPORANOX® (itraconazole) 200 mg dose administered under fed conditions; open circles represent the reference SPORANOX® (itraconazole) 200 mg dose administered under fasted conditions; closed squares represent the 110 mg LOZANOC dose administered under fed conditions; and open squares represent the 110 mg LOZANOC dose administered under fasted conditions.
Figure 6:
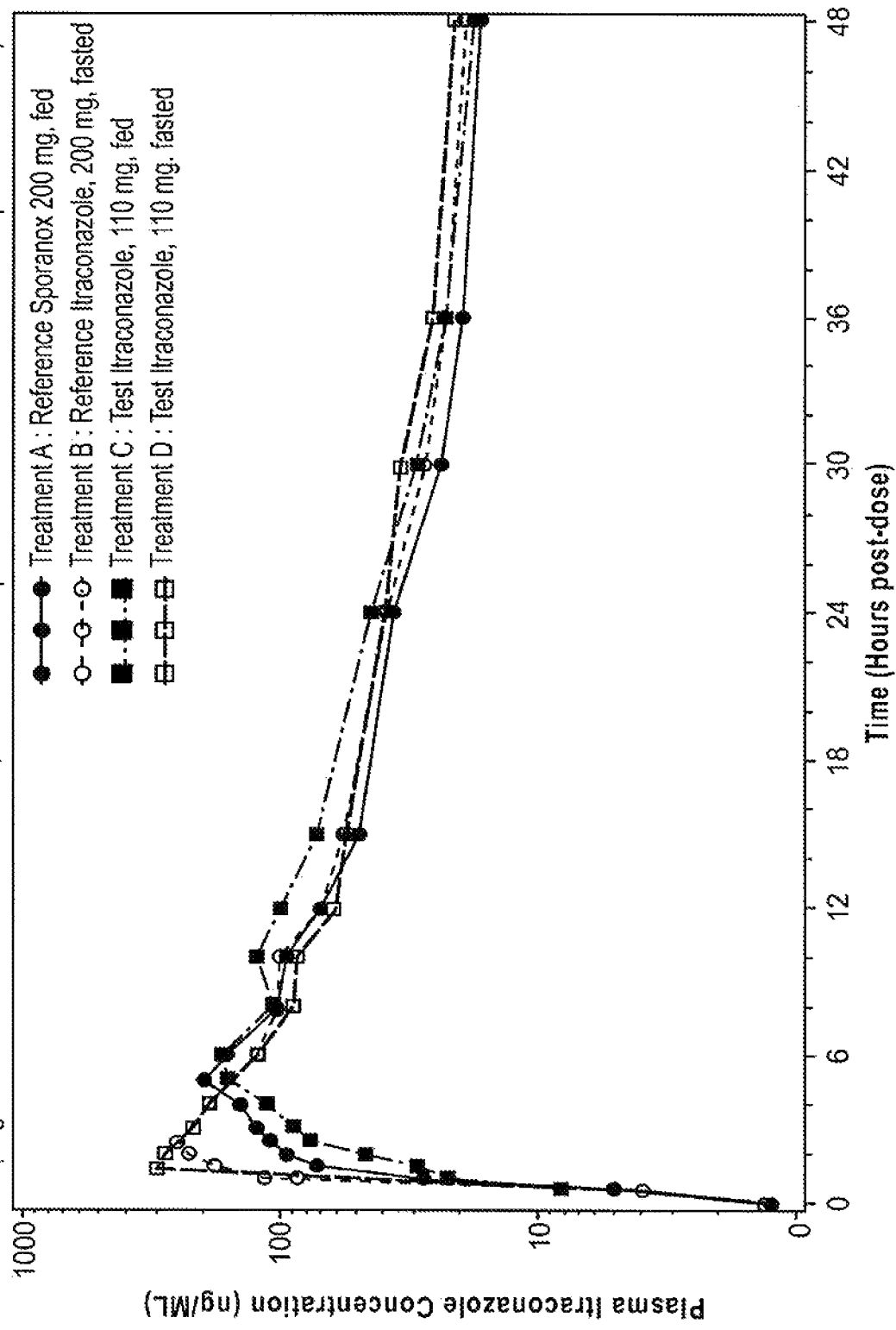
FIG. 6 shows the log-transformed scale graph of the plasma itraconazole concentration against time in a study assessing the relative bioavailability of a 110 mg LOZANOC dose with a 200 mg dose of SPORANOX® (itraconazole) under fed and fasted conditions. Closed circles represent the reference SPORANOX® (itraconazole) 200 mg dose administered under fed conditions; open circles represent the reference SPORANOX® (itraconazole) 200 mg dose administered under fasted conditions; closed squares represent the 110 mg LOZANOC dose administered under fed conditions; and open squares represent the 110 mg LOZANOC dose administered under fasted conditions.
Figure 7:
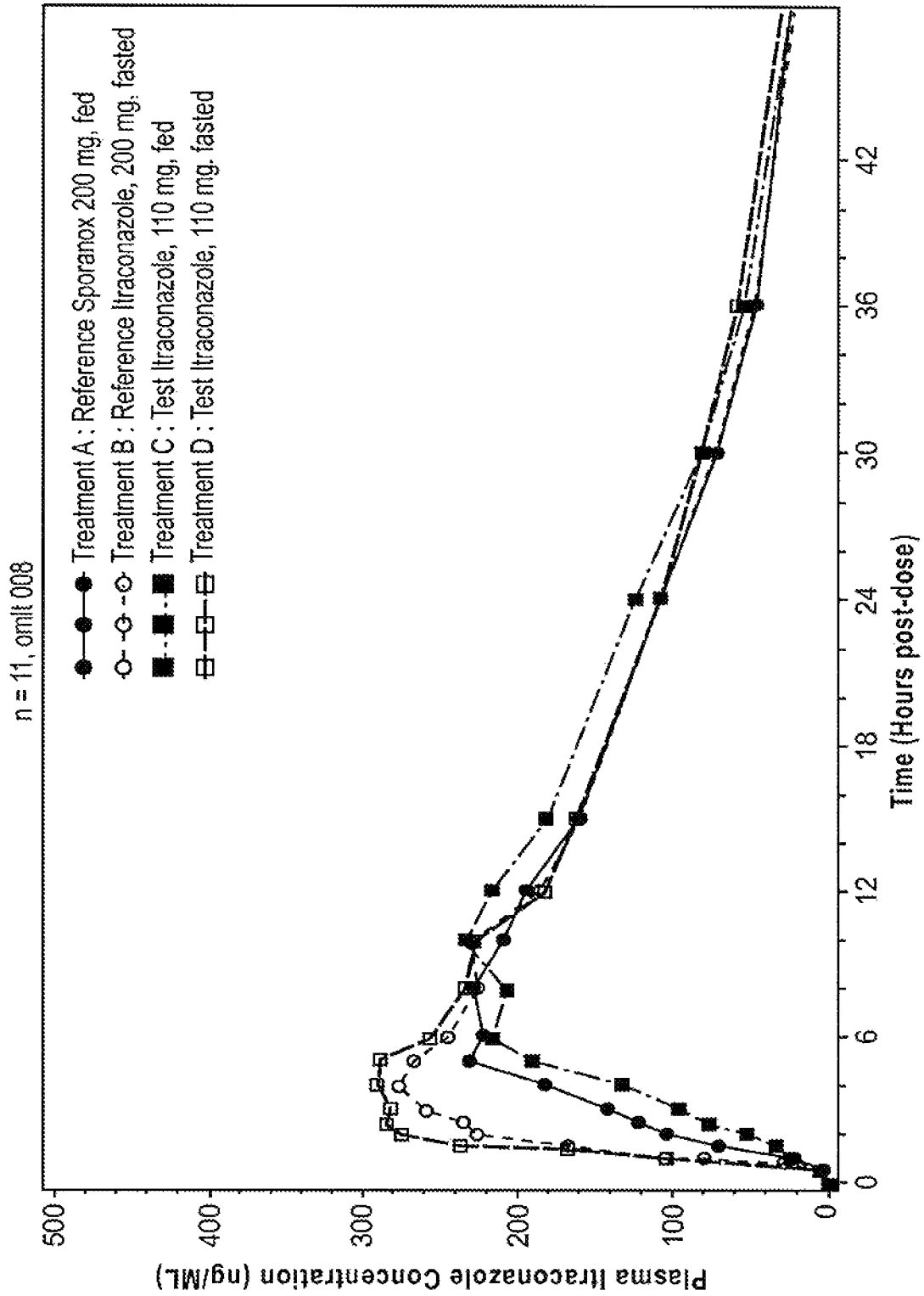
FIG. 7 shows the linear scale graph of the plasma hydroxyitraconazole concentration against time in a study assessing the relative bioavailability of a 110 mg LOZANOC dose with a 200 mg dose of SPORANOX® (itraconazole) under fed and fasted conditions. Closed circles represent the reference SPORANOX® (itraconazole) 200 mg dose administered under fed conditions; open circles represent the reference SPORANOX® (itraconazole) 200 mg dose administered under fasted conditions; closed squares represent the 110 mg LOZANOC dose administered under fed conditions; and open squares represent the 110 mg LOZANOC dose administered under fasted conditions.
Figure 8:
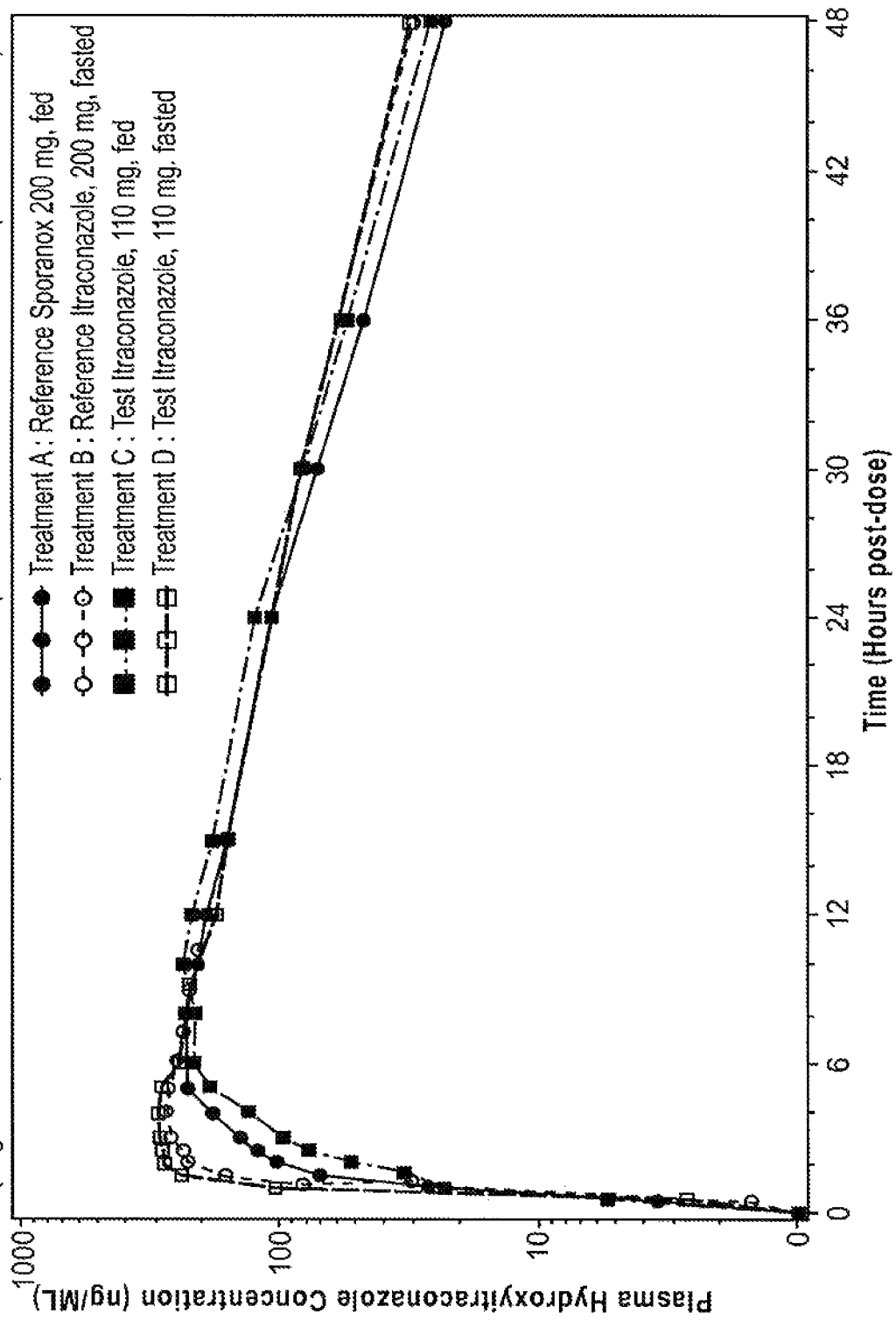
FIG. 8 shows the log-transformed scale graph of the plasma hydroxyitraconazole concentration against time in a study assessing the relative bioavailability of a 110 mg LOZANOC dose with a 200 mg dose of SPORANOX® (itraconazole) under fed and fasted conditions. Closed circles represent the reference SPORANOX® (itraconazole) 200 mg dose administered under fed conditions; open circles represent the reference SPORANOX® (itraconazole) 200 mg dose administered under fasted conditions; closed squares represent the 110 mg LOZANOC dose administered under fed conditions; and open squares represent the 110 mg LOZANOC dose administered under fasted conditions.

FIGS. 5 (linear) and 6 (semi-logarithmic) show the plasma itraconazole concentration against time. FIGS. 7 (linear) and 8 (semi-logarithmic) show the plasma hydroxyitraconazole concentration against time.

Table 7 shows the summary of the pharmacokinetic parameters of itraconazole and hydroxyitraconazole for each treatment for the eleven subjects.

The comparative bioavailability of the test formulation compared with the reference formulation (fed and fasted), and between fed and fasted administration of the test formulation, was determined in the usual manner for bioequivalence assessment, as the 90% confidence interval of the ratio of least squares means from analysis of variance of log-transformed Cmax, AUCt and AUCinf. Table 8 shows the comparative bioavailability of the test formulation compared with the reference treatment under fed and fasted conditions, determined as the ratios of at least squares means from analysis of variance of log-transformed data.

TABLE 8

Comparative bioavailability of itraconazole and hydroxyitraconazole

| Least Squares Mean Ratio (90% Confidence Interval) n = 11 | | Treatment C: 110 mg itraconazole test capsule (fed) vs Treatment A: 200 mg Sporanox ® capsule (fed) | Treatment D: 110 mg itraconazole test capsule (fasted) vs Treatment B: 200 mg Sporanox ® capsule (fasted) | Treatment C: 110 mg itraconazole test capsule (fed) vs Treatment D: 110 mg itraconazole test capsule (fasted) |
|---|---|---|---|---|
| Itraconazole | Cmax | 89.1% (67.1%-118.3%) | 122.0% (91.9%-162.0%) | 64.2% (48.4%-85.3%) |
| | AUCt | 103.0% (84.5%-125.6%) | 94.0% (77.1%-114.7%) | 97.4% (79.9%-118.7%) |
| | AUCinf | 111.2% (86.8%-142.4%) | 82.0% (61.3%-109.7%) | 111.6% (84.5%-147.4%) |
| Hydroxyitraconazole | Cmax | 97.8% (81.4%-117.7%) | 105.7% (89.7%-127.1%) | 77.9% (64.7%-93.6%) |
| | AUCt | 101.8% (80.9%-128.0%) | 98.6% (78.4%-124.0%) | 92.5% (73.6%-116.4%) |
| | AUCinf | 102.6% (81.7%-128.9%) | 98.2% (78.2%-123.3%) | 90.4% (72.0%-113.6%) |

For the fed comparison between the test 110 mg itraconazole capsules compared with the reference 200 mg SPORANOX®, Cmax of itraconazole was lower for the test formulation (LSMean=89.1%, 90% CI=67.1%-118.3%). However, for the fasted comparison between the test 110 mg itraconazole capsules compared with the reference 200 mg SPORANOX®, Cmax of itraconazole was higher for the test formulation (LSMean=122.0%, 90% CI=91.9%-162.0%). Comparisons of AUC parameters did not follow this trend.

TABLE 7

Summary of pharmacokinetics of itraconazole and hydroxyitraconazole

| Mean (Standard Deviation) | | Treatment A 200 mg Sporanox ® capsule (fed) n = 11 | Treatment B 200 mg Sporanox ® capsule (fasted) n = 11 | Test treatment 110 mg itraconazole capsule (fed) n = 11 | Test treatment 110 mg itraconazole capsule (fasted) n = 11 |
|---|---|---|---|---|---|
| Itraconazole | Cmax (ng/mL) | 230.4 (93.6) | 289.9 (215.3) | 225.3 (144.6) | 364.6 (215.4) |
| | AUCt (ng * h/mL) | 2384.0 (1114.4) | 2906.7 (1677.6) | 2658.0 (1197.0) | 2793.2 (1352.2) |
| | AUCinf (ng * h/mL) | 2509.7 (1111.7) | 3331.4 (2399.2) | 3163.6 (1461.7) | 2439.9 (1332.1) |
| Hydroxyitraconazole | Cmax (ng/mL) | 265.9 (109.2) | 308.4 (83.3) | 258.4 (77.5) | 335.9 (110.7) |
| | AUCt (ng * h/mL) | 5154.0 (2565.2) | 5816.7 (2710.4) | 5396.4 (2192.3) | 6034.1 (2753.9) |
| | AUCinf (ng * h/mL) | 5654.8 (3294.2) | 6629.3 (3458.2) | 5928.3 (2691.9) | 6916.9 (3796.3) |

For the comparison between fed and fasted administration of the test itraconazole, Cmax was considerably lower for fed administration, with mean ratios of 64.2% for itraconazole and 77.9% for hydroxyitraconazole. The mean ratios of AUCt were more similar between fasted and fed treatments, with mean ratios of 97.4% for itraconazole and 92.5% for hydroxyitraconazole.

A total of 12 adverse events (AEs) were reported by 5 of the 12 subjects (42%) during the conduct of the study. Most adverse events were mild in intensity, with 3 AEs of moderate severity and one AE of severe intensity (bacterial lower respiratory tract infection, deemed not related to study treatment). There were no AEs deemed to be probably or definitely related to the treatment. There were two AEs deemed by the Principal Investigator to be possibly related to the study treatment experienced by 1/12 subjects (8%), being diarrhea and headache after receiving the reference formulation 200 mg SPORANOX® under fed and fasted conditions, respectively. There were no deaths or other serious adverse events during the study. None of the subjects withdrew from the study due to adverse events deemed related to study treatments.

Example 6—Comparison of the Relative Bioavailability of Two LOZANOC 50 mg Capsules with Two SPORANOX® (Itraconazole) 100 mg Capsules Taken Daily Under Fed Conditions Study Rationale This study evaluated the relative bioavailability in healthy volunteers under fed conditions of two LOZANOC 50 mg capsules with that of two SPORANOX® (itraconazole) 100 mg capsules. Subjects were given 100 mg doses of LOZANOC or 200 mg doses of SPORANOX® (itraconazole) under fed conditions. The pharmacokinetics of both LOZANOC and SPORANOX® (itraconazole) were compared.

Twenty-four (24) volunteers were enrolled in a randomized, multi-dose, four-treatment, four-way crossover study conducted to compare the relative bioavailability of a 100 mg dose of LOZANOC given as 2×50 mg capsules compared to a 200 mg dose of SPORANOX® (itraconazole) (2×100 mg capsules), when administered under fed conditions. Twenty-two (22) subjects completed the study.

Blood samples were collected according to the following schedule:

Day 1—pre-dose (0) collected up to 60 minutes prior dosing and before breakfast

Day 13—immediately (within 5 minutes) prior to dosing

Day 14—immediately (within 5 minutes) prior to dosing

Day 15—pre-dose (0 immediately prior to dosing, within 5 minutes), and at 0.5, 1.0, 1.5, 2.0, 2.5, 3.0, 4.0, 5.0, 6.0, 8.0, 10, 12, 24, 36, 48, and 72 hours post dosing.

The blood samples were centrifuged at approximately 2500 rpm for 15 minutes, and the plasma collected. The plasma concentration of itraconazole and 2-hydroxyitraconazole (a metabolite of itraconazole) were measured by fully validated analytical procedures. Statistical analysis was performed to evaluate the relative bioavailability for the Test product compared to that of the Reference product after daily administration following a high fat, high calorie meal. The single-dose pharmacokinetics of each product was analyzed to identify the dose ranging characteristics of each formulation. Plasma samples were analyzed for itraconazole and 2-hydroxyitraconazole concentrations.

Study Design

In each period, subjects were given either:

Test A: Two doses of 50 mg (2×50 mg capsule LOZANOC;

Reference C: Two doses of 100 mg (2×100 mg capsule) SPORANOX® (itraconazole).

In each dosing period, a single dose of 100 mg (2×50 mg capsules) LOZANOC or 200 mg (2×100 mg capsules) SPORANOX® (itraconazole) was administered to all subjects once a day for 15 consecutive days. Each dose was given following a high fat, high calorie breakfast preceded by an overnight fast of at least 10 hours. The test formulation was LOZANOC 50 mg capsules and the reference formulation was SPORANOX® (itraconazole) 100 mg capsules. The subjects received the test product in one of the study periods and the reference product in the other study period; the order of administration was according to the two-treatment, two-sequence dosing randomization schedule. The interval between Day 1 in each study period was 28 days.

Twenty-four (24) subjects were dosed (12 Test A, 12 Test B) in Period I and 22 subjects were dosed (10 Test A, 12 Test B) in Period II. Subjects were dosed once a day for 15 consecutive days in each study period.

The subjects were monitored throughout the study for any adverse events. No serious adverse events were reported.

Pharmacokinetic Analysis

Concentrations and pharmacokinetics of itraconazole and hydroxyitraconazole in plasma were determined using fully validated analytical methods. The Statistical Analysis System (SAS, Version 9.1.3 or later) was used for all pharmacokinetic and statistical calculations. Linear and semi-logarithmic graphs of the concentration-time profiles for each subject were provided, using the actual times of sample collections. Graphical presentations of mean results use the scheduled times of sample collections. Concentration values reported for each collected sample are provided.

Data from subjects with missing concentration values (missed blood draws, lost samples, samples unable to be quantified) was used if the pharmacokinetic parameters could be estimated using remaining data points, otherwise data from these subjects was excluded from the final analysis.

For all treatments the peak exposure (Cmax) is the observed maximum plasma concentration; the time to peak exposure (Tmax) is the collection time at which Cmax is first observed.

Areas under the curve from time zero to the last measurable concentration (AUCt) were calculated by the linear trapezoidal method. No concentration estimates were provided for missing sample values. Any sample with a missing value was treated as if the sample had not been scheduled for collection. Area under the curve from time zero to time infinity (AUCinf) was calculated as follows:

$$(AUC_{inf}) = (AUCt) + Ct/Kel,$$

where Ct is the last measurable drug concentration and Kel is the elimination rate constant.

The apparent first-order elimination rate constant (Kel) was estimated, when possible, from the slope of the regression line for the terminal ln-linear concentration-time values. The values included in the regression lines were selected by examination of each subject's semi-logarithmic concentration-time plot.

The terminal half-life (Thalf) was estimated as ln(2)/Kel.

If a subject had pre-dose (0 hour sample) plasma levels greater than 5% of their measured Cmax value, all of their data for that analyte was excluded from the statistical analysis for that specific period. If they had measurable levels equal to or less than 5% of their measured Cmax, their data was included in the analysis without adjustment.

Analysis of Variance was performed using the General Linear Model (GLM) procedure of SAS, with hypothesis testing for treatment effects at α=0.05. The statistical model contains main effects of sequence, subject within sequence, treatment, and period. Sequence effects were tested against the Type III mean square term for subjects within sequence.

All other main effects were tested against the mean square error term. Least square means for the treatments (LSMEANS statement), the differences between adjusted treatment means, and the standard errors associated with these differences (ESTIMATE statement) were calculated.

Confidence intervals (90%) for the comparison of test and reference area and peak results were constructed to test two, one-sided hypotheses at the α=0.05 level of significance for AUCt, AUCinf, and Cmax. The confidence intervals were presented for the geometric mean ratios (obtained from logarithmic transformed data).

The Cmin was measured in the plasma concentrations from the blood samples collected on Days 13, 14, and 15. The mean Cmin for each subject is the mean of the observed plasma concentrations from the blood samples collected on these days. The Cav for each subject and treatment is calculated by finding the mean plasma concentrations over the plasma samples collected from 0.5 through 24 hours inclusive on Day 15 (one dosing interval of the reference product).

The Degree of fluctuation (Flux) is calculated for each subject and each treatment using the following calculation:

Flux=(Cmax following *Day* 15 dose−Cmin *on Day* 15)/*Cav on Day* 15.

Swing is calculated for each subject and each treatment using the following calculation:

Swing=(Cmax following *Day* 15 dose−Cmin *on Day* 15)/Cmin *on Day* 15

For calculations of the Flux and Swing, the plasma concentration reported from the pre-dose sample on Day 15 was used.

A comparison of Test A (2×50 mg capsule LOZANOC and Reference C (2×100 mg capsule) SPORANOX® (itraconazole) was computed. The mean concentration for each study agent was also determined over the 15 day treatment schedule.

The Confidence Intervals (90%) for the comparison of test and reference area and peak results are constructed to test two, one-sided hypotheses at the α=0.05 level of significance as follows: on Day 15, dosing for AUC0-72, AUCinf, and Cmax. The confidence intervals are presented for the geometric mean ratios (obtained from logarithmic transformed data). The primary determination of pharmacokinetic equivalence will be based on the log-transformed data for itraconazole. If the 90% confidence interval for the test/reference ratio for Day 15 AUC0-72, AUCinf, and Cmax for itraconazole fall within the range of 80.00 to 125.00%, then equivalence has been demonstrated under steady state conditions.

The same analysis was performed on the hydroxyitraconazole data for informational purposes.

For each serum sample, the mean concentration of the drug over time was determined. The pharmacokinetic parameters were also determined for each drug.

Figure 9:
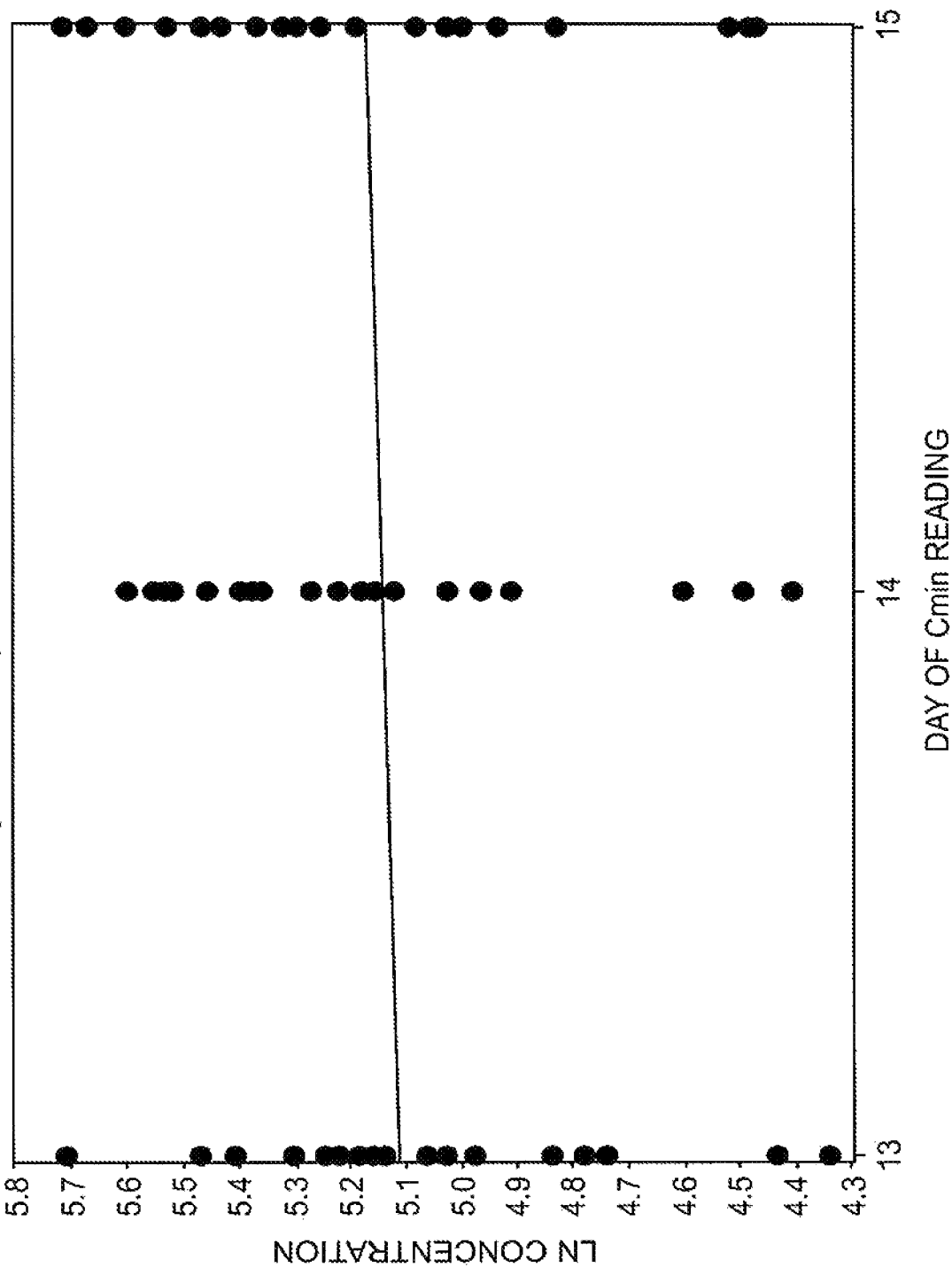
FIG. 9 shows the regression analysis for the concentration of a 100 mg LOZANOC itraconazole dose administered under fed conditions once daily for 15 consecutive days.
Figure 10:
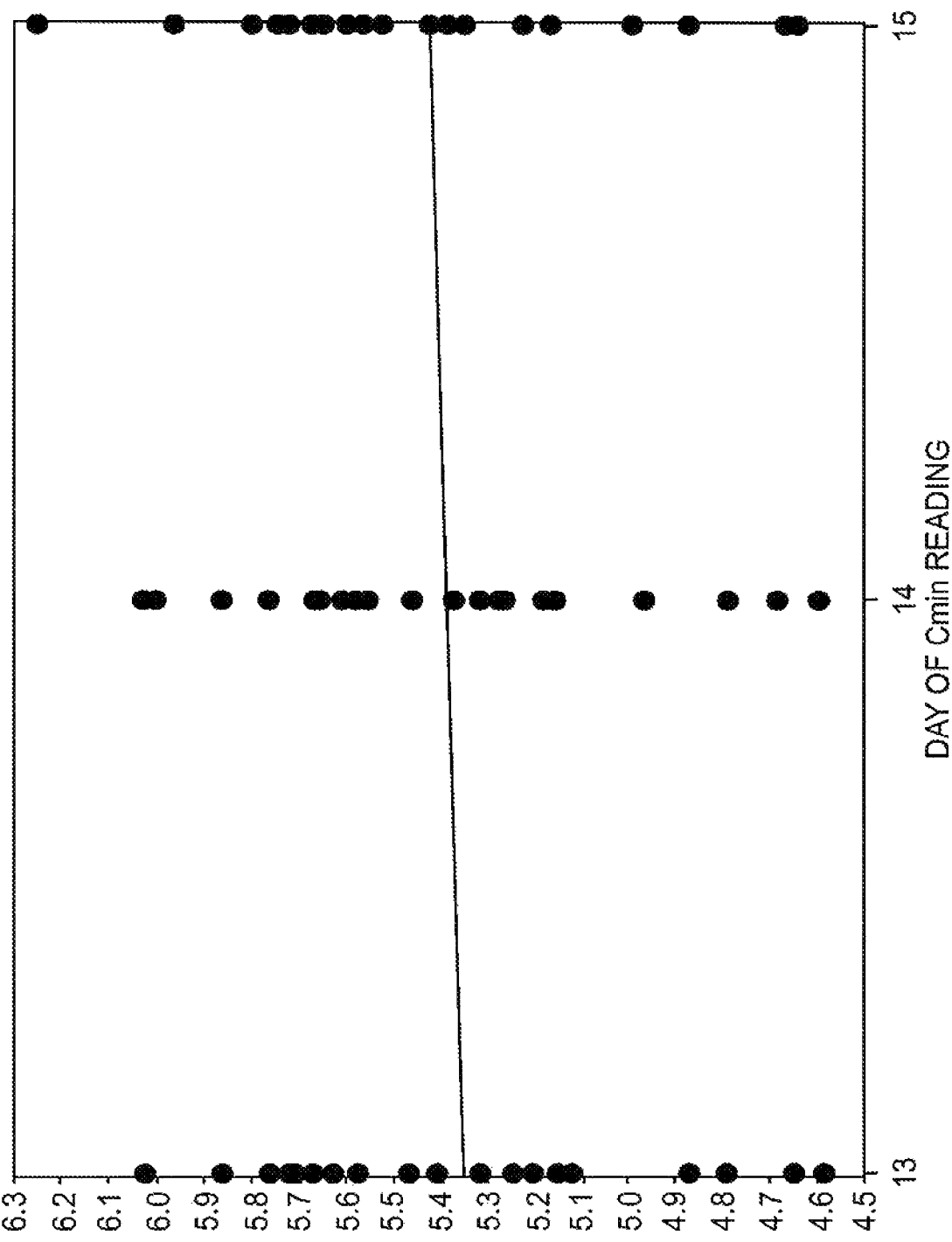
FIG. 10 shows the regression analysis for the concentration of a 200 mg SPORANOX® itraconazole dose administered under fed conditions once daily for 15 consecutive days.
Figure 11:
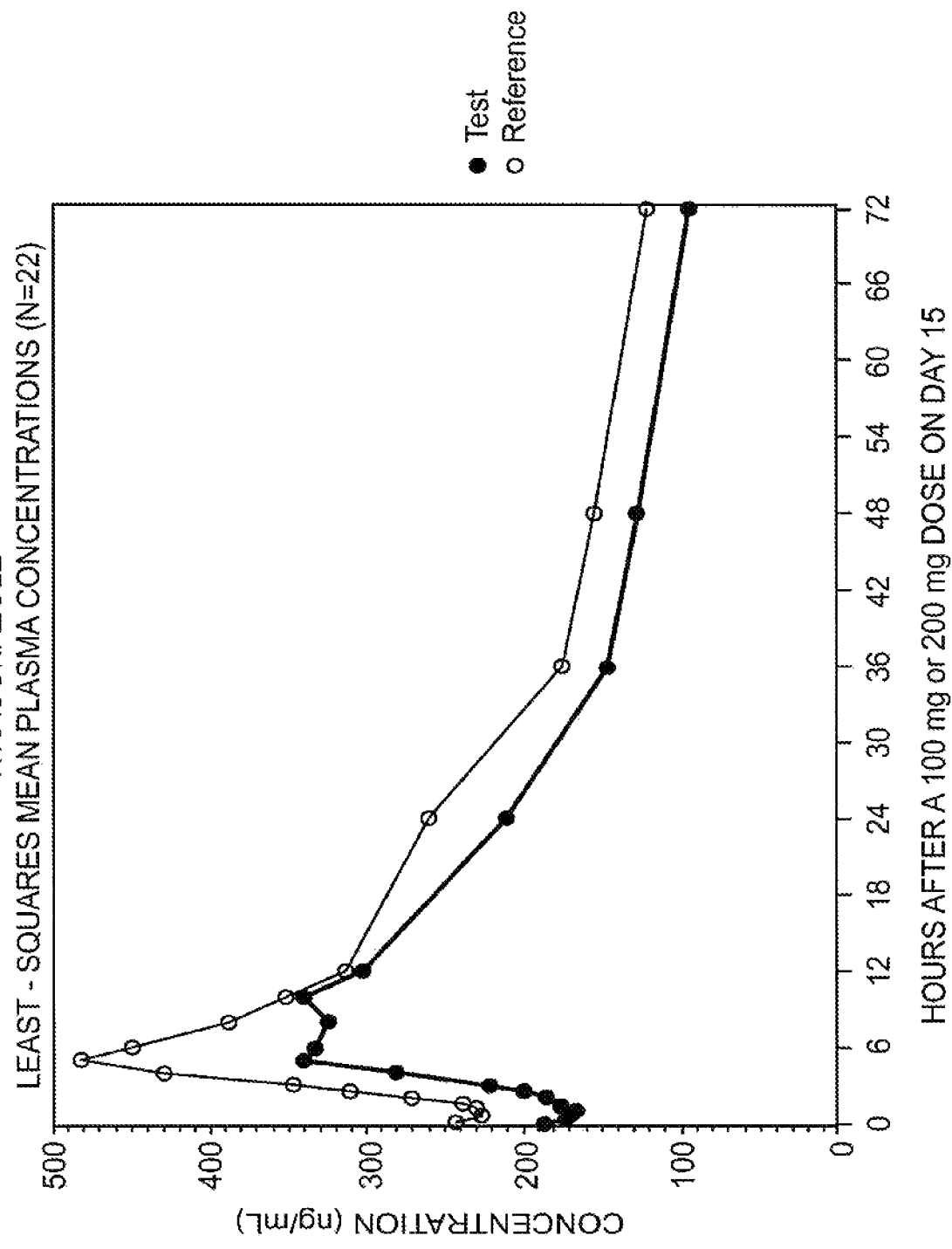
FIG. 11 shows a linear scale graph of the mean plasma itraconazole concentration over time in a study comparing the relative bioavailability of 100 mg LOZANOC dose administered under fed conditions with 200 mg SPORANOX® administered under fed conditions once daily for 15 consecutive days. Closed circles represent the 100 mg LOZANOC itraconazole dose administered under fed conditions; open circles represent the reference SPORANOX® 200 mg dose administered under fed conditions once daily for 15 consecutive days.
Figure 12:
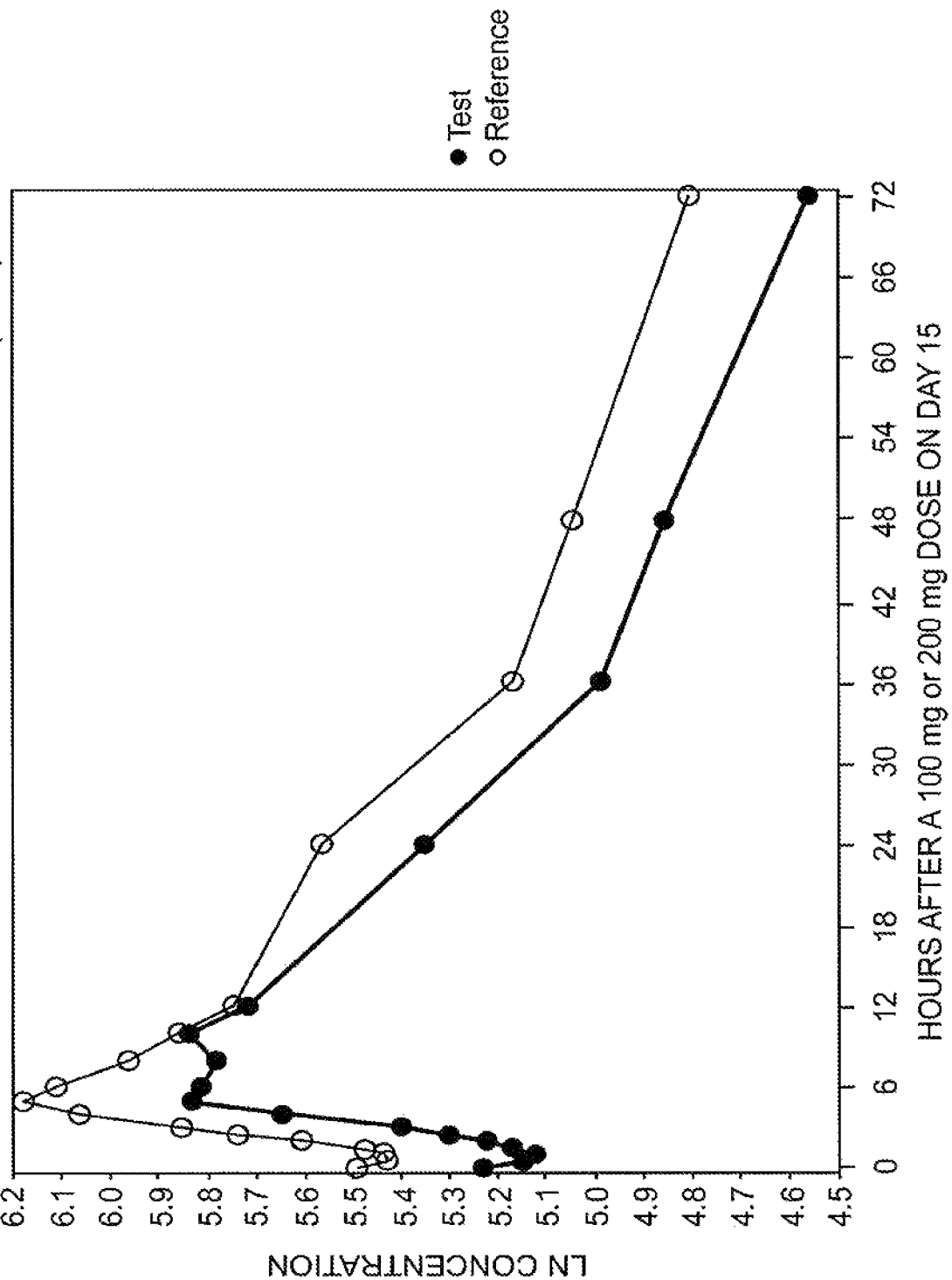
FIG. 12 shows a log-scale graph of the mean plasma itraconazole concentration over time in a study comparing the relative bioavailability of 100 mg LOZANOC dose administered under fed conditions with 200 mg SPORANOX® administered under fed conditions once daily for 15 consecutive days. Closed circles represent the 100 mg LOZANOC itraconazole dose administered under fed conditions; open circles represent the reference SPORANOX® 200 mg dose administered under fed conditions once daily for 15 consecutive days.

FIGS. 9 (Test A) and 10 (Reference B) show the mean itraconazole concentration (ln-linear) versus Study Day plots for Cmin. The mean concentration versus time plots are shown in FIGS. 11 (linear) and 12 (ln-linear).

The following key pharmacokinetic parameters were evaluated: Day 15 AUCt (AUC0-72), AUCinf, Cmax, Tmax, Median Tmax, Ke, Elimhalf (T1/2), Cmin, Cav, Flux, and Swing. Comparative statistics (ratios and 90% confidence interval calculations at steady state) are presented in the tables below.

Table 9 summarizes the pharmacokinetic parameters (untransformed) of itraconazole administered daily for 15 days in a fed state.

Table 10 shows the geometric means for itraconazole based on ANOVA of untransformed and ln-transformed data for itraconazole Test A (2×50 mg capsule of LOZANOC) with Reference B (2×100 mg dose of SPORANOX® (itraconazole)) after daily administration for 15 days in the fed state.

Table 11 shows the ratio of means and 90% confidence interval based on ANOVA of untransformed and ln-transformed data for itraconazole Test A (2×50 mg capsule of LOZANOC) with Reference B (2×100 mg dose of SPORANOX® (itraconazole)) after daily administration for 15 days in the fed state.

TABLE 9

Pharmacokinetic Parameters of Itraconazole Administered Daily in a Fed State

| Pharmacokinetic Parameter | Units | Arithmetic Mean ± SD | |
|---|---|---|---|
| | | Test A | Reference B |
| AUCt (0-72) | ng · hr/ml | 13007.6748 ± 4725.2118 | 15845.3411 ± 5743.7269 |
| AUCinf | ng · hr/ml | 20144.5525 ± 13330.5217 | 23464.8222 ± 10390.4699 |
| Cmax | ng/ml | 419.0909 ± 109.7998 | 524.7273 ± 159.8723 |
| Tmax | hr | 7.8636 ± 2.7132 | 5.2947 ± 1.5328 |
| Median Tmax | hr | 7.00 | 5.00 |
| Ke | 1/hr | 0.0192 ± 0.0086 | 0.0186 ± 0.0092 |
| Elimhalf | hr | 45.3011 ± 29.0137 | 48.5164 ± 33.8293 |
| Cmin Day 13 | ng/ml | 172.44 ± 51.96 | 224.40 ± 82.57 |
| Cmin Day 14 | ng/ml | 181.97 ± 54.23 | 234.63 ± 86.97 |
| Cmin Day 15 | ng/ml | 186.95 ± 61.86 | 244.86 ± 97.02 |
| Mean Cmin | ng/ml | 186.9500 ± 61.8644 | 244.8636 ± 97.0166 |
| Cav | ng/ml | 250.8973 ± 73.7361 | 334.3223 ± 99.0344 |
| Flux | — | 0.9668 ± 0.4120 | 0.8518 ± 0.2991 |
| Swing | — | 1.4100 ± 0.8949 | 1.3095 ± 0.7828 |

TABLE 10

Geometric Means of Itraconazole after daily administration in the fed state Geometric Means Based on ANOVA of Untransformed and Ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Test A | 12996.31 | 20346.30 | 415.73 | 12211.78 | 17437.69 | 401.90 |
| Reference B | 15700.92 | 24874.99 | 519.41 | 14649.35 | 21695.30 | 495.74 |

TABLE 11

Ratio of Means and 90% Confidence Interval of
Itraconazole after daily administration in the fed state
Ratio of Means, and 90% Confidence Intervals Based on
ANOVA of Untransformed and Ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.8277 | 0.8179 | 0.8004 | 0.8336 | 0.8038 | 0.8107 |
| CI | 0.7342-0.9213 | 0.6861-09498 | 0.7105-0.8902 | 0.7535-0.9222 | 0.6832-0.9456 | 0.7334-0.8962 |
| p-value | 0.0047 | 0.0283 | 0.0010 | 0.0055 | 0.0321 | 0.0018 |

Table 12 shows the statistical summary of the comparative bioavailability data from this study.

TABLE 12

Statistical Summary of Comparative Bioavailability
Data for Itraconazole

Drug SUBA ™-Itraconazole Capsules
Dose (Test 2 × 50 mg; Reference 2 × 100 mg)
Least Squares Geometric Means, Ratio of
Means, and 90% Confidence Intervals
Fed Bioequivalence Study (Study No. 1080705)

| Parameter | Test | Reference | Ratio | 90% C.I. |
|---|---|---|---|---|
| AUC0-t* | 12212 | 14649 | 0.8336 | 0.7535-0.9222 |
| AUC∞* | 17438 | 21695 | 0.8038 | 0.6832-0.9456 |
| Cmax* | 402 | 496 | 0.8107 | 0.7334-0.8962 |

Figure 13:
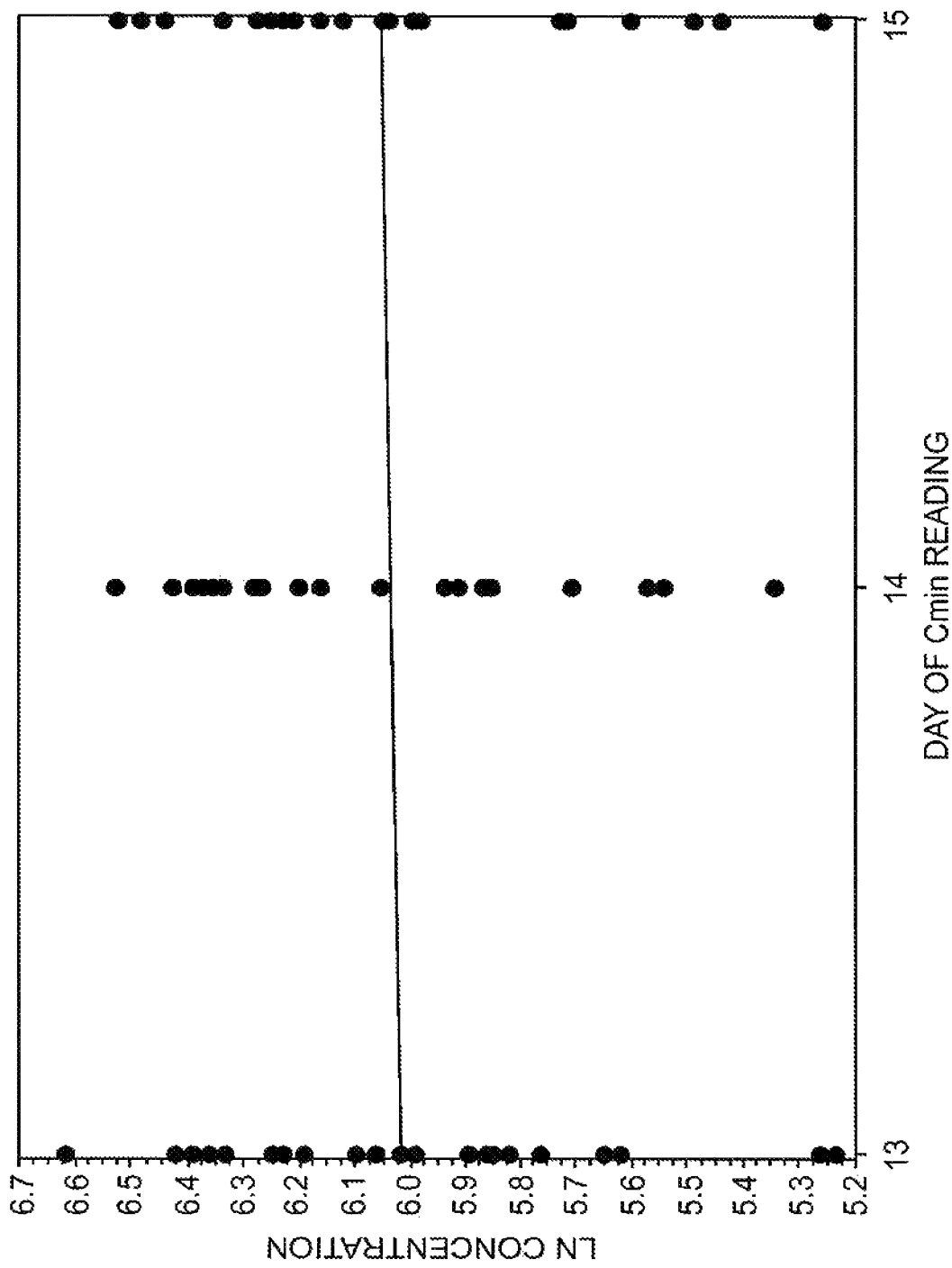
FIG. 13 shows the regression analysis for the concentration of hydroxyitraconazole after administration of a 100 mg LOZANOC itraconazole dose under fed conditions once daily for 15 consecutive days.
Figure 14:
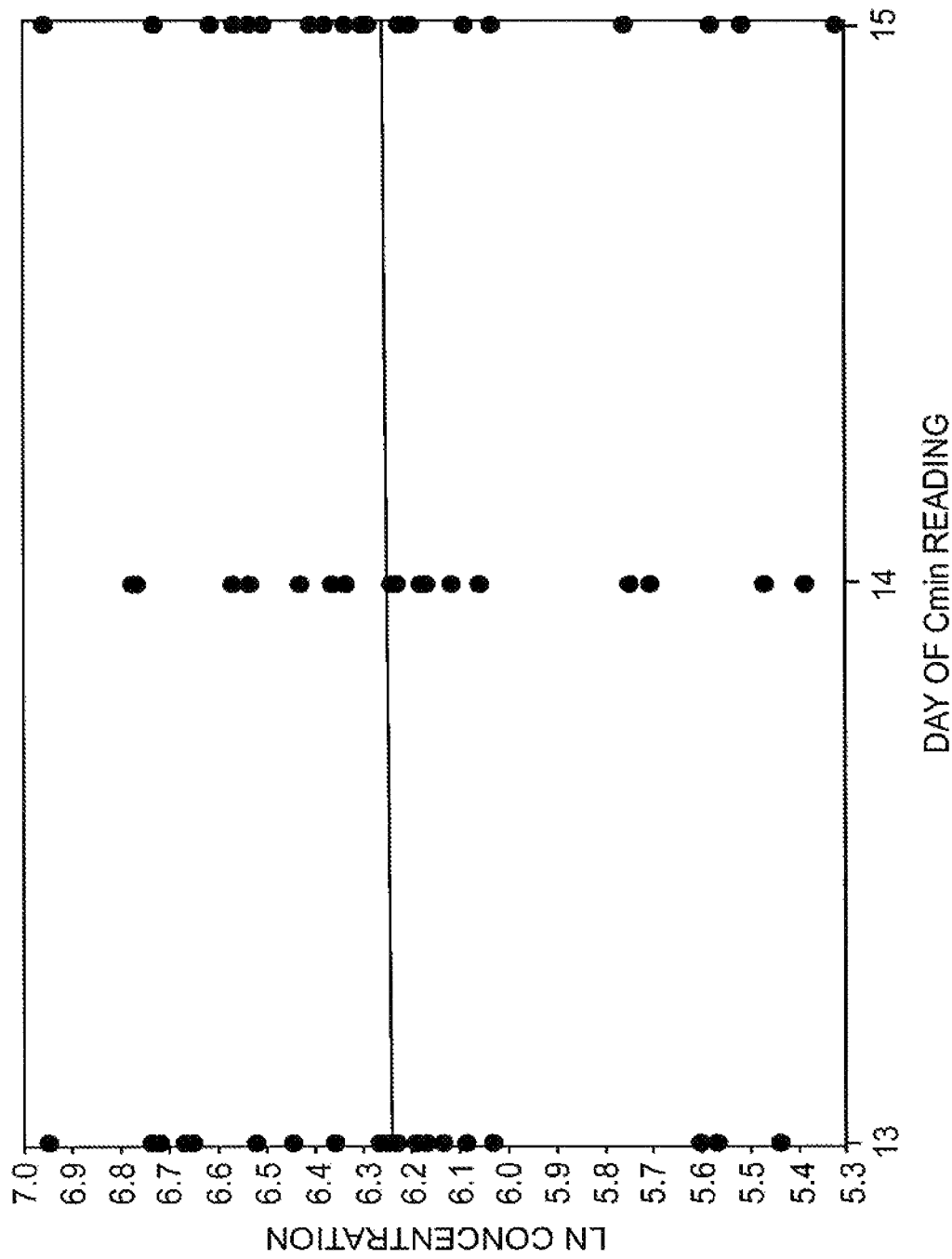
FIG. 14 shows the regression analysis for the concentration of hydroxyitraconazole after administration of a 200 mg SPORANOX® itraconazole dose under fed conditions once daily for 15 consecutive days.
Figure 15:
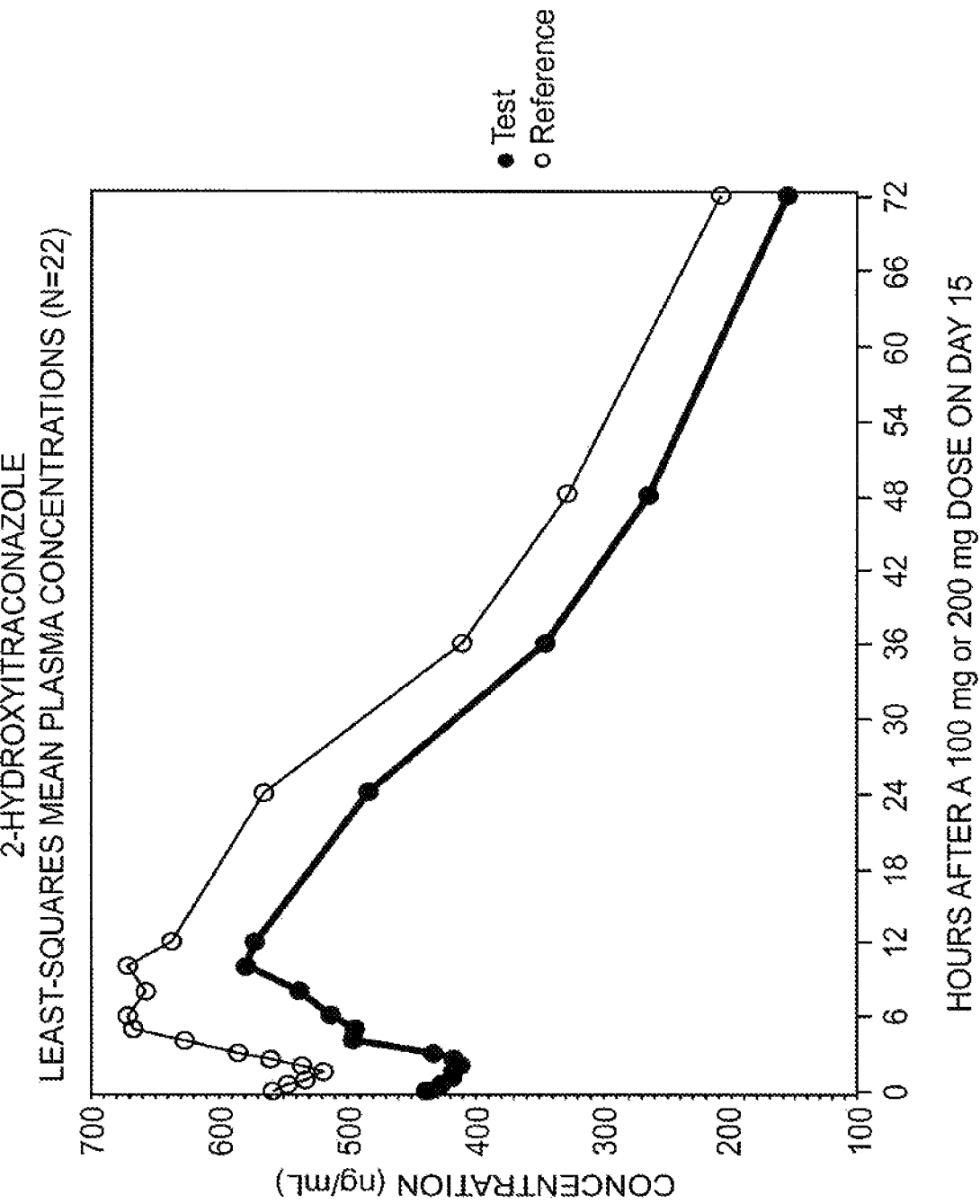
FIG. 15 shows a linear scale graph of the mean plasma hydroxyitraconazole concentration over time in a study comparing the relative bioavailability of 100 mg LOZANOC dose with 200 mg SPORANOX® administered under fed conditions once daily for 15 consecutive days. Closed circles represent the 100 mg LOZANOC itraconazole dose administered under fed conditions once daily for 15 consecutive days; open circles represent the reference SPORANOX® 200 mg dose administered under fed conditions once daily for 15 consecutive days.
Figure 16:
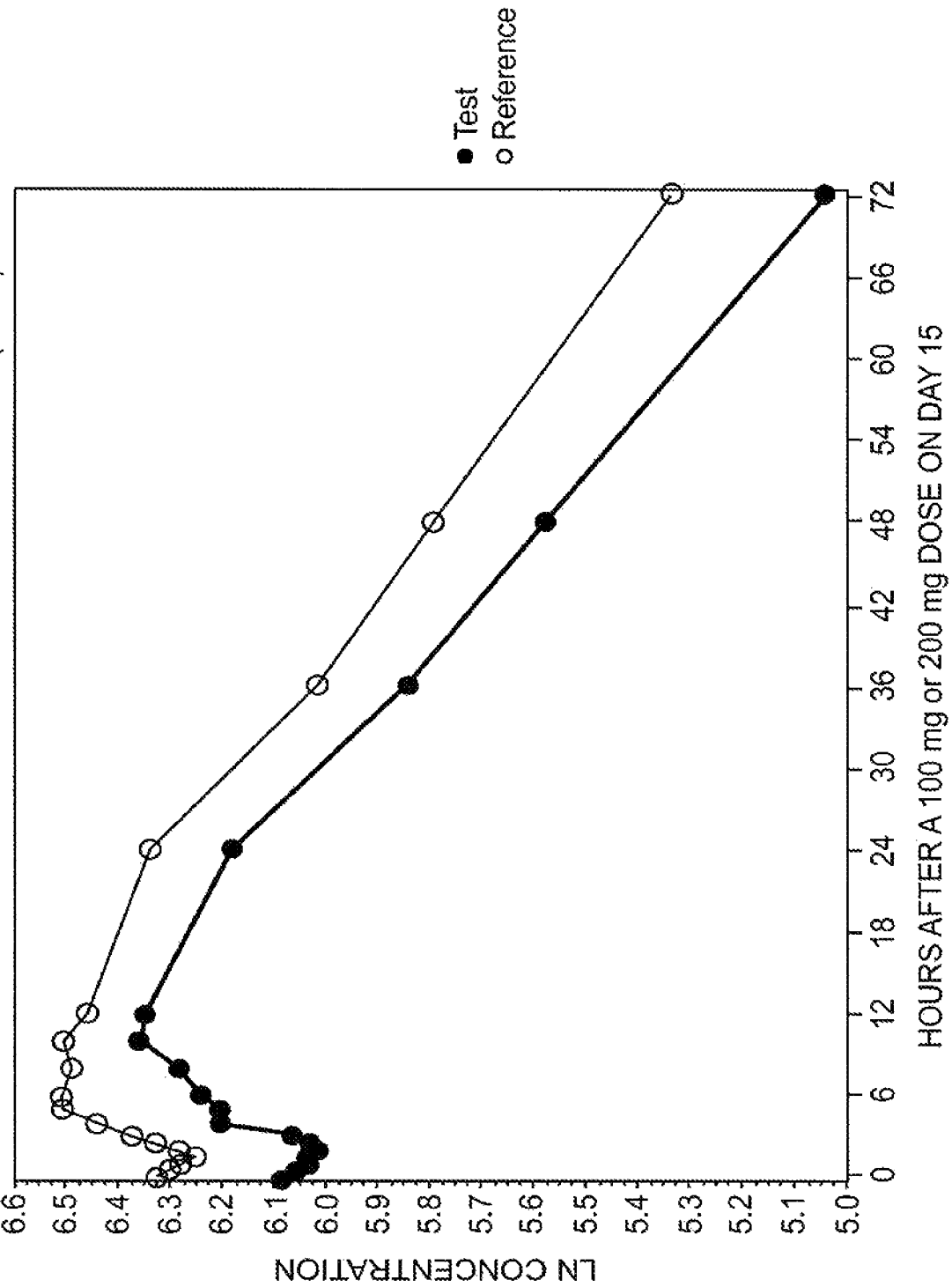
FIG. 16 shows a log-scale graph of the mean plasma hydroxyitraconazole concentration over time in a study comparing the relative bioavailability of 100 mg LOZANOC dose with 200 mg SPORANOX® administered under fed conditions once daily for 15 consecutive days. Closed circles represent the 100 mg LOZANOC itraconazole dose administered under fed conditions once daily for 15 consecutive days; open circles represent the reference SPORANOX® 200 mg dose administered under fed conditions once daily for 15 consecutive days.

The same analyses were performed for 2-hydroxyitraconazole, a metabolite of itraconazole. FIGS. 13 (Test A) and 14 (Reference C) show the mean concentration (ln-linear) versus Study Day plots for Cmin for 2-hydroxyitraconazole after daily administration of the itraconazole formulations under a fed state. The mean concentration versus time plots for 2-hydroxyitraconazole are shown in FIGS. 15 (linear) and 16 (ln-linear).

Table 13 summarizes the pharmacokinetic parameters (untransformed) of 2-hydroxyitraconazole after administration of the Test and Reference agents daily for 15 days in a fed state.

TABLE 13

Pharmacokinetic Parameters of 2-Hydroxyitraconazole
after Administration of Itraconazole Daily in a Fed State

| Pharmacokinetic Parameter | Units | Arithmetic Mean ± SD | |
|---|---|---|---|
| | | Test A | Reference B |
| AUCt (0-72) | ng · hr/ml | 25929.8512 ± 10133.4980 | 31583.4798 ± 12930.4733 |
| AUCinf | ng · hr/ml | 34366.0362 ± 18017.8441 | 45893.3050 ± 28163.7792 |
| Cmax | ng/ml | 613.7273 ± 156.0236 | 740.2273 ± 243.2432 |
| Tmax | hr | 8.5455 ± 2.9395 | 7.9530 ± 2.8695 |
| Median Tmax | hr | 10.00 | 8.00 |
| Ke | 1/hr | 0.0327 ± 0.0204 | 0.0281 ± 0.0183 |
| Elimhalf | hr | 28.6001 ± 14.5803 | 34.7349 ± 19.8660 |
| Cmin Day 13 | ng/ml | 424.27 ± 140.28 | 552.95 ± 212.59 |
| Cmin Day 14 | ng/ml | 451.59 ± 129.52 | 549.59 ± 194.02 |
| Cmin Day 15 | ng/ml | 437.55 ± 136.34 | 560.86 ± 203.09 |
| Mean Cmin | ng/ml | 437.5455 ± 136.3402 | 560.8636 ± 203.0860 |

TABLE 13-continued

Pharmacokinetic Parameters of 2-Hydroxyitraconazole
after Administration of Itraconazole Daily in a Fed State

| Pharmacokinetic Parameter | Units | Arithmetic Mean ± SD | |
|---|---|---|---|
| | | Test A | Reference B |
| Cav | ng/ml | 475.4873 ± 141.2199 | 603.1541 ± 185.5448 |
| Flux | — | 0.3977 ± 0.1912 | 0.3164 ± 0.1938 |
| Swing | — | 0.4559 ± 0.2812 | 0.3755 ± 0.2718 |

Table 14 shows the geometric means based on ANOVA of untransformed and ln-transformed data for 2-hydroxyitraconazole after daily administration of itraconazole Test A (2×50 mg capsule of LOZANOC) or Reference B (2×100 mg dose of SPORANOX® (itraconazole)) for 15 days in the fed state.

TABLE 14

Geometric Means of 2-Hydroxyitraconazole after daily
administration of itraconazole in the fed state
Geometric Means Based on ANOVA
of Untransformed and Ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Test A | 25972.58 | 34635.61 | 611.46 | 23932.62 | 29914.03 | 592.67 |
| Reference B | 31397.61 | 45873.13 | 732.43 | 28533.04 | 37918.58 | 696.31 |

Table 15 shows the ratio of means and 90% confidence intervals based on ANOVA of untransformed and ln-transformed data for 2-hydroxyitraconazole after daily administration of itraconazole Test A (2×50 mg capsule of LOZANOC) or Reference B (2×100 mg dose of SPORANOX® (itraconazole)) for 15 days in the fed state.

TABLE 15

Ratio of Means and 90% Confidence Interval of
Hydroxyitraconazole after daily administration of
itraconazole in the fed state
Ratio of Means, and 90% Confidence Intervals Based on
ANOVA of Untransformed and Ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.8272 | 0.7550 | 0.8348 | 0.8388 | 0.7889 | 0.8512 |
| CI | 0.7114-0.9430 | 0.5995-0.9105 | 0.7226-0.9471 | 0.7400-0.9507 | 0.6758-0.9210 | 0.7666-0.9450 |
| p-value | 0.0081 | 0.0133 | 0.0196 | 0.0252 | 0.0156 | 0.0151 |

Example 7—Comparison of the Relative Bioavailability of Two LOZANOC 50 mg Capsules with Two SPORANOX® (Itraconazole) 100 mg Capsules Taken Twice Daily Under Fed Conditions Study Rationale This study evaluated the relative bioavailability in healthy volunteers under fed conditions of two LOZANOC 50 mg capsules with that of two SPORANOX® (itraconazole) 100 mg capsules. Subjects were given 100 mg doses of LOZANOC or 200 mg doses of SPORANOX® (itraconazole) under fed conditions twice daily for 14.5 days. The pharmacokinetics of both LOZANOC and SPORANOX® (itraconazole) were compared.

Twenty-four (24) volunteers were enrolled in this randomized, multi-dose, steady-state, two-treatment, crossover study conducted to compare the relative bioavailability of twice-daily doses of 100 mg LOZANOC given as 2×50 mg capsules compared to 200 mg dose of SPORANOX® (itraconazole) (2×100 mg capsules), when administered under fed conditions. Twenty-one (21) subjects completed the study.

Blood samples were collected according to the following schedule:

Day 1—pre-dose (0) collected up to 60 minutes prior dosing and before breakfast

Day 13—immediately (within 5 minutes) prior to the morning dosing

Day 14—immediately (within 5 minutes) prior to the morning dosing

Day 15—pre-dose (0 immediately prior to dosing, within 5 minutes), and at 0.5, 1.0, 1.5, 2.0, 2.5, 3.0, 4.0, 5.0, 6.0, 8.0, 10, 12 (prior to evening dose), 24, 36, 48, and 72 hours post dosing.

The blood samples were centrifuged at approximately 2500 rpm for 15 minutes, and the plasma collected. The plasma concentration of itraconazole and 2-hydroxyitraconazole (a metabolite of itraconazole) were measured by fully validated analytical procedures. Statistical analysis was performed to evaluate the relative bioavailability for the Test product compared to that of the Reference product after twice-daily administration following under fed conditions. The single-dose pharmacokinetics of each product was analyzed to identify the dose ranging characteristics of each formulation. Plasma samples were analyzed for itraconazole and 2-hydroxyitraconazole concentrations.

Study Design

In each period, subjects were given either Test A or Reference C twice a day for 14.5 consecutive days. The agents tested were:

Test A: one dose of 100 mg (2×50 mg capsule LOZANOC;

Reference B: one dose of 200 mg (2×100 mg capsule) SPORANOX® (itraconazole).

In each dosing period, one dose of 100 mg (2×50 mg capsules) LOZANOC or 200 mg (2×100 mg capsules) SPORANOX® (itraconazole) was administered to all subjects twice a day for 14.5 consecutive days. Each morning dose (Days 1 to 15) was given following a full breakfast preceded by an overnight fast of at least 10 hours. On the last day of dosing (Day 15) the morning dosing occurred following subjects consuming the FDA standardized high fat, high calorie breakfast preceded by an overnight fast of at least 10 hours. Each evening dose (Days 1 to 14) was given within 30 minutes of consuming a standardized full dinner. The morning and evening doses were separated by 12 hours. The test formulation was LOZANOC 50 mg capsules and the reference formulation was SPORANOX® (itraconazole) 100 mg capsules. The subjects received the test product in one of the study periods and the reference product in the other study period; the order of administration was according to the two-treatment, two-sequence dosing randomization schedule. The interval between Day 1 in each study period was 28 days.

Twenty-four (24) subjects were dosed (12 Test A, 12 Reference B) in Period I and 21 subjects were dosed (12 Test A, 9 Reference B) in Period II. Subjects were dosed twice a day for 14.5 consecutive days in each study period.

The subjects were monitored throughout the study for any adverse events. No serious adverse events were reported.

Pharmacokinetic Analysis

Concentrations of itraconazole and hydroxyitraconazole in plasma were determined at using fully validated analytical methods. A definition of the pharmacokinetic parameters, AUC, AUC-INF, CMAX, TMAX, KEL and THALF, which were derived from the plasma itraconazole and hydroxyitraconazole concentration data, and a description of the statistical tests which were performed to compare the treatments are provided below:

Area Under the Curve (AUC and AUC-INF): Area under the plasma concentration-time curve from time zero to the time of the last measurable concentration (AUC), calculated by the linear trapezoidal method. Area under the curve from time zero to infinite time (AUC-INF), calculated from the sum of AUC plus the extrapolated area calculated from CLAST'/KEL, where CLAST' is the observed last measurable drug concentration and TLAST is the time of the last measurable concentration. i.e. AUC-INF=AUC+CLAST'/KEL.

Maximum Observed Plasma Concentration (CMAX): Maximum plasma concentration observed following dosing.

Time of Maximum Observed Plasma Concentration (TMAX): Sampling time of the observed CMAX, expressed as hours following dosing (obtained without interpolation)

Apparent First-order Elimination Rate Constant (KEL): Calculated from the slope of the regression line for the terminal log-linear plasma concentration-time values.

Apparent Elimination Half-Life (THALF): Calculated as 0.693/KEL

Analysis of Variance (ANOVA): ANOVA was performed at an alpha level of 0.05. The statistical model contained main effects of treatment, subject, period and sequence.

Confidence Intervals (90%): Confidence intervals (90%) for pair-wise pharmacokinetic comparisons were calculated by the t-test approach (two, one-sided) at an overall alpha level of 0.10 (=0.05 each side). The intervals were computed for the least squares mean differences, expressed as a percent of the reference treatment mean in the comparison, and mean ratios (following logarithmic transformation of the data, using natural logarithms).

Power: Power to detect a 20% difference for each pair-wise pharmacokinetic comparison was calculated at =0.05.

Mean Ratio (%): Mean ratios (expressed as percentages) were calculated for log-transformed parameters where: Mean ratio (%)=100×exp (least squares mean test–least squares mean reference).

Intrasubject Variability: Intrasubject coefficient of variation (CV %) was calculated for log-transformed parameters as: 100×(MSResidual)o.5

Intersubject Variability: Intersubject coefficient of variation (CV %) was calculated for log-transformed parameters as: 100×«MSSubject (Seq)–MSResidual/2)o.5.

Nominated sample collection times were used in the statistical analysis. A parametric (normaltheory) general linear model (GLM) was applied to each of the calculated pharmacokinetic parameters and observations derived from the plasma itraconazole and plasma hydroxyitraconazole concentrations using SA~ (Version 6.12) GLM Procedure. In addition, the parameters AUC, AUC-INF and CMAX were log-transformed using natural logarithms (LAUC, LAUC-INF and LCMAX) and were analyzed with the same model. The analysis of variance ANOVA) model included the effects of treatment, subject, period and sequence. Tukey's Studentized Range Test was performed on means of plasma itraconazole and plasma hydroxyitraconazole concentrations at individual sampling times at an alpha level of 0.05. Least squares means (LSMEANS) of each parameter for each treatment were used in the statistical analysis. Power to detect a 20% difference between formulations was calculated at =0.05. Ordinary 90% confidence intervals, based on the t-test, were calculated. The procedures correspond to Schuirmann's two one-sided tests at the 5% level of significance. The two one-sided hypothesis was tested at the 5% level for the parameters by constructing 90% confidence intervals for the ratios of the test and reference means. The 90% confidence intervals were obtained from the antilogs of the lower and upper bounds of the 90% confidence intervals for the difference in the means of the log-transformed data. Mean ratio values and intrasubject and intersubject variability (CV %) values were provided for the log-transformed parameters CMAX, AUC and AUC-INF.

The statistical tests were performed comparing Treatment A with Treatment B.

Areas under the curve from time zero to the last measurable concentration (AUC0-72) and truncated areas under the curve from time zero to the 12 hour concentration (AUC0-12) and the 24 hour concentration (AUC0-24), were calculated by the linear trapezoidal method.

The Cmin was measured in the plasma concentrations from the blood samples collected on Days 13, 14, and 15. The mean Cmin for each subject is the mean of the observed plasma concentrations from the blood samples collected on these days. Regression analysis was conducted on the Cmin values to determine that steady state was reached for both the test and reference agents.

The Cav for each subject and treatment was calculated by finding the mean plasma concentrations over the plasma samples collected from 0.5 through 12 hours inclusive on Day 15 (one dosing interval of the reference product).

The Degree of fluctuation (Flux) was calculated for each subject and each treatment using the following calculation:

Flux=(Cmax following *Day* 15 dose–Cmin *on Day* 15)/*Cav on Day* 15.

Swing was calculated for each subject and each treatment using the following calculation:

Swing=(Cmax following *Day* 15 dose–Cmin *on Day* 15)/Cmin *on Day* 15

For calculations of the Flux and Swing, the plasma concentration reported from the pre-dose sample on Day 15 was used.

A comparison of Test A (2×50 mg capsule LOZANOC) and Reference B (2×100 mg capsule) SPORANOX® (itraconazole) administered twice-daily for 14.5 days under a fed state was computed. The mean concentration for each study agent was also determined over the 15 day treatment schedule.

The Confidence Intervals (90%) for the comparison of test and reference area and peak results are constructed to test two, one-sided hypotheses at the α=0.05 level of significance as follows: on Day 15, dosing for AUC0-12, AUC0-24, AUC0-72, AUCinf, and Cmax. The confidence intervals are presented for the geometric mean ratios (obtained from logarithmic transformed data). The primary determination of pharmacokinetic equivalence will be based on the log-transformed data for itraconazole. If the 90% confidence interval for the test/reference ratio for Day 15 AUC0-12, AUC0-24, AUC0-72, AUCinf, and Cmax for the test agent falls within the range of 80.00 to 125.00%, then equivalence has been demonstrated under steady state conditions.

The same analysis was performed on the hydroxyitraconazole data for informational purposes.

For each serum sample, the mean concentration of the drug over time was determined. The pharmacokinetic parameters were also determined for each drug.

Figure 17:
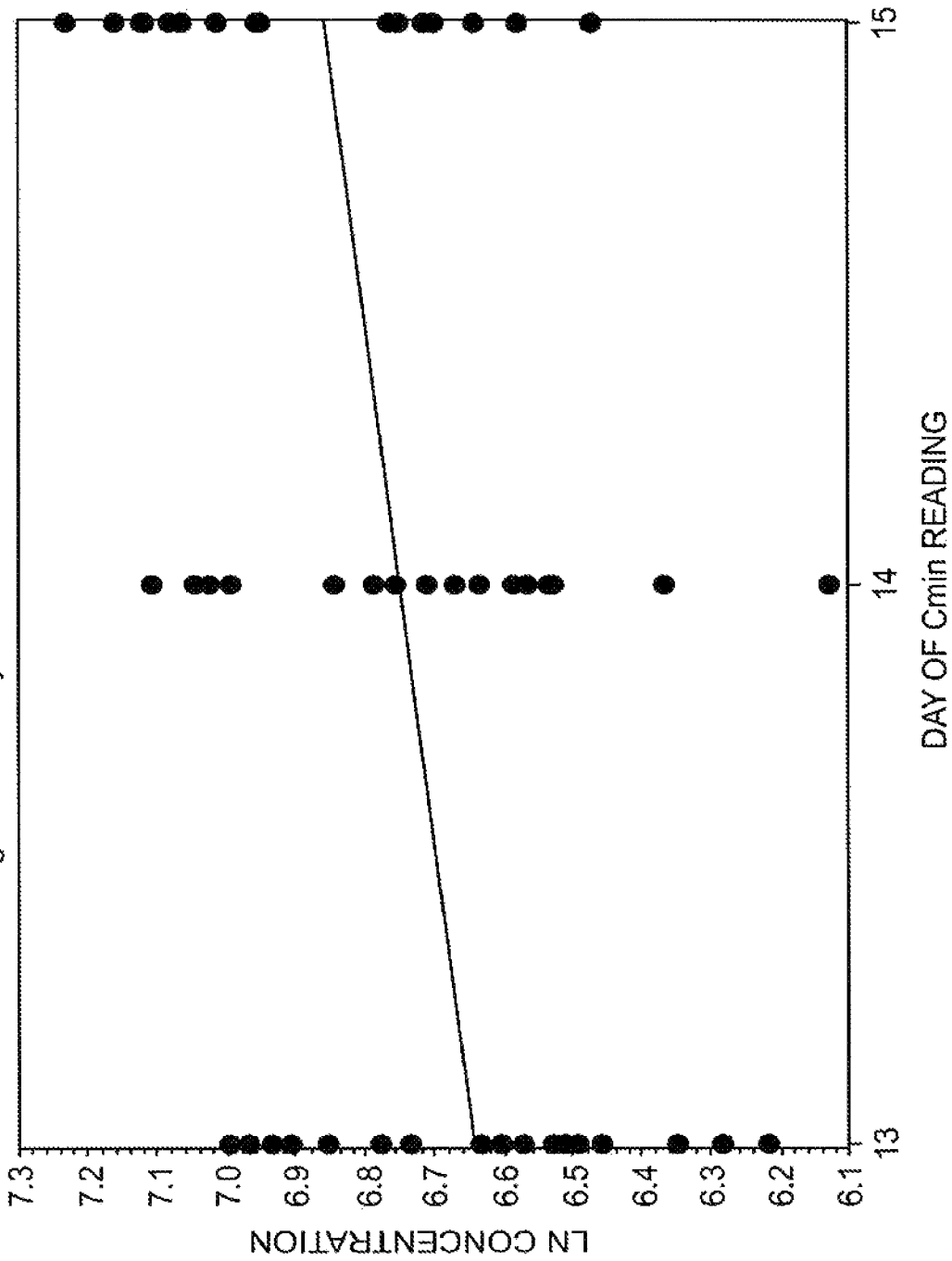
FIG. 17 shows the regression analysis for the concentration of a 100 mg LOZANOC itraconazole dose administered under fed conditions twice daily for 14. 5 consecutive days.
Figure 18:
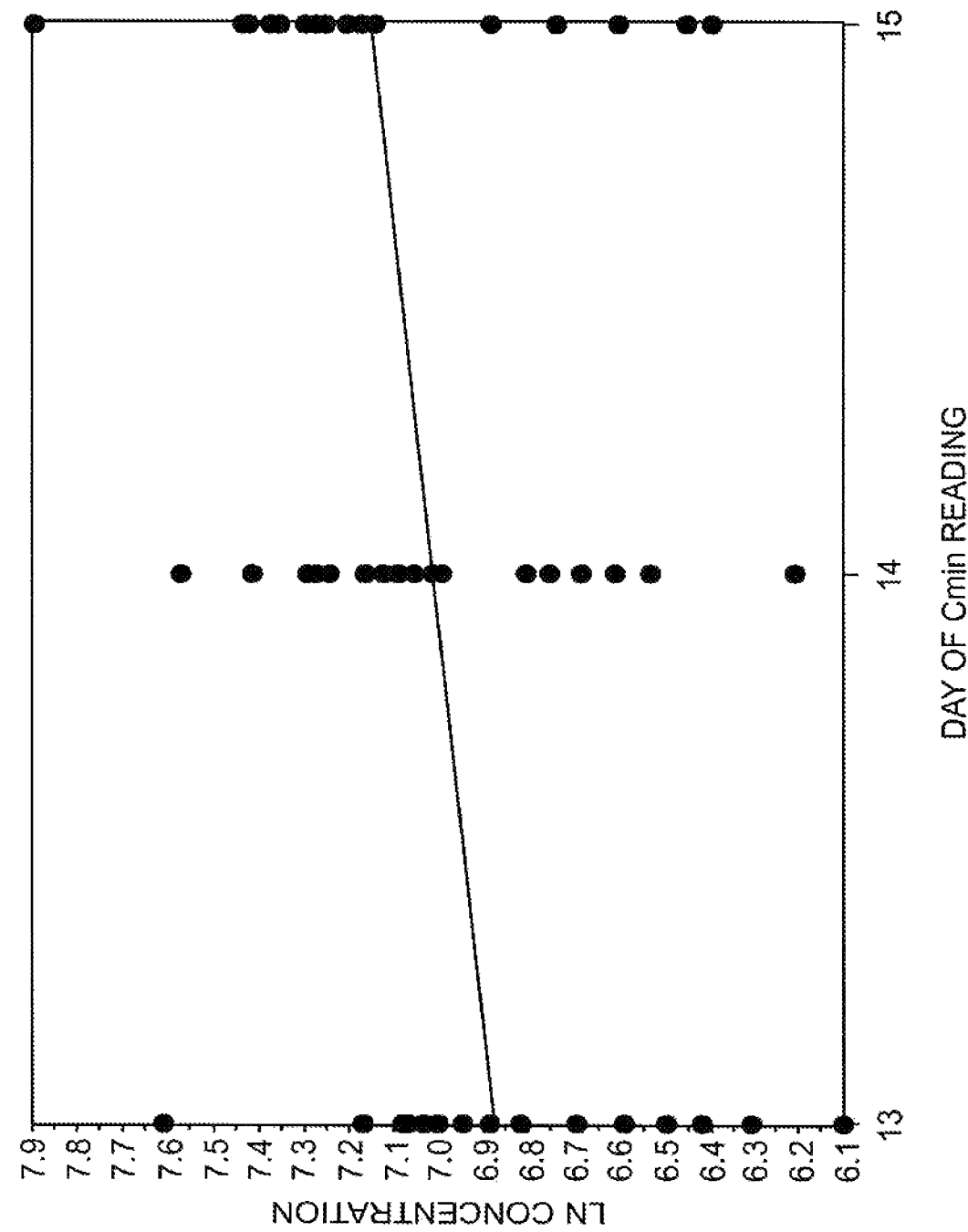
FIG. 18 shows the regression analysis for the concentration of a 200 mg SPORANOX® itraconazole dose administered under fed conditions twice daily for 14. 5 consecutive days.
Figure 19:
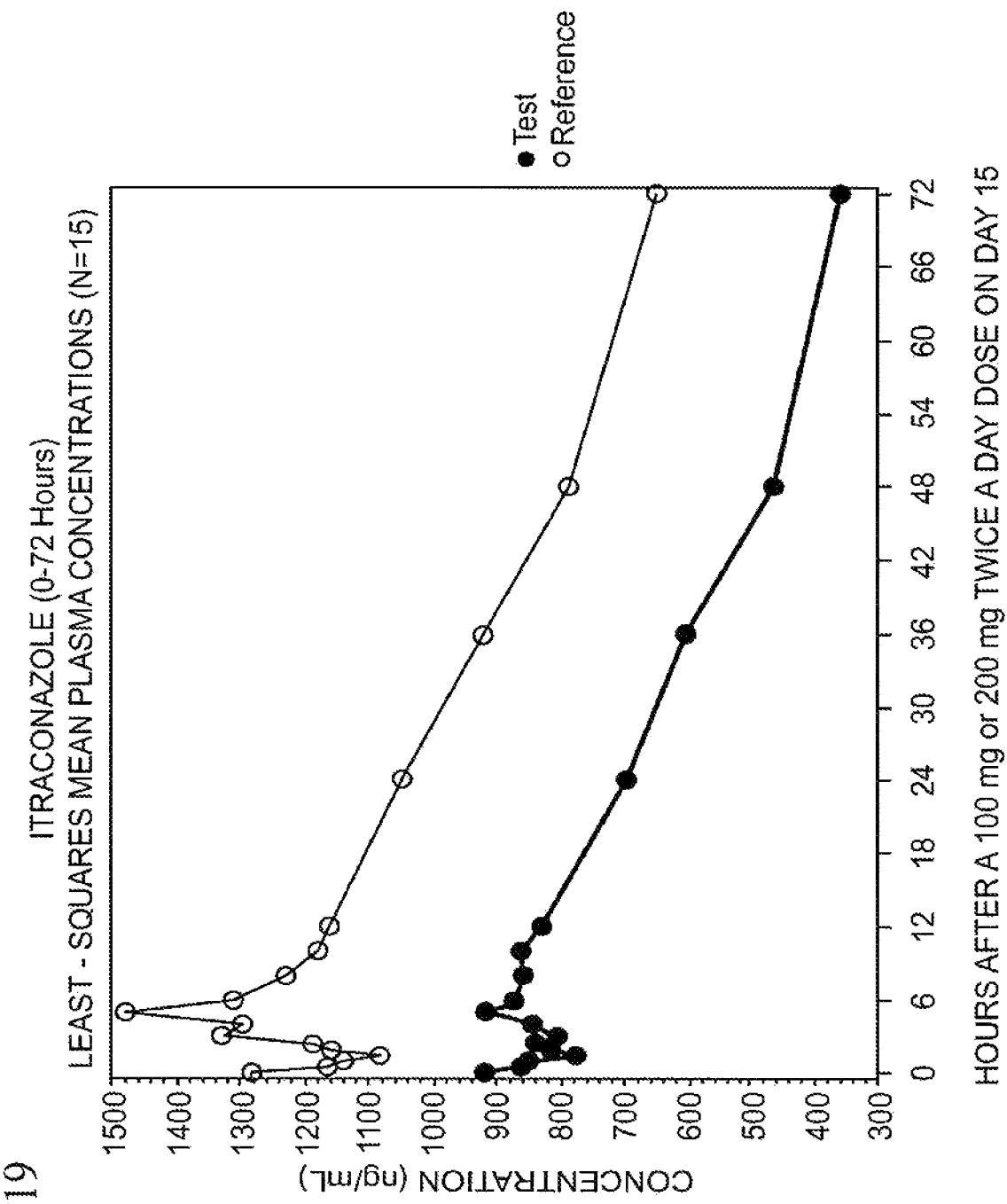
FIG. 19 shows a linear scale graph of the mean plasma itraconazole concentration over time in a study comparing the relative bioavailability of 100 mg LOZANOC dose with 200 mg SPORANOX® administered under fed conditions twice daily for 14. 5 consecutive days. Closed circles represent the 100 mg LOZANOC itraconazole dose administered under fed conditions twice daily for 14. 5 consecutive days; open circles represent the reference SPORANOX® 200 mg dose administered under fed conditions twice daily for 14. 5 consecutive days.
Figure 20:
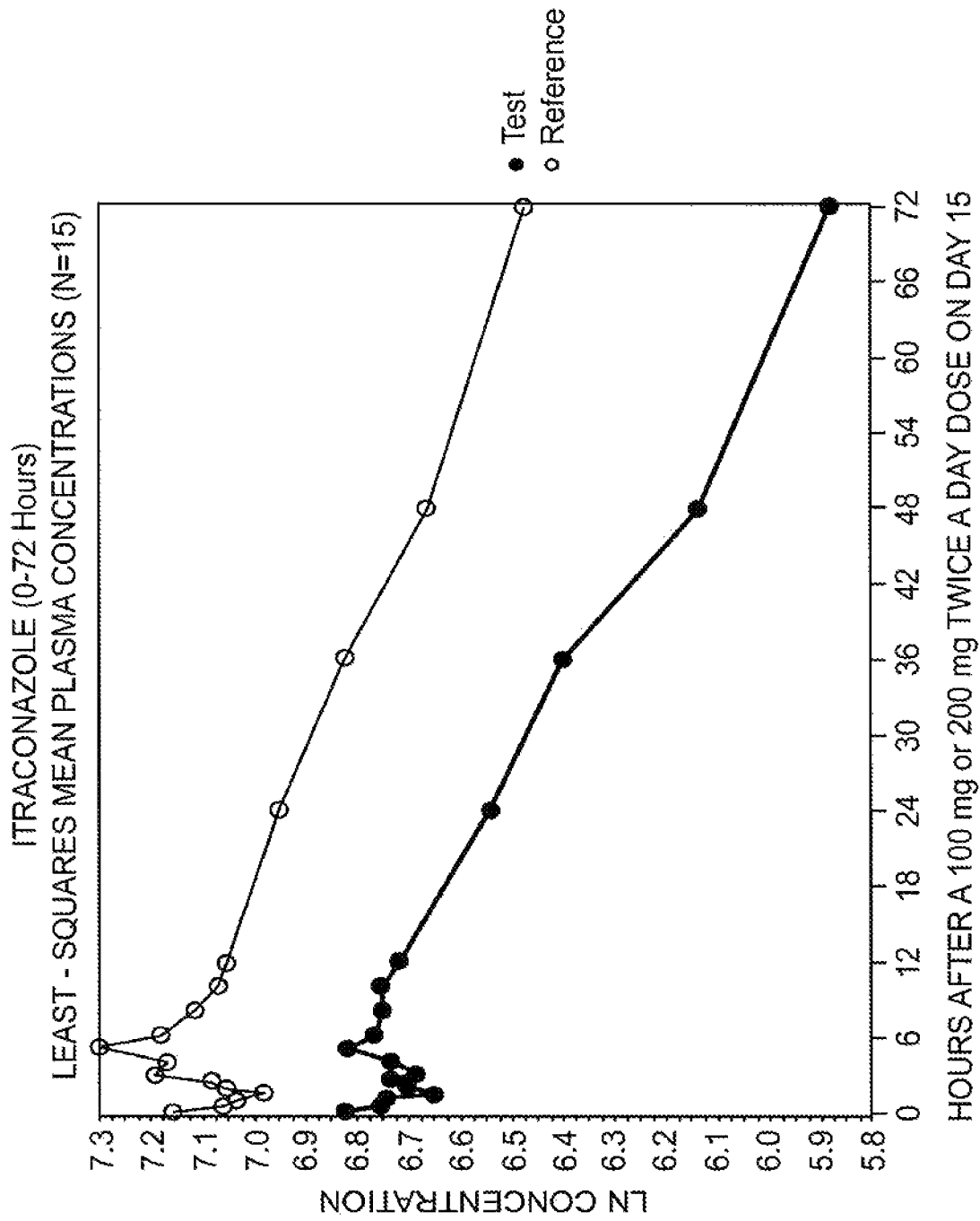
FIG. 20 shows a log-scale graph of the mean plasma itraconazole concentration over time in a study comparing the relative bioavailability of 100 mg LOZANOC dose with 200 mg SPORANOX® administered under fed conditions twice daily for 14. 5 consecutive days. Closed circles represent the 100 mg LOZANOC itraconazole dose administered under fed conditions twice daily for 14. 5 consecutive days; open circles represent the reference SPORANOX® 200 mg dose administered under fed conditions twice daily for 14. 5 consecutive days.

FIGS. 17 (Test A) and 18 (Reference B) show the mean concentration of itraconazole (ln-linear) versus Study Day plots for Cmin. FIGS. 19 (linear) and 20 (ln-linear) show the mean concentration of itraconazole versus time plots.

Table 16 shows the summary of pharmacokinetic parameters for itraconazole after twice-daily administration of either Test A (2×50 mg capsule LOZANOC) or Reference B (2×100 mg capsule) SPORANOX® (itraconazole) under a fed state.

The values for Cav, Flux, and Swing were less for the LOZANOC capsule than for SPORANOX® (itraconazole). The standard deviations for AUC, Cmax, and Cmin are less as well indicating that there was less variance among the test product as compared to the reference product.

Table 17 shows the geometric means and ratio of means and 90% confidence intervals based on ANOVA of untransformed data of the itraconazole after twice daily administration under fed conditions of 100 mg LOZANOC capsule or 200 mg SPORANOX® (itraconazole).

TABLE 16

Pharmacokinetic Parameters for itraconazole after twice-daily administration in a fed state

| Pharmacokinetic Parameter | Units | Arithmetic Mean ± SD | |
|---|---|---|---|
| | | Test A | Reference B |
| AUC0-12 | ng · hr/ml | 10166.0156 ± 2357.0887 | 14852.4889 ± 5507.3566 |
| AUC0-24 | ng · hr/ml | 19264.9856 ± 4620.6927 | 28041.6889 ± 10715.2182 |
| AUC0-72 | ng · hr/ml | 42216.3483 ± 8914.4673 | 67132.7800 ± 25020.7479 |
| AUCinf | ng · hr/ml | 71903.1025 ± 29372.9006 | 135997.1449 ± 63827.9360 |
| Cmax | ng/ml | 1011.4000 ± 229.7383 | 1579.1333 ± 555.2887 |
| Tmax | hr | 6.5000 ± 8.7770 | 5.000 ± 2.2991 |
| Median Tmax | hr | 5.00 | 5.00 |
| Ke | 1/hr | 0.0154 ± 0.0057 | 0.0127 ± 0.0054 |
| Elimhalf | hr | 54.2163 ± 30.9934 | 63.7492 ± 26.1447 |
| Cmin Day 13 | ng/ml | 750.07 ± 191.10 | 989.67 ± 390.95 |
| Cmin Day 14 | ng/ml | 834.80 ± 216.61 | 1124.60 ± 391.65 |
| Cmin Day 15 | ng/ml | 910.80 ± 219.86 | 1279.60 ± 520.63 |
| Mean Cmin | ng/ml | 910.8000 ± 219.8640 | 1279.6000 ± 520.6287 |
| Cav | ng/ml | 837.0000 ± 198.4605 | 1222.7613 ± 446.8402 |
| Flux | — | 0.1213 ± 0.0733 | 0.2667 ± 0.2921 |
| Swing | — | 0.1180 ± 0.0765 | 0.2900 ± 0.3835 |

TABLE 17

Geometric Means, ratio of means, and 90% CI of itraconazole after twice-daily administration

| | Geometric Means Based on ANOVA of Untransformed Data | | | |
|---|---|---|---|---|
| | AUC0-12 (ng · hr/ml) | AUC0-24 (ng · hr/ml) | AUC0-72 (ng · hr/ml) | Cmax (ng/ml) |
| Test A | 10201.40 | 19321.32 | 42313.30 | 1016.12 |
| Reference B | 14901.75 | 28145.89 | 67376.20 | 1576.84 |
| | Ratio of Means, and 90% Confidence Intervals Based on ANOVA of Untransformed Data | | | |
| Ratio | 0.6846 | 0.6865 | 0.6280 | 0.6444 |
| CI | 0.5567-0.8125 | 0.5525-0.8204 | 0.4843-0.7717 | 0.5216-0.7672 |
| p-value | 0.0008 | 0.0012 | 0.0005 | 0.0002 |

Table 18 shows the geometric means and ratio of means and 90% confidence intervals based on ANOVA of ln-transformed data of the itraconazole after twice daily administration under fed conditions of 100 mg LOZANOC capsule or 200 mg SPORANOX® (itraconazole).

Figure 21:
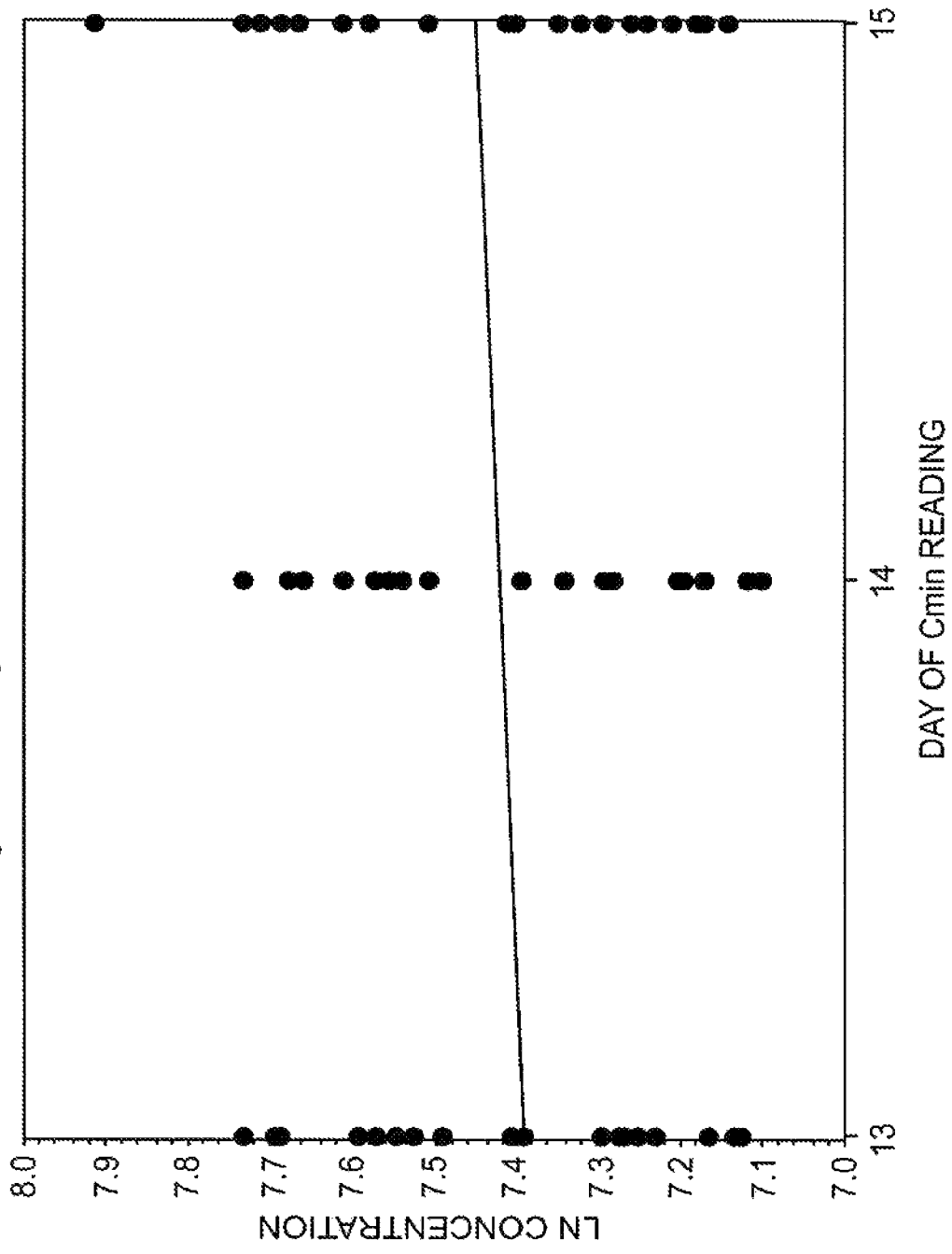
FIG. 21 shows the regression analysis for the concentration of hydroxyitraconazole after administration of a 100 mg LOZANOC itraconazole dose administered under fed conditions twice daily for 14. 5 consecutive days.
Figure 22:
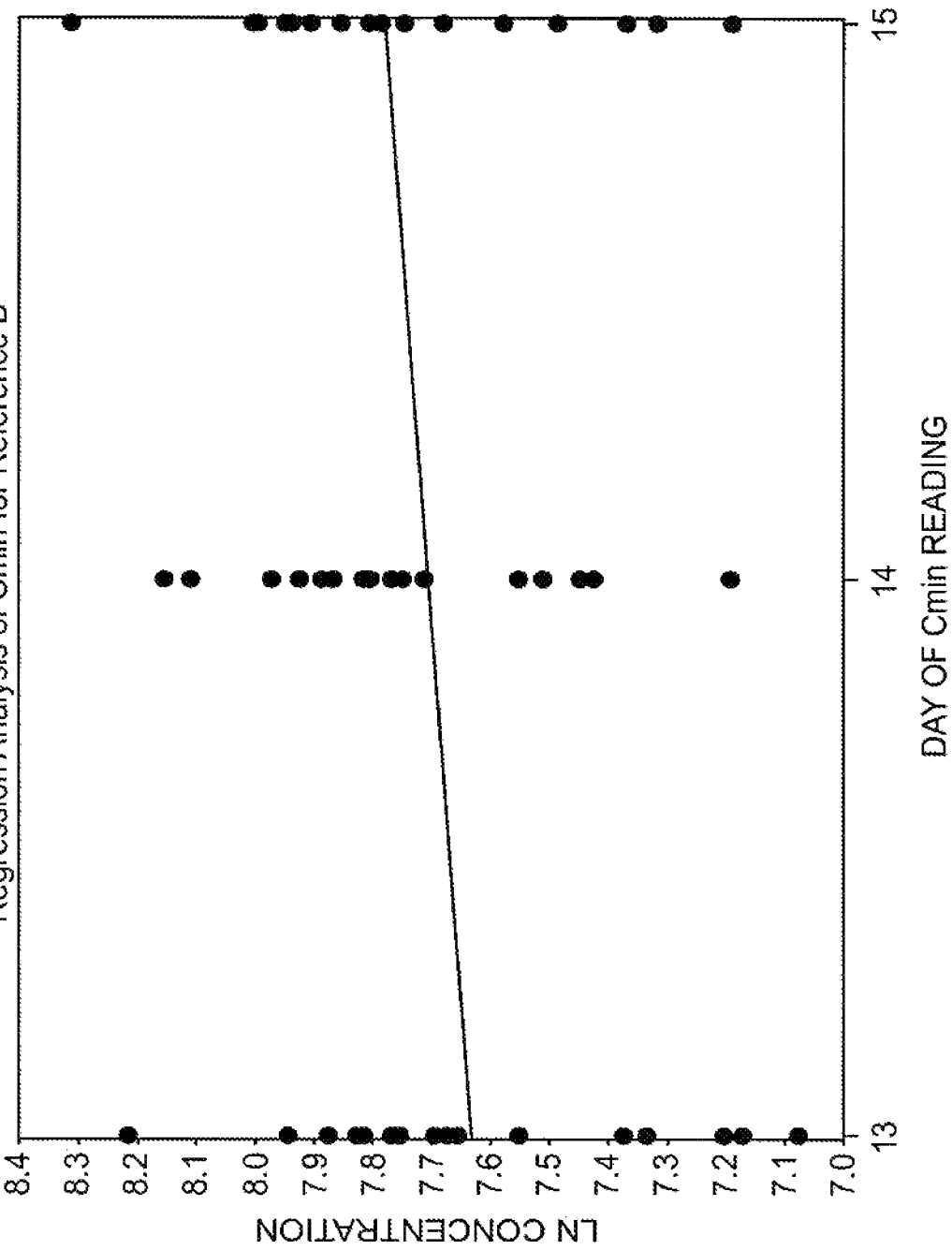
FIG. 22 shows the regression analysis for the concentration of hydroxyitraconazole after administration of a 200 mg SPORANOX® itraconazole dose administered under fed conditions twice daily for 14. 5 consecutive days.
Figure 23:
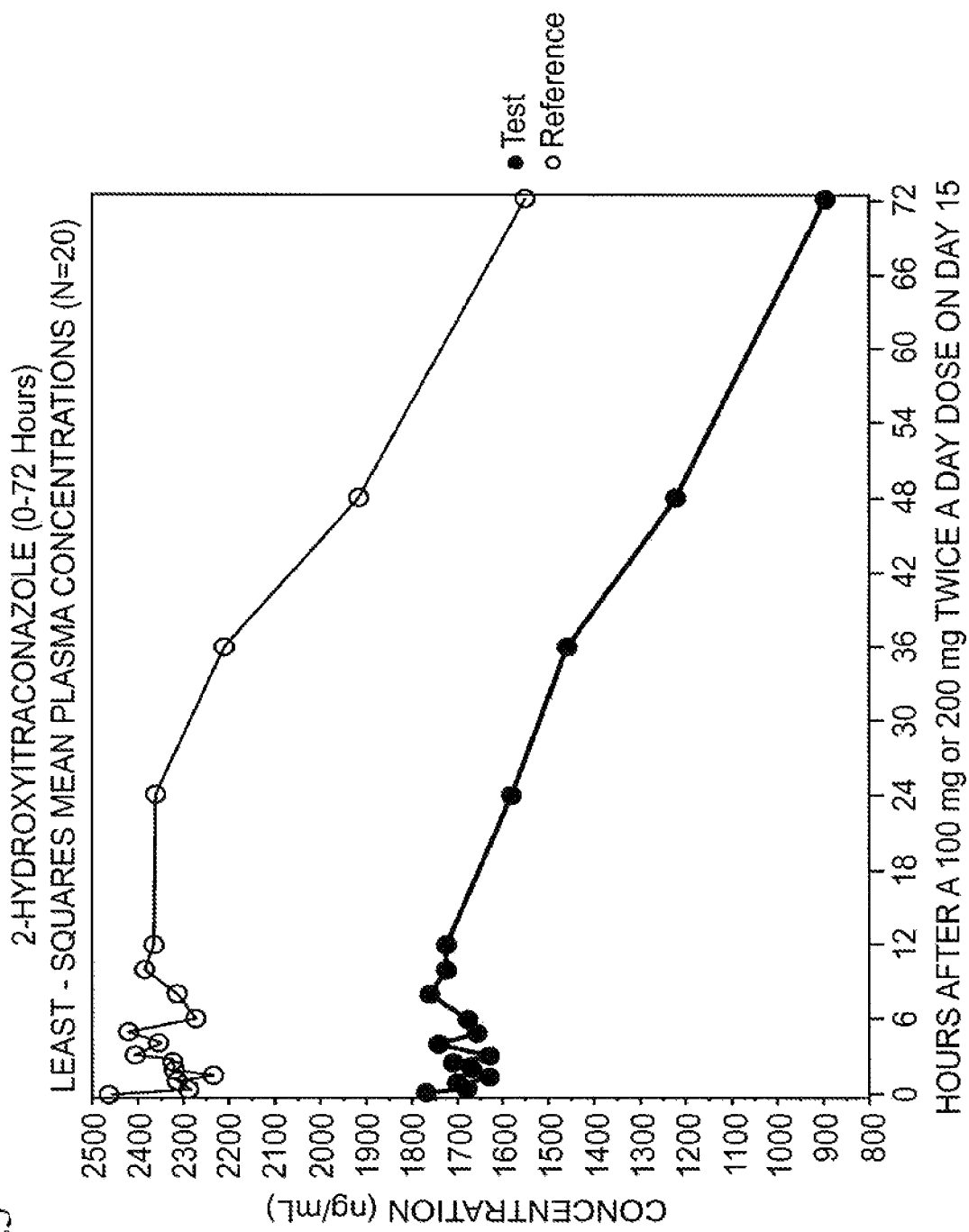
FIG. 23 shows a linear scale graph of the mean plasma hydroxyitraconazole concentration over time in a study comparing the relative bioavailability of 100 mg LOZANOC dose with 200 mg SPORANOX® administered under fed conditions twice daily for 14. 5 consecutive days. Closed circles represent the 100 mg LOZANOC itraconazole dose administered under fed conditions twice daily for 14. 5 consecutive days; open circles represent the reference SPORANOX® 200 mg dose administered under fed conditions twice daily for 14. 5 consecutive days.
Figure 24:
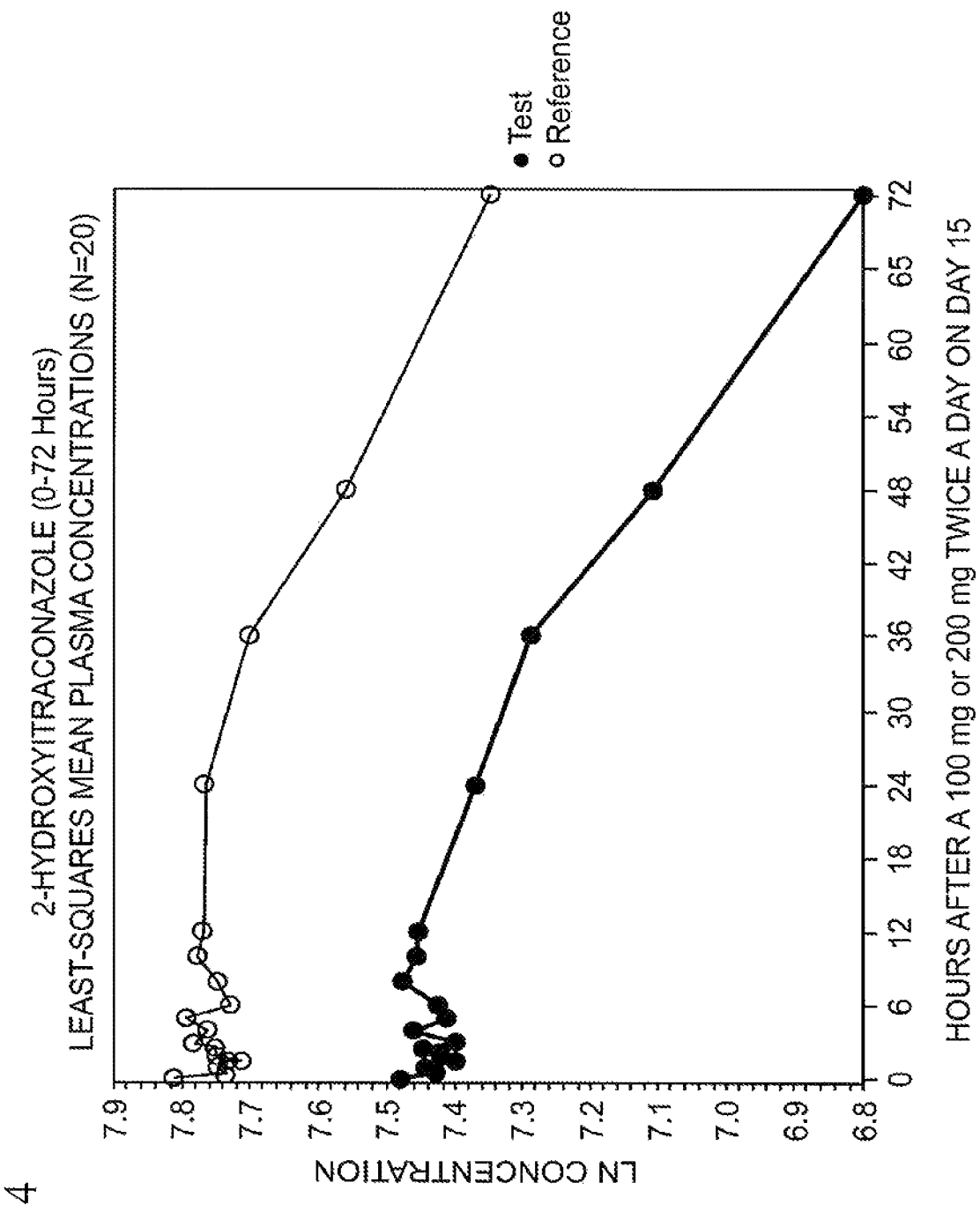
FIG. 24 shows a log-scale graph of the mean plasma hydroxyitraconazole concentration over time in a study comparing the relative bioavailability of 100 mg LOZANOC dose with 200 mg SPORANOX® administered under fed conditions twice daily for 14. 5 consecutive days. Closed circles represent the 100 mg LOZANOC itraconazole dose administered under fed conditions twice daily for 14. 5 consecutive days; open circles represent the reference SPORANOX® 200 mg dose administered under fed conditions twice daily for 14. 5 consecutive days.

FIGS. 21 (Test A) and 22 (Reference B) show the mean concentration of 2-hydroxyitraconazole (ln-linear) versus Study Day plots for Cmin after twice-daily administration of itraconazole in the 100 mg LOZANOC capsule or 200 mg SPORANOX® (itraconazole) formulations. FIGS. 23 (linear) and 24 (ln-linear) show the mean concentration of 2-hydroxyitraconazole versus time plots after the twice-daily administration of the test and reference formulations under fed conditions.

Table 19 shows the summary of pharmacokinetic parameters for 2-hydroxyitraconazole after twice-daily administration of either Test A (2×50 mg capsule LOZANOC) or Reference B (2×100 mg capsule) SPORANOX® (itraconazole) under a fed state.

TABLE 18

Geometric Means, ratio of means, and 90% CI of itraconazole after twice-daily administration

| | Geometric Means Based on ANOVA of Untransformed Data | | | |
|---|---|---|---|---|
| | AUC0-12 (ng · hr/ml) | AUC0-24 (ng · hr/ml) | AUC0-72 (ng · hr/ml) | Cmax (ng/ml) |
| Test A | 9965.16 | 18842.36 | 41448.45 | 993.26 |
| Reference B | 13967.48 | 26302.19 | 63076.86 | 1478.94 |
| | Ratio of Means, and 90% Confidence Intervals Based on ANOVA of LN-Transformed Data | | | |
| Ratio | 0.7135 | 0.7164 | 0.6571 | 0.6716 |
| CI | 0.6321-0.8054 | 0.6327-0.8111 | 0.5738-0.7525 | 0.5948-0.7584 |
| p-value | 0.0003 | 0.0004 | 0.0001 | <0.0001 |

TABLE 19

Pharmacokinetic Parameters for 2-hydroxyitraonazole after twice-daily administration of itraconazole in a fed state

| Pharmacokinetic Parameter | Units | Arithmetic Mean ± SD | |
|---|---|---|---|
| | | Test A | Reference B |
| AUC0-12 | (ng · hr/ml) | 20514.0750 ± 4477.1446 | 28111.7875 ± 6713.6147 |
| AUC0-24 | (ng · hr/ml) | 40356.6958 ± 8773.9782 | 56539.7875 ± 14275.8765 |
| AUC0-72 | (ng · hr/ml) | 97974.8975 ± 25878.4345 | 150740.2667 ± 44934.3294 |
| AUCinf | (ng · hr/ml) | 192315.6015 ± 139127.0685 | 362654.0343 ± 237849.5437 |
| Cmax | ng/ml | 1943.0000 ± 488.9204 | 2746.5000 ± 681.4171 |
| Tmax | hr | 6.9525 ± 7.6539 | 6.3000 ± 7.2645 |
| Median Tmax | hr | 5.00 | 3.50 |
| Ke | 1/hr | 0.0151 ± 0.0068 | 0.0100 ± 0.0044 |
| Elimhalf | hr | 60.9200 ± 44.1098 | 86.2167 ± 46.1494 |
| Cmin Day 13 | ng/ml | 1657.00 ± 331.47 | 2142.50 ± 587.61 |
| Cmin Day 14 | ng/ml | 1678.50 ± 370.01 | 2287.50 ± 586.25 |

TABLE 19-continued

Pharmacokinetic Parameters for 2-hydroxyitraonazole after twice-daily administration of itraconazole in a fed state

| Pharmacokinetic Parameter | Units | Arithmetic Mean ± SD | |
| --- | --- | --- | --- |
| | | Test A | Reference B |
| Cmin Day 15 | ng/ml | 1773.00 ± 424.13 | 2464.50 ± 637.87 |
| Mean Cmin | ng/ml | 1773.0000 ± 424.1288 | 2464.5000 ± 637.8704 |
| Cav | ng/ml | 1696.1655 ± 375.9869 | 2333.5010 ± 559.5159 |
| Flux | — | 0.1025 ± 0.0737 | 0.1285 ± 0.2389 |
| Swing | — | 0.1020 ± 0.0745 | 0.1395 ± 0.2843 |

Table 20 shows the geometric means and ratio of means and 90% confidence intervals based on ANOVA of untransformed data of 2-hydroxyitraconazole after twice daily administration under fed conditions of 100 mg LOZANOC capsule or 200 mg SPORANOX® (itraconazole).

TABLE 20

Geometric Means, ratio of means, and 90% CI of 2-hydroxyitraconazole after twice-daily administration of itraconazole

| | Geometric Means Based on ANOVA of Untransformed Data | | | | |
| --- | --- | --- | --- | --- | --- |
| | AUC0-12 (ng · hr/ml) | AUC0-24 (ng · hr/ml) | AUC0-72 (ng · hr/ml) | AUCinf (ng · hr/ml) | Cmax (ng/ml) |
| Test A | 20472.40 | 40333.92 | 97855.05 | 194562.03 | 1936.16 |
| Reference B | 28102.58 | 56463.79 | 150380.58 | 351817.47 | 2752.58 |

| | Ratio of Means, and 90% Confidence Intervals Based on ANOVA of Untransformed Data | | | | |
| --- | --- | --- | --- | --- | --- |
| Ratio | 0.7285 | 0.7143 | 0.6507 | 0.5530 | 0.7034 |
| CI | 0.6705-0.7864 | 0.6486-0.7800 | 0.5668-0.7346 | 0.2727-0.8333 | 0.6395-0.7673 |
| p-value | <0.0001 | <0.0001 | <0.0001 | 0.0136 | <0.0001 |

Table 21 shows the geometric means and ratio of means and 90% confidence intervals based on ANOVA of ln-transformed data of 2-hydroxyitraconazole after twice daily administration under fed conditions of 100 mg LOZANOC capsule or 200 mg SPORANOX® (itraconazole).

TABLE 21

Geometric Means, ratio of means, and 90% CI of 2-hydroxyitraconazole after twice-daily administration of itraconazole

| | Geometric Means Based on ANOVA of LN-Transformed Data | | | | |
| --- | --- | --- | --- | --- | --- |
| | AUC0-12 (ng · hr/ml) | AUC0-24 (ng · hr/ml) | AUC0-72 (ng · hr/ml) | AUCinf (ng · hr/ml) | Cmax (ng/ml) |
| Test A | 20022.29 | 39429.62 | 94670.73 | 162427.06 | 1883.69 |
| Reference B | 27311.97 | 54689.33 | 143845.88 | 306557.86 | 2666.26 |

| | Ratio of Means, and 90% Confidence Intervals Based on ANOVA of Ln-Transformed Data | | | | |
| --- | --- | --- | --- | --- | --- |
| Ratio | 0.7331 | 0.7210 | 0.6581 | 0.5298 | 0.7065 |
| CI | 0.6861-0.7833 | 0.6707-0.7750 | 0.5998-0.7222 | 0.4114-0.6824 | 0.6558-0.7611 |
| p-value | <0.0001 | <0.0001 | <0.0001 | 0.0005 | <0.0001 |

Example 8—Comparison of the Relative Bioavailability of LOZANOC 50 mg Capsules with SPORANOX® (Itraconazole) 100 mg Capsules Under Fasting Conditions Study Rationale This study compared the relative bioavailability of LOZANOC 50 mg capsules with that of SPORANOX® (itraconazole) 100 mg capsules already on the market in healthy volunteers. Subjects were given 50 mg or 100 mg doses of LOZANOC, or 100 mg or 200 mg doses of SPORANOX® (itraconazole) under fasted conditions. The pharmacokinetics of both LOZANOC and SPORANOX® (itraconazole) were compared when each was given at two different doses.

Twenty-four volunteers were enrolled in this randomized, multi-dose, four-treatment, four-way crossover study conducted to compare the relative bioavailability under fasting conditions of LOZANOC 50 mg capsules when given as a single 50 mg dose and a single 100 mg dose (2×50 mg capsules) compared to SPORANOX® (itraconazole) 100 mg capsules, when given as a single 100 mg dose and a single 200 mg dose (2×100 mg capsules). In each dosing period, either a single dose of 50 mg (1×50 mg capsules) or 100 mg (2×50 mg capsules) LOZANOC or 100 mg (1×100 mg capsule) or 200 mg (2×100 mg capsules) SPORANOX® (itraconazole) was administered to all subjects following an overnight fast of at least 10 hours. The test formulation was LOZANOC 50 mg capsules and the reference formulation was SPORANOX® (itraconazole) 100 mg capsules. The subjects received each of the four treatments according to the four sequence dosing randomization schedule. There was a 7-day interval between treatments.

Blood samples were collected at 0.5, 1.0, 1.5, 2.0, 2.5, 3.0, 4.0, 5.0, 6.0, 8.0, 10, 12, 24, 36, 48, and 72 hours after dosing. Pre-dose samples were collected up to 60 minutes prior to dosing. The blood samples were centrifuged at approximately 2500 rpm for 15 minutes, and the plasma collected for evaluation. Plasma samples were analyzed for itraconazole and 2-hydroxyitraconazole concentrations and agent pharmacokinetics.

The plasma concentration of itraconazole and 2-hydroxyitraconazole (a metabolite of itraconazole) were measured by fully validated analytical procedures. Statistical analysis was performed to evaluate the relative bioavailability for the two different doses of the Test product to that of the two different doses of the Reference product under fasted conditions. The single-dose pharmacokinetics of the two different doses of each product was analyzed to identify the dose ranging characteristics of each formulation.

LOZANOC (50 mg capsules) is a new formulation of oral itraconazole capsules that, in pilot bioavailability studies in healthy normal volunteers, has been shown to have comparable bioavailability to SPORANOX® (itraconazole) 100 mg capsules. (1,2). This study was designed based on the known pharmacokinetics of both LOZANOC (previously known as SUBA-Itraconazole®) 50 mg capsules and SPORANOX® (itraconazole) 100 mg capsules.

Study Design

In each period, subjects were given either:
Test A: A single dose of 50 mg (1×50 mg capsule) LOZANOC;
Test B: Two doses of 50 mg (2×50 mg capsule LOZANOC;
Reference C: One dose of 100 mg (1×100 mg capsule) SPORANOX® (itraconazole); or
Reference D: Two doses of 100 mg (2×100 mg capsule) SPORANOX® (itraconazole).

The drug was administered to all subjects following an overnight fast of at least 10 hours. The subjects were randomized and received each of the four treatments according to a four-sequence randomization schedule with a seven-day interval between each treatment.

Twenty-four (24) subjects were dosed (6 Test A, 6 Test B, 6 Reference C, 6 Reference D) in Period I, 22 subjects were dosed (5 Test A, 6 Test B, 6 Reference C, 5 Reference D) in Period II, 23 subjects were dosed (5 Test A, 6 Test B, 6 Reference C, 6 Reference D) in Period III on, and 23 subjects were dosed (6 Test A, 5 Test B, 6 Reference C, 6 Reference D) in Period IV. Data from subjects who completed at least two periods of the study were included in the statistical analysis.

The subjects were monitored throughout the study for any adverse events. No serious adverse events were reported.

Pharmacokinetic Analysis

Concentrations of itraconazole and hydroxyitraconazole in plasma were determined at using fully validated analytical methods as described in Example 6.

The following comparisons were computed.
Test A v Reference C (N=22)—comparison of a single 50 mg dose of LOZANOC capsule with a single 100 mg dose of SPORANOX® (itraconazole) capsule in the fasted state.
Test B v Reference D (N=22)—comparison of a single 100 mg dose of LOZANOC (2×50 mg capsules) with a single 200 mg dose of SPORANOX® (itraconazole) (2×100 mg capsules) in the fasted state.
Test A v Test B (N=22)—comparison of a single 50 mg dose of LOZANOC capsule with a single 100 mg dose of LOZANOC (2×50 mg capsules) in the fasted state.
Reference C v Reference D (N=22)—comparison of a single 100 mg dose of SPORANOX® (itraconazole) capsule with a single 200 mg dose of SPORANOX® (itraconazole) (2×100 mg capsules) in the fasted state The first two sets of analysis primary determination of pharmacokinetic equivalence of LOZANOC compared with twice the dose of SPORANOX® (itraconazole) in the fasted state was based on the log-transformed data for itraconazole. If the 90% confidence interval for the test/reference ratio for AUCt, AUCinf, and Cmax for itraconazole fall within the range 80.00-125.00%, then equivalence has been demonstrated.

The relative bioavailability of a single 50 mg dose of the test product compared to a single 100 mg dose of the test product (A v B), and the relative bioavailability of a single 100 mg dose of the reference product compared to a single 200 mg dose of the reference product (C v D) are presented for informational purposes. If the ratio of mean Cmax and mean AUC for A/B or C/D are approximately 0.5 then it may be considered that the single dose pharmacokinetics of itraconazole are approximately linear in the dose range tested for that specific formulation.

The same analysis was performed on the hydroxyitraconazole data for informational purposes.

For each serum sample, the mean concentration of itraconazole in the serum for each agent and dose over time was determined. The pharmacokinetic parameters were also determined for each agent and dose.

Figure 25:
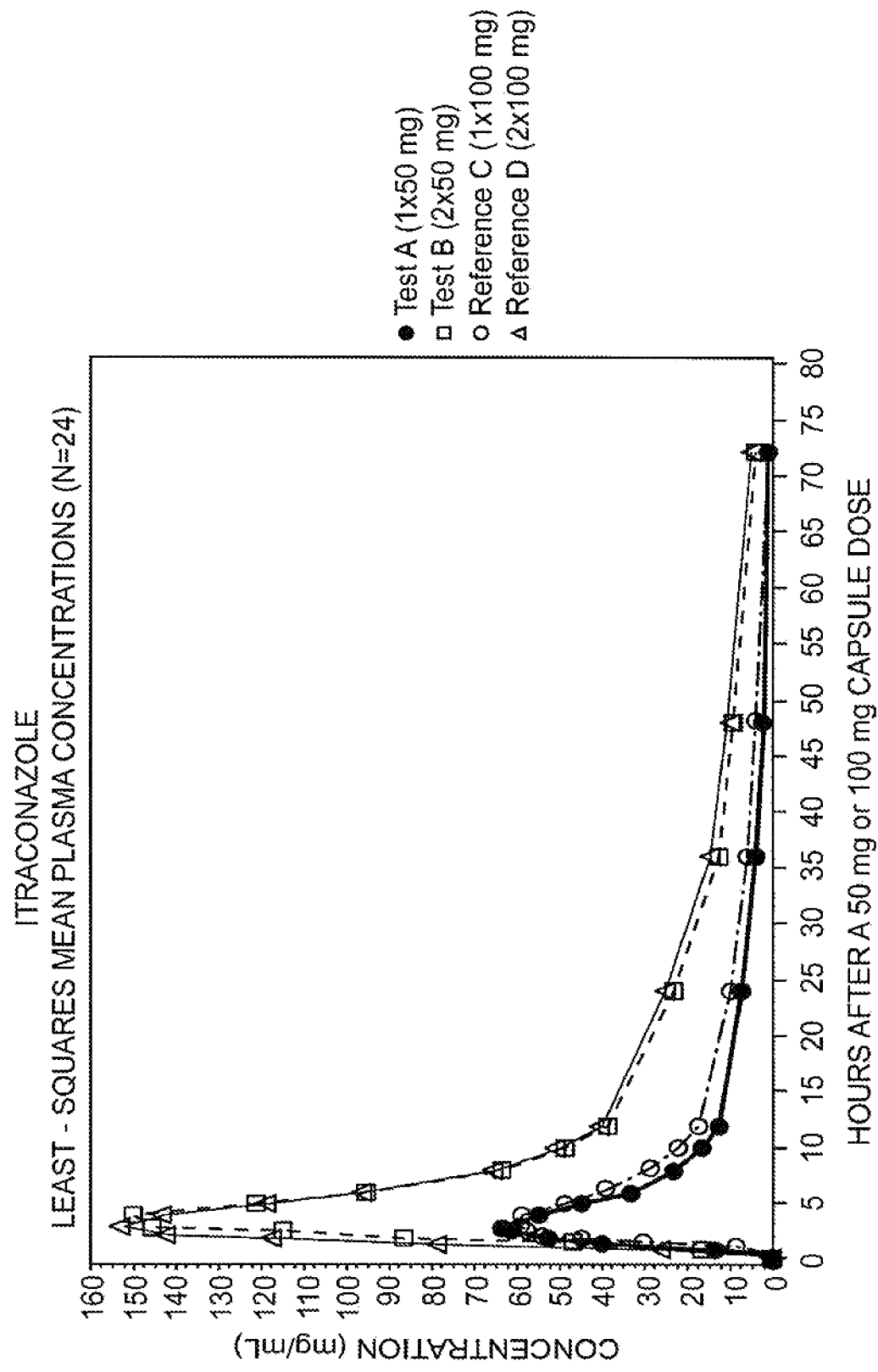
FIG. 25 shows a linear scale graph comparing the mean plasma itraconazole concentration over time in a study assessing the bioavailability of a 50 mg or 100 mg LOZANOC dose with a 100 mg or 200 mg dose of SPORANOX® administered under fasted conditions. Closed circles represent the 50 mg LOZANOC dose administered under fasted conditions; open squares represent the 100 mg LOZANOC dose administered under fasted conditions; open circles represent the reference SPORANOX® 100 mg dose administered under fasted conditions; open triangles represent the reference SPORANOX® 200 mg dose administered under fasted conditions.
Figure 26:
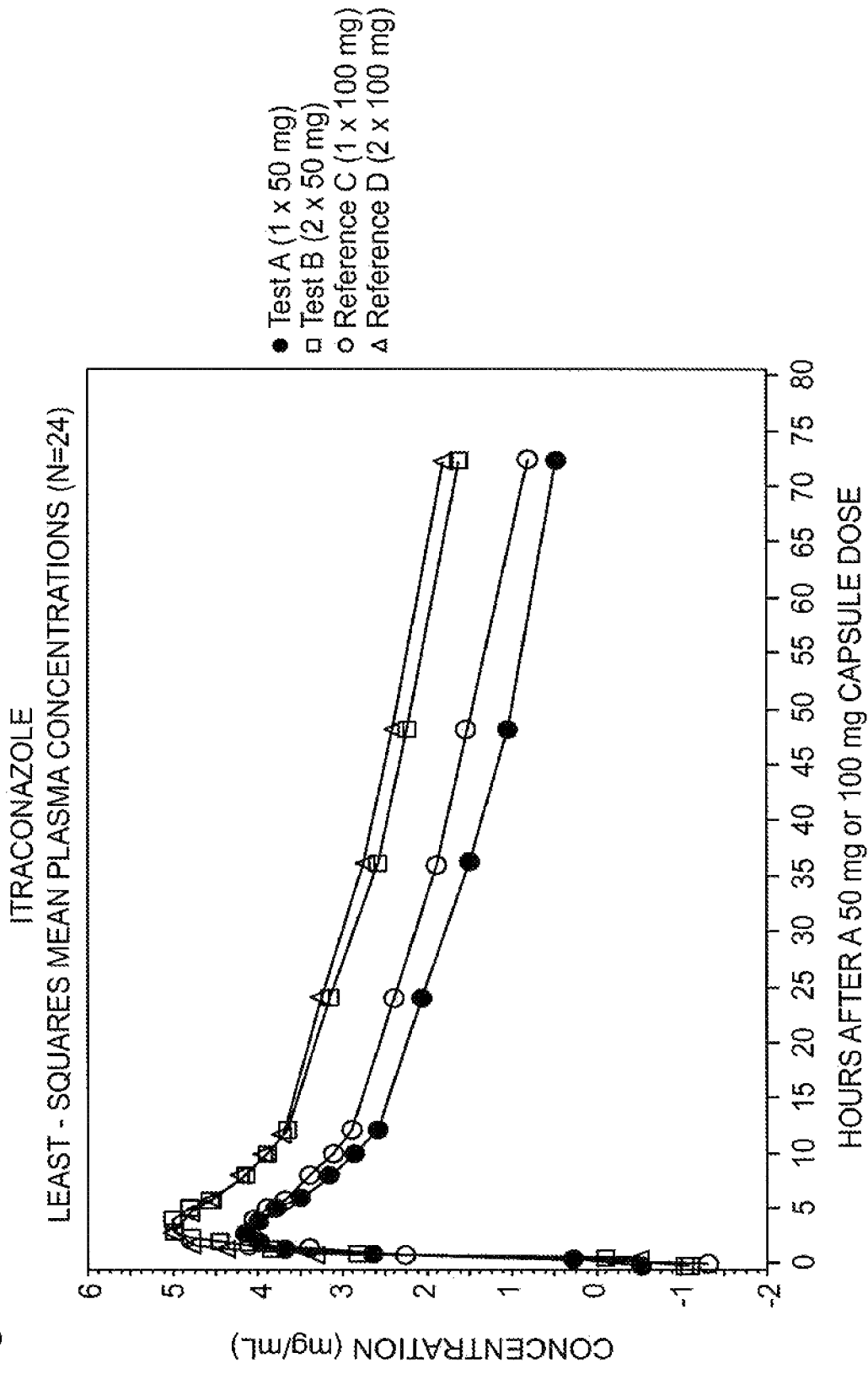
FIG. 26 shows a log-transformed graph comparing the mean plasma itraconazole concentration over time in a study assessing the bioavailability of a 50 mg or 100 mg LOZANOC dose with a 100 mg or 200 mg dose of SPORANOX® administered under fasted conditions. Closed circles represent the 50 mg LOZANOC dose administered under fasted conditions; open squares represent the 100 mg LOZANOC dose administered under fasted conditions; open circles represent the reference SPORANOX® 100 mg dose administered under fasted conditions; open triangles represent the reference SPORANOX® 200 mg dose administered under fasted conditions.

FIGS. 25 (linear plot) and 26 (ln-linear plot) show the mean concentration of itraconazole in the blood serum over time.

Figure 27:
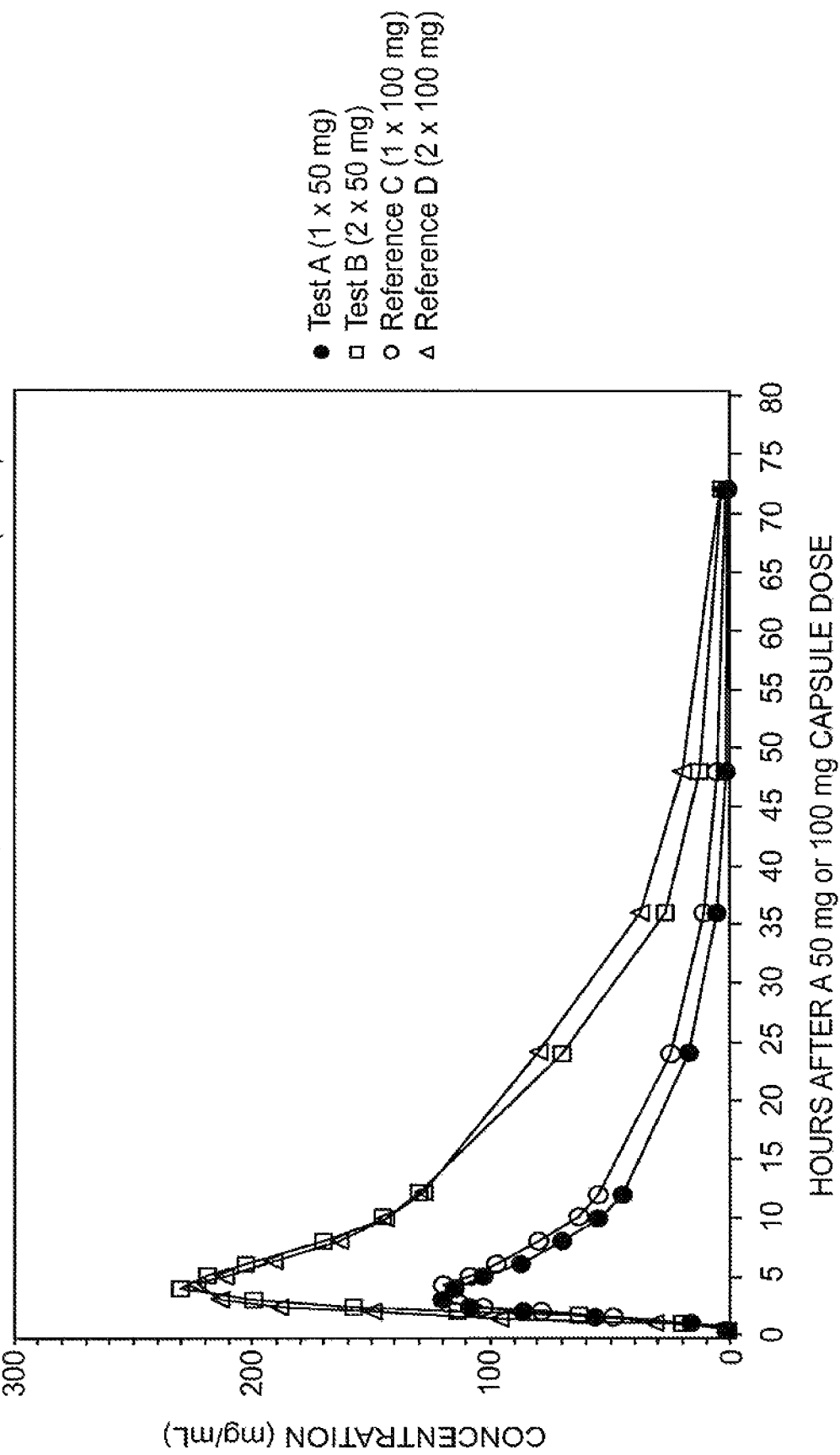
FIG. 27 shows a linear scale graph comparing the mean plasma hydroxyitraconazole concentration over time in a study assessing the bioavailability of a 50 mg or 100 mg LOZANOC dose with a 100 mg or 200 mg dose of SPORANOX® administered under fasted conditions. Closed circles represent the 50 mg LOZANOC dose administered under fasted conditions; open squares represent the 100 mg LOZANOC dose administered under fasted conditions; open circles represent the reference SPORANOX® 100 mg dose administered under fasted conditions; open triangles represent the reference SPORANOX® 200 mg dose administered under fasted conditions.
Figure 28:
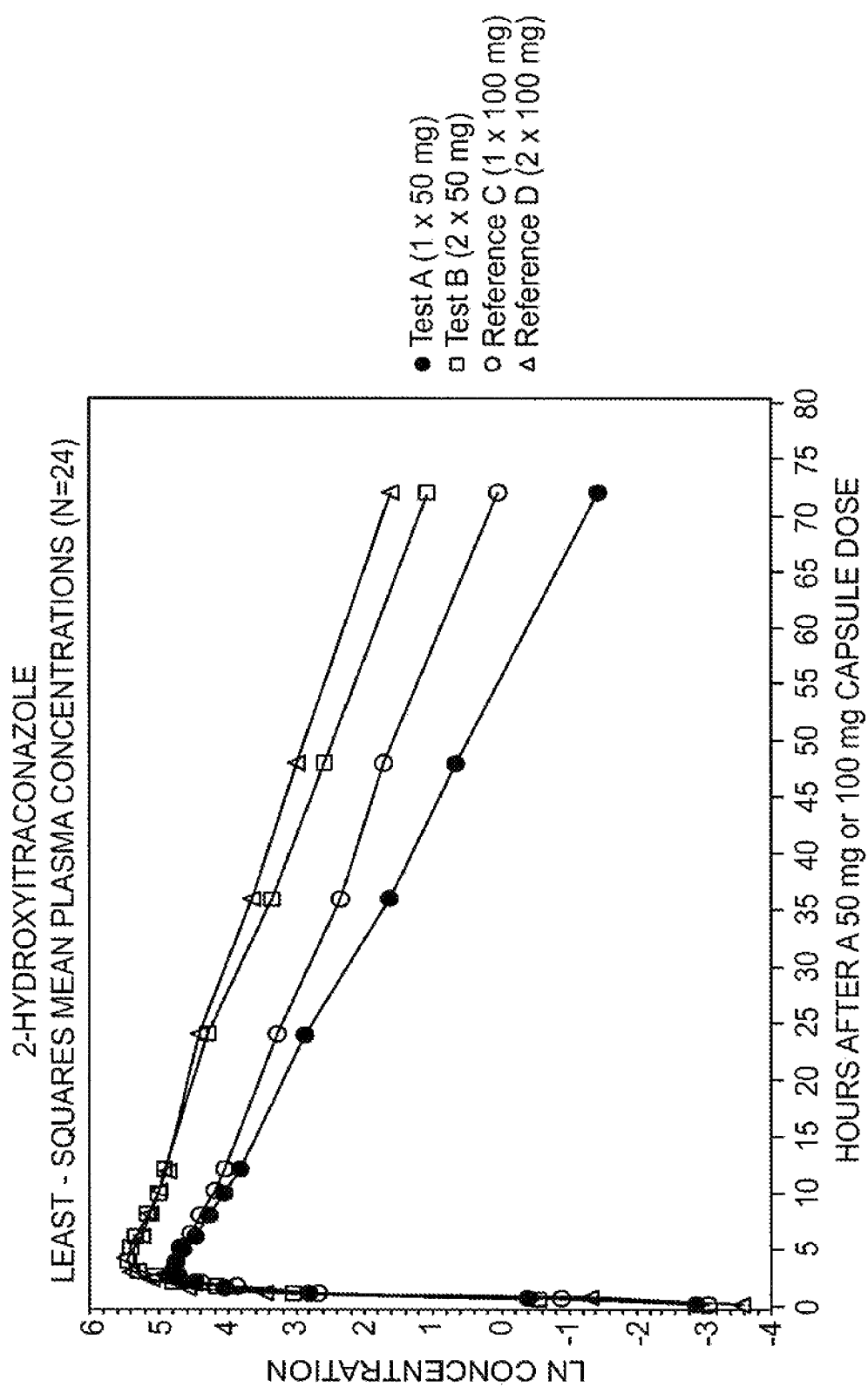
FIG. 28 shows a log-transformed graph comparing the mean plasma hydroxyitraconazole concentration over time in a study assessing the bioavailability of a 50 mg or 100 mg LOZANOC dose with a 100 mg or 200 mg dose of SPORANOX® administered under fasted conditions. Closed circles represent the 50 mg LOZANOC dose administered under fasted conditions; open squares represent the 100 mg LOZANOC dose administered under fasted conditions; open circles represent the reference SPORANOX® 100 mg dose administered under fasted conditions; open triangles represent the reference SPORANOX® 200 mg dose administered under fasted conditions.

FIGS. 27 (linear plot) and 28 (ln-linear plot) show the mean concentration of 2-hydroxyitraconazole in the blood serum over time for each itraconazole agent and dose.

Table 22 summarizes the pharmacokinetic parameters (untransformed) of itraconazole for the various agents and doses described above.

TABLE 22

Pharmacokinetic Parameters of Itraconazole Agents
Summary of Pharmacokinetic Parameters

| Pharmacokinetic Parameter | Arithmetic mean ± SD (% CV) | | | |
|---|---|---|---|---|
| | Test A | Test B | Reference C | Reference D |
| AUCt (ng · hr/ml) | 714.9464 ± 293.2184 (41.0126) | 1876.8254 ± 733.005 (39.0556) | 789.3709 ± 318.1479 (40.3040) | 2015.6652 ± 1332.6396 (66.1141) |
| AUCinf (ng · hr/ml) | 773.1397 ± 335.4541 (43.3885) | 2041.3007 ± 798.8421 (39.1340) | 853.0783 ± 347.3570 (40.7181) | 2222.5795 ± 1488.8634 (66.9881) |
| Cmax (ng/ml) | 79.5500 ± 29.8543 (37.5289) | 178.0000 ± 71.4344 (40.1317) | 64.6348 ± 28.0251 (43.3592) | 164.6043 ± 111.6715 (67.8423) |
| Tmax (hr) | 2.8432 ± 0.9565 (33.6408) | 3.4783 ± 0.9229 (26.5339) | 3.2181 ± 0.8218 (25.5352) | 3.3275 ± 0.8752 (26.3009) |
| Median Tmax (hr) | 2.7500 | 3.0000 | 3.0000 | 3.0000 |
| Ke (1/hr) | 0.0372 ± 0.0085 (22.8796) | 0.0362 ± 0.0093 (25.7917) | 0.0381 ± 0.0127 (33.2712) | 0.0337 ± 0.0082 (24.3801) |
| Elimhalf (hr) | 19.5320 ± 4.2499 (21.7589) | 20.3115 ± 4.9224 (24.2344) | 19.6020 ± 4.8500 (24.7426) | 21.6492 ± 4.7155 (21.7812) |

Table 23 shows the geometric means based on ANOVA of untransformed and Ln-transformed data for the various comparisons of itraconazole agents and doses.

TABLE 23

Geometric Means of Itraconazole Agents
Geometric Means Based on ANOVA
of Untransformed and Ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Test A | 670.27 | 725.03 | 74.96 | 635.81 | 683.56 | 70.72 |
| Test B | 1836.35 | 1995.40 | 175.00 | 1674.84 | 1814.68 | 156.50 |
| Reference C | 823.62 | 892.81 | 66.87 | 744.98 | 805.34 | 59.45 |
| Reference D | 2029.15 | 2236.33 | 164.90 | 1570.63 | 1722.77 | 122.01 |

Table 24 shows the ratio of means and 90% confidence intervals based on ANOVA of untransformed and Ln-transformed data for Test A (1×50 mg LOZANOC) v Reference C (1×100 mg SPORANOX® (itraconazole)).

TABLE 24

Ratio of Means and Confidence Intervals for Test A v. Reference C
Ratio of Means, and 90% Confidence Intervals
Based on ANOVA of Untransformed and Ln-Transformed Data
Test A (1 × 50 mg) v Reference C (1 × 100 mg)

| | | Untransformed Data | | | Ln-Transformed Data | | |
|---|---|---|---|---|---|---|---|
| | | AUCt (ng · hr/ml) | AUCinf (ng · hr/ml) | Cmax (ng/ml) | AUCt (ng · hr/ml) | AUCinf (ng · hr/ml) | Cmax (ng/ml) |
| | Ratio | 0.8138 | 0.8121 | 1.1211 | 0.8535 | 0.8488 | 1.1894 |
| | CI | 0.4279-1.1997 | 0.4221-1.2020 | 0.6983-1.5439 | 0.7035-1.0354 | 0.7007-1.0282 | 0.9517-1.4865 |
| | p-value | 0.4234 | 0.4240 | 0.6341 | 0.1758 | 0.1584 | 0.1987 |

When a single-dose of 50 mg LOZANOC is given in the fasted state, the peak and overall bioavailability as measured by Cmax and AUC is approximately 120% and 85% respectively, of that seen following a single 100 mg dose of SPORANOX® (itraconazole) capsules under fasting conditions. Based on the statistical analysis of itraconazole, the comparison of a single 50 mg dose of capsule LOZANOC with a single 100 mg dose of SPORANOX® (itraconazole) capsule in the fasted state does not meet the 90% confidence interval (CI) for log-transformed AUCt, AUCinf, and Cmax.

Table 25 shows the ratio of means and 90% Confidence Interval based on ANOVA of untransformed and ln-transformed data of Test B (2×50 mg LOZANOC) and Reference D (2×100 mg SPORANOX® (itraconazole)).

TABLE 25

Ratio of Means and Confidence Intervals for Test B v. Reference D
Ratio of Means, and 90% Confidence Intervals
Based on ANOVA of Untransformed and Ln-Transformed Data
Test B (2 × 50 mg) v Reference D (2 × 100 mg)

|  | Untransformed Data | | | Ln-Transformed Data | | |
| --- | --- | --- | --- | --- | --- | --- |
|  | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.9050 | 0.8923 | 1.0612 | 1.0664 | 1.0534 | 1.2827 |
| CI | 0.7505-1.0595 | 0.7387-1.0458 | 0.8921-1.2304 | 0.8813-1.2903 | 0.8718-1.2727 | 1.0295-1.5982 |
| p-value | 0.3084 | 0.2458 | 0.5475 | 0.5756 | 0.6479 | 0.0634 |

When a single dose of 100 mg of LOZANOC (2×50 mg capsules) is given in the fasted state the peak and overall bioavailability as measured by Cmax and AUC is approximately 130% and 106% respectively, of that seen following a single 200 mg dose of SPORANOX® (itraconazole) (2×100 mg capsules) under fasting conditions. Based on the statistical analysis of itraconazole, the comparison of a single 100 mg dose of capsule LOZANOC with a single 200 mg dose of SPORANOX® (itraconazole) capsule in the fasted state does not meet the 90% Confidence Interval for log-transformed AUCt, AUCinf, and Cmax.

Table 26 shows the ratio of means and 90% Confidence Interval based on ANOVA of untransformed and Ln-transformed data of Test A (1×50 mg LOZANOC) and Test B (2×50 mg LOZANOC).

TABLE 26

Ratio of Means and Confidence Intervals for Test A v. Test B
Ratio of Means, and 90% Confidence Intervals
Based on ANOVA of Untransformed and Ln-Transformed Data
Test A (1 × 50 mg) v Test B (2 × 50 mg)

|  | Untransformed Data | | | Ln-Transformed Data | | |
| --- | --- | --- | --- | --- | --- | --- |
|  | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.3650 | 0.3634 | 0.4284 | 0.3796 | 0.3767 | 0.4519 |
| CI | 0.1934-0.5366 | 0.1904-0.5363 | 0.2682-0.5886 | 0.3134-0.4598 | 0.3115-0.4556 | 0.3623-0.5637 |
| p-value | <0.0001 | <0.0001 | <0.0001 | <0.0001 | <0.0001 | <0.0001 |

When a single 50 mg dose of LOZANOC capsules is given in the fasted state, the ratio of mean, Cmax is approximately 45% of that seen following a single 100 mg dose of LOZANOC (2×50 mg capsules) in the fasted state.

Table 27 shows the ratio of means and 90% Confidence Interval based on ANOVA of untransformed and ln-transformed data of Reference C (1×100 mg SPORANOX® (itraconazole)) and Reference D (2×100 mg SPORANOX® (itraconazole)).

TABLE 27

Ratio of Means and Confidence Intervals for Reference C v. Reference D
Ratio of Means, and 90% Confidence Intervals
Based on ANOVA of Untransformed and Ln-Transformed Data
Reference C (1 × 100 mg) v Reference D (2 × 100 mg)

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.4059 | 0.3992 | 0.4055 | 0.4743 | 0.4675 | 0.4873 |
| CI | 0.2520-0.5598 | 0.2463-0.5522 | 0.2371-0.5739 | 0.3923-0.5735 | 0.3872-0.5644 | 0.3915-0.6066 |
| p-value | <0.0001 | <0.0001 | <0.0001 | <0.0001 | <0.0001 | <0.0001 |

When a single 100 mg dose of SPORANOX® (itraconazole) capsules is given in the fasted state, the ratio of mean Cmax and mean AUC are approximately 50% of that seen following a single 200 mg dose of SPORANOX® (itraconazole) (2×100 mg capsules) in the fasted state.

Table 28 summarizes the pharmacokinetic parameters (untransformed) of 2-hydroxyitraconazole after administration of the various itraconazole agents and doses described above.

Table 29 shows the ratio of means and 90% Confidence Interval based on ANOVA of untransformed and ln-transformed data for the comparisons performed in this study. As would be anticipated, the comparative results of the metabolite data (2-hydroxyitraconazole) are consistent to that observed with the parental product (itraconazole).

TABLE 28

Summary of Pharmacokinetic Parameters for 2-hydroxyitraconazole
Summary of Pharmacokinetic Parameters

| Pharmacokinetic Parameter | Arithmetic mean ± SD (% CV) | | | |
|---|---|---|---|---|
| | Test A | Test B | Reference C | Reference D |
| AUCt (ng · hr/ml) | 1514.7223 ± 630.4316 (41.6203) | 4162.1861 ± 1862.0149 (44.7365) | 1765.8720 ± 694.9582 (39.3550) | 4455.4271 ± 2891.5105 (64.8986) |
| AUCinf (ng · hr/ml) | 1529.9022 ± 637.1077 (41.6437) | 4215.9561 ± 1883.7742 (44.6820) | 1792.6811 ± 704.0504 (39.2736) | 4546.9988 ± 2972.9973 (65.3837) |
| Cmax (ng/ml) | 136.6273 ± 39.1386 (28.6463) | 246.4565 ± 73.8615 (29.9694) | 123.4500 ± 36.6698 (29.7042) | 234.9087 ± 117.1553 (49.8727) |
| Tmax (hr) | 3.1394 ± 0.8621 (27.4617) | 3.8913 ± 0.8251 (21.2043) | 3.6250 ± 0.7974 (21.9976) | 3.8493 ± 0.8320 (21.6142) |
| Median Tmax (hr) | 3.0000 | 4.0000 | 4.0000 | 4.0000 |
| Ke (1/hr) | 0.0992 ± 0.0252 (25.3748) | 0.0783 ± 0.0263 (33.5392) | 0.0762 ± 0.0253 (33.2301) | 0.0681 ± 0.0230 (33.7645) |
| Elimhalf (hr) | 7.4683 ± 2.0431 (27.3569) | 9.7261 ± 2.9654 (30.4886) | 10.5333 ± 5.4746 (51.9749) | 11.2233 ± 3.5688 (31.7976) |

Based on the statistical analysis of itraconazole under fasted conditions, using the comparisons of Test A (1×50 mg LOZANOC capsules) v Reference C (1×100 mg SPORANOX® (itraconazole) capsules) and Test B (2×50 mg LOZANOC capsules) v Reference D (2×100 mg SPORANOX® (itraconazole) capsules), LOZANOC capsules does not meet the 90% Confidence Interval for log transformed AUCt, AUCinf, and Cmax.

For both the test and reference formulations, doubling the dose resulted in approximately a two-fold increase in bioavailability as measured by Cmax. This would suggest that itraconazole follows non-linear pharmacokinetics.

reference product) following a standardized high fat, high calorie breakfast preceded by an overnight fast of at least 10 hours. The test formulation was LOZANOC 50 mg capsules and the reference formulation was SPORANOX® (itraconazole) 100 mg capsules. The subjects received the test product in two of the study periods and the reference product in the other two study periods; the order of administration was according to the four sequence dosing randomization schedule. There was a 7-day interval between treatments.

Blood samples were collected at 0.5, 1.0, 1.5, 2.0, 2.5, 3.0, 4.0, 5.0, 6.0, 8.0, 10, 12, 24, 36, 48, and 72 hours after dosing. Pre-dose samples were collected up to 60 minutes

TABLE 29

Ratio of Means and Confidence Intervals for 2-hydroxyitraconazole
Geometric Means, Ratio of Means, and 90% Confidence Intervals
Based on ANOVA of Untransformed and Ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Test A | 1429.73 | 1443.12 | 132.77 | 1353.80 | 1367.47 | 128.50 |
| Test B | 4079.74 | 4131.68 | 244.61 | 3657.49 | 3703.58 | 232.95 |
| Reference C | 1765.87 | 1792.68 | 123.45 | 1634.24 | 1660.54 | 118.12 |
| Reference D | 4486.28 | 4577.18 | 235.76 | 3499.97 | 3564.93 | 203.72 |
| | | | Test A (1 × 50 mg) v Reference C (1 × 100 mg) | | | |
| Ratio | 0.8096 | 0.8050 | 1.0755 | 0.8284 | 0.8235 | 1.0879 |
| CI | 0.4164-1.2029 | 0.4089-1.2011 | 0.8248-1.3263 | 0.6780-1.0122 | 0.6746-1.0054 | 0.9189-1.2880 |
| p-value | 0.4220 | 0.4142 | 0.6168 | 0.1217 | 0.1092 | 0.4081 |
| | | | Test B (2 × 50 mg) v Reference D (2 × 100 mg) | | | |
| Ratio | 0.9094 | 0.9027 | 1.0375 | 1.0450 | 1.0389 | 1.1435 |
| CI | 0.7545-1.0643 | 0.7474-1.0579 | 0.9061-1.1689 | 0.8551-1.2770 | 0.8509-1.2685 | 0.9657-1.3540 |
| p-value | 0.3324 | 0.2992 | 0.6351 | 0.7152 | 0.7507 | 0.1901 |
| | | | Test A (1 × 50 mg) v Test B (2 × 50 mg) | | | |
| Ratio | 0.3504 | 0.3493 | 0.5428 | 0.3701 | 0.3692 | 0.5516 |
| CI | 0.1792-0.5217 | 0.1764-0.5222 | 0.4155-0.6701 | 0.3026-0.4528 | 0.3021-0.4513 | 0.4654-0.6537 |
| p-value | <0.0001 | <0.0001 | <0.0001 | <0.0001 | <0.0001 | <0.0001 |
| | | | Reference C (1 × 100 mg) v Reference D (2 × 100 mg) | | | |
| Ratio | 0.3936 | 0.3917 | 0.5236 | 0.4669 | 0.4658 | 0.5798 |
| CI | 0.2414-0.5458 | 0.2391-0.5442 | 0.3945-0.6527 | 0.3834-0.5686 | 0.3828-0.5668 | 0.4911-0.6845 |
| p-value | <0.0001 | <0.0001 | <0.0001 | <0.0001 | <0.0001 | <0.0001 |

Example 9—Comparison of the Relative Bioavailability of LOZANOC 50 mg Capsules with SPORANOX® (Itraconazole) 100 mg Capsules Under Fasting and Fed Conditions Study Rationale This study evaluated the relative bioavailability of LOZANOC 50 mg capsules with that of SPORANOX® (itraconazole) 100 mg capsules. The pharmacokinetics of both LOZANOC and SPORANOX® (itraconazole) were compared when administered to subjects under fasted and fed conditions.

This randomized, single-dose, four-treatment, four-period, crossover study was conducted to compare single doses of LOZANOC 50 mg capsules to SPORANOX® (itraconazole) 100 mg capsules under fasted and fed conditions. The study was conducted with 36 (35 completing at least two periods of the study) healthy, nontobacco using, adults. In each study period, a single dose (1×50 mg LOZANOC capsule or 1×100 mg SPORANOX® (itraconazole) capsule) was administered to all subjects. In two of the study periods subjects were dosed (with either a test or reference product) following an overnight fast of at least 10 hours. In the other two periods, subjects were dosed (with either a test or prior to dosing. The blood samples were centrifuged at approximately 2500 rpm for 15 minutes, and the plasma collected. The plasma concentration of itraconazole and 2-hydroxyitraconazole (a metabolite of itraconazole) were measured by fully validated analytical procedures. Statistical analysis was performed to evaluate the relative bioavailability for the test and reference agents under fasting or fed conditions. Plasma samples were analyzed for itraconazole and 2-hydroxyitraconazole concentrations.

Study Design

In each period, subjects were given either:
Test A: A single dose of 50 mg (1×50 mg capsule) LOZANOC; fasting conditions;
Test B: A single dose of 50 mg (1×50 mg capsule) LOZANOC; fed conditions;
Reference C: One dose of 100 mg (1×100 mg capsule) SPORANOX® (itraconazole); fasting conditions; or
Reference D: Two doses of 100 mg (2×100 mg capsule) SPORANOX® (itraconazole); fed conditions.

Thirty-six (36) subjects were dosed (9 Test A, 9 Test B, 9 Reference C, 9 Reference D) in Period I, 35 subjects were dosed (9 Test A, 9 Test B, 9 Reference C, 8 Reference D) in Period II, 35 subjects were dosed (9 Test A, 8 Test B, 9 Reference C, 9 Reference D) in Period III, and 34 subjects were dosed (9 Test A, 9 Test B, 7 Reference C, 9 Reference D) in Period IV.

The subjects were monitored throughout the study for any adverse events. No serious adverse events were reported.

Pharmacokinetic Analysis

Concentrations of itraconazole and hydroxyitraconazole in plasma were determined at using fully validated analytical methods as described in Example 6. Subjects who completed at least 2 periods of the study were included in the final data set.

The following comparisons were computed.

Test A v Reference C—comparison of a single 50 mg dose of LOZANOC capsule with a single 100 mg dose of SPORANOX® (itraconazole) capsule in the fasting state.

Test B v Reference D—comparison of a single 50 mg dose of LOZANOC (1×50 mg capsules) with a single 100 mg dose of SPORANOX® (itraconazole) (1×100 mg capsules) in the fed state.

Test A v Test B—comparison of a single 50 mg dose of LOZANOC capsule in the fasting state with a single 50 mg dose of LOZANOC (1×50 mg capsule) in the fed state.

Reference C v Reference D—comparison of a single 100 mg dose of SPORANOX® (itraconazole) capsule in the fasting state with a single 100 mg dose of SPORANOX® (itraconazole) (1×100 mg capsules) in the fed state Test A v Reference D—comparison of a single 50 mg dose of LOZANOC capsule in the fasting state compared with 100 mg dose of SPORANOX® (itraconazole) (1×100 mg capsules) in the fed state.

Primary determination of pharmacokinetic equivalence was based on the log-transformed data for itraconazole. If the 90% confidence interval for the test/reference ratio for AUCt, AUCinf, and Cmax for itraconazole falls within the range 80.00-125.00%, then equivalence has been demonstrated. Equivalence was tested under fasting conditions.

The effect of food on each formulation was based on the log-transformed data for itraconazole by comparing Test A v Test B and Reference C v Reference D. If the 90% confidence interval for the test/reference ratio for AUCt, AUCinf, and Cmax for itraconazole falls within the range 80.00-125.00%, in the fed state compared to the fasted state then food was considered not to have any effect on the bioavailability of that formulation.

The relative bioavailability of a single 50 mg capsule dose of the test product under fasted conditions compared to a single 100 mg capsule dose of the reference product under fed conditions (Test A v Reference D) was presented for information purposes.

The same analysis was performed on the hydroxyitraconazole data for informational purposes.

For each serum sample, the mean concentration of itraconazole over time and the pharmacokinetic parameters were determined after administration of the agents under fasted or fed conditions.

Figure 29:
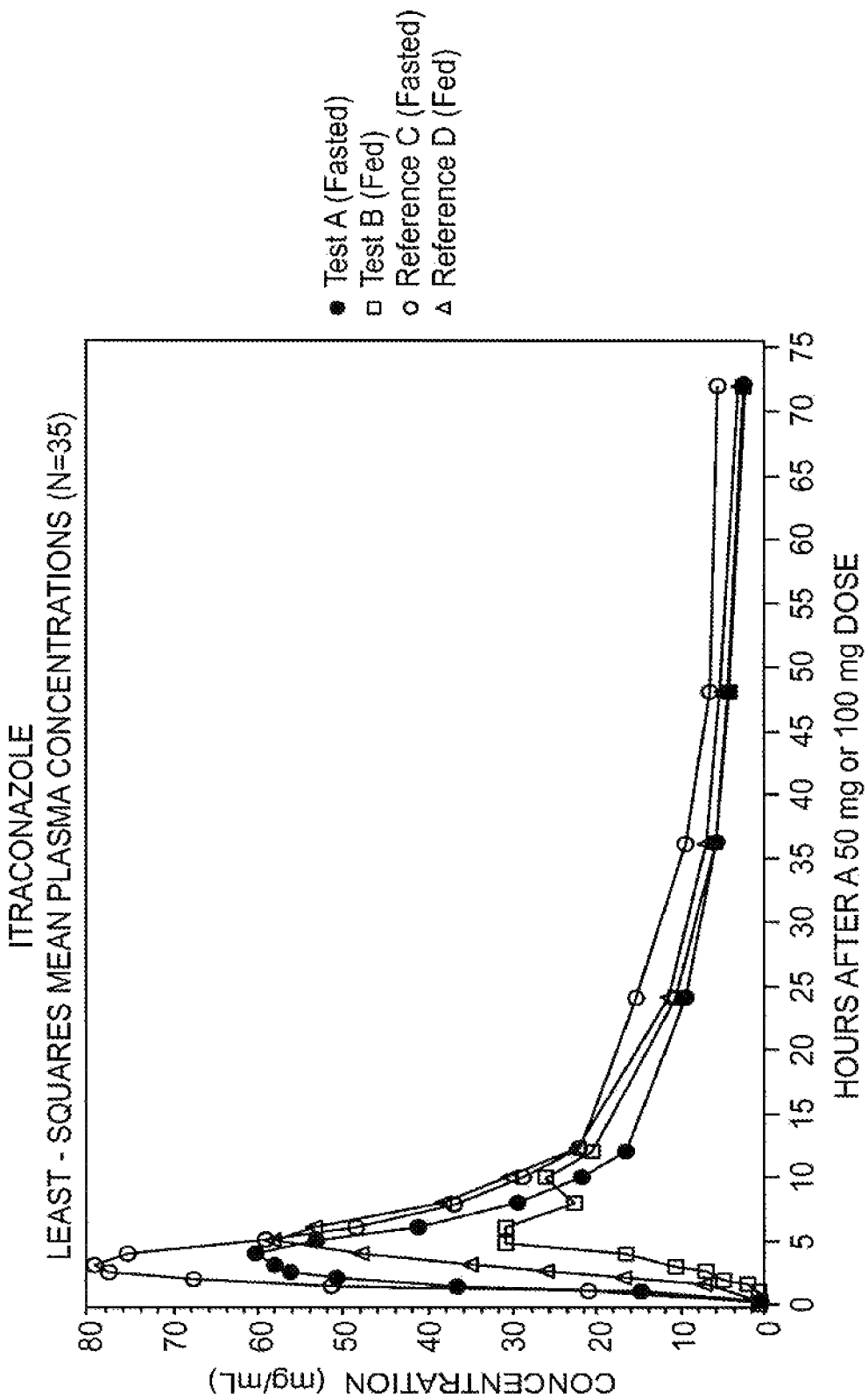
FIG. 29 shows a linear scale graph of the mean plasma itraconazole concentration over time in a study comparing the relative bioavailability of a 100 mg LOZANOC dose with a 100 mg dose of SPORANOX® administered under fed and fasted conditions. Closed circles represent the 50 mg LOZANOC dose administered under fasted conditions; open squares represent the 50 mg LOZANOC dose administered under fed conditions; open circles represent the reference SPORANOX® 100 mg dose administered under fasted conditions; open triangles represent the reference SPORANOX® 100 mg dose administered under fed conditions.
Figure 30:
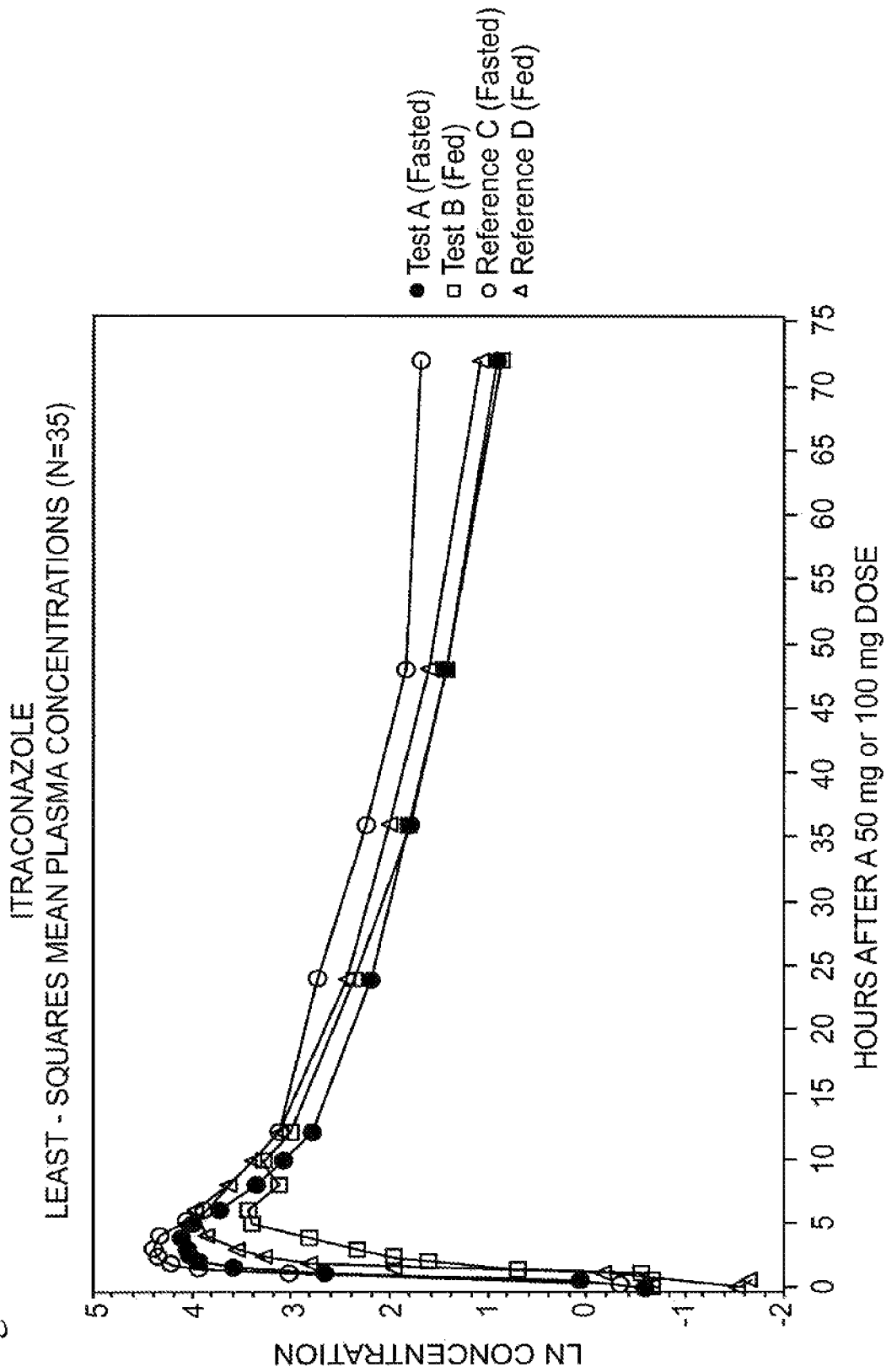
FIG. 30 shows a log-transformed scale graph of the mean plasma itraconazole concentration over time in a study comparing the relative bioavailability of a 100 mg LOZANOC dose with a 100 mg dose of SPORANOX® administered under fed and fasted conditions. Closed circles represent the 50 mg LOZANOC dose administered under fasted conditions; open squares represent the 50 mg LOZANOC dose administered under fed conditions; open circles represent the reference SPORANOX® 100 mg dose administered under fasted conditions; open triangles represent the reference SPORANOX® 100 mg dose administered under fed conditions.

FIGS. 29 (linear plot) and 30 (ln-linear plot) show the mean concentration of itraconazole in fasted and fed subjects in the blood serum over time.

Figure 31:
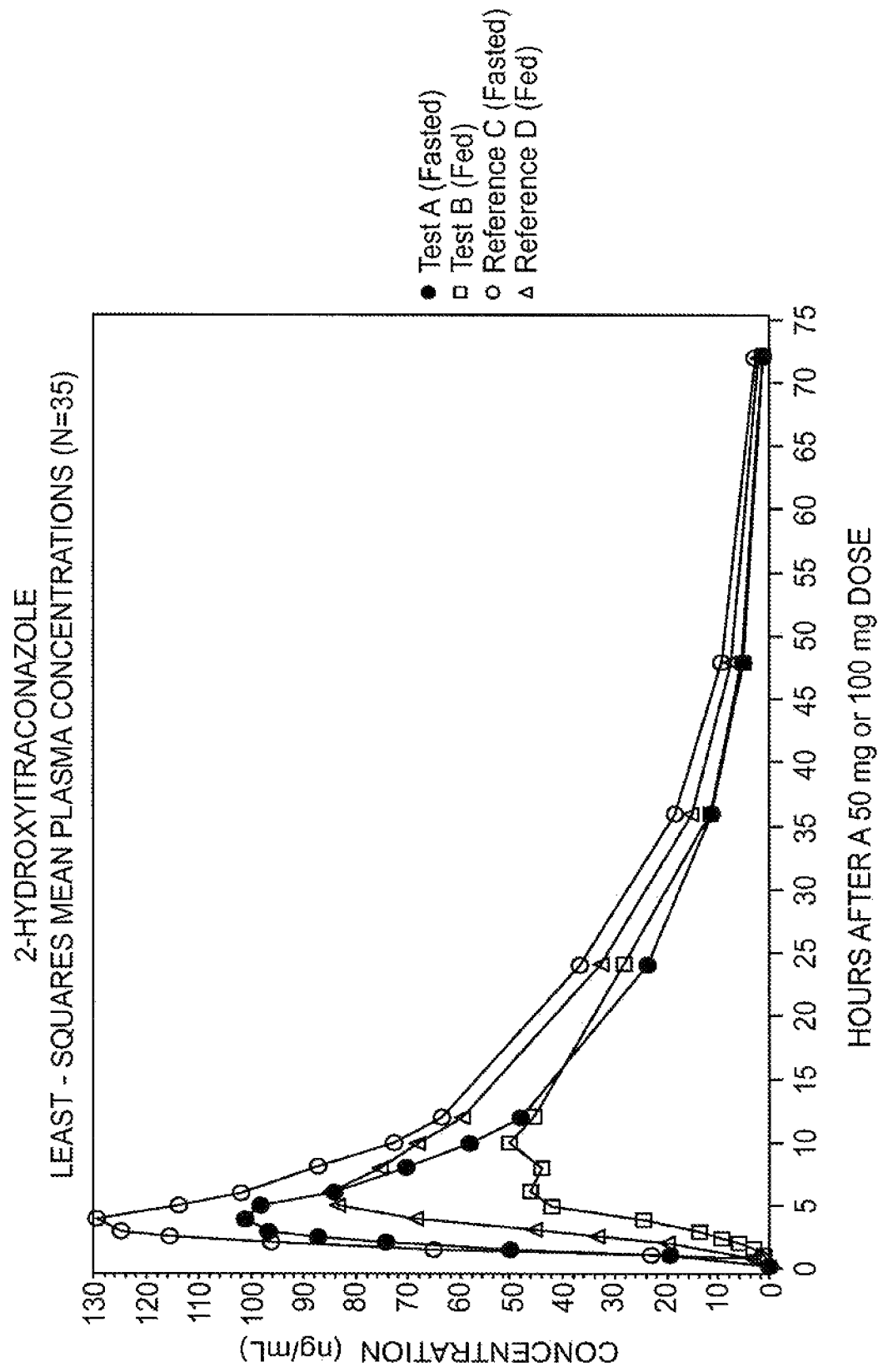
FIG. 31 shows a linear scale graph of the mean plasma hydroxyitraconazole concentration over time in a study comparing the relative bioavailability of a 100 mg LOZANOC dose with a 100 mg dose of SPORANOX® administered under fed and fasted conditions. Closed circles represent the 50 mg LOZANOC dose administered under fasted conditions; open squares represent the 50 mg LOZANOC dose administered under fed conditions; open circles represent the reference SPORANOX® 100 mg dose administered under fasted conditions; open triangles represent the reference SPORANOX® 100 mg dose administered under fed conditions.
Figure 32:
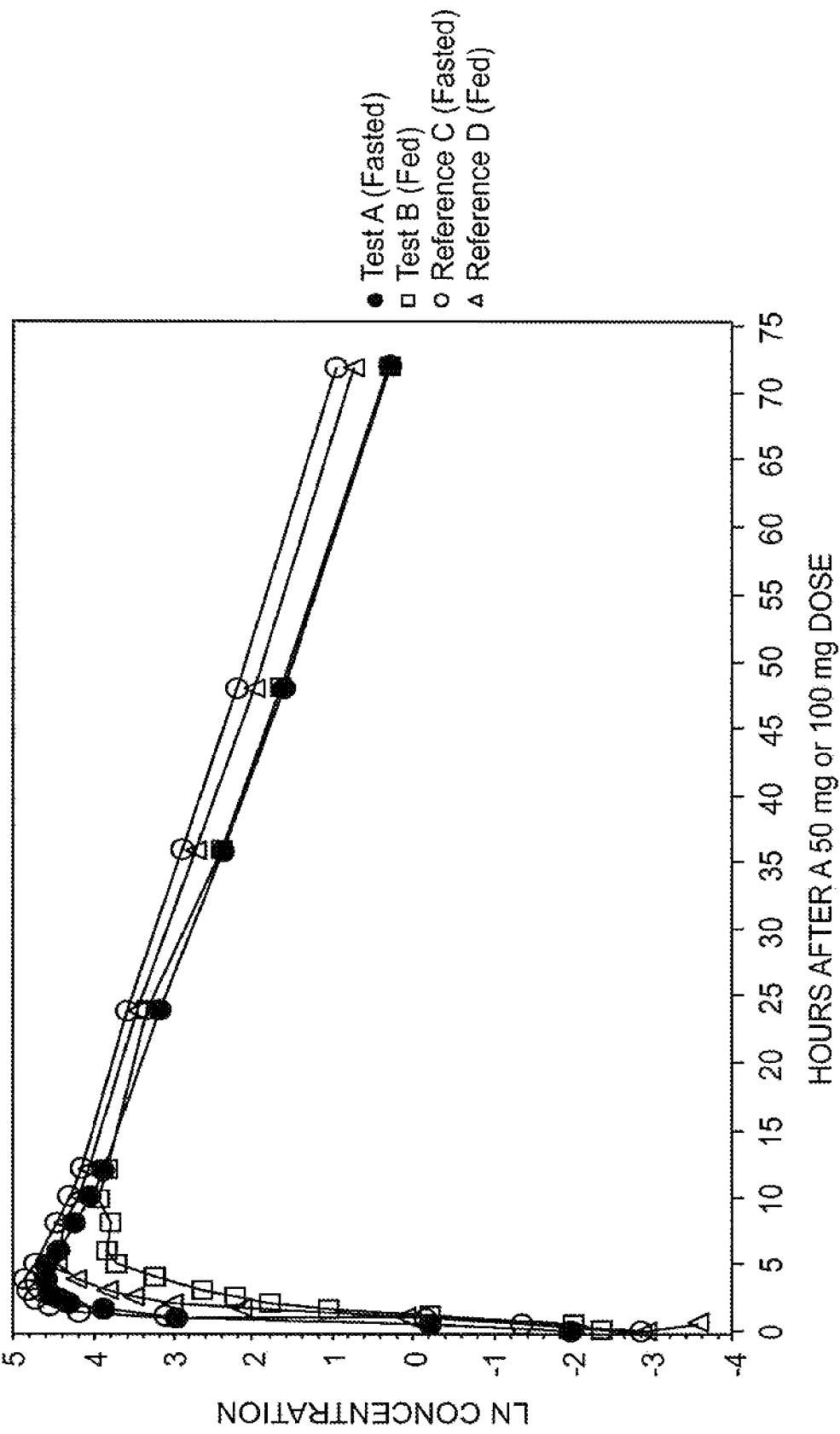
FIG. 32 shows a log-transformed scale graph of the mean plasma hydroxyitraconazole concentration over time in a study comparing the relative bioavailability of a 100 mg LOZANOC dose with a 100 mg dose of SPORANOX® administered under fed and fasted conditions. Closed circles represent the 50 mg LOZANOC dose administered under fasted conditions; open squares represent the 50 mg LOZANOC dose administered under fed conditions; open circles represent the reference SPORANOX® 100 mg dose administered under fasted conditions; open triangles represent the reference SPORANOX® 100 mg dose administered under fed conditions.

FIGS. 31 (linear plot) and 32 (ln-linear plot) show the mean concentration of 2-hydroxyitraconazole in fasted and fed subjects in the blood serum over time.

Table 30 summarizes the pharmacokinetic parameters (untransformed) of itraconazole for the agents administered under fasted and fed conditions described above.

TABLE 30

Summary of Pharmacokinetic Parameters of Itraconazole in Fasted and Fed Conditions
Summary of Pharmacokinetic Parameters

| Pharmacokinetic Parameter | Arithmetic mean ± SD (% CV) | | | |
|---|---|---|---|---|
| | Test A | Test B | Reference C | Reference D |
| AUCt (ng · hr/ml) | 804.51 ± 483.41 (60.09) | 604.14 ± 417.14 (69.05) | 1147.09 ± 719.49 (62.72) | 855.51 ± 581.34 (67.95) |
| AUCinf (ng · hr/ml) | 898.33 ± 607.78 (67.66) | 684.05 ± 541.50 (79.16) | 1208.35 ± 843.46 (69.80) | 959.01 ± 686.94 (71.63) |
| Cmax (ng/ml) | 80.17 ± 38.71 (48.29) | 39.04 ± 25.79 (66.05) | 87.62 ± 54.98 (62.76) | 63.17 ± 41.89 (66.32) |
| Tmax (hr) | 3.03 ± 1.16 (38.35) | 7.64 ± 3.81 (49.85) | 3.16 ± 0.94 (29.58) | 5.71 ± 1.80 (31.57) |
| Median Tmax (hr) | 2.50 | 6.00 | 3.00 | 5.00 |
| Ke (1/hr) | 0.04 ± 0.01 (31.85) | 0.04 ± 0.01 (33.67) | 0.03 ± 0.01 (28.25) | 0.04 ± 0.01 (31.94) |
| Elimhalf (hr) | 20.74 ± 6.65 (32.07) | 19.14 ± 5.83 (30.47) | 21.52 ± 5.66 (26.32) | 19.86 ± 5.87 (29.58) |

Table 31 shows the geometric means based on ANOVA of untransformed and ln-transformed data for the itraconazole agents tested in this study under fasting and fed conditions.

TABLE 31

Geometric Means of Itraconazole Agents in Fasted and Fed Conditions c
Geometric Means Based on ANOVA of Untransformed and ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Test A | 804.08 | 897.51 | 80.12 | 676.00 | 735.77 | 69.92 |
| Test B | 644.86 | 738.20 | 40.40 | 533.30 | 588.76 | 32.76 |

TABLE 31-continued

Geometric Means of Itraconazole Agents in Fasted and Fed Conditions c
Geometric Means Based on ANOVA of Untransformed and ln-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Reference C | 1137.56 | 1238.78 | 87.19 | 927.60 | 1011.63 | 71.26 |
| Reference D | 879.58 | 987.71 | 64.38 | 692.62 | 762.64 | 50.11 |

Table 32 shows the ratio of means and 90% Confidence Interval based on ANOVA of untransformed and ln-transformed data for Test A (50 mg dose of LOZANOC capsule) with Reference C (100 mg dose of SPORANOX® (itraconazole) capsule) in the fasting state.

TABLE 32

Ratio of Means and Confidence Intervals for Test A v Reference C
Ratio of Means, and 90% Confidence Intervals
Based on ANOVA of Untransformed and ln-Transformed Data
Test A (fasted) v Reference C (fasted)

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.7068 | 0.7245 | 0.9189 | 0.7288 | 0.7273 | 0.9813 |
| CI | 0.6069-0.8068 | 0.6188-0.8303 | 0.7892-1.0485 | 0.6299-0.8432 | 0.6268-08440 | 0.8113-1.1870 |
| p-value | <0.0001 | <0.0001 | 0.3013 | 0.0005 | 0.0006 | 0.8694 |

This comparison showed that the mean peak plasma concentration (Cmax) of a single dose of the Test product LOZANOC 50 mg capsules under fasted conditions are equivalent to that of the Reference product SPORANOX® (itraconazole) 100 mg capsules under fasted conditions.

Table 33 shows the ratio of means and 90% Confidence Interval based on ANOVA of untransformed and ln-transformed data for Test B (50 mg dose of LOZANOC capsule) with Reference D (100 m dose of SPORANOX® (itraconazole) capsule) in the fed state.

TABLE 33

Ratio of Means and Confidence Intervals for Test B v Reference D
Ratio of Means, and 90% Confidence Intervals
Based on ANOVA of Untransformed and ln-Transformed Data
Test B (fed) v Reference D (fed)

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Ratio | 0.7331 | 0.7474 | 0.6274 | 0.7700 | 0.7720 | 0.6538 |
| CI | 0.6017-0.8646 | 0.6152-0.8796 | 0.4489-0.8060 | 0.6639-0.8930 | 0.6656-0.8954 | 0.5388-0.7934 |
| p-value | 0.0011 | 0.0020 | 0.0008 | 0.0043 | 0.0047 | 0.0004 |

When a single 50 mg dose of the LOZANOC 50 mg capsules is given following a high fat meal, the peak and overall bioavailability as measured by Cmax and AUC is approximately 70% of that seen following a single 100 mg capsule dose of the Reference product (100 mg dose of SPORANOX® (itraconazole) under fed conditions.

Table 34 shows the ratio of means and 90% Confidence Interval based on ANOVA of untransformed and ln-transformed data for Test A (50 mg dose of LOZANOC capsule under the fasted state) with Test B (50 mg dose of LOZANOC capsule under the fed state).

TABLE 34

Ratio of Means and Confidence Intervals for Test B v Reference D
Ratio of Means, and 90% Confidence Intervals
Based on ANOVA of Untransformed and ln-Transformed Data
Test A (fasted) v Test B (fed)

| | Untransformed Data | | | Ln-Transformed Data | | |
|---|---|---|---|---|---|---|
| | AUCt (ng·hr/ml) | AUCinf (ng·hr/ml) | Cmax (ng/ml) | AUCt (ng·hr/ml) | AUCinf (ng·hr/ml) | Cmax (ng/ml) |
| Ratio | 1.2469 | 1.2158 | 1.9833 | 1.2676 | 1.2497 | 2.1342 |
| CI | 1.0683-1.4255 | 1.0396-1.3920 | 1.6998-2.2668 | 1.0935-1.4693 | 1.0781-1.4487 | 1.7600-2.5880 |
| p-value | 0.0239 | 0.0447 | <0.0001 | 0.0090 | 0.0139 | <0.0001 |

When given in the fasted state, the single dose Cmax of the Test product (50 mg dose of LOZANOC capsule) is approximately twice that of the same dose of LOZANOC capsule given following a high fat meal. Overall bioavailability as measured by AUC is approximately 25% higher in the fasted state compared to the fed state. Time to peak concentration (Tmax) increases from around 2.5 hours to 6 hours when LOZANOC 50 mg capsules are given with a high fat meal.

Table 35 shows the ratio of means and 90% Confidence Interval based on ANOVA of untransformed and ln-transformed data for Reference C (100 mg dose of SPORANOX® (itraconazole) under the fasted state) with Reference D (100 mg dose of SPORANOX® (itraconazole) under the fed state).

TABLE 35

Ratio of Means and Confidence Intervals for Reference C v Reference D
Ratio of Means, and 90% Confidence Intervals
Based on ANOVA of Untransformed and ln-Transformed Data
Reference C (fasted) v Reference D (fed)

| | Untransformed Data | | | Ln-Transformed Data | | |
|---|---|---|---|---|---|---|
| | AUCt (ng·hr/ml) | AUCinf (ng·hr/ml) | Cmax (ng/ml) | AUCt (ng·hr/ml) | AUCinf (ng·hr/ml) | Cmax (ng/ml) |
| Ratio | 1.2933 | 1.2542 | 1.3542 | 1.3393 | 1.3265 | 1.4220 |
| CI | 1.1624-1.4242 | 1.1199-1.3884 | 1.1765-1.5320 | 1.1555-1.5523 | 1.1410-1.5421 | 1.1728-1.7240 |
| p-value | 0.0003 | 0.0022 | 0.0013 | 0.0014 | 0.0024 | 0.0031 |

When given in the fasted state, the single dose Cmax for SPORANOX® (itraconazole) 100 mg capsules is approximately 40% higher and the AUC is approximately 30% higher than that of the same dose of SPORANOX® (itraconazole) 100 mg capsules given following a high fat meal. Time to peak concentration (Tmax) increases from around 3 hours to 5 hours when SPORANOX® (itraconazole) 100 mg capsules are given following a high fat meal.

Table 36 shows the ratio of means and 90% Confidence Interval based on ANOVA of untransformed and ln-transformed data for Test A (50 mg dose of LOZANOC capsule under the fasted state) with Reference D (100 mg dose of SPORANOX® (itraconazole) under the fed state).

TABLE 36

Ratio of Means and Confidence Intervals for Test A v Reference D
Ratio of Means, and 90% Confidence Intervals
Based on ANOVA of Untransformed and ln-Transformed Data
Test A (fasted) v Reference D (fed)

|  | Untransformed Data | | | Ln-Transformed Data | | |
| --- | --- | --- | --- | --- | --- | --- |
|  | AUCt (ng·hr/ml) | AUCinf (ng·hr/ml) | Cmax (ng/ml) | AUCt (ng·hr/ml) | AUCinf (ng·hr/ml) | Cmax (ng/ml) |
| Ratio | 0.9142 | 0.9087 | 1.2444 | 0.9760 | 0.9648 | 1.3954 |
| CI | 0.7847-1.0436 | 0.7785-1.0388 | 1.0686-1.4202 | 0.8434-1.1294 | 0.8337-1.1164 | 1.1533-1.6882 |
| p-value | 0.2734 | 0.2467 | 0.0231 | 0.7829 | 0.6841 | 0.0046 |

The overall bioavailability (AUC) of a single dose of LOZANOC 50 mg capsules under fasted conditions are equivalent to that of the Reference product SPORANOX® (itraconazole) 100 mg capsules when given under fed conditions, although the Cmax is approximately 30% higher.

Table 37 summarizes the pharmacokinetic parameters (untransformed) of 2-hydroxyitraconazole metabolized from the Test and Reference products administered under fasting and fed conditions.

TABLE 37

Summary of Pharmacokinetic Parameters for 2-hydroxyitraconazole under fasted and fed conditions
Summary of Pharmacokinetic Parameters

| Pharmacokinetic Parameter | Arithmetic mean ± SD (% CV) | | | |
| --- | --- | --- | --- | --- |
|  | Test A | Test B | Reference C | Reference D |
| AUCt (ng·hr/ml) | 1611.12 ± 851.06 (52.82) | 1224.98 ± 800.59 (65.36) | 2262.65 ± 1307.43 (57.78) | 1760.13 ± 1233.23 (70.06) |
| AUCinf (ng·hr/ml) | 1646.61 ± 907.11 (55.09) | 1263.28 ± 874.05 (69.19) | 2329.99 ± 1404.64 (60.29) | 1814.12 ± 1304.81 (71.92) |
| Cmax (ng/ml) | 121.09 ± 34.77 (28.71) | 63.30 ± 27.76 (43.86) | 135.48 ± 49.82 (36.78) | 94.13 ± 48.79 (51.83) |
| Tmax (hr) | 3.46 ± 1.34 (38.77) | 9.54 ± 5.81 (60.86) | 3.59 ± 0.87 (24.13) | 7.11 ± 3.59 (50.42) |
| Median Tmax (hr) | 3.00 | 6.00 | 4.00 | 6.00 |
| Ke (1/hr) | 0.09 ± 0.03 (34.24) | 0.09 ± 0.03 (32.59) | 0.07 ± 0.02 (29.09) | 0.09 ± 0.03 (33.97) |
| Elimhalf (hr) | 8.75 ± 3.38 (38.67) | 8.44 ± 3.57 (42.34) | 10.71 ± 3.50 (32.63) | 8.98 ± 3.77 (41.97) |

Table 38 shows the ratio of means and 90% Confidence Interval based on ANOVA of untransformed and ln-transformed data for the comparisons performed in this study. As would be anticipated, the comparative results of the metabolite data (2-hydroxyitraconazole) are consistent to that observed with the parental product (itraconazole).

female subjects. A total of 36 subjects participated in the study. Thirty-five subjects completed the study. Screening was performed in the 28-day period prior to the first dose. Each subject participated in 4 treatment periods, residing at the CRU from Day −1 (the day before dosing) to Day 3 (48 hours post dose). Dosing occurred on Day 1 for each subject.

TABLE 38

Ratio of Means and Confidence Intervals for 2-hydroxyitraconazole
Geometric Means, Ratio of Means, and 90% Confidence Intervals
Based on ANOVA of Untransformed and In-Transformed Data

| | Untransformed Data | | | Ln-Transformed Data | | |
|---|---|---|---|---|---|---|
| | AUCt (ng · hr/ml) | AUCinf (ng · hr/ml) | Cmax (ng/ml) | AUCt (ng · hr/ml) | AUCinf (ng · hr/ml) | Cmax (ng/ml) |
| Test A | 1614.60 | 1650.23 | 121.27 | 1393.44 | 1415.14 | 115.92 |
| Test B | 1228.80 | 1267.09 | 63.42 | 1027.06 | 1047.24 | 57.84 |
| Reference C | 2247.52 | 2313.99 | 135.43 | 1864.27 | 1906.30 | 123.78 |
| Reference D | 1764.19 | 1818.55 | 94.28 | 1356.53 | 1384.97 | 82.20 |
| Test A (fasted) v Reference C (fasted) | | | | | | |
| Ratio | 0.7184 | 0.7132 | 0.8955 | 0.7474 | 0.7424 | 0.9365 |
| CI | 0.6181-0.8187 | 0.6137-0.8127 | 0.8034-0.9876 | 0.6429-0.8690 | 0.6394-0.8619 | 0.8065-10875 |
| p-value | <0.0001 | <0.0001 | 0.0625 | 0.0018 | 0.0013 | 0.4678 |
| Test B (fed) v Reference D (fed) | | | | | | |
| Ratio | 0.6965 | 0.6968 | 0.6727 | 0.7571 | 0.7562 | 0.7037 |
| CI | 0.5701-0.8229 | 0.5715-0.8220 | 0.5418-0.8036 | 0.6522-0.8789 | 0.6523-0.8765 | 0.6070-0.8159 |
| p-value | 0.0001 | 0.0001 | <0.0001 | 0.0025 | 0.0022 | 0.0002 |
| Test A (fasted) v Test B (fed) | | | | | | |
| Ratio | 1.3140 | 1.3024 | 1.9121 | 1.3567 | 1.3513 | 2.0039 |
| CI | 1.1325-1.4954 | 1.1226-1.4822 | 1.7175-2.1068 | 1.1688-1.5749 | 1.1658-1.5664 | 1.7284-2.3234 |
| p-value | 0.0050 | 0.0063 | <0.0001 | 0.0010 | 0.0010 | <0.0001 |
| Reference C (fasted) v Reference D (fed) | | | | | | |
| Ratio | 1.2740 | 1.2724 | 1.4364 | 1.3743 | 1.3764 | 1.5059 |
| CI | 1.1462-1.4017 | 1.1458-1.3990 | 1.3040-1.5687 | 1.1820-1.5979 | 1.1856-1.5980 | 1.2968-1.7487 |
| p-value | 0.006 | 0.0005 | <0.0001 | 0.0007 | 0.0006 | <0.0001 |
| Test A (fasted) v Reference D (fed) | | | | | | |
| Ratio | 0.9152 | 0.9074 | 1.2862 | 1.0272 | 1.0218 | 1.4102 |
| CI | 0.7888-1.0416 | 0.7822-1.0327 | 1.1553-1.4172 | 0.8849-1.1924 | 0.8815-1.1844 | 1.2163-1.6350 |
| p-value | 0.2680 | 0.2228 | 0.0005 | 0.7656 | 0.8091 | 0.0002 |

Example 10—Bioavailability Study Comparing 50 mg LOZANOC Itraconazole to SPORANOX® (Itraconazole) Under Fed and Fasted Conditions Study Rationale This study was performed to determine the relative bioavailability of a new formulation of itraconazole capsules (SUBA®-itraconazole), 50 mg under fed and fasted conditions compared to currently marketed itraconazole capsules (SPORANOX® purchased from a European state), 100 mg under fed and fasted conditions when administered to healthy male and female subjects as a single oral dose. SPORANOX® capsules demonstrate high between-patient variability in the absorption of itraconazole, where occasionally very high or sub-therapeutic plasma levels are experienced. Due to higher bioavailability, a 50 mg dose of LOZANOC is expected to result in similar exposure to itraconazole as seen following a 100 mg dose of SPORANOX®. A fed/fasted comparison was included in the study to investigate the effect of food on the new LOZANOC capsules due to the significant impact that food is known to have on the bioavailability of the current marketed SPORANOX® capsules.

Study Design

This was a randomized, single dose, open-label, 4-way crossover, relative bioavailability study in healthy male and female subjects. Subjects then returned for an outpatient visit on Day 4 (72 hours post dose). There was a minimum of 7 days between each dose administration.

Study Treatments

Test Formulation: capsules containing 50 mg itraconazole (LOZANOC).

Reference Formulation: 100 mg capsules SPORANOX® (itraconazole)

Treatment A: LOZANOC capsules, 50 mg administered following at least a 10-hour overnight fast.

Treatment B: LOZANOC capsules, 50 mg administered following a high-fat, high-calorie breakfast after at least a 10-hour fast.

Treatment C: SPORANOX® (itraconazole) capsules, 100 mg administered following at least a 10-hour overnight fast.

Treatment D: SPORANOX® (itraconazole) capsules, 100 mg administered following a high-fat, high-calorie breakfast after at least a 10-hour fast.

Each subject received a total of 4 doses of itraconazole during the study (2 doses of LOZANOC capsules and 2 doses of SPORANOX®).

Blood samples were collected pre-dose and at the following times after administration of each dose: 0.5 1, 1.5, 2, 2.5, 3, 3.5, 4, 5, 6, 8, 10, 12, 16, 24, 36, 48 and 72 hours. Following collection, plasma was separated from blood cells by centrifugation. All plasma samples were stored frozen at −20.0 (±5° C.) until analysis.

Sample Analysis

The analysis of itraconazole and hydroxyitraconazole in plasma samples was performed by the Department of Bioanalytical Services at Covance Laboratories Europe (CLE), Harrogate, UK using a validated analytical method. The plasma samples were prepared by solid phase extraction. The centrifuged eluates were quantified by liquid chromatography with tandem mass spectrometric detection (LC-MS/MS).

Pharmacokinetic Analysis

The pharmacokinetic analysis was conducted by Covance CRU using WinNonlin Professional Version 5.2 (Pharsight Corporation, Mountain View, Calif., USA). Pharmacokinetic parameters were determined from the plasma concentrations of itraconazole and hydroxyitraconazole using non-compartmental procedures.

The pharmacokinetic parameters determined are presented in Table 1.

For the assessment of relative bioavailability, SUBA®-itraconazole (itraconazole) capsules (50 mg under fed and fasted conditions) were the test formulation and SPORANOX® (itraconazole) capsules (100 mg under fed and fasted conditions) were the reference formulation. Statistical analyses were performed separately for the fed and fasted conditions and were repeated for hydroxyitraconazole. As the variance for all pharmacokinetic parameters increases as the mean increases, the pharmacokinetic parameters AUC0-tlast, AUC0-∞ and Cmax were log-transformed (base e) prior to analysis and were analyzed using a mixed model. The model included sequence, period and treatment as fixed effects and subject within sequence as a random effect. The least squares (LS) means were calculated for these pharmacokinetic parameters for the test and reference investigational products. Mean differences between the test and reference investigational products were calculated. The residual variance from the mixed model was used to calculate 90% and 95% confidence intervals (CIs) for the difference between the test and reference investigational products. These values were back-transformed to give geometric LS means, a point estimate and 90% and 95% CIs for the ratio of the test relative to the reference investigational product. This procedure was equivalent to Schuirmann's two one-sided tests at the 0.05 level of significance. The parameter tmax was analyzed nonparametrically using the Wilcoxon signed-rank test. The median difference between the test and reference treatments and the corresponding 90% and 95% CIs were calculated.

Food Effect

The food assessment was tested separately for the itraconazole formulations and was repeated for hydroxyitraconazole. The pharmacokinetic parameters AUC0-tlast, AUC0-∞ and Cmax were log-transformed (base e) prior to analysis and were analyzed using a mixed model. The model included sequence, period and treatment as fixed effects, and subject with sequence as a random effect. For these pharmacokinetic parameters, LS means were calculated for the fed and fasted conditions. Mean differences between the fed and fasted treatments were calculated. The residual variance from the mixed model was used to calculate 90% and 95% CIs for the difference between the fed and fasted conditions. These values were back-transformed to give geometric LS means, a point estimate and 90% and 95% CIs for the ratio of the fed relative to the fasted condition.

The parameter tmax was analyzed nonparametrically using the Wilcoxon signed-rank test. The median difference between the dietary conditions and the corresponding 90% and 95% CIs were calculated.

Pharmacokinetic Results

Figure 33:
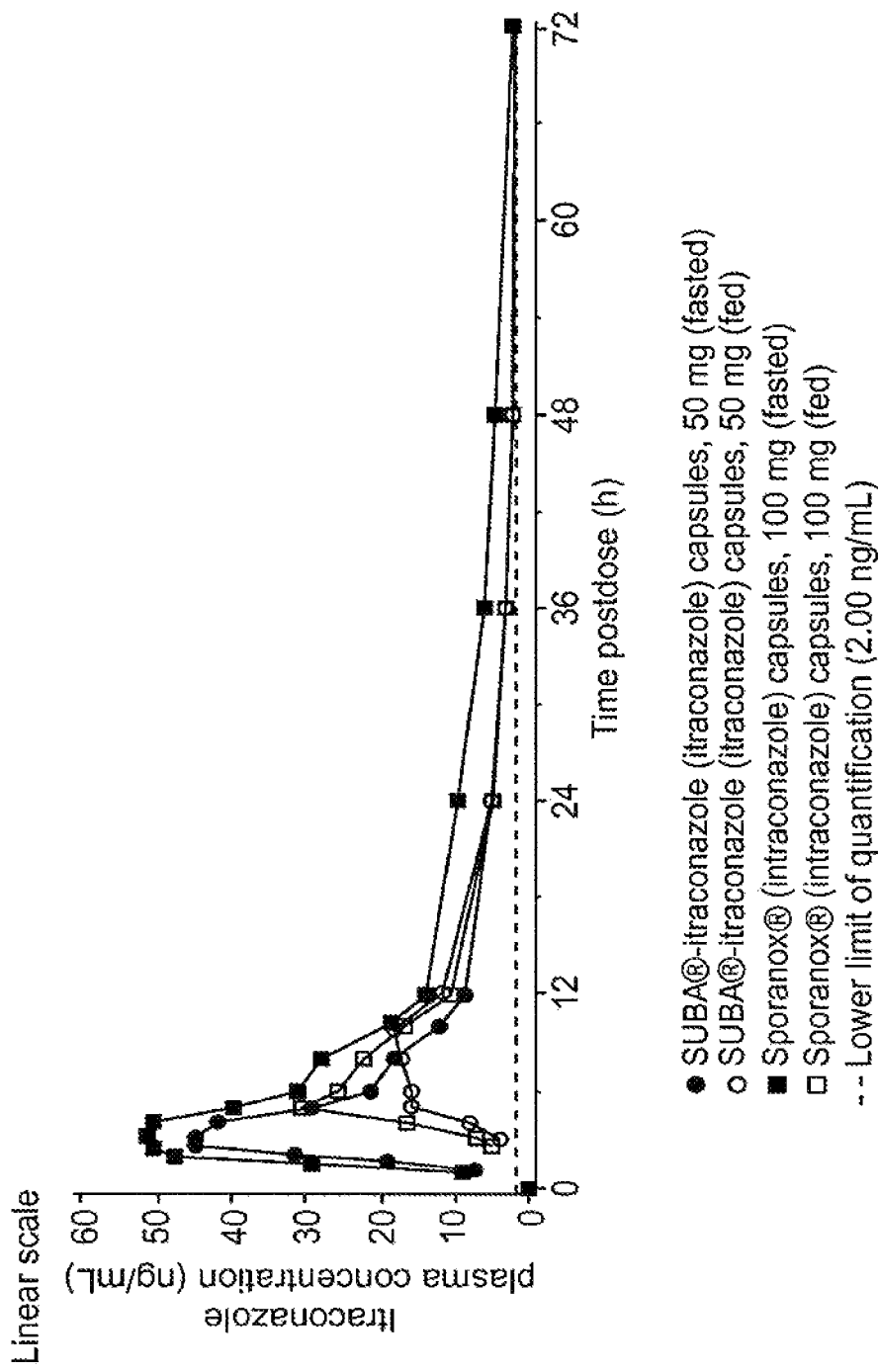
FIG. 33 shows a linear graph of the mean plasma itraconazole concentration over time in a study assessing the relative bioavailability of a 50 mg LOZANOC dose with a 100 mg dose of SPORANOX® administered under fed and fasted conditions. Closed circles represent the 50 mg LOZANOC dose administered under fasted conditions; open circles represent the 100 mg LOZANOC dose administered under fed conditions; closed squares represent the reference SPORANOX® 100 mg dose administered under fasted conditions; and closed circles represent the reference SPORANOX® 100 mg dose administered under fed conditions.
Figure 34:
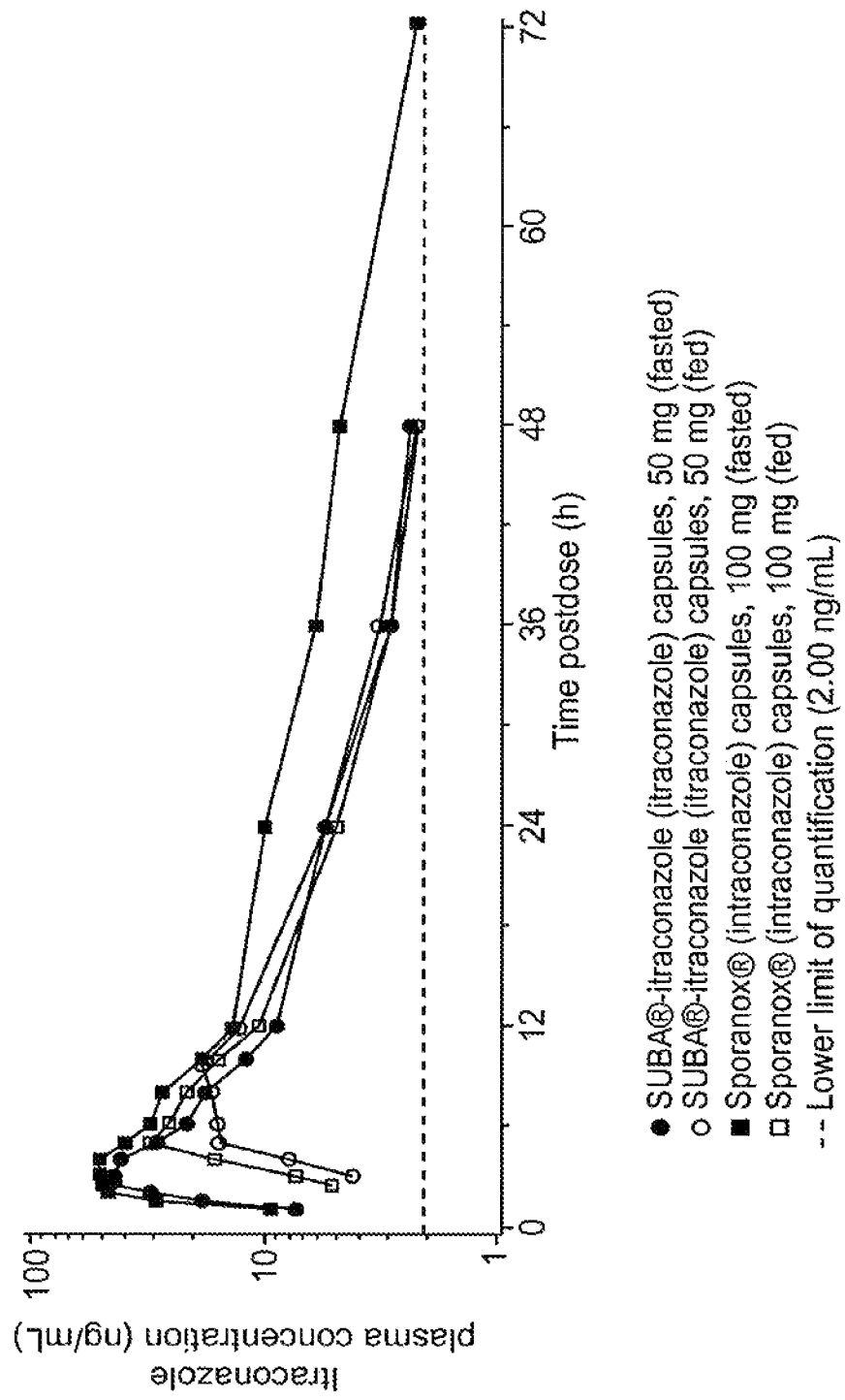
FIG. 34 shows a log-transformed graph of the mean plasma itraconazole concentration over time in a study assessing the relative bioavailability of a 50 mg LOZANOC dose with a 100 mg dose of SPORANOX® administered under fed and fasted conditions. Closed circles represent the 50 mg LOZANOC dose administered under fasted conditions; open circles represent the 100 mg LOZANOC dose administered under fed conditions; closed squares represent the reference SPORANOX® 100 mg dose administered under fasted conditions; and closed circles represent the reference SPORANOX® 100 mg dose administered under fed conditions.

Plasma concentrations of itraconazole following administration of LOZANOC and SPORANOX® (itraconazole) formulations in both the fasted and fed conditions are summarized in FIGS. 33 (linear) and 34 (log-transformed).

Figure 35:
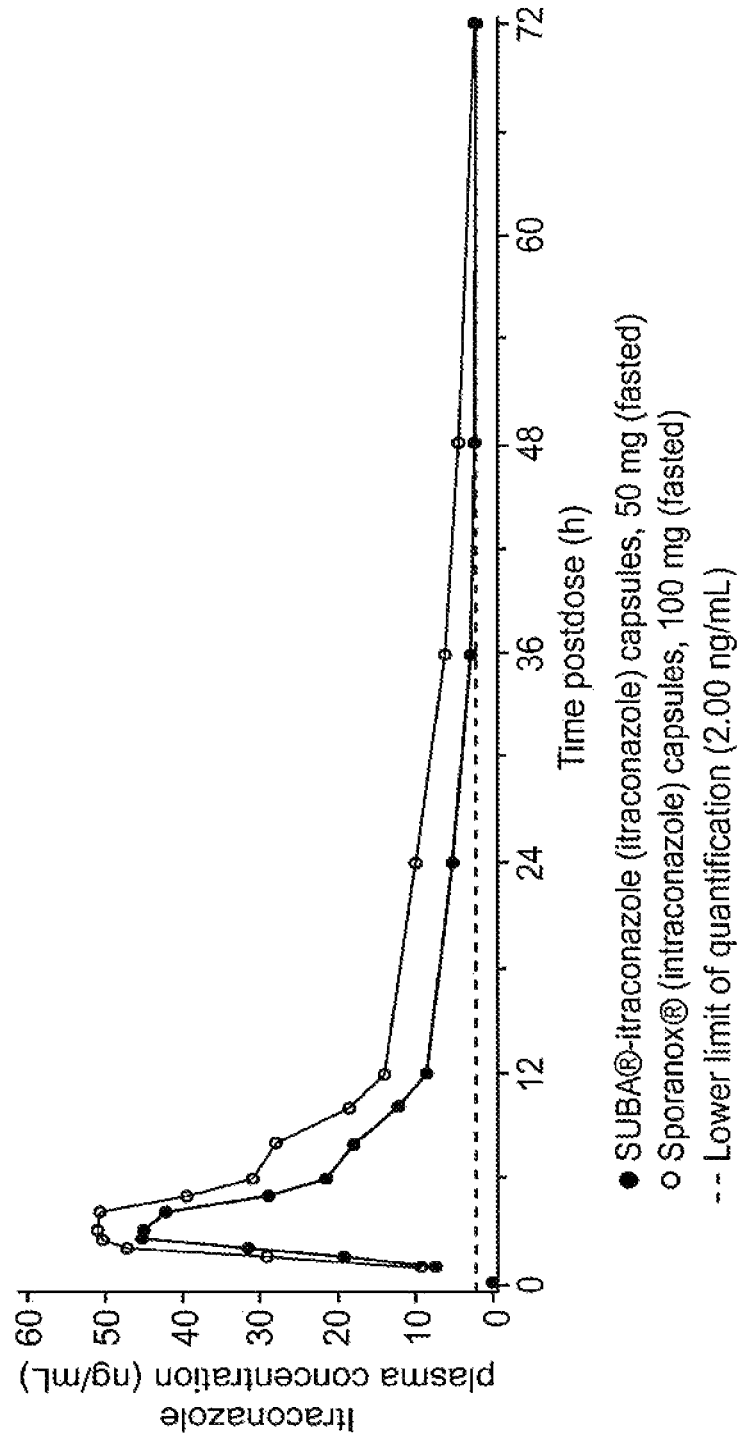
FIG. 35 shows a linear scale graph comparing the mean plasma itraconazole concentration over time in a study assessing the relative bioavailability of a 50 mg LOZANOC dose with a 100 mg dose of SPORANOX® administered under fasted conditions. Closed circles represent the 50 mg LOZANOC dose administered under fasted conditions; open circles represent the reference SPORANOX® 100 mg dose administered under fasted conditions.
Figure 36:
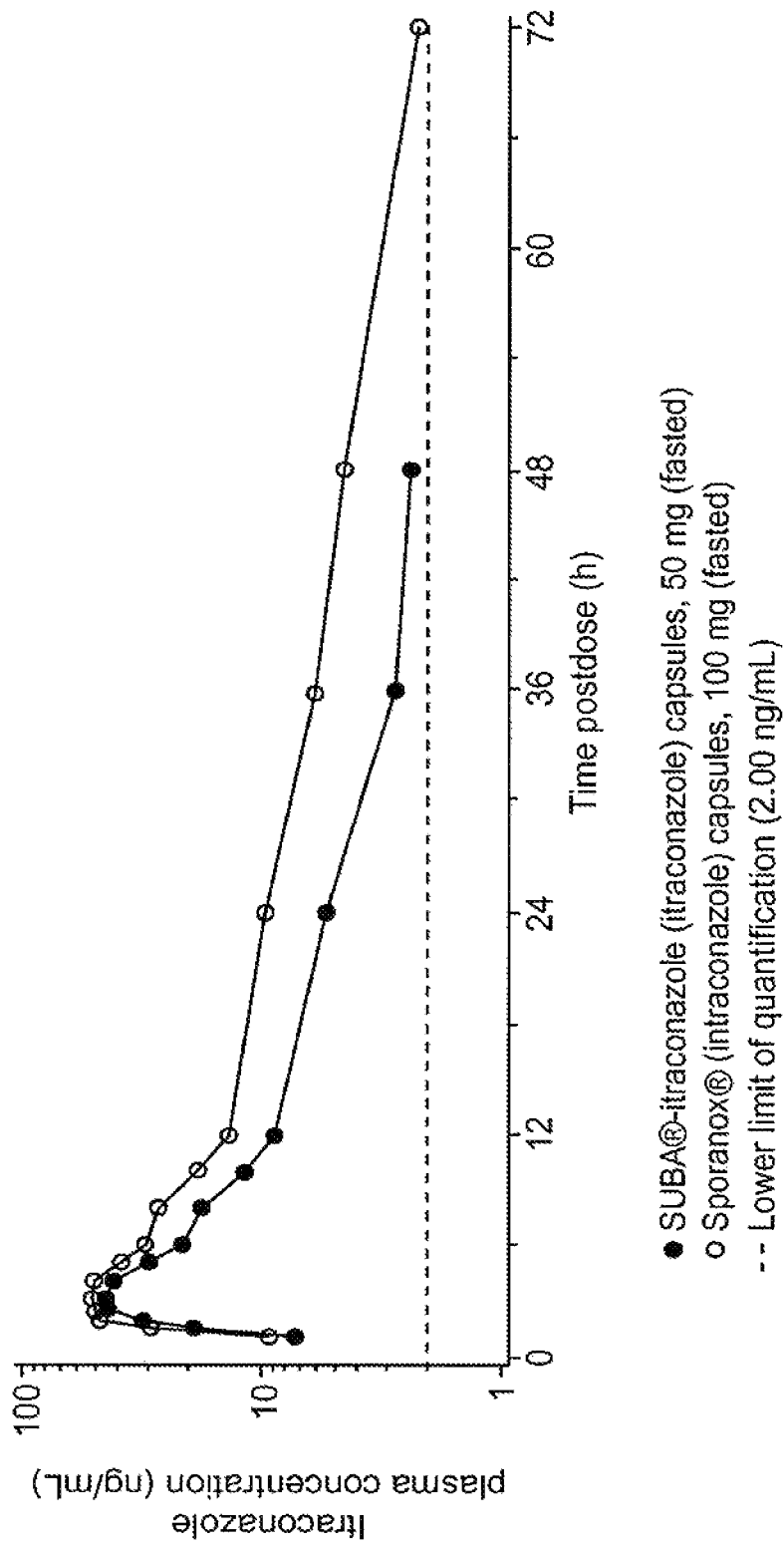
FIG. 36 shows a log-transformed scale graph comparing the mean plasma itraconazole concentration over time in a study assessing the relative bioavailability of a 50 mg LOZANOC dose with a 100 mg dose of SPORANOX® administered under fasted conditions. Closed circles represent the 50 mg LOZANOC dose administered under fasted conditions; open circles represent the reference SPORANOX® 100 mg dose administered under fasted conditions.

Plasma concentrations of itraconazole following administration of LOZANOC and SPORANOX® (itraconazole) formulations in the fasted condition are summarized in FIGS. 35 (linear) and 36 (log-transformed).

Figure 37:
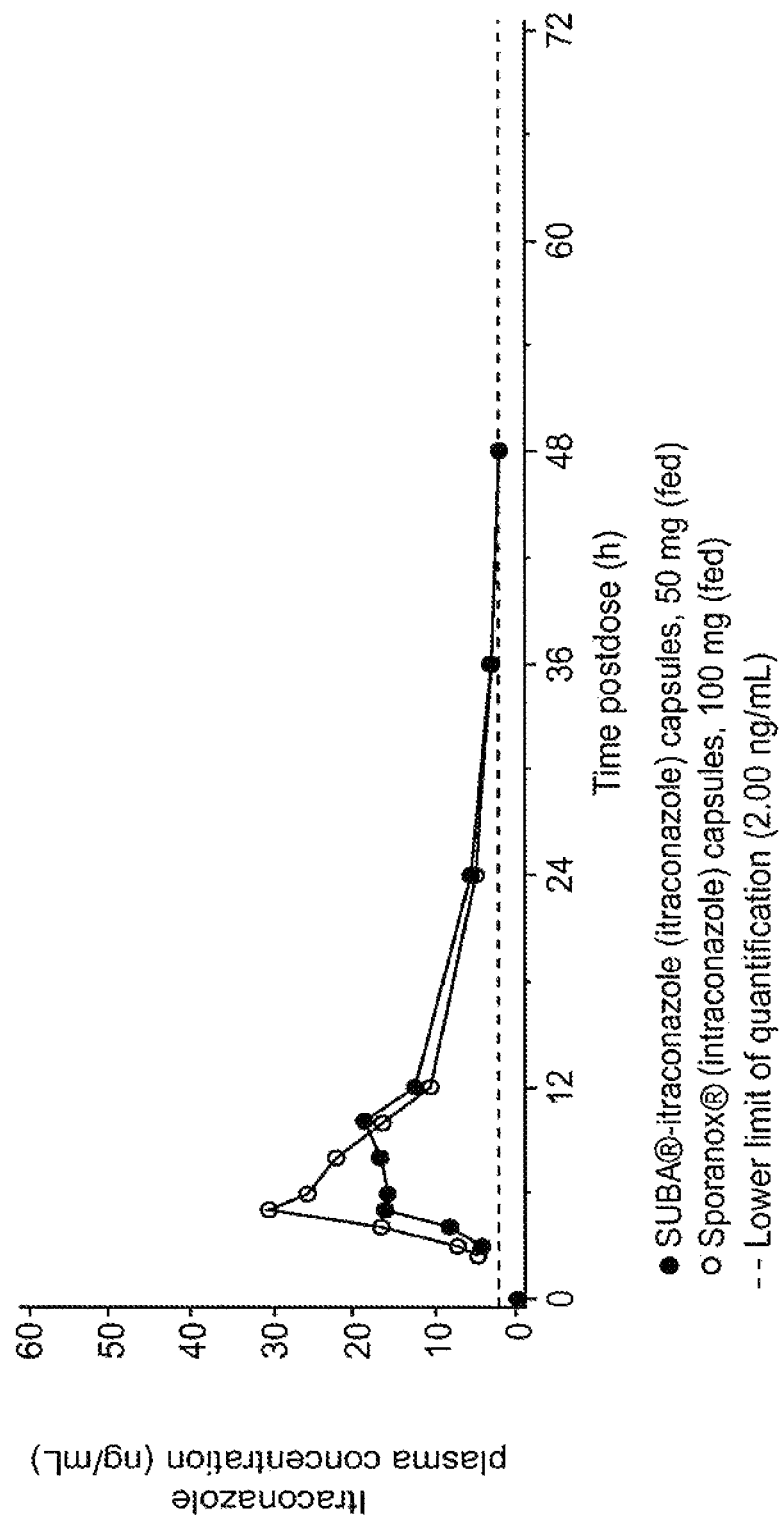
FIG. 37 shows a linear scale graph comparing the mean plasma itraconazole concentration over time in a study assessing the relative bioavailability of a 50 mg LOZANOC dose with a 100 mg dose of SPORANOX® administered under fed conditions. Closed circles represent the 50 mg LOZANOC dose administered under fed conditions; open circles represent the reference SPORANOX® 100 mg dose administered under fed conditions.
Figure 38:
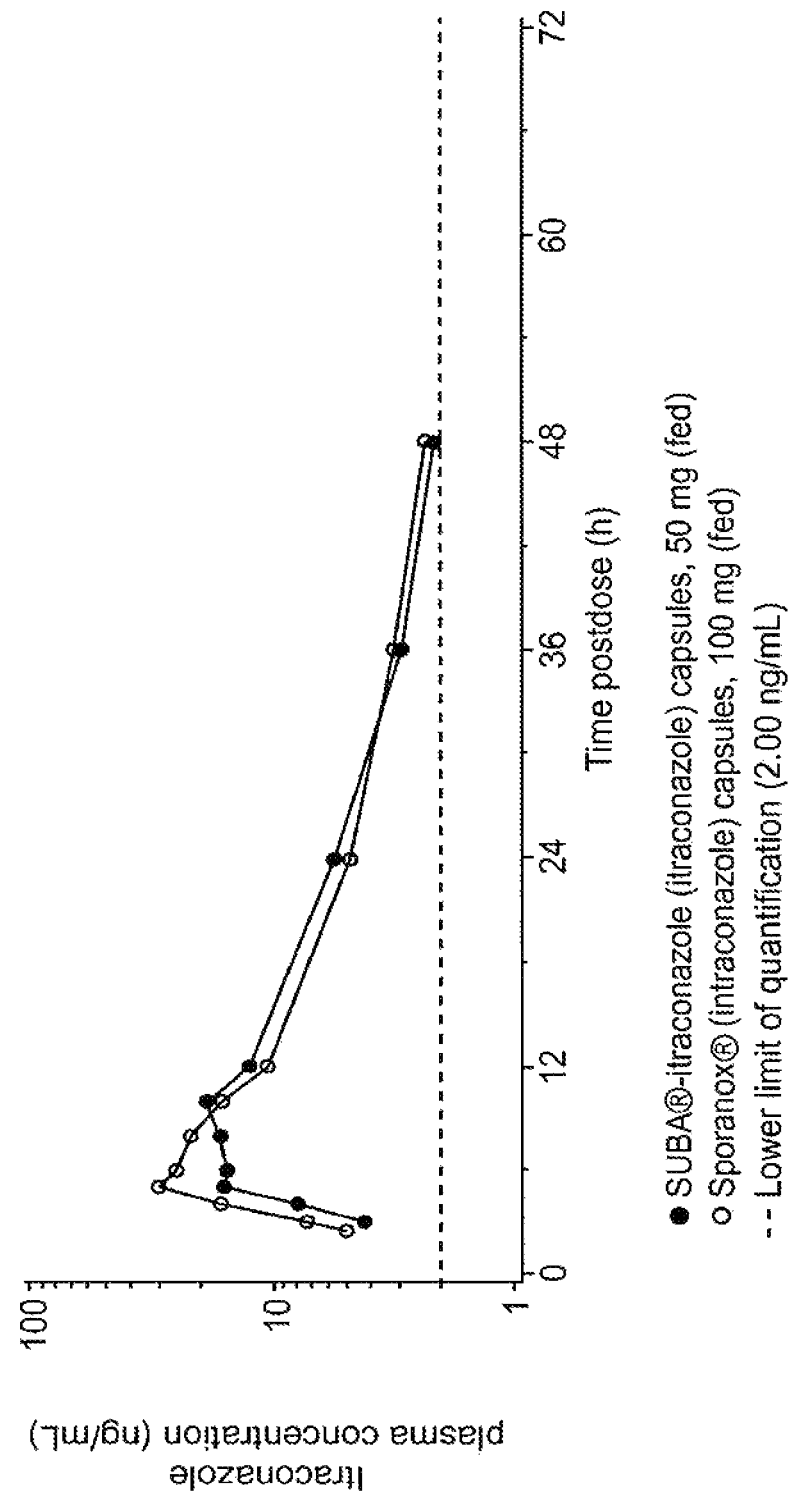
FIG. 38 shows a log-transformed scale graph comparing the mean plasma itraconazole concentration over time in a study assessing the relative bioavailability of a 50 mg LOZANOC dose with a 100 mg dose of SPORANOX® administered under fed conditions. Closed circles represent the 50 mg LOZANOC dose administered under fed conditions; open circles represent the reference SPORANOX® 100 mg dose administered under fed conditions.

Plasma concentrations of itraconazole following administration of LOZANOC and SPORANOX® (itraconazole) formulations in the fed condition are summarized in FIGS. 37 (linear) and 38 (log-transformed).

The pharmacokinetic parameters of itraconazole are summarized in Table 39.

TABLE 39

Summary of the Pharmacokinetic Parameters for Itraconazole Following Administration of LOZANOC and SPORANOX ® (Itraconazole) Formulations in the Fasted and Fed Conditions

| | Treatments | | | |
|---|---|---|---|---|
| | 50 mg SUBA ®— itraconazole capsules | | 100 mg Sporanox ®— itraconazole capsules | |
| Parameters | Fasted (N = 35) | Fed (N = 36) | Fasted (N = 36) | Fed (N = 36) |
| $AUC_{0-tlast}$ (ng · h/mL) | 450 (56.8) | 359 (65.4) | 733 (52.6) | 358 (102) |
| $AUC_{0-\infty}$ (ng · h/mL) | 659[b] (34.7) | 532[c] (46.0) | 920[d] (37.3) | 589[b] (54.4) |
| $C_{max}$ (ng/mL) | 64.0 (57.5) | 33.6 (68.9) | 63.8 (62.0) | 36.2 (88.2) |
| $t_{max}$ (h) | 2.50 (1.00-5.15) | 6.00 (1.00-12.0) | 2.50 (1.50-5.00) | 5.00 (2.00-8.05) |
| $T_{lag}$[a] (h) | 0.500 (0-1.50) | 2.50 (0-8.02) | 0.500 (0-1.00) | 1.77 (0.500-4.00) |
| $T_{1/2}$ (h) | 24.5[c] (35.7) | 21.5[c] (34.6) | 24.8 (33.2) | 21.8[e] (49.7) |
| CL/F (mL/min) | 1245 (35.0) | 1566[c] (46.0) | 1924 (45.5) | 2815[e] (51.8) |
| $V_z/F$ (L) | 2637[c] (36.3) | 2919[c] (38.7) | 4138 (60.5) | 5303[e] (53.2) |

Geometric mean (CV %) data are presented
N = Number of subjects studied
[a] Median (min-max)
[b] N = 25,
[c] N = 26,
[d] N = 34,
[e] N = 28

Following the oral administration of each of the LOZANOC (50 mg) and SPORANOX® (100 mg) formulations in the fasted condition, itraconazole was rapidly absorbed, appearing in plasma at 0.5 hours after administration. Maximum plasma concentrations were attained at median tmax of 2.5 hours post dose, with values for individual subjects ranging from 1.0 to 5.2 hours and 1.5 to 5.0 hours post-dose, respectively. After reaching Cmax, plasma concentrations declined in an apparent biphasic manner, with the start of the elimination phase generally occurring at 10 to 24 hours post dose for both formulations and a mean apparent elimination half-life of 25 hours (range in individual subjects from 13.8 to 67.4 hours and 9.3 to 46.2 hours for the LOZANOC and SPORANOX® formulations, respectively). The statistical comparison of relative bioavailability of itraconazole in the fasted condition is summarized in Table 40.

TABLE 40

Statistical Comparison of the Relative Bioavailability of Itraconazole Following Administration of 50 mg LOZANOC and 100 mg SPORANOX ® (Itraconazole) in the Fasted Condition

| Parameters | Geometric LS mean | | Ratio of |
|---|---|---|---|
| | 50 mg SUBA ®— itraconazole (fasted) | 100 mg Sporanox ®— itraconazole capsules | geometric LS means SUBA ®: Sporanox ® (90% CI) |
| $AUC_{0-tlast}$ (ng · h/mL) | 448 | 733 | 0.611 (0.557, 0.670) |
| $AUC_{0-\infty}$ (ng · h/mL) | 591 | 866 | 0.682 (0.629, 0.740) |
| $C_{max}$ (ng/mL) | 63.4 | 63.8 | 0.993 (0.859, 1.15) |
| $t_{max}{}^a$ (h) | 2.5 | 2.5 | 0 (−0.500, 0.258) |

[a] Median difference (SUBA ®—itraconazole − Sporanox ® [itraconazole])

In the fasted condition, systemic exposure to itraconazole, based upon AUC0-tlast and AUC0-∞, was lower (by approximately 32 to 39%) when administered as the LOZANOC formulation (50 mg) compared to the SPORANOX® formulation (100 mg). Maximum plasma concentrations were similar and rapidly attained at median tmax of 2.5 hours post dose for both formulations. The between-subject variability (geometric CV %,) was high and generally similar for both formulations in the fasted condition, ranging from 35% and 37% for AUC0-∞ and 58% and 62% for Cmax. The magnitude of difference in the maximum and minimum exposure between individual subjects was similar for both formulations in terms of AUC0-∞ (3.8- and 3.6-fold for the SPORANOX® compared to the SUBA® formulation), however for Cmax, the SPORANOX® formulation was markedly higher than LOZANOC (17.3- and 8.8-fold, respectively). The statistical comparison of relative bioavailability of itraconazole in the fed condition is summarized in Table 41.

TABLE 41

Statistical Comparison of Relative Bioavailability of Itraconazole Following Administration of 50 mg LOZANOC and 100 mg SPORANOX ® (Itraconazole) in the Fed Condition

| Parameters | Geometric LS mean | | Ratio of |
|---|---|---|---|
| | 50 mg SUBA ®— itraconazole (fed) | 100 mg Sporanox ®— itraconazole (fed) | geometric LS means SUBA ®: Sporanox ® (90% CI) |
| $AUC_{0-tlast}$ (ng · h/mL) | 359 | 358 | 1.00 (0.827, 1.22) |
| $AUC_{0-\infty}$ (ng · h/mL) | 521 | 591 | 0.883 (0.774, 1.05) |
| $C_{max}$ (ng/mL) | 33.6 | 36.2 | 0.927 (0.763, 1.12) |
| $t_{max}{}^a$ (h) | 6 | 5 | 1.98 (0.500, 2.75) |

[a] Median difference (SUBA ®—itraconazole − Sporanox ® [itraconazole])

Statistical analysis showed itraconazole systemic exposure (based on AUC and Cmax) to be similar between the 2 formulations when administered in the fed condition. In addition, median tmax for the LOZANOC and SPORANOX® formulations was similar (occurring at 6 and 5 hours, respectively). Higher between-subject variability (geometric CV %) in AUC0-∞ and Cmax occurred in the fed condition compared to the fasted for both formulations. The magnitude of difference in the maximum and minimum exposure between individual subjects in the fed condition was higher for the LOZANOC formulation than observed in the fasted condition being 5.8- and 18.2-fold for AUC0-∞ and Cmax, respectively. For the SPORANOX® formulation, the differences observed between individual subjects were 5.8-fold for AUC0-∞ and 20.3-fold for Cmax. The statistical comparison of relative bioavailability of itraconazole administered as 50 mg LOZANOC in the fasted condition and 100 mg SPORANOX® in the fed condition is summarized in Table 42.

TABLE 42

Statistical Comparison of the Relative Bioavailability of Itraconazole Following Administration of 50 mg LOZANOC in the Fasted Condition and 100 mg SPORANOX ® (Itraconazole) in the Fed Condition

| Parameters | Geometric LS mean | | Ratio of |
|---|---|---|---|
| | 50 mg SUBA ®— itraconazole (fasted) | 100 mg Sporanox ®— itraconazole (fed) | geometric LS means SUBA ®: Sporanox ® (90% CI) |
| $AUC_{0-tlast}$ (ng · h/mL) | 451 | 358 | 1.26 (1.03, 1.54) |
| $AUC_{0-\infty}$ (ng · h/mL) | 650 | 593 | 1.10 (0.925, 1.30) |
| $C_{max}$ (ng/mL) | 63.6 | 36.2 | 1.76 (1.44, 2.14) |
| $t_{max}{}^a$ (h) | 2.5 | 5 | −2.50 (−3.00, −1.98) |

[a] Median difference (SUBA ®—itraconazole fasted − Sporanox ® [itraconazole] fed)

Systemic exposure to itraconazole, based upon AUC0-∞, was similar for the SUBA® formulation (50 mg) given in the fasted condition and the SPORANOX® formulation (100 mg) given in the fed condition. Statistical analysis showed Cmax to be higher for the LOZANOC formulation with median tmax occurring more rapidly compared to the SPORANOX® formulation. The between-subject variability (geometric CV %) Table 42 for itraconazole was lower when given as the LOZANOC formulation in the fasted condition compared to the SPORANOX® formulation in the fed condition, being 35% and 54% for AUC0-∞ and 58% and 88% for Cmax, respectively. The magnitude of difference in the maximum and minimum exposure between individual subjects was also lower for the LOZANOC formulation, being 3.8- and 8.8-fold for AUC0-∞ and Cmax, respectively, compared to 5.8- and 20.3-fold, respectively, for the SPORANOX® formulation.

Effect of Dietary Condition on Itraconazole Exposure

The statistical assessment of the effect of dietary condition on the pharmacokinetics of itraconazole is summarized in Table 43 and Table 44.

TABLE 43

Statistical Comparison of the Effect of Dietary Condition on Itraconazole Exposure Following Administration of 50 mg LOZANOC in the Fed and Fasted Conditions

| Parameters | Geometric LS mean 50 mg SUBA ®— itraconazole capsules | | Ratio of geometric LS means Fed:Fasted |
|---|---|---|---|
| | Fed | Fasted | (90% CI) |
| $AUC_{0-tlast}$ (ng · h/mL) | 359 | 454 | 0.792 (0.718, 0.873) |
| $AUC_{0-\infty}$ (ng · h/mL) | 524 | 649 | 0.808 (0.734, 0.891) |

TABLE 43-continued

Statistical Comparison of the Effect of Dietary Condition on
Itraconazole Exposure Following Administration of 50 mg
LOZANOC in the Fed and Fasted Conditions

| Parameters | Geometric LS mean 50 mg SUBA ®— itraconazole capsules | | Ratio of geometric LS means Fed:Fasted |
|---|---|---|---|
| | Fed | Fasted | (90% CI) |
| $C_{max}$ (ng/mL) | 33.6 | 63.9 | 0.525 |
| | | | (0.446, 0.618) |
| $t_{max}{}^a$ (h) | 6 | 2.5 | 4.23 |
| | | | (3.00, 5.00) |

$^a$ Median difference (fed − fasted)

TABLE 44

Statistical Comparison of the Effect of Dietary Condition on
Itraconazole Exposure Following Administration of 100 mg
SPORANOX ® (Itraconazole) in the Fed and Fasted Conditions

| Parameters | Geometric LS mean 100 mg Sporanox ®— itraconazole capsules | | Ratio of geometric LS means Fed:Fasted |
|---|---|---|---|
| | Fed | Fasted | (90% CI) |
| $AUC_{0-tlast}$ (ng · h/mL) | 358 | 733 | 0.488 (0.405, 0.587) |
| $AUC_{0-\infty}$ (ng · h/mL) | 567 | 866 | 0.654 (0.568, 0.754) |
| $C_{max}$ (ng/mL) | 36.2 | 63.8 | 0.568 (0.474, 0.681) |
| $t_{max}{}^a$ (h) | 5 | 2.5 | 2.25 (1.75, 2.75) |

$^a$ Median difference (fed − fasted)

Statistical assessment showed AUC0-tlast, AUC0-∞ and Cmax for itraconazole to be lower for both formulations when administered in the fed compared to the fasted condition. The effect of food appeared more marked for the SPORANOX® formulation compared to the LOZANOC formulation, with AUC0-∞ being 35% and 19% lower, respectively, in the fed condition. Cmax was similar for both formulations in the fed condition and ranged from 43% to 48% lower than the fasted condition.

Figure 39:
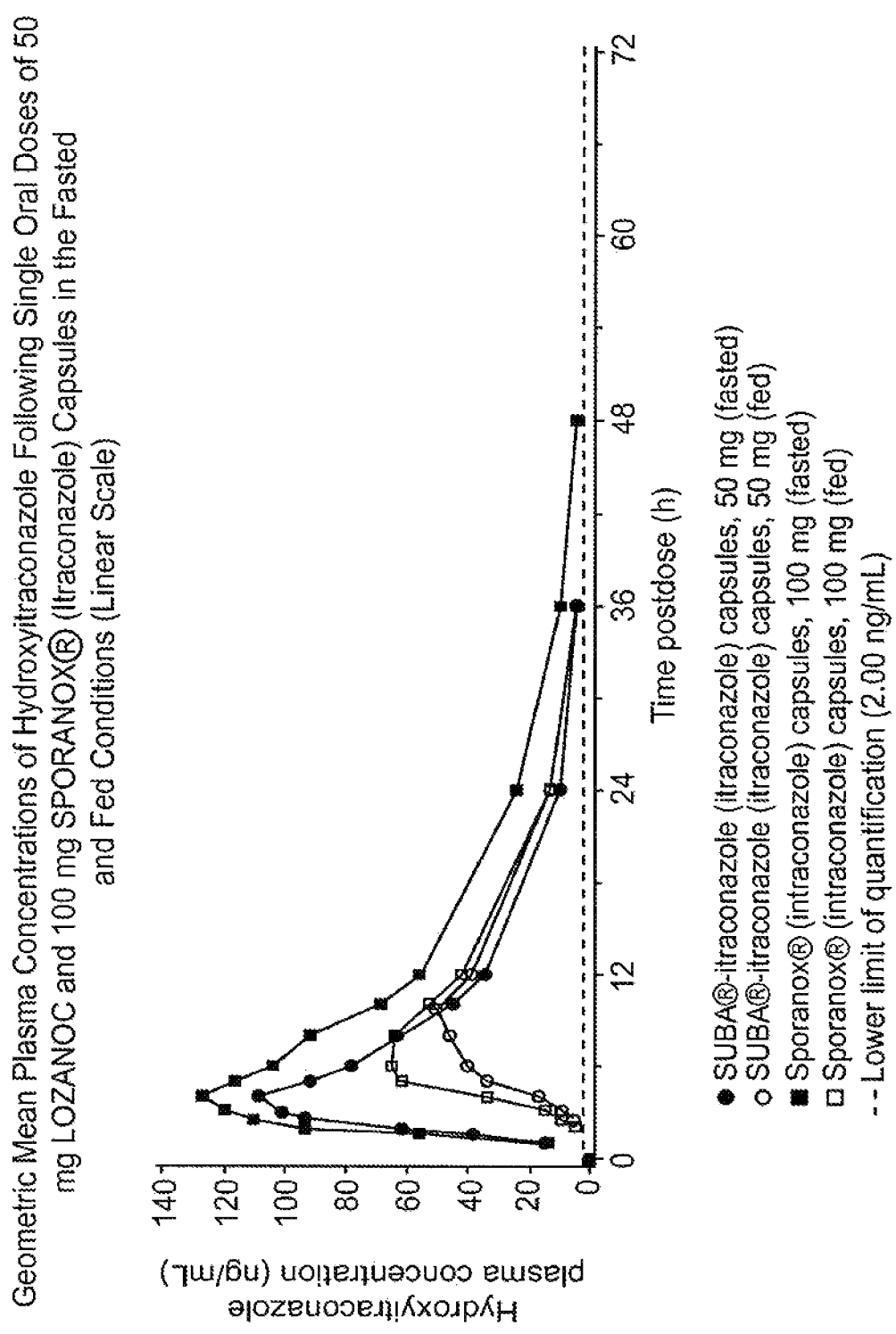
FIG. 39 shows a linear graph of the mean plasma hydroxyitraconazole concentration over time in a study assessing the relative bioavailability of a 50 mg LOZANOC dose with a 100 mg dose of SPORANOX® administered under fed and fasted conditions. Closed circles represent the 50 mg LOZANOC dose administered under fasted conditions; open circles represent the 100 mg LOZANOC dose administered under fed conditions; closed squares represent the reference SPORANOX® 100 mg dose administered under fasted conditions; and closed circles represent the reference SPORANOX® 100 mg dose administered under fed conditions.
Figure 40:
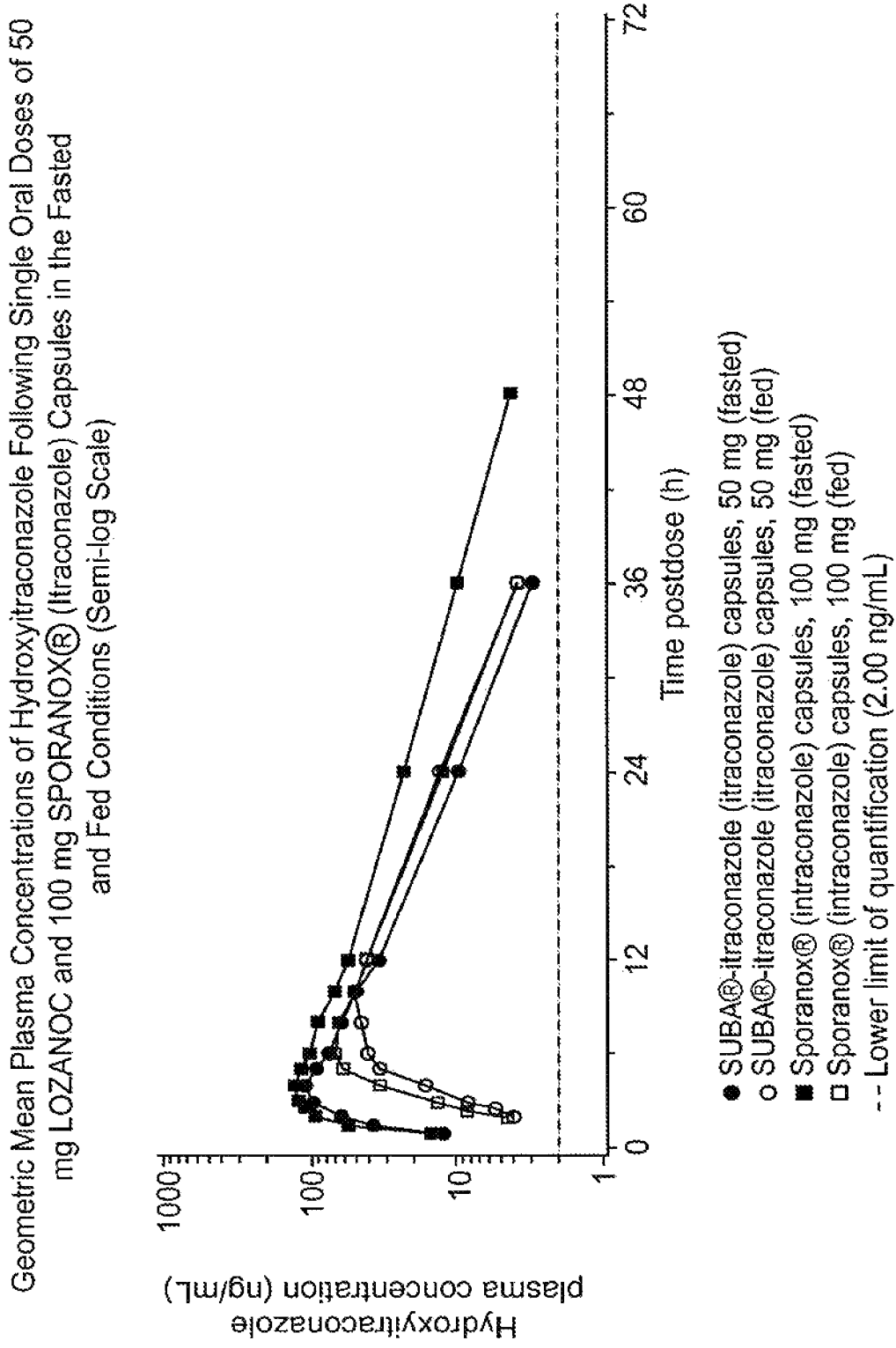
FIG. 40 shows a log-transformed graph of the mean plasma hydroxyitraconazole concentration over time in a study assessing the relative bioavailability of a 50 mg LOZANOC dose with a 100 mg dose of SPORANOX® administered under fed and fasted conditions. Closed circles represent the 50 mg LOZANOC dose administered under fasted conditions; open circles represent the 100 mg LOZANOC dose administered under fed conditions; closed squares represent the reference SPORANOX® 100 mg dose administered under fasted conditions; and closed circles represent the reference SPORANOX® 100 mg dose administered under fed conditions.

Plasma concentrations of hydroxyitraconazole following administration of the LOZANOC and SPORANOX® (itraconazole) formulations in both the fasted and fed conditions are summarized in FIGS. 39 (linear) and 40 (log-transformed).

Figure 41:
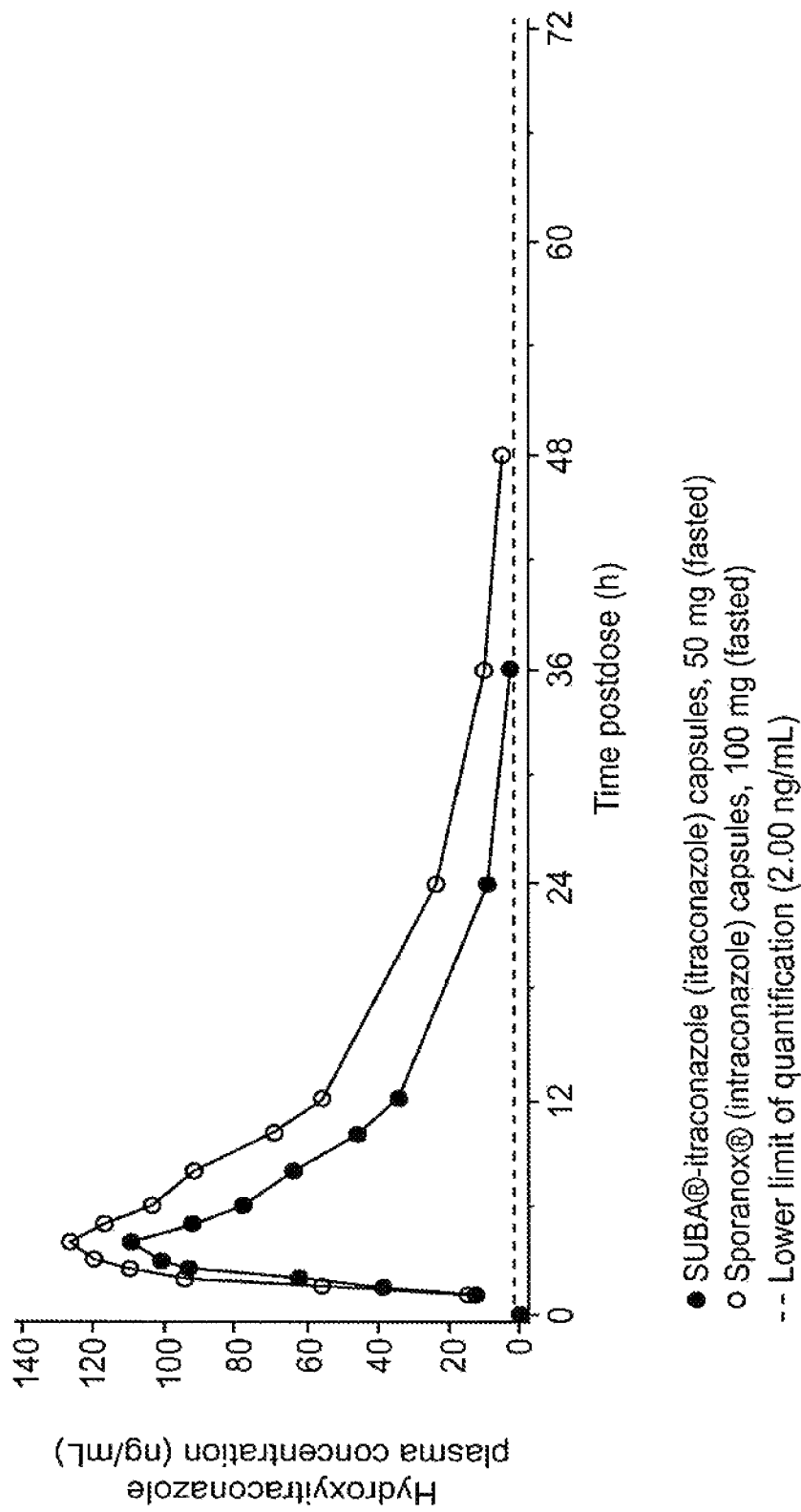
FIG. 41 shows a linear scale graph comparing the mean plasma hydroxyitraconazole concentration over time in a study assessing the relative bioavailability of a 50 mg LOZANOC dose with a 100 mg dose of SPORANOX® administered under fasted conditions. Closed circles represent the 50 mg LOZANOC dose administered under fasted conditions; open circles represent the reference SPORANOX® 100 mg dose administered under fasted conditions.
Figure 42:
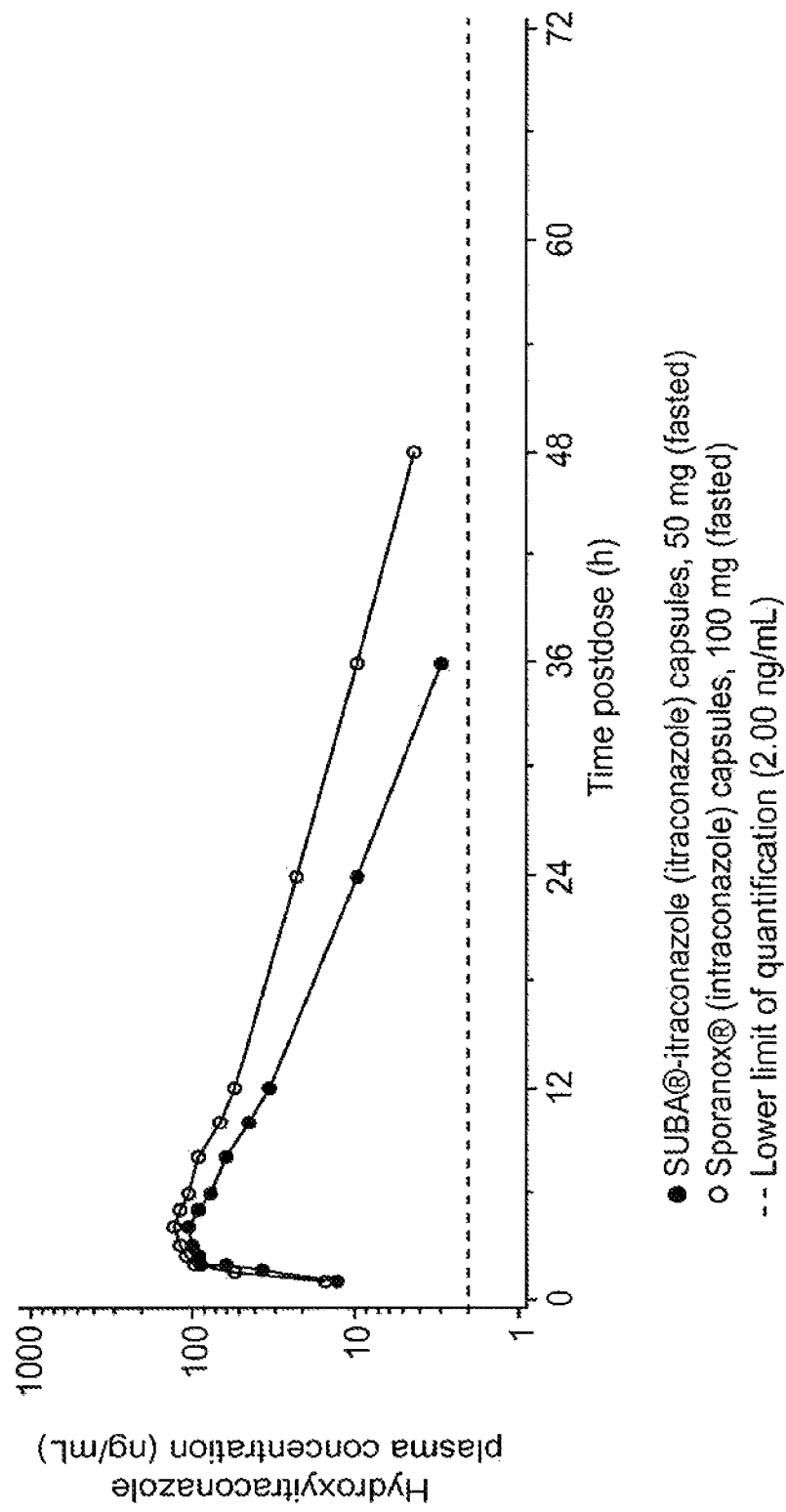
FIG. 42 shows a log-transformed scale graph comparing the mean plasma hydroxyitraconazole concentration over time in a study assessing the relative bioavailability of a 50 mg LOZANOC dose with a 100 mg dose of SPORANOX® administered under fasted conditions. Closed circles represent the 50 mg LOZANOC dose administered under fasted conditions; open circles represent the reference SPORANOX® 100 mg dose administered under fasted conditions.

Plasma concentrations of hydroxyitraconazole following administration of the LOZANOC and SPORANOX® (itraconazole) formulations in the fasted conditions are summarized in FIGS. 41 (linear) and 42 (log-transformed).

Figure 43:
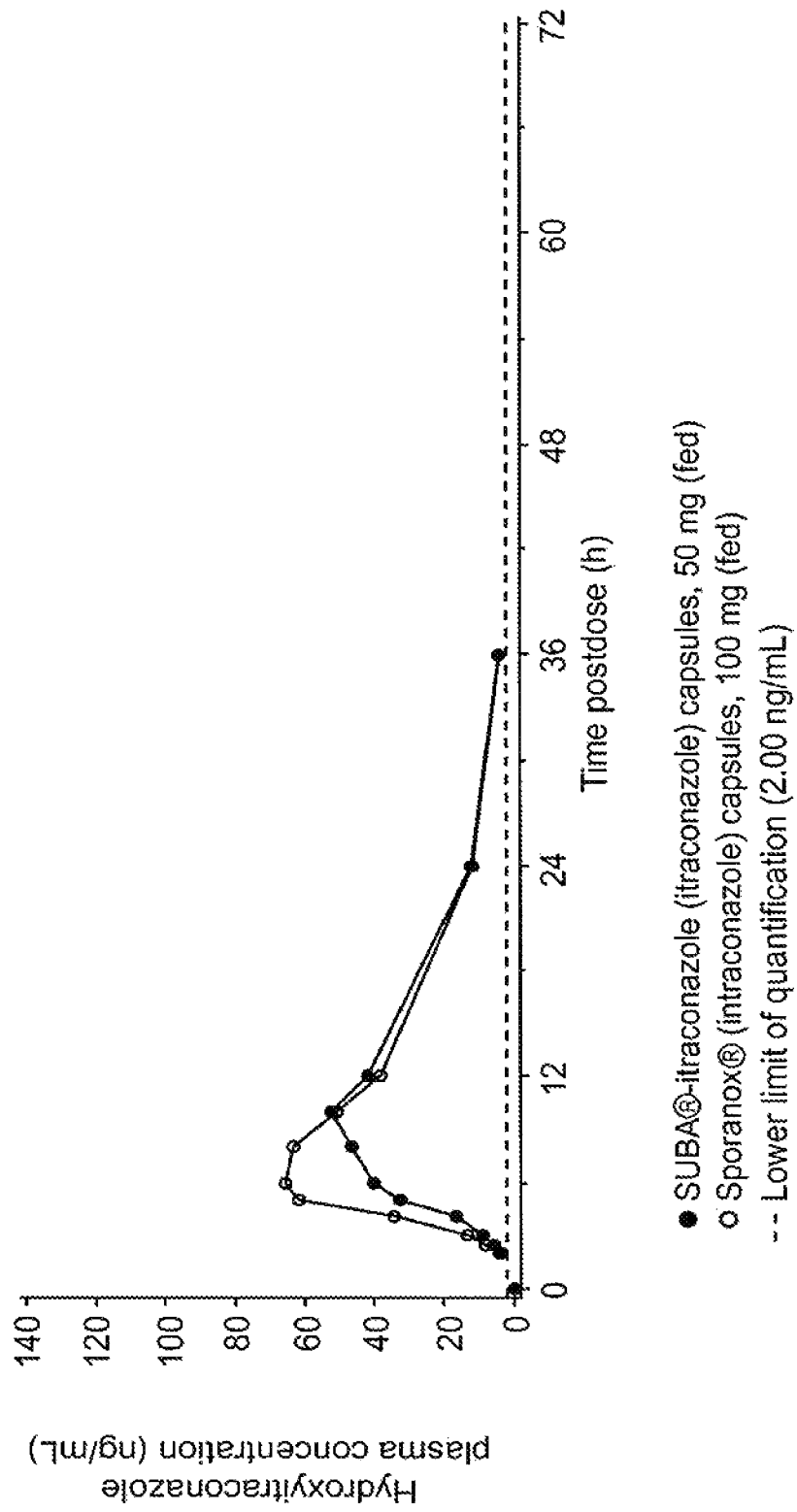
FIG. 43 shows a linear scale graph comparing the mean plasma hydroxyitraconazole concentration over time in a study assessing the relative bioavailability of a 50 mg LOZANOC dose with a 100 mg dose of SPORANOX® administered under fed conditions. Closed circles represent the 50 mg LOZANOC dose administered under fed conditions; open circles represent the reference SPORANOX® 100 mg dose administered under fed conditions.
Figure 44:
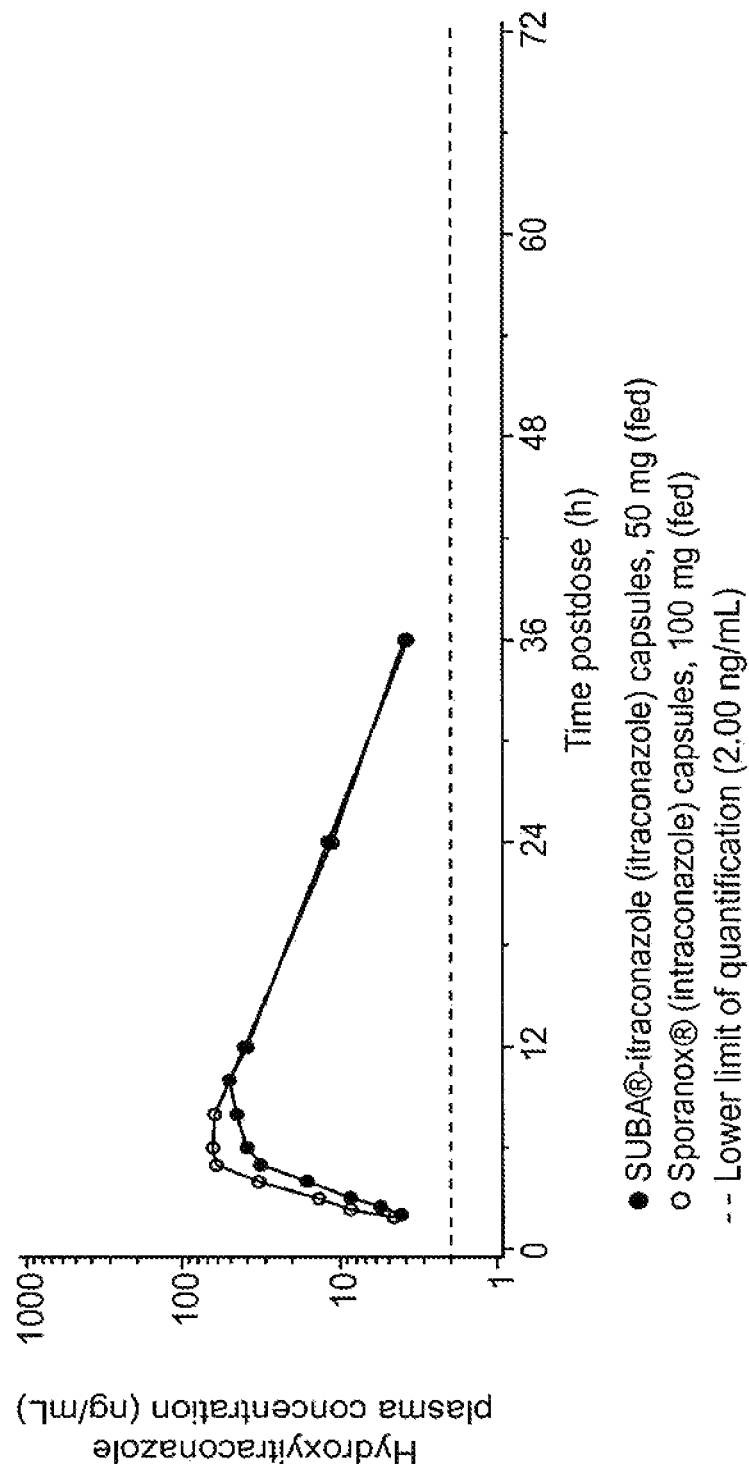
FIG. 44 shows a log-transformed scale graph comparing the mean plasma hydroxyitraconazole concentration over time in a study assessing the relative bioavailability of a 50 mg LOZANOC dose with a 100 mg dose of SPORANOX® under fed conditions. Closed circles represent the 50 mg LOZANOC dose administered under fed conditions; open circles represent the reference SPORANOX® 100 mg dose administered under fed conditions.

Plasma concentrations of hydroxyitraconazole following administration of the LOZANOC and SPORANOX® (itraconazole) formulations in the fed conditions are summarized in FIGS. 43 (linear) and 44 (log-transformed).

The pharmacokinetic parameters for hydroxyitraconazole are summarized in Table 45.

The metabolite hydroxyitraconazole was rapidly formed following administration of both the LOZANOC (50 mg) and SPORANOX® (100 mg) formulations in the fasted condition, with quantifiable levels in plasma being observed 0.5 hours after dosing. Maximum plasma concentrations of hydroxyitraconazole occurred at a median tmax of 3 to 4 hours for both formulations, with values ranging from 1.5 to 6 hours post dose in individual subjects). After reaching Cmax, plasma concentrations of hydroxyitraconazole appeared to decline in an apparent mono-phasic manner, with the start of the elimination phase generally ranging from 2.0 to 6.0 hours post dose for the LOZANOC formulation and 3.0 to 12.0 hours post dose for the SPORANOX® formulation. The mean apparent elimination half-life for hydroxyitraconazole was 6.4 and 10.0 hours for the LOZANOC and SPORANOX® formulations, respectively, with values ranging from 3.1 to 15.6 hours and 5.8 to 18.6 hours, respectively, in individual subjects. Systemic exposure to hydroxyitraconazole was higher than the parent drug following the administration of itraconazole as both the LOZANOC and SPORANOX® formulations. The extent of formation of the metabolite was similar for both formulations in the fed and fasted conditions as shown by the mean metabolic ratios with MRAUC ranging from 2.4 to 2.5 and MRCmax ranging from 2.0 to 2.1.

The statistical comparison of relative bioavailability of hydroxyitraconazole in the fasted condition is summarized in Table 46.

TABLE 45

Summary of the Pharmacokinetic Parameters for Hydroxyitraconazole
Following Administration of the LOZANOC and SPORANOX ®
(Itraconazole) Formulations in the Fasted and Fed Conditions

| | Treatments | | | |
|---|---|---|---|---|
| | 50 mg SUBA ®- itraconazole capsules | | 100 mg Sporanox ®- itraconazole capsules | |
| Parameters | Fasted (N = 35) | Fed (N = 36) | Fasted (N = 36) | Fed (N = 36) |
| $AUC_{0-tlast}$ (ng · h/mL) | 1132 (45.5) | 868 (49.1) | 1802 (50.2) | 890 (77.5) |
| $AUC_{0-\infty}$ (ng · h/mL) | 1163 (44.7) | 938$^b$ (46.2) | 1875 (47.6) | 931 (74.4) |
| $C_{max}$ (ng/mL) | 129 (31.1) | 71.2 (43.2) | 137 (42.0) | 76.7 (56.1) |
| $t_{max}$ (h) | 3.00 (1.50-5.15) | 8.00 (1.50-12.0) | 4.00 (2.00-6.02) | 6.00 (2.00-10.0) |
| $T_{lag}{}^a$ (h) | 0.500 (0-1.00) | 1.50 (0-8.02) | 0.500 (0-1.00) | 1.50 (0.500-4.00) |
| $T_{1/2}$ (h) | 644 (34.7) | 71.5$^b$ (27.7) | 10.0 (27.8) | 6.92 (28.8) |
| $MR_{AUC}$ | 2.51 (20.2) | 2.42 (24.7) | 2.46 (17.6) | 2.49 (30.1) |
| $MR_{Cmax}$ | 2.01 (31.5) | 2.12 (29.8) | 2.14 (29.2) | 2.12 (38.9) |

Geometric mean (CV %) data are presented
N = Number of subjects studied
$^a$Median (min-max)
$^b$N = 34

TABLE 46

Statistical Comparison of Relative Bioavailability of
Hydroxyitraconazole Following Administration of
50 mg LOZANOC and 100 mg SPORANOX ®
(Itraconazole) in the Fasted Condition

| Parameters | Geometric LS mean | | Ratio of geometric LS means SUBA ®:Sporanox ® 90% CI) |
|---|---|---|---|
| | 50 mg SUBA ®- itraconazole Fed | 100 mg Sporanox ® (itraconazole) Fasted | |
| $AUC_{0-tlast}$ (ng · h/mL) | 1127 | 1802 | 0.625 (0.569, 0.687) |

TABLE 46-continued

Statistical Comparison of Relative Bioavailability of
Hydroxyitraconazole Following Administration of
50 mg LOZANOC and 100 mg SPORANOX ®
(Itraconazole) in the Fasted Condition

| | Geometric LS mean | | |
|---|---|---|---|
| Parameters | 50 mg SUBA ®-itraconazole Fed | 100 mg Sporanox ® (itraconazole) Fasted | Ratio of geometric LS means SUBA ®:Sporanox ® 90% CI) |
| $AUC_{0-\infty}$ (ng · h/mL) | 1158 | 1875 | 0.618 (0.567, 0.673) |
| $C_{max}$ (ng/mL) | 128 | 137 | 0.935 (0.847, 1.03) |
| $t_{max}{}^a$ (h) | 3 | 4 | −0.508 (−1.00, −0.233) |

[a] Median difference (SUBA ®-itraconazole − Sporanox ®[itraconazole])

As for the parent drug, the extent of exposure to hydroxyitraconazole was lower (by up to 38% for AUC) when itraconazole was administered as the LOZANOC formulation compared to the SPORANOX® formulation. Maximum plasma concentrations were similar for both formulations and were attained at a median of 3 and 4 hours post dose for the LOZANOC and SPORANOX® formulations, respectively. The between-subject variability (geometric CV %, Table 47) was high for both formulations in the fasted condition and was generally similar, ranging from 45% to 48% for $AUC_{0-\infty}$ and 31% to 42% for Cmax. Differences in $AUC_{0-\infty}$ and Cmax of 5.5- and 3.9-fold for the LOZANOC formulation and 7.8- and 6.3-fold for the SPORANOX® formulation were observed in the maximum and minimum exposure for individual subjects.

Systemic exposure (based on AUC and Cmax) to hydroxyitraconazole mirrored that of the parent drug and was similar for both formulations when administered in the fed condition, with greater between-subject variability (geometric CV %) compared to the fasted condition also observed. The statistical comparison of the relative bioavailability of hydroxyitraconazole administered as 50 mg LOZANOC in the fasted condition and SPORANOX® in the fed condition is summarized in Table 48.

TABLE 47

Statistical Comparison of the Relative Bioavailability of
Hydroxyitraconazole Following Administration of
50 mg LOZANOC and 100 mg SPORANOX ®
(Itraconazole) in the Fed Condition

| | Geometric LS mean | | Ratio of geometric |
|---|---|---|---|
| Parameters | 50 mg SUBA ®-itraconazole | 100 mg Sporanox ® (itraconazole) | LS means SUBA ®:Sporanox ® (90% CI) |
| $AUC_{0-tlast}$ (ng · h/mL) | 868 | 890 | 0.975 (0.809, 1.18) |
| $AUC_{0-\infty}$ (ng · h/mL) | 941 | 931 | 1.01 (0.838, 1.22) |
| $C_{max}$ (ng/mL) | 71.2 | 76.7 | 0.928 (0.791, 1.09) |
| $t_{max}{}^a$ (h) | 8 | 6 | 1.99 (0.975, 2.50) |

[a] Median difference (SUBA ®-itraconazole − Sporanox ® [itraconazole])

TABLE 48

Statistical Comparison of Relative Bioavailability of
Hydroxyitraconazole Following Administration of
50 mg LOZANOC in the Fasted Condition and
100 mg SPORANOX ® (Itraconazole) in the Fed Condition

| | Geometric LS mean | | Ratio of geometric |
|---|---|---|---|
| Parameters | 50 mg SUBA ®-itraconazole | 100 mg Sporanox ® (itraconazole) | LS means SUBA ®:Sporanox ® (90% CI) |
| $AUC_{0-tlast}$ (ng · h/mL) | 1127 | 890 | 1.27 (1.07, 1.50) |
| $AUC_{0-\infty}$ (ng · h/mL) | 1159 | 931 | 1.24 (1.06, 1.46) |
| $C_{max}$ (ng/mL) | 128 | 76.7 | 1.67 (1.44, 1.93) |
| $t_{max}{}^a$ (h) | 3 | 6 | −2.75 (−3.25, −2.25) |

[a] Median difference (SUBA ®-itraconazole − Sporanox ® [itraconazole] fed)

Statistical assessment showed that systemic exposure, based upon AUC0-tlast, $AUC_{0-\infty}$ and Cmax for hydroxyitraconazole, was higher for the LOZANOC formulation (fasted) compared to the SPORANOX® formulation (fed). Median tmax occurred earlier for the SUBA® formulation (fasted) compared to the SPORANOX® formulation (fed). As for the parent drug, the between-subject variability (geometric CV %, Table 46) for hydroxyitraconazole was similar for each formulation and was generally higher when administered in the fed compared to the fasted condition. The magnitude of differences in the maximum and minimum exposure for individual subjects was lower for the LOZANOC formulation (fasted) compared to the SPORANOX® formulation (fed) i.e. 5.5- and 3.9-fold for $AUC_{0-\infty}$ and Cmax and 12.5- and 8.3-fold, respectively.

Effect of Dietary Condition on Hydroxyitraconazole Exposure

The statistical assessment of the effect of dietary condition on the pharmacokinetics of hydroxyitraconazole is summarized in Table 49 and Table 50.

As for the parent drug, statistical assessment showed AUC0-tlast, $AUC_{0-\infty}$ and Cmax for hydroxyitraconazole to be lower for each formulation when administered in the fed compared to the fasted condition. The effect of food appeared more marked for the SPORANOX® formulation compared to the LOZANOC formulation.

TABLE 49

Statistical Comparison of the Effect of Dietary
Condition on Hydroxyitraconazole Exposure
Following Administration of 50 mg
LOZANOC in the Fed and Fasted Conditions

| | Geometric LS mean 50 mg SUBA ®-itraconazole capsules | | Ratio of geometric LS means Fed:Fasted |
|---|---|---|---|
| Parameters | Fed | Fasted | (90% CI) |
| $AUC_{0-tlast}$ (ng · h /mL) | 868 | 1136 | 0.764 (0.705, 0.829) |
| $AUC_{0-\infty}$ (ng · h/mL) | 929 | 1170 | 0.794 (0.733, 0.861) |
| $C_{max}$ (ng/mL) | 71.2 | 129 | 0.553 (0.493, 0.622) |
| $t_{max}{}^a$ (h) | 8 | 3 | 4.50 (3.50, 5.49) |

[a] Median difference (fed − fasted)

TABLE 50

Statistical Comparison of the Effect of Dietary Condition on
Hydroxyitraconazole Exposure Following Administration
of 100 mg SPORANOX ®
(Itraconazole) in the Fed and Fasted Conditions

| Parameters | Geometric LS mean 100 mg Sporanox ®- itraconazole capsules | | Ratio of geometric LS means Fed:Fasted |
| --- | --- | --- | --- |
| | Fed | Fasted | (90% CI) |
| $AUC_{0\text{-}tlast}$ (ng · h/mL) | 890 | 1802 | 0.494 (0.425, 0.574) |
| $AUC_{0\text{-}\infty}$ (ng · h/mL) | 931 | 1875 | 0.497 (0.428, 0.576) |
| $C_{max}$ (ng/mL) | 76.7 | 137 | 0.561 (0.494, 0.636) |
| $t_{max}^{a}$ (h) | 6 | 4 | 2.01 (1.51, 2.75) |

$^{a}$ Median difference (fed – fasted)

Between-subject variability was high for itraconazole AUC and Cmax for both formulations. Higher variability was noted in the fed compared to the fasted condition and also for the SPORANOX® compared to the LOZANOC formulation.

Administration of itraconazole as the 50 mg LOZANOC formulation in the fasted condition provided similar overall exposure (AUC0-∞) compared to the 100 mg SPORANOX® formulation in the fed condition with approximately 1.8-fold higher Cmax and lower between-subject variability.

The pharmacokinetics of hydroxyitraconazole reflected those of the parent drug following administration of the LOZANOC and SPORANOX® formulations in the fed and fasted conditions.

Analysis of Adverse Events

Headache was the most frequently reported drug-related adverse event. A total of 7 episodes were reported by 4 subjects, with 3 of these subjects reporting headache in at least 2 treatment periods. One subject experienced single episodes of mild to moderate headache following 100 mg SPORANOX® in both the fed and fasted conditions; one subject experienced single episodes of mild headache following 50 mg LOZANOC in both the fed and fasted conditions; one subject experienced a single episode of moderate headache following 50 mg LOZANOC (fasted) and Subject 23 experienced single episodes of mild to moderate headache following 50 mg LOZANOC (fasted) and 100 mg SPORANOX® (fasted). Episodes of headache occurred between approximately 2 hours and 6 days post dose and lasted between approximately 3 hours and 7 days. All 4 subjects required concomitant medication (paracetamol) for the treatment of headache.

Fatigue was the second most frequently reported drug-related adverse event, with single episodes reported by 4 subjects (2 subjects following 50 mg LOZANOC [fed] and 2 subjects following 100 mg SPORANOX® [fasted]). All episodes of fatigue were mild in severity and resolved without treatment, occurring between 33 minutes and 5 hours post dose and lasting from 30 minutes to approximately 23 hours. The only other drug-related adverse event reported by 2 subjects was rash following 50 mg LOZANOC in the fed condition. All other drug-related adverse events were single episodes only and included lethargy, abdominal pain, diarrhea and dry lips.

Discussion

This study investigated the relative bioavailability of itraconazole when administered as 50 mg LOZANOC and 100 mg SPORANOX® (itraconazole) capsule formulations in both the fed and fasted conditions. The administration of itraconazole as the 50 mg LOZANOC formulation compared to the clinically used 100 mg SPORANOX® formulation in the fasted condition was found to provide similar maximum plasma concentrations, however systemic exposure (based upon AUC) was lower overall. In the fed condition, exposure to itraconazole was lower than observed in the fasted condition for both formulations and, although food appeared to have a greater impact on the SPORANOX® formulation compared to the LOZANOC formulation, AUC0-∞ and Cmax were similar for both formulations.

The between-subject variability for AUC and Cmax was also high for both itraconazole formulations, being greater in the fed compared to the fasted condition, as was the magnitude of difference in the maximum and minimum exposure for individual subjects. Higher between-subject variability, however, was noted for the SPORANOX® compared to the LOZANOC formulation in the fed condition.

Administration of the LOZANOC formulation in the fasted condition was shown to have advantages over the SPORANOX® formulation in the fed condition regarding itraconazole exposure. The LOZANOC formulation provided a more rapidly attained and higher Cmax (1.8-fold higher), similar AUC0-∞, and lower between-subject variability for administration of half the required itraconazole dose (50 mg vs. 100 mg).

Single oral doses of itraconazole as 50 mg LOZANOC and 100 mg SPORANOX® formulations were safe and well tolerated by healthy male and female subjects in this study. Both adverse events observed during this study were not considered to be drug-related. There were no severe adverse events reported for the study. The overall incidence of drug-related adverse events was low and slightly higher for the LOZANOC formulation compared to the SPORANOX® formulation in both the fed and fasted conditions, respectively.

Between-subject variability was noted for itraconazole AUC and Cmax for both formulations. Higher variability was noted in the fed compared to the fasted condition and also for the SPORANOX® compared to the LOZANOC formulation.

Administration of itraconazole as the 50 mg LOZANOC formulation in the fasted condition provided similar overall exposure (AUC0-∞) compared to the 100 mg SPORANOX® formulation in the fed condition with approximately 1.8-fold higher Cmax and lower between-subject variability.

The pharmacokinetics of hydroxyitraconazole reflected those of the parent drug following administration of the LOZANOC and SPORANOX® formulations in the fed and fasted conditions.

Single oral doses of itraconazole administered as the 50 mg LOZANOC and 100 mg SPORANOX® formulations were considered to be safe and well tolerated when administered to healthy male and female subjects in the fed and fasted conditions in this study.

Example 11—Variability Analysis of the Studies Described in Examples 10 and 9

The main purpose of the studies conducted was to assess bioequivalence of 50 mg capsules of the oral solid dosage form of the present invention with SPORANOX® 100 mg capsules. However, we also assessed the data from the two SPORANOX® 100 mg capsules administrations for "bioequivalence" to itself. The results of this analysis are shown in Table 51.

TABLE 51

"Bioequivalence" analysis of SPORANOX® 100 mg
capsules first and second occurrence

|  | AUC Ratio | $C_{max}$ Ratio |
|---|---|---|
| Sporanox | 0.802 (0.654-0.984) | 0.792 (0.648-0.969) |

The AUC data show that the ratio of means fell just within 80-125% but the lower boundary of the 90% confidence interval was at only 65.4% of nominal. Furthermore, the upper boundary of the AUC ratio did not include 1.00. The Cmax data were similar (ratio of means very close 5 to 80%; lower boundary of 90% CI at 64.8%; upper boundary of 90% CI below 1.00). The data shows a difference in bioavailability between consecutive SPORANOX® 100 mg capsule administrations. This demonstrates that the bioavailability of itraconazole from SPORANOX® 100 mg capsules is subject to wide variation, even when dosed on separate occasions in the same subject population.

The outcome of the corresponding analysis for the oral solid dosage form of the present invention in the form of 50 mg capsules is shown in Table 52. The ratio of AUC means is close to unity and the 90% CI falls within 80-125%. For Cmax, the intra-subject CV % for both administrations was 33.3% and so the lower boundary of the required 90% CI for the ratio of means will fall slightly below 0.80.

TABLE 52

"Bioequivalence" analysis of SUBACAP ™ 50
mg capsules first and second occurrence

|  | AUC Ratio | $C_{max}$ Ratio |
|---|---|---|
| SUBACAP | 0.985 (0.811-1.110) | 0.901 (0.778-1.04) |

It is known that the absorption of itraconazole from SPORANOX® 100 mg capsules is highly variable. By reducing the variability prescribers can be more confident of the exposure obtained by each patient. It is therefore relevant, when comparing 50 mg capsules of the oral solid dosage form of the present invention and SPORANOX® 100 mg capsules, to use clinical pharmacology data to understand:
  1) The probability that a patient receiving a 50 mg capsule oral solid dosage form of the present invention will achieve a lower exposure than is necessary for therapeutic effect, compared to the corresponding probability with SPORANOX® 100 mg capsules.
  2) The probability that a patient receiving a 50 mg capsule oral solid dosage form of the present invention will achieve a much greater exposure than is necessary compared to the corresponding probability with SPORANOX® 100 mg capsules.

In order to assess the performance of 50 mg capsules of the oral solid dosage form of the present invention in this way the data was analyzed at the individual level. Accordingly, the following analyses, all based on AUC0-∞ following single administration in the fed state, are presented below:

Analysis of median, range and inter-quartile range (IQR) for Study 1 (Example 9) and Study 2 (Example 10).
  1) Comparative graphs of AUC values in Study 1.
  2) Comparative graphs of AUC values in Study 2.
  3) Box plots and Bartlett's tests (to investigate differences in variability between formulations).
  4) Ratio of AUC0-00 to minimum inhibitory concentration (AUC/MIC) data 5 for Study 1 and Study 2.

AUC0-∞ was selected for the above analyses based on recommendations by Moulton et al (Mouton, Dudley et al. 2005). Data were excluded in cases where AUC0-∞ required >30% extrapolation from AUC(0-t last).

For all Box-plots presented, height of box and whiskers indicate variability of AUC. Box-plots show: lower hinge=25% quantile, middle=median (50% quantile), upper hinge=75% quantile. Lower whisker=lower hinge−1.5×interquartile range (IQR), and upper whisker=upper hinge+1.5×IQR. Outliers outside the lower and upper whiskers are shown as points.

The Bartlett's test (Snedecor and Cochran, (1989), Statistical Methods, Eighth Edition, Iowa State University Press) is used to test if k samples have equal variances. Bartlett's test is sensitive to departures from normality. The Bartlett's test examines the hypothesis that two distributions have different variability (e.g. as characterized by standard deviation) regardless of mean or median value of the distribution. A p-value of 0.05 was used as the cut-off for statistical significance. The Bartlett's test outcome is presented under each Box-plot, with a comparison of the results presented in Table 53.

Study 1

Figure 45:
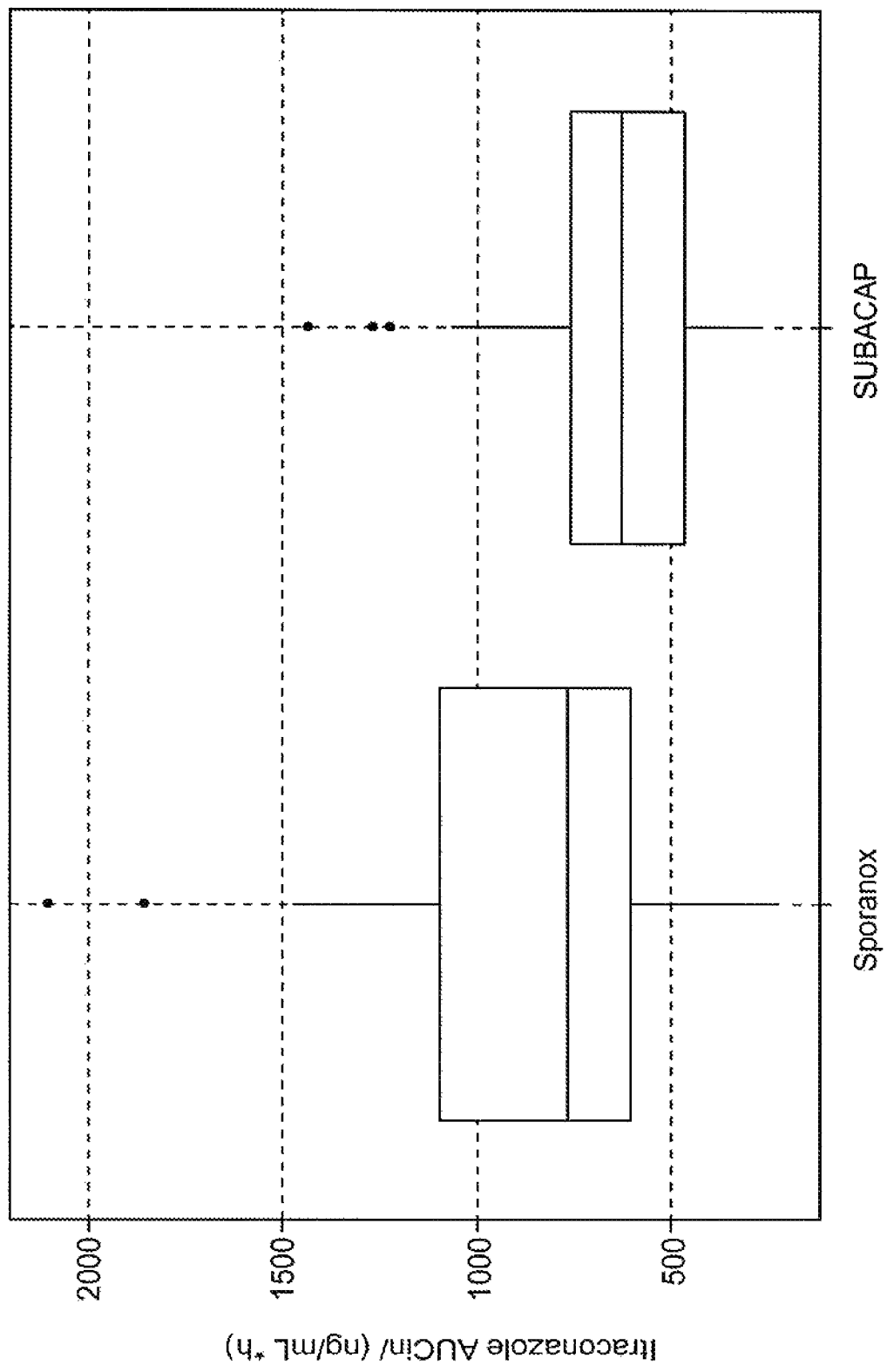
FIG. 45 shows a Box-plot analysis by formulation of the combined fed state and fasted state AUC(0-∞) data in Example 9.

The median, IQR and range of 50 mg capsule oral solid dosage forms of the present invention and SPORANOX® 100 mg Capsules AUC0-∞ in Study 1 are shown in Table 53. The corresponding Box-plots are presented in FIGS. 45-47.

TABLE 53

Analysis of median, IQR and range in Study 1

AUC0-∞ (ng.h/ml)

| Parameter | 50 mg capsule oral solid dosage forms of the present invention | | | Sporanox | | |
|---|---|---|---|---|---|---|
|  | FASTED | FED | FED & FASTED | FASTED | FED | FED & FASTED |
| Number of data points | N = 25 | N = 26 | N = 50 | N = 33 | N = 28 | N = 58 |
| Median | 699 | 515 | 632 | 868 | 527 | 765 |
| IQR | 534-812 | 681 | 472-755 | 701-1168 | 423-922 | 608-1092 |
| $Q_3$-$Q_1$ | 278 | 297 | 284 | 467 | 499 | 483 |
| Range | 336-1267 | 249-1435 | 249-1435 | 576-2101 | 216-1254 | 216-2101 |

The Bartlett's test of homogeneity of variances for untransformed AUC gave a p-value of 0.002, which indicates that the variance was significantly different between the two formulations when the results of each formulation with and without food are pooled. It is apparent from FIG. 45 that the 50 mg capsule oral solid dosage form of the present invention has a less variable AUC0-∞ than the SPORANOX® 100 mg capsule formulation.

Figure 46:
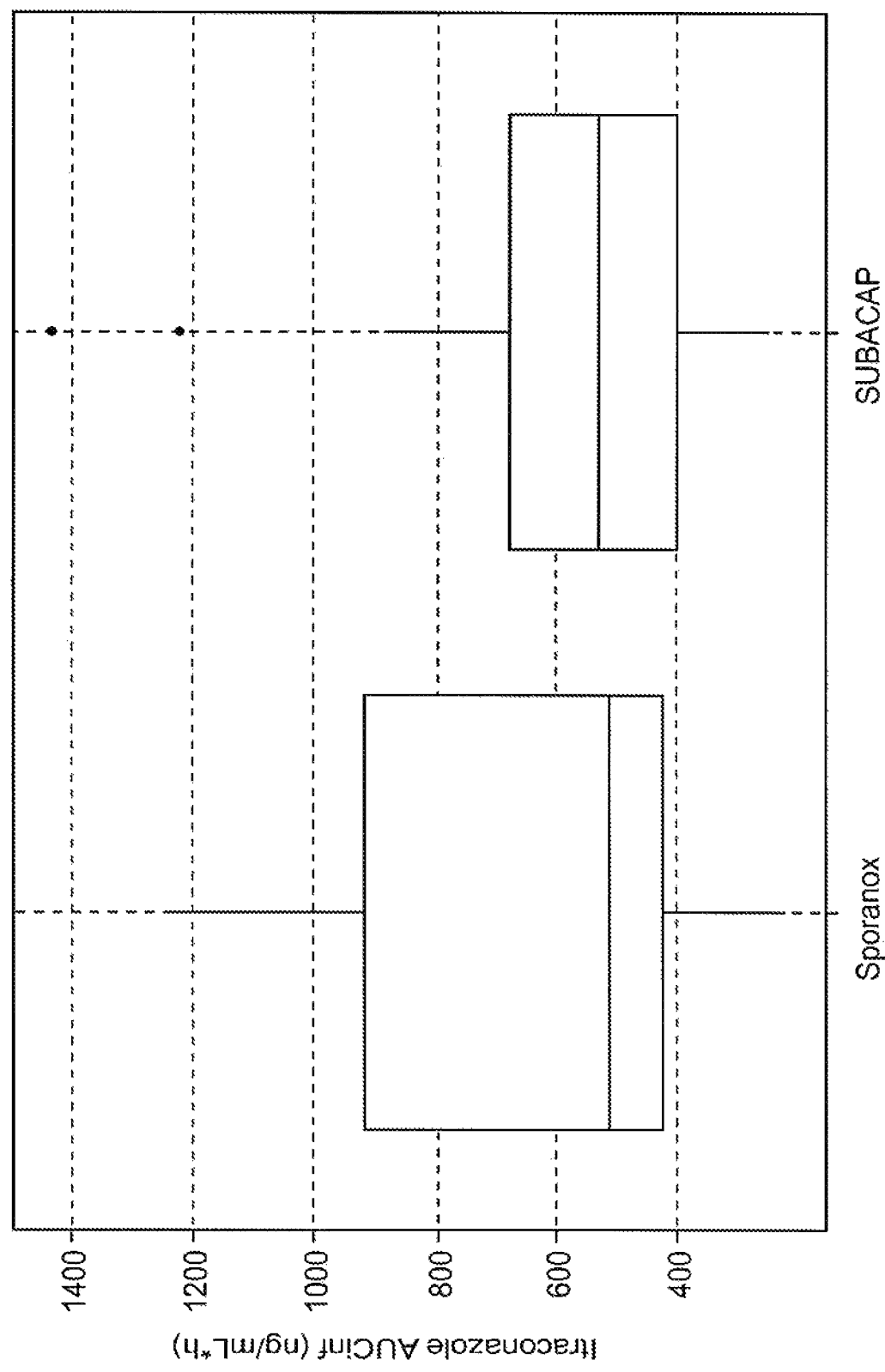
FIG. 46 shows a Box-plot analysis of AUC(0-∞) in Example 9 by formulation in a fed state only.

It is apparent from the Box-plot of FIG. 46 that the 50 mg capsule oral solid dosage form of the present invention is less variable with respect to AUC0-∞ than the SPORANOX® 100 mg capsule formulation in the fed state.

Figure 47:
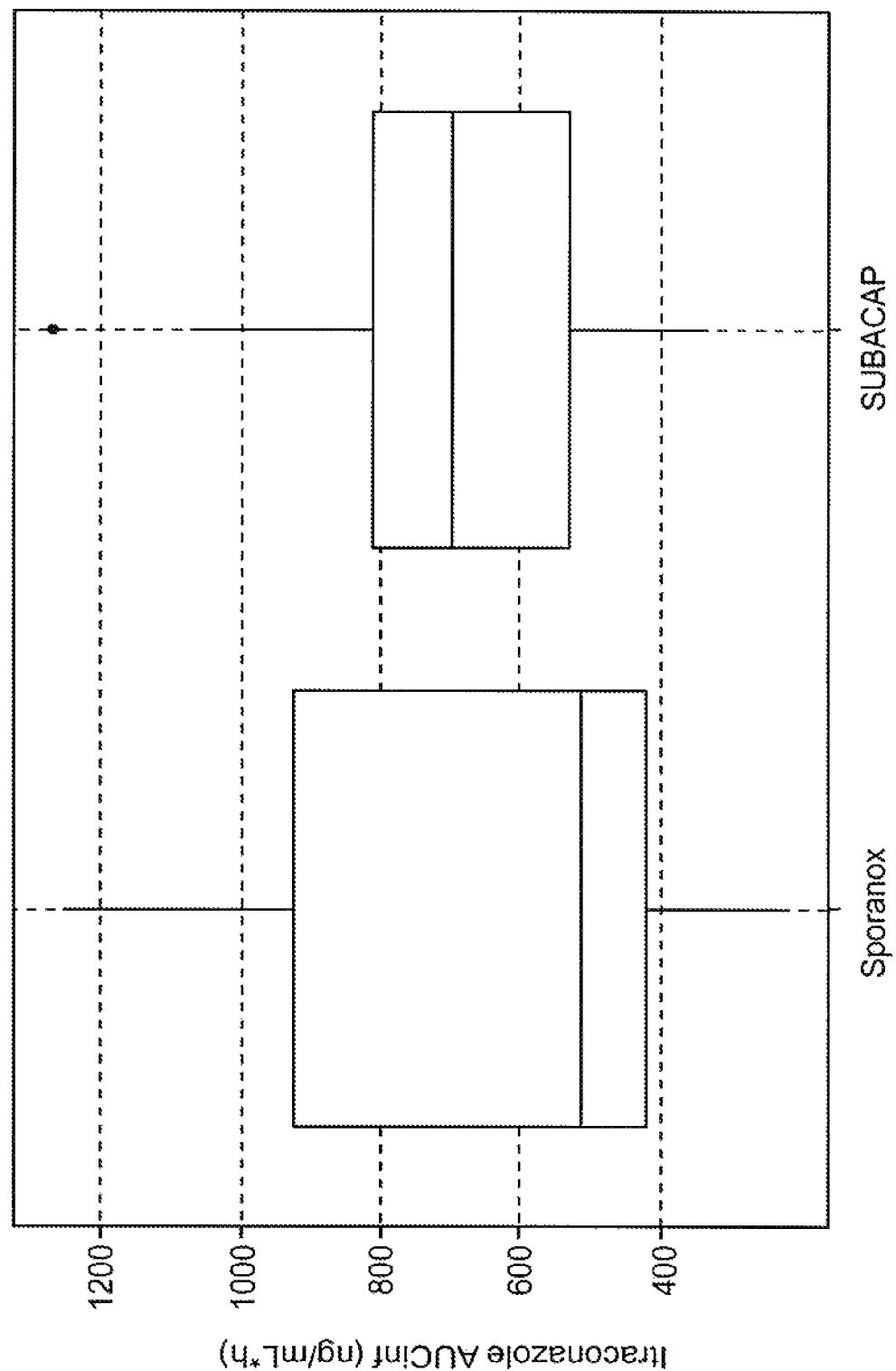
FIG. 47 shows a Box-plot analysis of AUC(0-∞) in Example 9—Sporanox® 100 mg capsules in a fed state versus 50 mg capsules of the solid oral dosage form of LOZANOC in a fasted state.

It is apparent from the Box-plot of FIG. 47 that the 50 mg capsule oral solid dosage form of the present invention in the fasted state is less variable than the Sporanox® 100 mg capsule formulation in the fed state.

Figure 48:
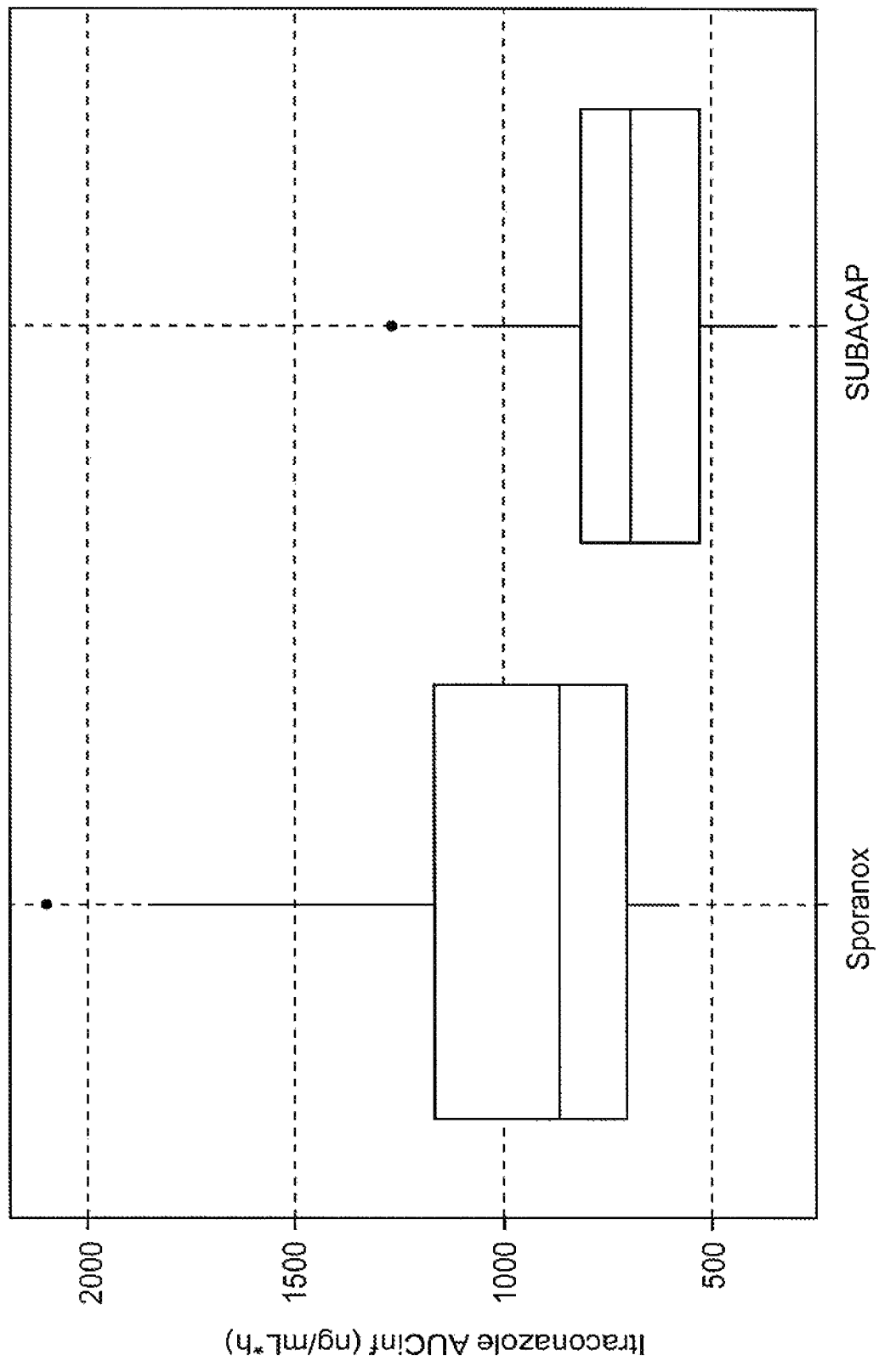
FIG. 48 shows a Box-plot analysis of AUC(0-∞) in Example 9 by formulation in a fasted state only.

It is apparent from FIG. 48 that the 50 mg capsule oral solid dosage form of the present invention is less variable than the SPORANOX® 100 mg capsule formulation, both in the fasted state. The Bartlett's test of homogeneity of variances for untransformed AUC gave a p-value of 0.006, which indicates that the variance was significantly different between the two formulations in the fasted state.

Study 2

Figure 49:
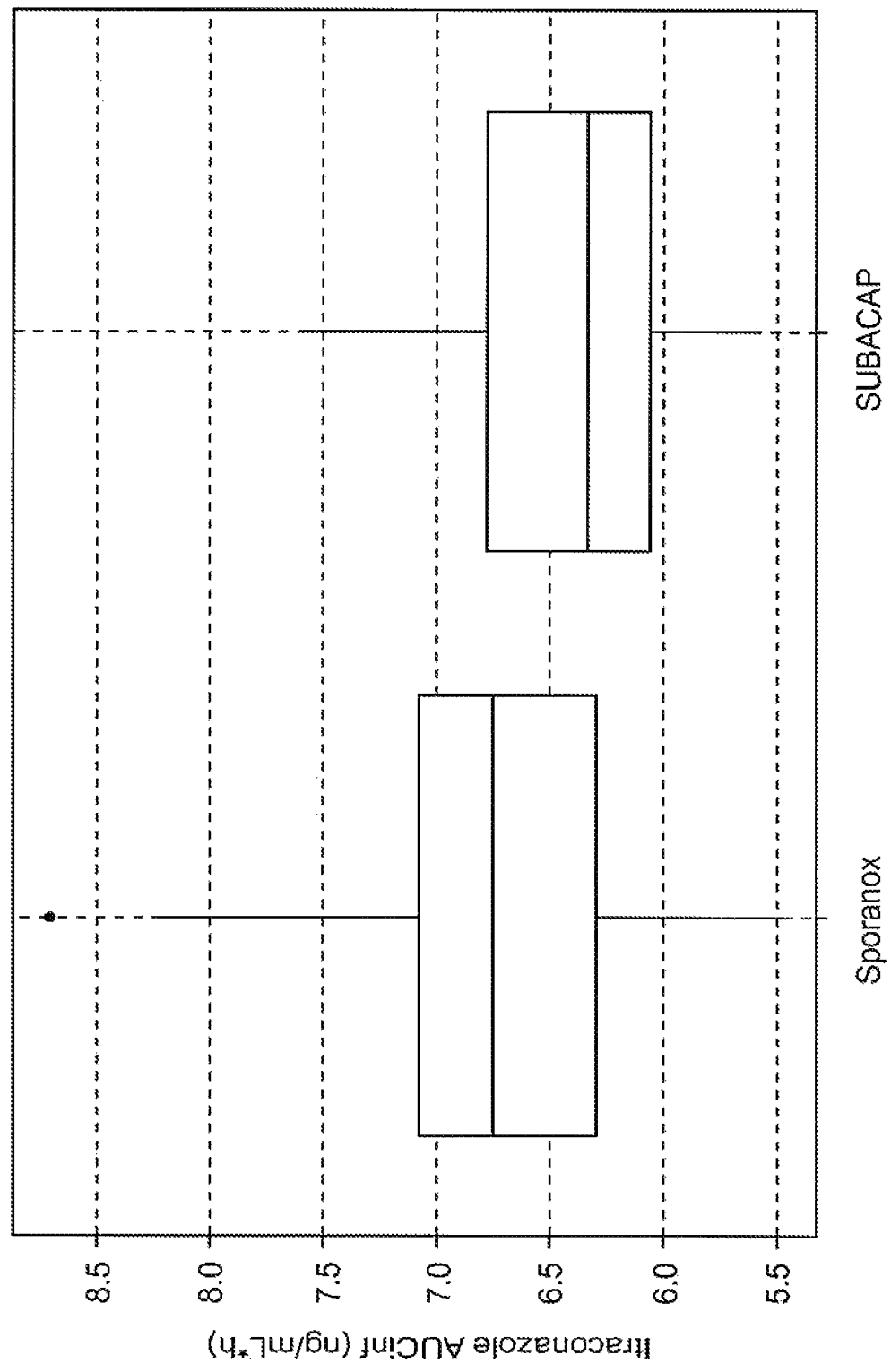
FIG. 49 shows a Box-plot analysis of AUC(0-∞) in Example 10 by formulation—both occurrences combined.
Figure 50:
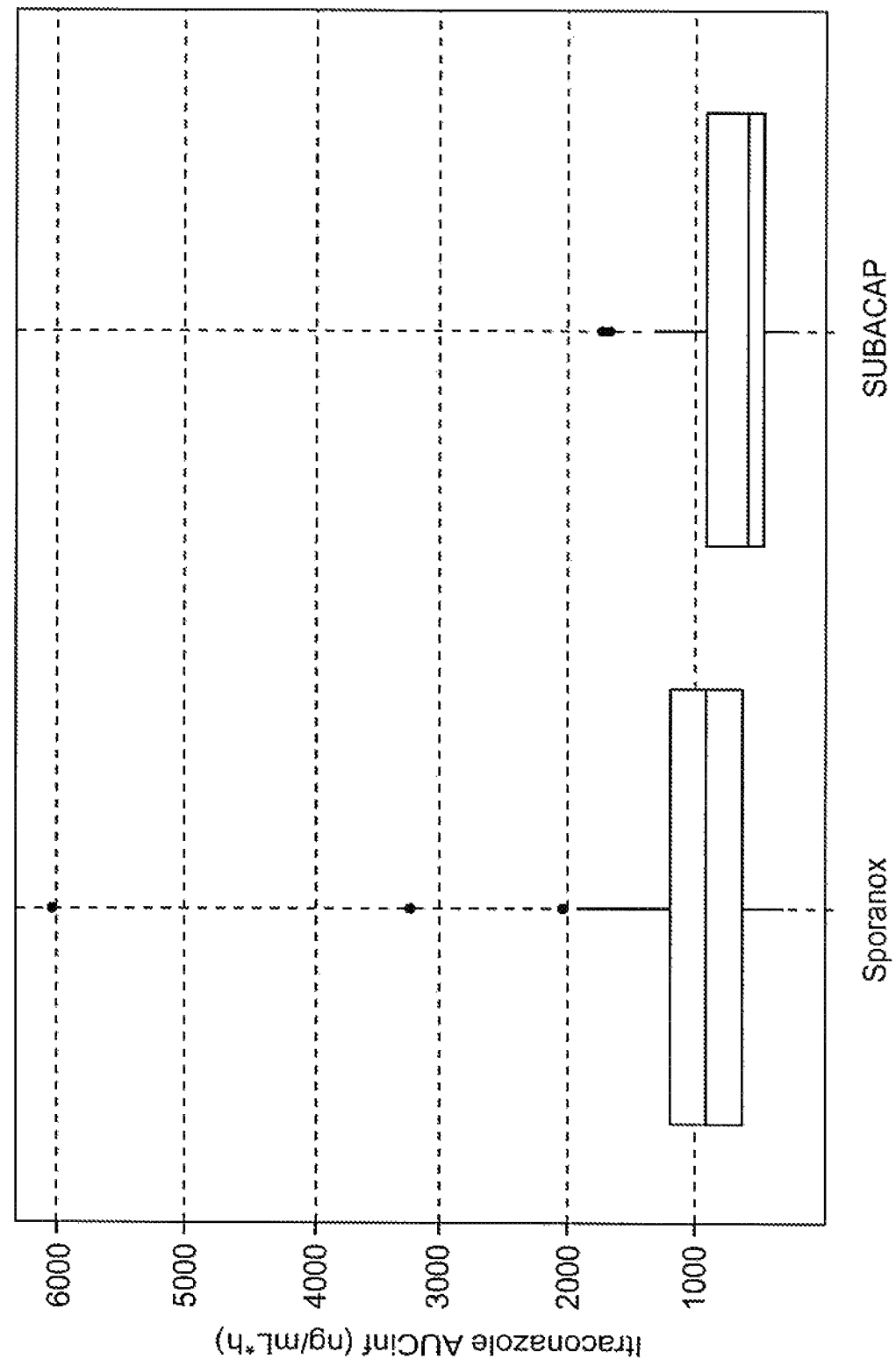
FIG. 50 shows a Box-plot analysis of AUC(0-∞) in Example 10 by formulation—second occurrence only.

The median, IQR and range of 50 mg capsule oral solid dosage forms of the present invention and SPORANOX® 100 mg capsules AUC0-∞ in Study 2 are shown in Table 54. Corresponding Box-plot analyses are shown in FIGS. 49 and 50.

TABLE 54

Analysis of median, IQR and range in Study 2 (fed only)

| | $AUC_{0-\infty}$ (ng · h/ml) | |
| --- | --- | --- |
| Parameter | 50 mg capsule oral solid dosage forms of the present invention | Sporanox |
| First administration | | |
| Number of data points | N = 32 | N = 38 |
| Median | 505 | 765 |
| IQR | 416-882 | 456-1155 |
| $Q_3$-$Q_1$ | 466 | 699 |
| Range | 299-1981 | 239-1816 |
| Second administration | | |
| Number of data points | N = 35 | N = 38 |
| Median | 596 | 922 |
| IQR | 463-935 | 656-1211 |
| $Q_3$-$Q_1$ | 472 | 555 |
| Range | 267-1723 | 269-6026 |

The Bartlett's test of homogeneity of variances for untransformed AUC gave a p-value of <0.001, which indicates that the variance was significantly different between the two formulations when the results from each occurrence are pooled. FIG. 49 shows that the 50 mg capsule oral solid dosage form of the present invention is less variable than the SPORANOX® 100 mg capsule formulation.

The Bartlett's test of homogeneity of variances for untransformed AUC gave a p-value of <0.001, which indicates that the variance is significantly different between the two formulations for the second occurrence. FIG. 50 shows that the 50 mg capsule oral solid dosage form of the present invention is less variable than the SPORANOX® 100 mg capsule formulation, with two high outlying observations in the SPORANOX® 100 mg capsule group.

Figure 51:
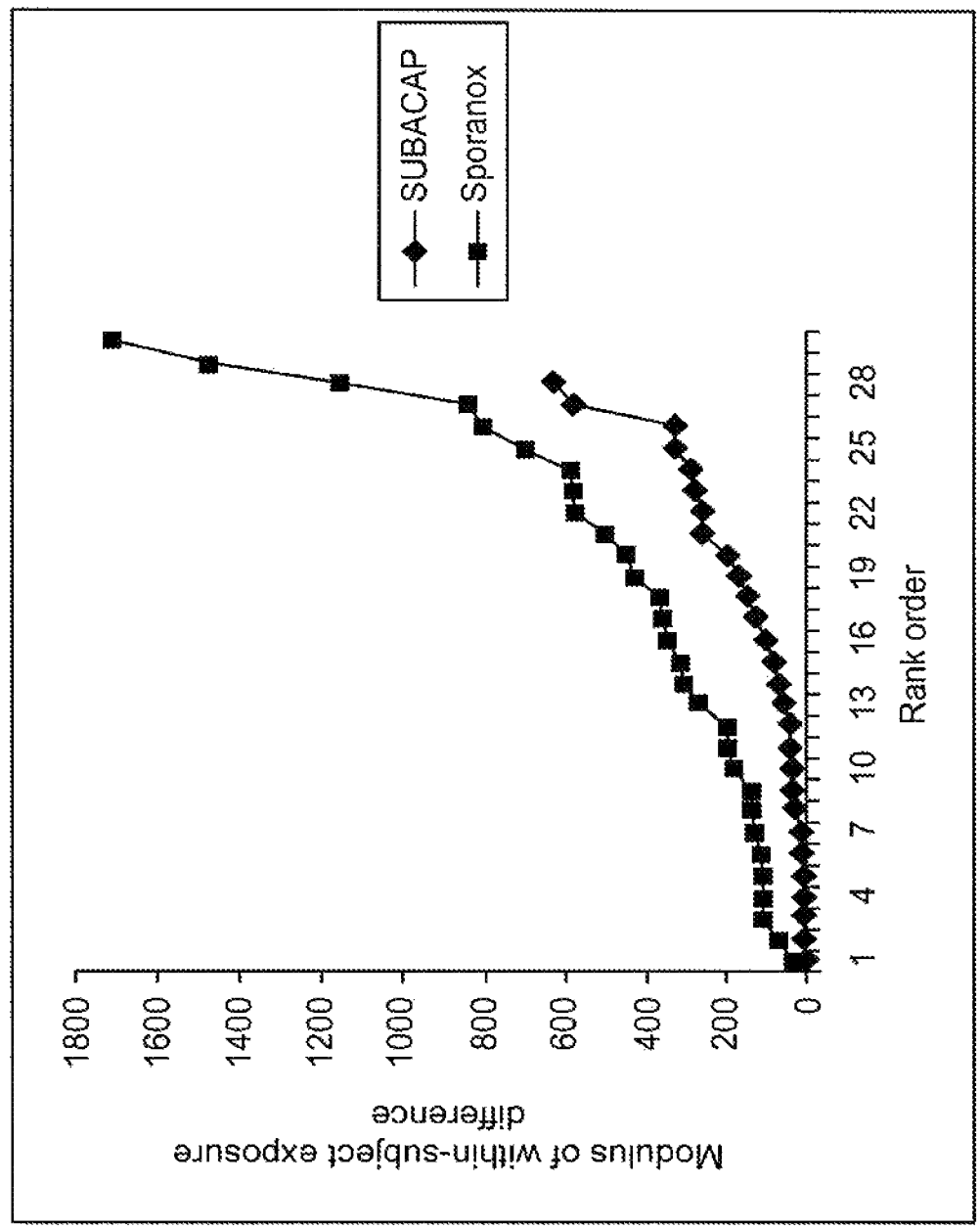
FIG. 51 is a plot showing the magnitude of within-subject variability of AUC(0-∞) in Study 2—50 mg capsules of the solid oral dosage form of LOZANOC versus Sporanox® 100 mg capsules.

The fact that Study 2 was of replicate design also allowed investigation of the within-patient variability between two separate administrations. The modulus (|m|) of the difference between the two AUC0-∞ values was calculated for each data pair. These datasets were then used to assess the within-subject variability of 50 mg capsule oral solid dosage form of the present invention as compared to SPORANOX® 100 mg capsule formulation (Table 55). The greater within-subject variability associated with Sporanox is easily visualized when the ranked modulus values are plotted according to magnitude (FIG. 51). Note that FIG. 51 excludes an outlier SPORANOX® 100 mg capsule formulation modulus value of 4934 ng·h/ml. Thus, it can be concluded that there is a dramatic difference in favor of the oral solid dosage form of the present invention regarding the within-subject reproducibility of dosing.

As mentioned, the Bartlett's test examines the hypothesis that two distributions have different variability (e.g. as characterized by standard deviation) regardless of mean or median value of the distribution. A p-value of 0.05 was used as the cut-off for statistical significance. Table 56 summarizes the Bartlett's test results from the AUC distribution analyses on Studies 1 and 2.

TABLE 55

Within subject variability of AUC0-∞ in Study 2-50 mg capsule oral solid dosage form of the present invention versus SPORANOX ® 100 mg capsules

| | Within-Subject Variation in $AUC_{(0-\infty}$ (ng · hr/ml) | |
| --- | --- | --- |
| Parameter | 50 mg capsule oral solid dosage forms of the present invention | Sporanox |
| Number of replicate values | N = 28 | N = 31 |
| $\Sigma^{|m|}$ | 4141 | 18091 |
| Arithmetic mean | 147.9 | 583.6 |
| Geometric mean | 60.5 | 320.8 |
| Median | 77 | 337 |
| IQR | 16-258 | 132-585 |
| Range | 1-624 | 33-4934 |
| Bartlett's test result | P < 0.001 | |

TABLE 56

Summary of Bartlett's test Results-Study 1 and 2

| STUDY | COMPARISON | p-VALUE |
| --- | --- | --- |
| 1 | 50 mg capsule oral solid dosage forms of the present invention vs Sporanox-fed and fasted pooled | 0.002* |
| | 50 mg capsule oral solid dosage forms of the present invention vs Sporanox-fed state only | 0.494 |
| | 50 mg capsule oral solid dosage forms of the present invention vs Sporanox-fasted state only | 0.087 |
| | 50 mg capsule oral solid dosage forms of the present invention fasted vs Sporanox fed | 0.006* |
| 2 | 50 mg capsule oral solid dosage forms of the present invention vs Sporanox-both occurances pooled | <0.001* |

TABLE 56-continued

Summary of Bartlett's test Results-Study 1 and 2

| STUDY | COMPARISON | p-VALUE |
|---|---|---|
| | 50 mg capsule oral solid dosage forms of the present invention vs Sporanox-1$^{st}$ occurance | 0.660 |
| | 50 mg capsule oral solid dosage forms of the present invention vs Sporanox-2$^{nd}$ occurance | <0.001* |

*Statiscally significant as p < 0.05

The following conclusions can be made from review of Table 56:

1) In Study 1, the variance in AUC0-∞ for the 50 mg capsule oral solid dosage form of the present invention is significantly lower than SPORANOX® 100 mg capsules when the fed and fasted data are pooled, which in part is due to the variance being significantly less when the 50 mg capsule oral solid dosage form of the present invention is taken in the fasted state versus SPORANOX® 100 mg capsules in the fed state.

2) In Study 2, the variance in AUC0-∞ for the 50 mg capsule oral solid dosage form of the present invention is significantly lower than SPORANOX® 100 mg capsules due to the "second occurrence" effect that was observed for SPORANOX® 100 mg capsules but not for the 50 mg capsule oral solid dosage form of the present invention.

Thus, one would expect that the exposure following administration of a 50 mg capsule oral solid dosage form of the present invention can be more reliably predicted than for SPORANOX® 100 mg capsules, regardless of whether taken in the fed or the fasted state.

It may be noted that the Box-plot analyses also indicate that less drug is delivered from a 50 mg capsule oral solid dosage form of the present invention than a SPORANOX® 100 mg capsule. However, this observation is consistent with bioequivalence analyses conducted from Study 1 and Study 2 (Table 57), where in the fed state the AUC(0-72 h) exposure from 50 mg capsule oral solid dosage forms of the present invention was bioequivalent in Study 1 and more than 20% lower in Study 2.

TABLE 57

Relative bioavailability of 50 mg capsules of the oral solid dosage form of the present invention and SPORANOX ® 100 mg capsules in Studies 1 and 2

| STUDY | Food status | AUC$_{(0-72h)}$ ratio (SUBACAP/Sporanox) (90% CI) |
|---|---|---|
| 1 | Fed | 1.00 |
| | | (0.827, 1.22) |
| | Fasted | 0.611 |
| | | (0.557, 0.670) |
| 2 | Fed | 0.774 |
| | | (0.696, 0.861) |

Figure 52:
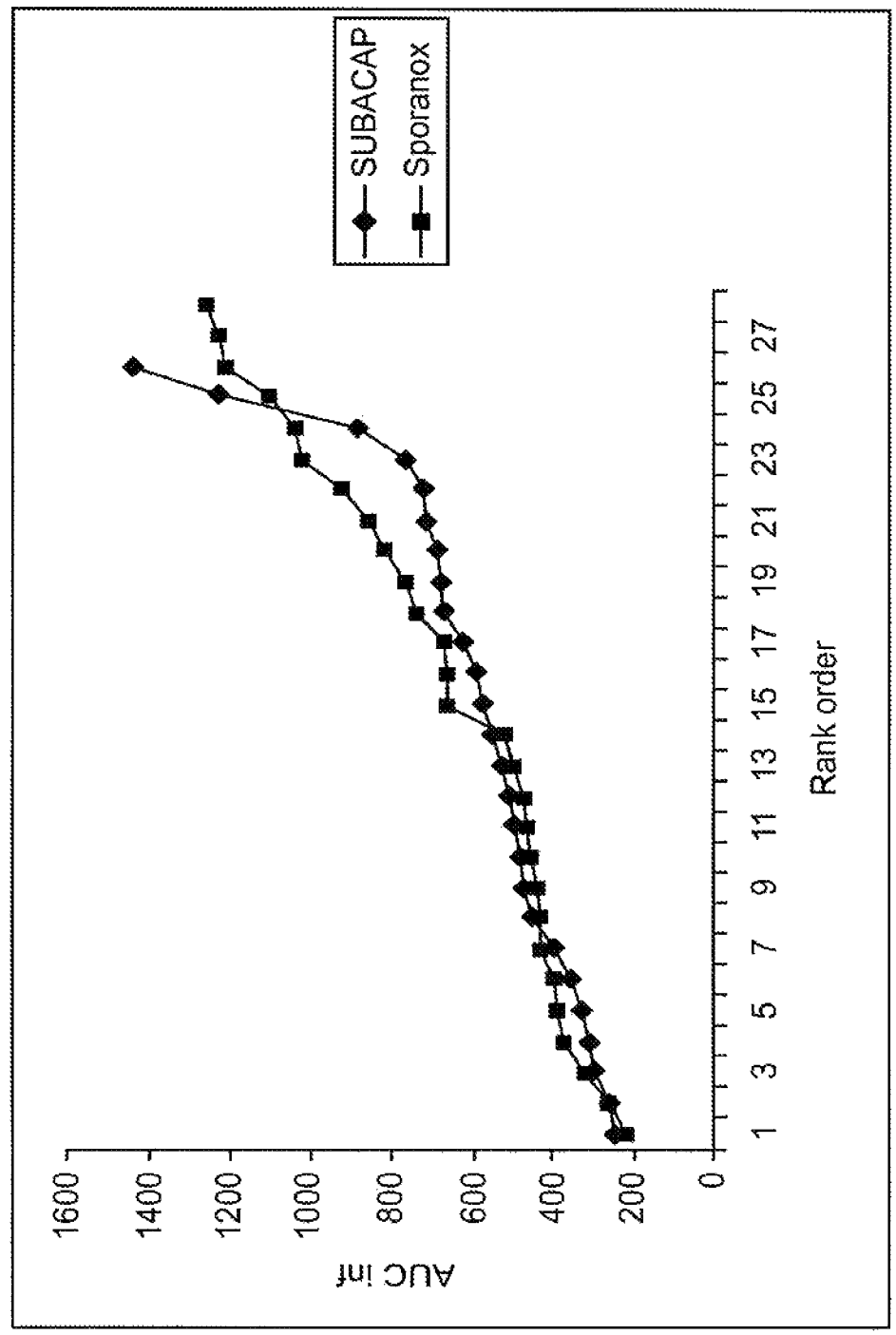
FIG. 52 is a plot showing individual AUC(0-∞) values from Example 9 (fed state).

Apart from the Box-plots, another way of looking at the raw AUC0-∞ data is to rank them according to size and plot them. FIG. 52 shows that exposure to 50 mg capsule oral solid dosage forms of the present invention and SPORANOX® 100 mg capsules is essentially the same for the 50% of subjects who absorb the least drug.

There is a slightly greater exposure to SPORANOX®100 mg capsules in the 50% of subjects who absorb the most drug (as would be expected given that double the quantity of drug substance is present in SPORANOX® 100 mg capsules).

Bioequivalence Study

Example 12—Bioequivalence Study Comparing Single Oral Doses of SUBA®-Itraconazole 50 mg Capsules with Sporanox® (Itraconazole) 100 mg Capsules Under Fed Conditions Study Rationale This study was performed to determine the bioequivalence of LOZANOC (SUBA®-itraconazole) and SPORANOX®. Due to enhanced bioavailability, a 50 mg dose of SUBA®-itraconazole has been shown to result in similar exposure to itraconazole as observed following a 100 mg dose of SPORANOX® with lower inter- and intra-subject variability. Due to the known high intra-subject variability of the reference product (SPORANOX®), this study will assess the bioequivalence of the two products (i.e. a 50 mg dose of LOZANOC compared to a 100 mg dose of SPORANOX®) using a replicate two-treatment, four-period, two-sequence study design. In addition, the study will be conducted under fed conditions since it is known that the bioavailability of itraconazole approximately doubles when administered with food.

This study was an open-label, analytically-blinded investigation as the main objectives were based on pharmacokinetic parameters, which are not believed to be subject to bias. A crossover design was chosen to minimize the effect of between-subject variability. The subjects were randomized such that an equal number of subjects received the treatments in the same order in each of the two sequences. As the SPORANOX® itraconazole is considered to be a highly variable drug product; the study was conducted as a replicate cross-over design to assess the within-subject variability of the maximum observed plasma concentration (Cmax) of the SPORANOX® itraconazole. If intra-variability of Cmax was found to be greater than 30% the acceptance criteria for bioequivalence could be widened. In each treatment period, blood sampling up to 120 hours post dose allowed the pharmacokinetic parameters of itraconazole and hydroxyitraconazole to be adequately described, based on the expected apparent plasma terminal elimination half-life (t1/2) for itraconazole and hydroxyitraconazole of 22 hours and 7 hours, respectively. A washout period of 14 days was chosen for this study, as this was deemed to be an appropriate amount of time to guarantee that the dose of itraconazole administered in the previous treatment period will have cleared from the subjects' bloodstream prior to the commencement of the next treatment period.

Study Design

This was a 2 treatment, 4-period, 2-sequence, single dose, cross-over, randomized, replicate-design bioequivalence study in healthy male and female subjects. Forty-eight (48) subjects participated in the study. Screening was performed in the 28-day period prior to the first dose. There was a minimum of 14 days between each dose administration.

Subjects had post-study visit assessments performed at their Day 6 visit in Treatment Period 4.

Study Treatments

Test Formulation: capsules containing 50 mg itraconazole (LOZANOC).

Reference Formulation: 100 mg capsules SPORANOX® (itraconazole)

In each treatment period subjects received one of the following 2 treatments:

Treatment A: 1×50 mg LOZANOC capsule administered following a high-fat breakfast.

Treatment B: 1×100 mg LOZANOC capsule administered following a high-fat breakfast.

Each subject received Treatment A in 2 treatment periods and Treatment B in 2 treatment periods in accordance with a randomization schedule.

Blood samples were collected pre-dose and at the following times after administration of each dose: 1, 2, 3, 3.5, 4, 4.5, 5, 5.5, 6, 6.5, 7, 8, 10, 12, 24, 36, 48, 72, 96 and 120 hours post dose Following collection, The samples were centrifuged, within 1 hour of collection, at 1500 g for 10 minutes at approximately 4° C. The serum was stored at −20° C.

Sample Analysis

The analysis of itraconazole and hydroxyitraconazole in plasma samples was performed by the Department of Bioanalytical Services at Covance Laboratories Europe (CLE), Harrogate, UK using a validated analytical method. The plasma samples were prepared by solid phase extraction. The centrifuged eluates were quantified by liquid chromatography with tandem mass spectrometric detection (LC-MS/MS).

Pharmacokinetic Analysis

The pharmacokinetic analysis was conducted by Covance CRU using WinNonlin Professional Version 5.2 (Pharsight Corporation, Mountain View, Calif., USA). Pharmacokinetic parameters were determined from the plasma concentrations of itraconazole and hydroxyitraconazole using non-compartmental procedures.

The pharmacokinetic parameters determined are presented in Table 1.

For the assessment of bioequivalence 50 mg SUBA® itraconazole was the test formulation and 100 mg SPORANOX® was the reference formulation. Statistical analysis was performed separately for itraconazole and hydroxyitraconazole. The pharmacokinetic parameters AUC0-72 h, AUC0-tlast, AUC0-∞, and Cmax were log-transformed and analyzed using a repeated measures, linear mixed-effects model where formulation, period and sequence were considered as fixed factors, and subject as a random effect. From the model, the difference in least squares (LS) mean estimates and the corresponding 90% confidence intervals (CIs) for the difference were estimated and back-transformed from the log scale to provide estimates of the ratio of geometric means and 90% CI for the ratio of these means.

If the 90% CI for treatment ratios (test/reference) for AUC0-72 h was contained within 0.80 to 1.25 for itraconazole, then the formulations could be considered bioequivalent. As the reference formulation is considered to be a highly variable drug product, the 90% CI bioequivalence acceptance range for Cmax was widened. The extent of widening was based on the calculated within-subject variability (CV %) for Cmax. The widened Cmax lower and upper limits permitted according to the European Medicines Agency (EMEA) Guidance7 are displayed in Table 58.

TABLE 58

| Confidence Interval Acceptance range | | |
|---|---|---|
| Within-subject CV (%) | Lower Limit | Upper Limit |
| 30 | 80.00 | 125.00 |
| 35 | 77.23 | 129.48 |
| 40 | 74.62 | 134.02 |
| 45 | 72.15 | 138.59 |
| ≥50 | 69.84 | 143.19 |

Residual plots were produced to assess the adequacy of the model. The model was used to investigate the within- and between-subject variability for each treatment.

Pharmacokinetic Analysis

Figure 53:
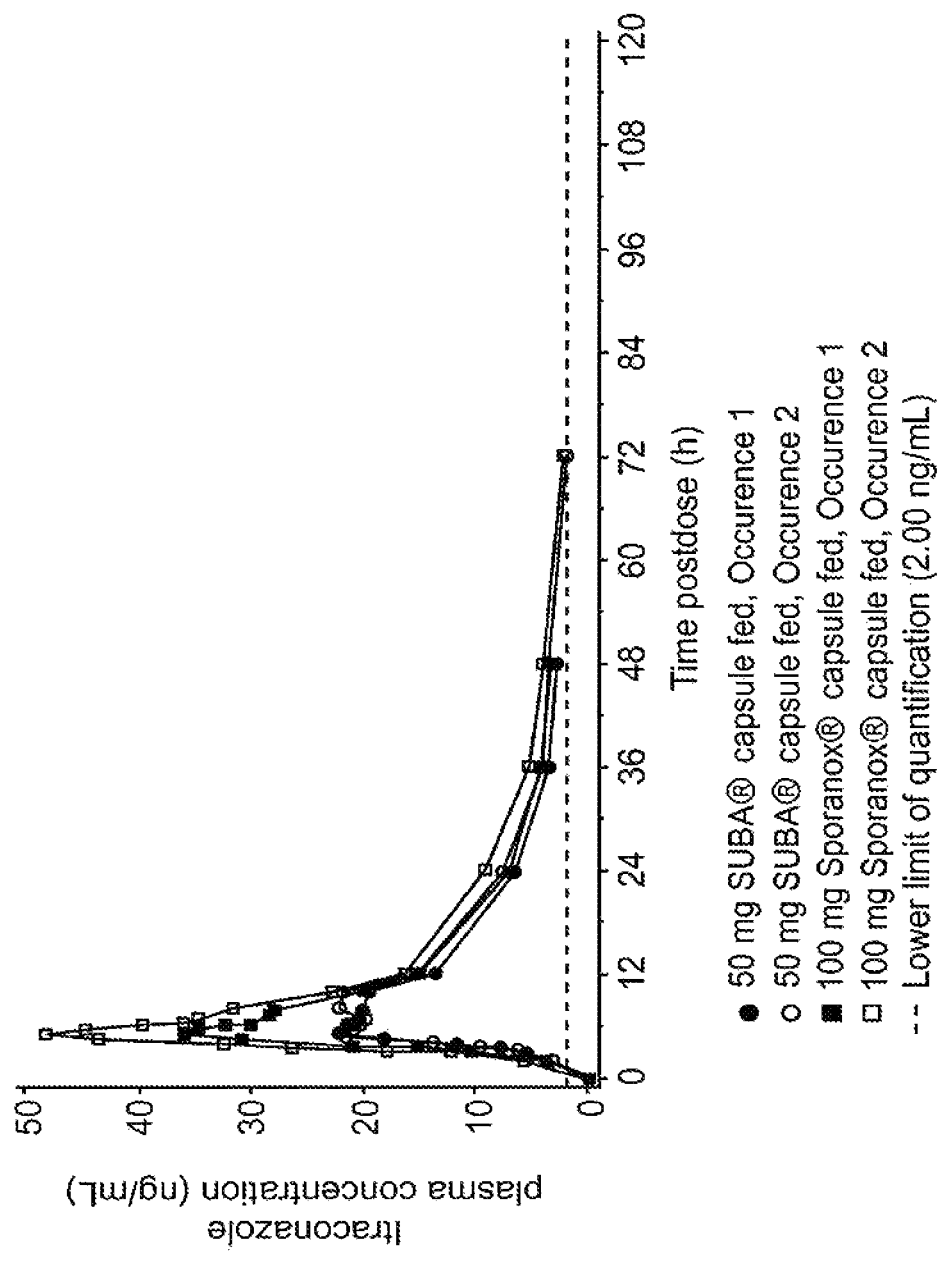
FIG. 53 shows a linear scale graph comparing the mean plasma itraconazole concentration over time in a study assessing the bioequivalence of two treatments of a 50 mg LOZANOC dose with a 100 mg dose of SPORANOX® administered under fed conditions. Closed circles represent the 50 mg LOZANOC dose administered under fed conditions (Occurrence 1); open circles represent the 50 mg LOZANOC dose administered under fed conditions (Occurrence 2); open squares represent the reference SPORANOX® 100 mg dose administered under fed conditions (Occurrence 1); closed squares represent the reference SPORANOX® 100 mg dose administered under fed conditions (Occurrence 2).
Figure 54:
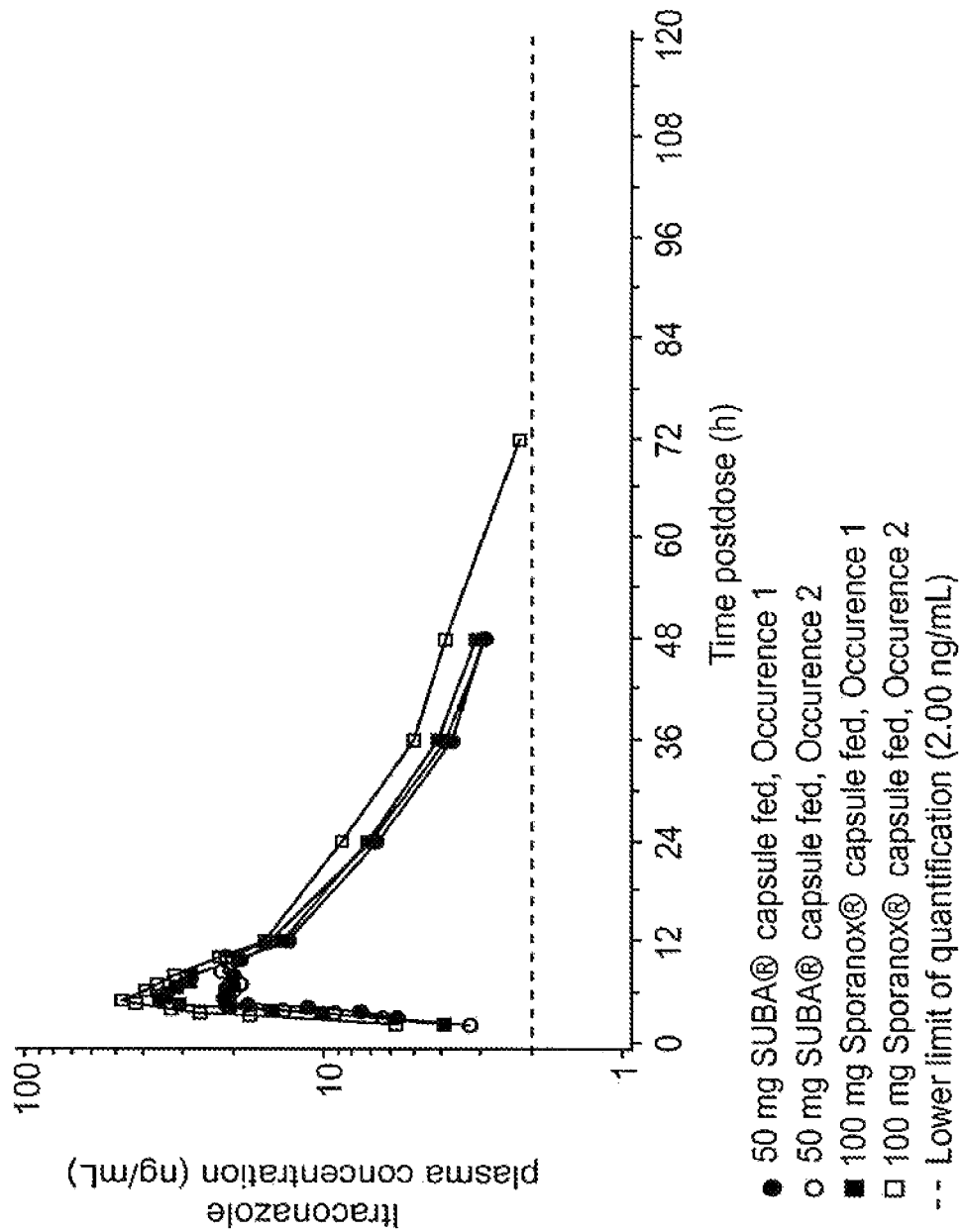
FIG. 54 shows a log-transformed scale graph comparing the mean plasma itraconazole concentration over time in a study assessing the bioequivalence of two treatments of a 50 mg LOZANOC dose with a 100 mg dose of SPORANOX® administered under fed conditions. Closed circles represent the 50 mg LOZANOC dose administered under fed conditions (Occurrence 1); open circles represent the 50 mg LOZANOC dose administered under fed conditions (Occurrence 2); open squares represent the reference SPORANOX® 100 mg dose administered under fed conditions (Occurrence 1); closed squares represent the reference SPORANOX® 100 mg dose administered under fed conditions (Occurrence 2).

Single Oral Dose Pharmacokinetics of Itraconazole Following Administration of Two Different Formulations (SUBA®-Itraconazole and SPORANOX® [Itraconazole]) in the Fed Condition on Two Dosing Occasions Each Plasma concentrations of itraconazole following administration of the SUBA-itraconazole and SPORANOX® (itraconazole) formulations in the fed condition on two dosing occasions each are summarized in FIGS. 53 (linear) and 54 (log-transformed).

The pharmacokinetic parameters of itraconazole are summarized in Table 59.

Following the oral administration of each of the SUBA® (50 mg) and SPORANOX® (100 mg) formulations in the fed condition, itraconazole was steadily absorbed, appearing in plasma at 1.0 hour after administration. Median tmax for the SUBA® and SPORANOX® formulations was similar (occurring at 5.50 and 5.00 hours, respectively), with values for individual subjects ranging from 1.0 to 24.0 hours and 1.0 to 10.0 hours post-dose, respectively. Mean maximum plasma concentrations were lower for the SUBA® formulation than for the SPORANOX®, being 41.4 ng/mL and 52.8 ng/mL, respectively. After reaching Cmax, plasma concentrations declined in an apparent biphasic manner, with the start of the elimination phase generally occurring at 12 to 24 hours post dose for both formulations and a mean t1/2 of 20.2 and 23.9 hours (range in individual subjects from 9.57 to 46.4 hours and 10.8 to 45.7 hours) for the SUBA® and SPORANOX® formulations, respectively.

In general, as assessed from the geometric CV %, high between-subject variability was noted for AUC0-72 h, AUC0-tlast, AUC0-∞ and Cmax for each of the formulations. However, between-subject variability in total exposure was consistently lower for the SUBA® formulation than the Sporanox® with respective values of 41.8% and 59.8% for AUC0-72 h, 57.7% and 84.7% for AUC0-tlast, and 51.3% and 67.0% for AUC0-∞. Between-subject variability in Cmax was similar for the SUBA® and the SPORANOX® formulations (59.8% and 65.2%, respectively).

Statistical analysis of occurrence on the pharmacokinetic parameters of itraconazole is summarized in Table 60.

TABLE 59

Summary of the Pharmacokinetic Parameters for Itraconazole Following Administration of the SUBA ®-itraconazole and SPORANOX ® (Itraconazole) Formulations in Fed Condition

| | Treatment | | | | | |
|---|---|---|---|---|---|---|
| | 50 mg SUBA ® capsule fed | | | 100 mg Sporanox ® capsule fed | | |
| Parameters | Occurrence 1 | Occurrence 2 | Average | Occurrence 1 | Occurrence 2 | Average |
| $AUC_{0-72\,h}$ (ng.h/mL) | 547 (42.3) | 556 (41.9) | 552 (41.8) | 637 (52.4) | 794 (64.7) | 712 (59.8) |
| N | 40 | 41 | 81 | 39 | 40 | 79 |
| $AUC_{0-tlast}$ (ng.h/mL) | 465 (60.7) | 496 (55.0) | 480 (57.7) | 535 (81.4) | 683 (86.1) | 604 (84.7) |
| N | 47 | 47 | 94 | 47 | 47 | 94 |
| $AUC_{0-\infty}$ (ng.h/mL) | 608 (52.8) | 625 (50.8) | 616 (51.3) | 733 (61.8) | 919 (70.2) | 822 (67.0) |
| N | 32 | 34 | 66 | 37 | 38 | 75 |
| $C_{max}$ (ng/mL) | 39.3 (63.0) | 43.6 (56.6) | 41.4 (59.8) | 47.0 (61.2) | 59.3 (67.1) | 52.8 (65.2) |
| N | 47 | 47 | 94 | 47 | 47 | 94 |
| $t_{max}^{a}$ (h) | 5.50 (2.00-12.0) | 5.50 (1.00-24.0) | 5.50 (1.00-24.0) | 5.00 (1.00-10.0) | 5.00 (1.00-10.0) | 5.00 (1.00-10.0) |
| N | 47 | 47 | 94 | 47 | 47 | 94 |
| $T_{lag}^{a}$ (h) | 2.00 (0-8.00) | 1.00 (0-8.00) | 2.00 (0-8.00) | 1.00 (0-4.00) | 1.00 (0-4.02) | 1.00 (0-4.02) |
| N | 47 | 47 | 94 | 47 | 47 | 94 |
| $T_{1/2}$ (h) | 20.2 (37.6) | 20.2 (41.9) | 20.2 (39.5) | 23.3 (47.6) | 24.5 (40.5) | 23.9 (43.9) |
| N | 32 | 34 | 66 | 37 | 38 | 75 |
| CL/F (mL/min) | 1371 (52.8) | 1334 (50.8) | 1352 (51.3) | 2275 (61.8) | 1813 (70.2) | 2028 (67.0) |
| N | 32 | 34 | 66 | 37 | 38 | 75 |
| $V_z/F$ (L) | 2400 (30.6) | 2332 (29.8) | 2365 (30.0) | 4598 (37.5) | 3845 (54.3) | 4200 (47.3) |
| N | 32 | 34 | 66 | 37 | 38 | 75 |

Geometric mean (CV %) data are presented.
N = Number of subjects studied,
$AUC_{0-72\,h}$ = Area under the plasma concentration-time curve from time zero up to 72 hours postdose,
$AUC_{0-tlast}$ = Area under the plasma concentration-time curve from time zero up to the last quantifiable concentration,
$AUC_{0-\infty}$ = Area under the plasma concentration-time curve from time zero to infinity,
$C_{max}$ = Maximum observed plasma concentration,
$t_{max}$ = Time of maximum observed plasma concentration,
$t_{lag}$ = Time before the start of absorption,
$t_{1/2}$ = Apparent plasma terminal elimination half-life,
CL/F = Apparent total plasma clearance,
$V_z/F$ = Apparent volume of distribution during the terminal phase.
[a]Median (min-max).

TABLE 60

Occurrence Analysis of the Pharmacokinetic Parameters of Itraconazole

| | | Geometric LS mean | | Ratio (occurrence 1:Occurrence 2) |
|---|---|---|---|---|
| Parameter | Treatment | Occurrence 1 | Occurrence 2 | (90% CI) |
| $AUC_{0-72h}$ (ng · h /mL) | 50 mg SUBA ® capsule fed | 539 | 546 | 0.987 (0.914, 1.07) |
| | 100 mg Sporanox ® capsule fed | 615 | 780 | 0.789 (0.672, 0.925) |

TABLE 60-continued

Occurrence Analysis of the Pharmacokinetic Parameters of Itraconazole

| Parameter | Treatment | Geometric LS mean | | Ratio (occurrence 1:Occurrence 2) (90% CI) |
|---|---|---|---|---|
| | | Occurrence 1 | Occurrence 2 | |
| $AUC_{0\text{-}tlast}$ (ng · h/mL) | 50 mg SUBA ® capsule fed | 464 | 496 | 0.936 (0.851, 1.03) |
| | 100 mg Sporanox ® capsule fed | 533 | 680 | 0.784 (0.665, 0.925) |
| $AUC_{0\text{-}\infty}$ (ng · h/mL) | 50 mg SUBA ® capsule fed | 593 | 631 | 0.939 (0.854, 1.03) |
| | 100 mg Sporanox ® capsule fed | 703 | 911 | 0.771 (0.645, 0.921) |
| $C_{max}$ (ng/mL) | 50 mg SUBA ® capsule fed | 39.2 | 43.5 | 0.902 (0.807, 1.01) |
| | 100 mg Sporanox ® capsule fed | 46.8 | 59.1 | 0.792 (0.704, 0.891) |

$AUC_{0\text{-}72h}$ = Area under the plasma concentration-time curve from time zero up to 72 hours postdose,
$AUC_{0\text{-}tlast}$ = Area under the plasma concentration-time curve from time zero up to the last quantifiable concentration,
$AUC_{0\text{-}\infty}$ = Area under the plasma concentration-time curve from time zero to infinity,
$C_{max}$ = Maximum observed plasma concentration, LS = least squares.

Figure 55:
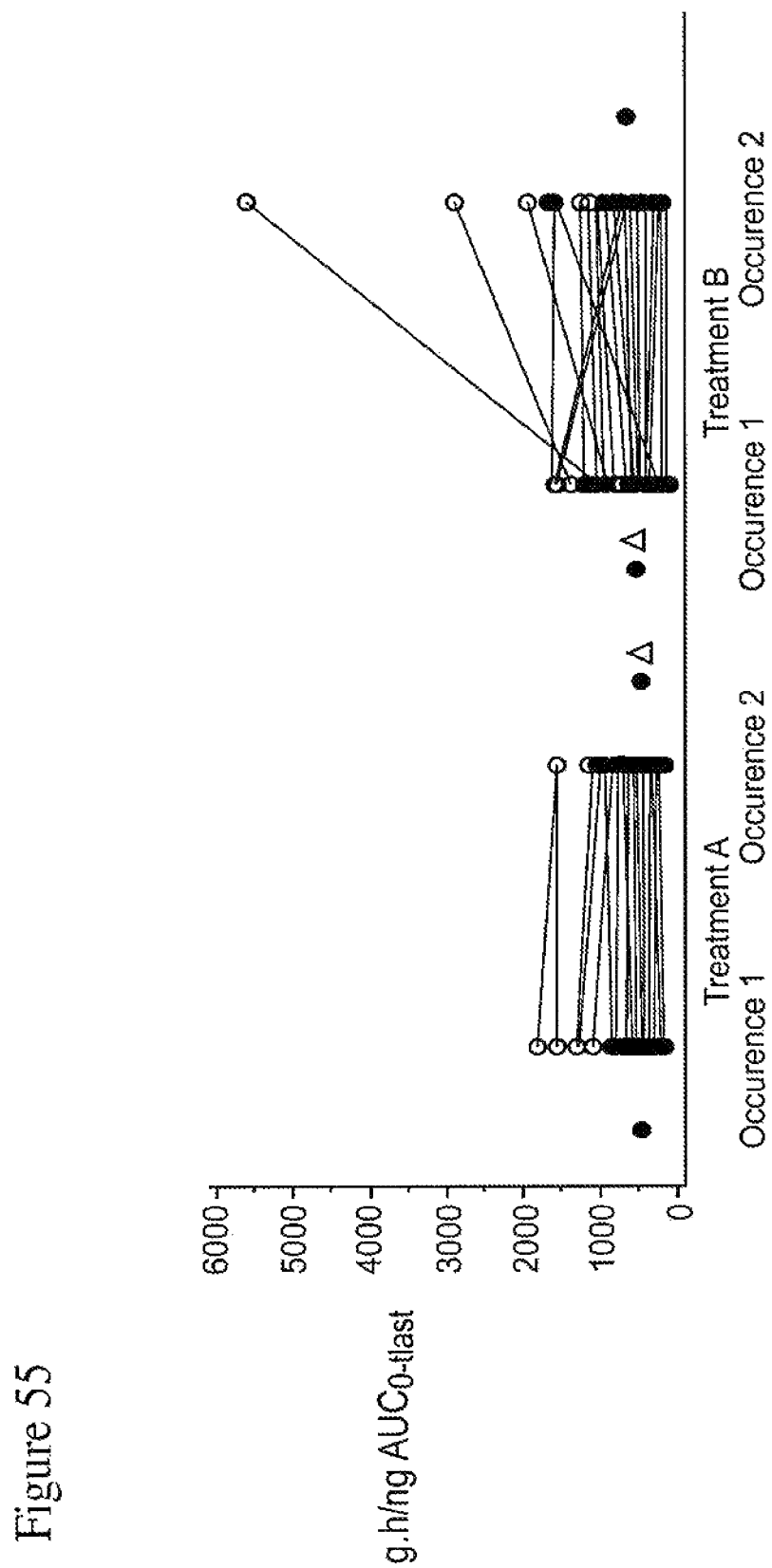
FIG. 55 is a graph which shows that the systemic exposure (based on AUC and Cmax) from the 50 mg SUBA® formulation was less variable between dosing occurrences than that of the Sporanox® in the study assessing the bioequivalence of two treatments of a 50 mg dose of LOZANOC to a 100 mg dose of SPORANOX® when administered under fed conditions.

Statistical analysis showed that the systemic exposure (based on AUC and Cmax) from the 50 mg SUBA® formulation was less variable between dosing occurrences than that of the SPORANOX® (FIG. 55). The ratios of geometric LS means for the SUBA® formulation were close to unity (ranging from 0.902 to 0.987); whereas the ratios for the SPORANOX® were considerably lower (ranging from 0.771 to 0.792) due to the higher exposure seen in Occurrence 2. A review of individual subject profiles found 2 subjects (Subject 27 and Subject 42) with outlying results. The increased exposure and variability between dosing occurrences with 100 mg SPORANOX® can be partially explained by these values (Table 61).

The statistical analysis of bioequivalence for itraconazole in the fed condition is summarized in Table 62.

TABLE 61

Pharmacokinetic Parameters for Outlying Subjects Following Dosing with 100 mg SPORANOX ®

| | Subject 27 | | Subject 42 | |
|---|---|---|---|---|
| Parameter | Occurrence 1 | Occurrence 2 | Occurrence 1 | Occurrence 2 |
| $AUC_{0\text{-}72h}$ (ng · h/mL) | 1209 | 2449 | 904 | 4842 |

TABLE 61-continued

Pharmacokinetic Parameters for Outlying Subjects Following Dosing with 100 mg SPORANOX ®

| | Subject 27 | | Subject 42 | |
|---|---|---|---|---|
| Parameter | Occurrence 1 | Occurrence 2 | Occurrence 1 | Occurrence 2 |
| $AUC_{0\text{-}tlast}$ (ng · h/mL) | 1389 | 2883 | 980 | 5601 |
| $AUC_{0\text{-}\infty}$ (ng · h/mL) | 1519 | 3232 | 1092 | 6026 |
| $C_{max}$ (ng/mL) | 108 | 171 | 83.4 | 329 |

$AUC_{0\text{-}72h}$ = Area under the plasma concentration-time curve from time zero up to 72 hours postdose,
$AUC_{0\text{-}tlast}$ = Area under the plasma concentraton-time curve from time zero up to the last quantifiable concentration,
$AUC_{0\text{-}\infty}$ = Area under the plasma concentration-time curve from time zero to infinity,
$C_{max}$ = Maximum observed plasma concentration.

TABLE 62

Bioequivalence Analysis of the Pharmacokinetic Parameters of Itraconazole Following Administration of 50 mg SUBA®-itraconazole and 100 mg SPORANOX® (Itraconazole) in the Fed Condition

| | Geometric LS mean | | Ratio (50 mg SUBA® capsule fed: 100 mg Sporanox® capsule fed (90% CI) | Within-subject CV % (90% CI) | |
|---|---|---|---|---|---|
| Parameter | 50 mg SUBA® capsule fed | 100 mg Sporanox® capsule fed | | 50 mg SUBA® capsule fed | 100 mg Sporanox® capsule fed |
| $AUC_{0\text{-}72h}$ (ng · h/mL) | 536 | 692 | 0.774 (0.696, 0.861) | 20.9 (17.4, 26.3) | 44.8 (36.9, 57.6) |
| $AUC_{0\text{-}tlast}$ (ng · h/mL) | 479 | 602 | 0.797 (0.704, 0.901) | 27.8 (23.6, 34.0) | 51.2 (43.1, 63.7) |
| $AUC_{0\text{-}\infty}$ (ng · h/mL) | 611 | 800 | 0.763 (0.678, 0.859) | 22.2 (18.1, 29.3) | 47.4 (38.7, 62.1) |
| $C_{max}$ (ng/mL) | 41.3 | 52.6 | 0.785 (0.695, 0.888) | 33.3 (28.3, 40.9) | 35.5 (30.1, 43.5) |

$AUC_{0\text{-}72h}$ = Area under the plasma concentration-time curve from time zero up to 72 hours postdose, $AUC_{0\text{-}tlast}$ = Area under the plasma concentraton-time curve from time zero up to the last quantifiable concentration, $AUC_{0\text{-}\infty}$ = Area under the plasma concentration-time curve from time zero to infinity, $C_{max}$ = Maximum observed plasma concentration.

Statistical analysis of the systemic exposure results (based on AUC and Cmax) showed that the 50 mg SUBA® capsule was not bioequivalent with the 100 mg SPORANOX® capsule with respect to itraconazole. For the measures of AUC, the ratio of the geometric means ranged from 0.763 to 0.797, with none of the associated 90% CI for the geometric LS mean ratios fully contained within the predefined equivalence limits of 0.80 to 1.25. For Cmax, the ratio of geometric LS mean ratios was 0.785 and within-subject CV % for the SUBA® and the SPORANOX® formulation was 33.3% and 35.5%, respectively. Therefore, using the expanded 0.746 to 1.340 equivalence range allowed, based on the reference formulation and within-subject CV %, bioequivalence can not be concluded for Cmax.

Within-subject variability in Cmax was similar for the SUBA® and the SPORANOX® formulations (33.3% and 35.5%, respectively).

Figure 56:
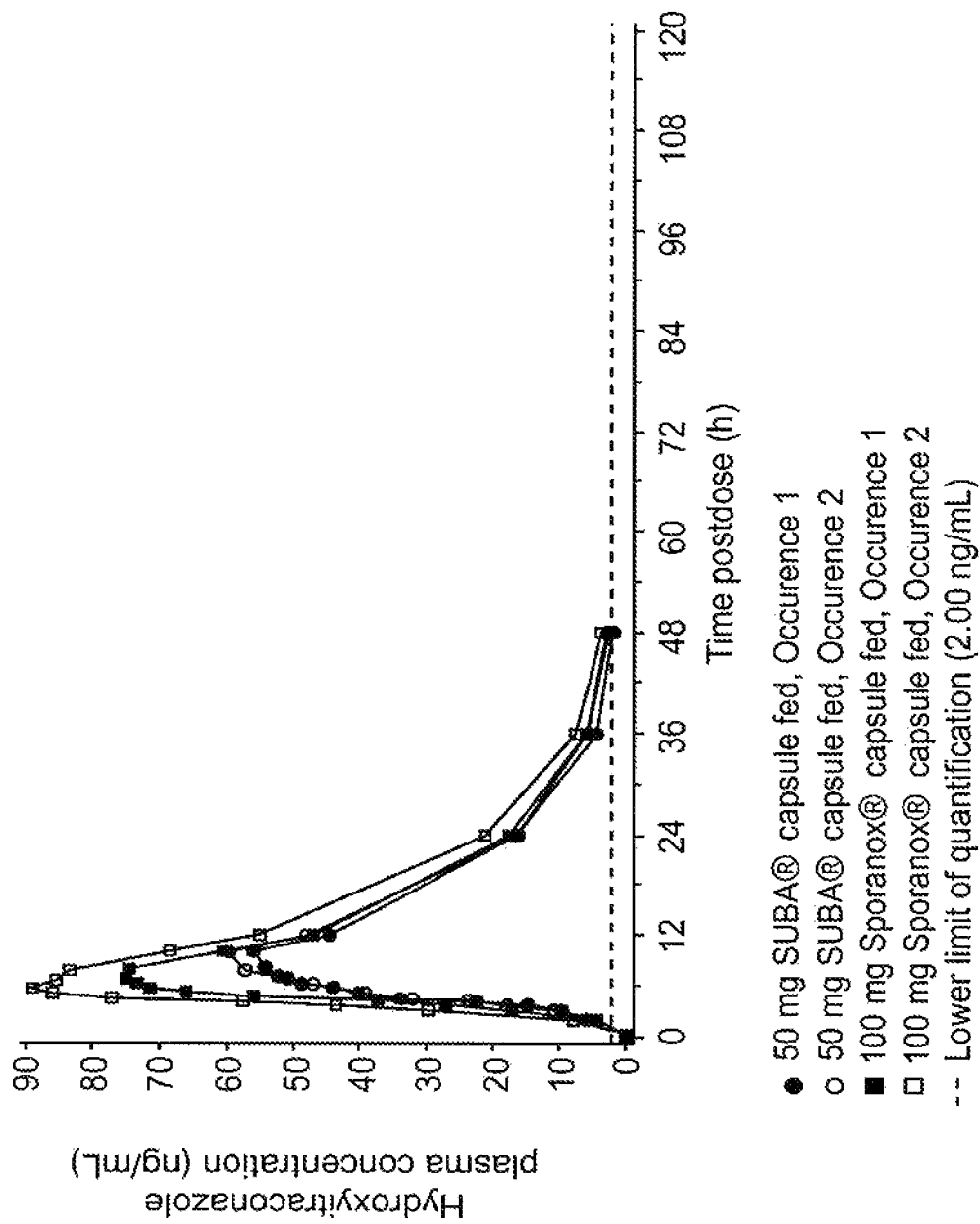
FIG. 56 shows a log-transformed scale graph comparing the mean plasma hydroxyitraconazole concentration over time in a study assessing the bioequivalence of two treatments of a 50 mg LOZANOC dose with a 100 mg dose of SPORANOX® administered under fed conditions. Closed circles represent the 50 mg LOZANOC dose administered under fed conditions (Occurrence 1); open circles represent the 50 mg LOZANOC dose administered under fed conditions (Occurrence 2); open squares represent the reference SPORANOX® 100 mg dose administered under fed conditions (Occurrence 1); closed squares represent the reference SPORANOX® 100 mg dose administered under fed conditions (Occurrence 2).
Figure 57:
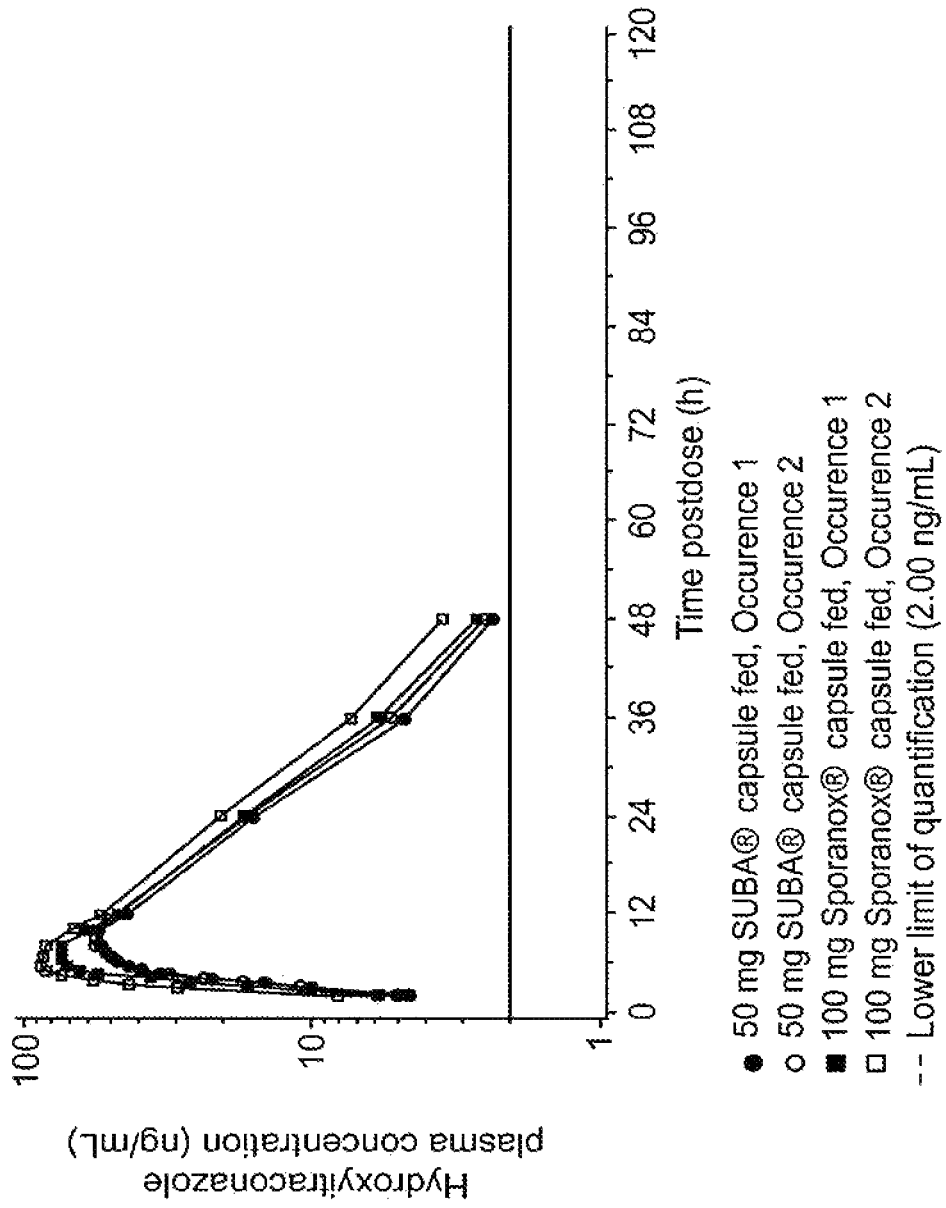
FIG. 57 shows a log-transformed scale graph comparing the mean plasma hydroxyitraconazole concentration over time in a study assessing the bioequivalence of two treatments of a 50 mg LOZANOC dose with a 100 mg dose of SPORANOX® administered under fed conditions. Closed circles represent the 50 mg LOZANOC dose administered under fed conditions (Occurrence 1); open circles represent the 50 mg LOZANOC dose administered under fed conditions (Occurrence 2); open squares represent the reference SPORANOX® 100 mg dose administered under fed conditions (Occurrence 1); closed squares represent the reference SPORANOX® 100 mg dose administered under fed conditions (Occurrence 2).

Single Oral Dose Pharmacokinetics of Hydroxyitraconazole Following Administration of Two Different Formulations (SUBA®-Itraconazole and SPORANOX® [Itraconazole]) in the Fed Condition on Two Dosing Occasions Each Plasma concentrations of hydroxyitraconazole following administration of the SUBA®-itraconazole and SPORANOX® (itraconazole) formulations in the fed condition on two dosing occasions each are summarized in FIG. 56 (linear) and FIG. 57 (log-transformed).

The pharmacokinetic parameters of hydroxyitraconazole are summarized in Table 63.

TABLE 63

Summary of the Pharmacokinetic Parameters for Hydroxyitraconazole Following Administration of the SUBA®-itraconazole and SPORANOX® (Itraconazole) Formulations in Fed Condition

| | Treatments | | | | | |
|---|---|---|---|---|---|---|
| | 50 mg SUBA® capsule fed | | | 100 mg Sporanox® capsule fed | | |
| Parameters | Occurrence 1 | Occurrence 2 | Average | Occurrence 1 | Occurrence 2 | Average |
| $AUC_{0-72\,h}$ (ng.h/mL) | 1089 (54.2) | 1159 (49.3) | 1123 (51.6) | 1212 (72.8) | 1492 (82.2) | 1345 (78.1) |
| N | 46 | 45 | 91 | 47 | 47 | 94 |
| $AUC_{0-tlast}$ (ng.h/mL) | 1025 (59.2) | 1073 (54.9) | 1049 (56.8) | 1173 (75.8) | 1455 (85.6) | 1307 (81.4) |
| N | 47 | 47 | 94 | 47 | 47 | 94 |
| $AUC_{0-\infty}$ (ng.h/mL) | 1098 (55.5) | 1169 (50.1) | 1133 (52.6) | 1223 (73.9) | 1509 (84.2) | 1358 (79.7) |
| N | 46 | 45 | 91 | 47 | 47 | 94 |
| $C_{max}$ (ng/mL) | 78.7 (36.3) | 82.6 (35.8) | 80.6 (35.9) | 90.3 (43.1) | 106 (50.2) | 97.8 (47.3) |
| N | 47 | 47 | 94 | 47 | 47 | 94 |
| $t_{max}^{a}$ (h) | 6.50 (2.00-24.3) | 6.50 (2.00-24.0) | 6.50 (2.00-24.3) | 5.50 (2.00-10.0) | 5.00 (2.00-10.0) | 5.50 (2.00-10.0) |
| N | 47 | 47 | 94 | 47 | 47 | 94 |
| $t_{lag}^{a}$ (h) | 1.00 (0-7.00) | 1.00 (0-5.50) | 1.00 (0-7.00) | 1.00 (0-4.00) | 1.00 (0-3.52) | 1.00 (0-4.00) |
| N | 47 | 47 | 94 | 47 | 47 | 94 |
| $t_{1/2}$ (h) | 7.99 (32.8) | 8.16 (29.7) | 8.07 (31.1) | 8.25 (34.6) | 8.54 (35.1) | 8.40 (34.7) |
| N | 32 | 34 | 66 | 37 | 38 | 75 |
| $MR_{AUC}$ | 2.00 (17.4) | 1.97 (17.4) | 1.98 (17.2) | 1.97 (16.7) | 1.95 (17.2) | 1.96 (16.8) |
| N | 32 | 34 | 66 | 37 | 38 | 75 |
| $MR_{Cmax}$ | 2.00 (32.3) | 1.90 (28.9) | 1.95 (30.6) | 1.92 (28.0) | 1.78 (26.6) | 1.85 (27.4) |
| N | 47 | 47 | 94 | 47 | 47 | 94 |

Geometric mean (CV %) data are presented.
N = Number of subjects studied,
$AUC_{0-72\,h}$ = Area under the plasma concentration-time curve from time zero up to 72 hours postdose,
$AUC_{0-tlast}$ = Area under the plasma concentration-time curve from time zero up to the last quantifiable concentration,
$AUC_{0-\infty}$ = Area under the plasma concentration-time curve from time zero to infinity,
$C_{max}$ = Maximum observed plasma concentration,
$t_{max}$ = Time of maximum observed plasma concentration,
$t_{lag}$ = Time before the start of absorption,
$t_{1/2}$ = Apparent plasma terminal elimination half-life,
$MR_{AUC}$ = Metabolic ratio based on AUC,
$MR_{Cmax}$ = Metabolic ratio based on $C_{max}$.
[a]Median (min-max).

Within-subject variability in total exposure was considerably lower for the SUBA® formulation than for the SPORANOX® with values of 20.9% and 44.8% for AUC0-72 h, 27.8% and 51.2% for AUC0-tlast and 22.2% and 47.4% for AUC0-∞, respectively. There was no overlap in the 90% confidence interval ranges obtained for the 2 formulations at each AUC measure. Therefore the difference in within-subject variability was statistically significant at the 90% level.

Following the oral administration of each of the SUBA® (50 mg) and SPORANOX® (100 mg) formulations in the fed condition, hydroxyitraconazole was steadily formed, appearing in formulations was similar (occurring at 6.50 and 5.50 hours, respectively), with values for individual subjects ranging from 2.0 to 24.3 hours and 2.0 to 10.0 hours post-dose, respectively. Mean maximum plasma concentrations were lower for the SUBA® formulation than for the SPORANOX®, being 80.6 ng/mL and 97.8 ng/mL, respectively. After reaching Cmax, plasma concentrations of hydroxyitraconazole declined in an apparent mono-phasic manner, with the start of the elimination phase generally occurring at 8 to 12 hours post dose for both formulations and a mean t1/2 of 8.07 and 8.40 hours (range in individual subjects from 4.59 to 19.2 hours and 4.15 to 21.5 hours) for the SUBA® and SPORANOX® formulations, respectively. Systemic exposure to hydroxyitraconazole was higher than the parent drug following the administration of itraconazole as both the SUBA® and SPORANOX® formulations. The extent of formation of the metabolite was similar for both formulations as shown by the mean metabolic ratios with MRAUC ranging from 1.95 to 2.0 and MRCmax ranging from 1.78 to 2.0.

In general, as assessed from the geometric CV %, high between-subject variability was noted for AUC0-72 h, AUC0-tlast and AUC0-∞, with moderate between-subject variability in Cmax for the SUBA® formulation. The between-subject variability in exposure was lower for the SUBA® formulation than for the SPORANOX® with values of 51.6% and 78.1% for AUC0-72 h, 56.8% and 81.4% for AUC0-tlast, 52.6% and 79.7% for AUC0-∞, and 35.9% and 47.3% for Cmax, respectively.

Statistical analysis of occurrence on the pharmacokinetic parameters of hydroxyitraconazole is summarized in Table 64.

As observed with itraconazole pharmacokinetic parameters, Subjects 27 and 42 again showed outlying results in AUC measures for dosing Occurrence 2.

The statistical analysis of bioequivalence for hydroxyitraconazole in the fed condition is summarized in Table 65.

TABLE 64

Occurrence Analysis of the Pharmacokinetic Parameters of Hydroxyitraconazole

| Parameter | Treatment | Geometric LS mean Occurrence 1 | Geometric LS mean Occurrence 2 | Ratio (occurrence 1:Occurrence 2) (90% CI) |
|---|---|---|---|---|
| $AUC_{0-72h}$ | 50 mg SUBA ® capsule fed | 1085 | 1144 | 0.949 (0.867, 1.04) |
| (ng · h/mL) | 100 mg Sporanox ® capsule fed | 1206 | 1485 | 0.813 (0.704, 0.938) |
| $AUC_{0-tlast}$ | 50 mg SUBA ® capsule fed | 1022 | 1071 | 0.954 (0.873, 1.04) |
| (ng · h/mL) | 100 mg Sporanox ® capsule fed | 1167 | 1448 | 0.806 (0.695, 0.935) |
| $AUC_{0-\infty}$ | 50 mg SUBA ® capsule fed | 1094 | 1153 | 0.949 (0.868, 1.04) |
| (ng · h/mL) | 100 mg Sporanox ® capsule fed | 1217 | 1501 | 0.811 (0.701, 0.938) |
| $C_{max}$ | 50 mg SUBA ® capsule fed | 78.5 | 82.4 | 0.952 (0.876, 1.04) |
| (ng/mL) | 100 mg Sporanox ® capsule fed | 90.1 | 105 | 0.854 (0.767, 0.951) |

$AUC_{0-72h}$ = Area under the plasma concentration-time curve from time zero up to 72 hours postdose, $AUC_{0-tlast}$ = Area under the plasma concentraton-time curve from time zero up to the last quantifiable concentration, $AUC_{0-\infty}$ = Area under the plasma concentration-time curve from time zero to infinity, $C_{max}$ = Maximum observed plasma concentration, LS = least squares.

TABLE 65

Bioequivalence Analysis of the Pharmacokinetic Parameters of Hydroxyitraconazole Following Administration of 50 mg SUBA ®-itraconazole and 100 mg SPORANOX ® (Itraconazole) in the Fed Condition

| Parameter | Geometric LS mean 50 mg SUBA ® capsule fed | Geometric LS mean 100 mg Sporanox ® capsule fed | Ratio (50 mg SUBA ® capsule fed: 100 mg Sporanox ® capsule fed (90% CI) | Within-subject CV % (90% CI) 50 mg SUBA ® capsule fed | Within-subject CV % (90% CI) 100 mg Sporanox ® capsule fed |
|---|---|---|---|---|---|
| $AUC_{0-72h}$ (ng · h/mL) | 1108 | 1338 | 0.828 (0.737, 0.929) | 25.8 (21.9, 31.7) | 44.0 (37.2, 54.4) |
| $AUC_{0-tlast}$ (ng · h/mL) | 1046 | 1300 | 0.805 (0.716, 0.905) | 26.1 (22.2, 31.9) | 45.7 (38.6, 56.6) |
| $AUC_{0-\infty}$ (ng · h/mL) | 1117 | 1352 | 0.826 (0.736, 0.927) | 25.9 (22.0, 31.8) | 44.5 (37.6, 55.0) |
| $C_{max}$ (ng/mL) | 80.4 | 97.5 | 0.825 (0.754, 0.904) | 24.7 (21.0, 30.1) | 32.1 (27.3, 39.3) |

$AUC_{0-72h}$ = Area under the plasma concentration-time curve from time zero up to 72 hours postdose, $AUC_{0-tlast}$ = Area under the plasma concentraton-time curve from time zero up to the last quantifiable concentration, $AUC_{0-\infty}$ = Area under the plasma concentration-time curve from time zero to infinity, $C_{max}$ = Maximum observed plasma concentration Statistical analysis of the systemic exposure to hydroxyitraconazole (based on AUC and Cmax) for the 50 mg SUBA® capsule was lower than that with the 100 mg SPORANOX® capsule. For the measures of AUC, the ratio of the geometric means ranged from 0.805 to 0.828, with the associated 90% CIs excluding unity. Similarly for Cmax, the ratio of the geometric means was 0.825, and the associated 90% CIs excluded unity.

Within-subject variability in total exposure was considerably lower for the SUBA® formulation than for the SPORANOX® with values of 25.8% and 44.0% for AUC0-72 h, 26.1% and 45.7% for AUC0-tlast, and 25.9% and 44.5% for AUC0-∞, respectively. There was no overlap in the 90% confidence interval ranges obtained for the 2 formulations at each AUC measure. Therefore the difference in within-subject variability was statistically significant at the 90% level.

Within subject variability for Cmax was lower for the SUBA® formulation than for the SPORANOX® with values of 24.7% and 32.1%, respectively. However, this difference was not statistically significant at the 90% level.

The systemic exposure to itraconazole, based upon AUC and Cmax, was 20% to 24% lower when administered as the SUBA® itraconazole formulation compared to the SPORANOX® formulation in the fed condition (AUC0-72 h, 536 nigh/mL and 692 ng·h/mL; AUC0-tlast, 479 ng·h/mL and 602 ng·h/mL; AUC0-00, 611 ng·h/mL and 800 ng·h/mL; and Cmax, 41.3 ng/mL and 52.6 ng·h/mL, respectively).

Between-subject variability was noted for itraconazole AUC and Cmax for both formulations. However, between-subject variability in total exposure was consistently lower for the SUBA® formulation compared to the SPORANOX® formulation.

Systemic exposure for the SUBA® formulation was considerably less variable between dosing occurrences than that of the 100 mg SPORANOX®.

Within-subject variability in total exposure to itraconazole was statistically significantly lower for the SUBA® formulation compared to the SPORANOX® at the 90% level. Within-subject variability in Cmax was similar for both formulations.

The pharmacokinetics of hydroxyitraconazole reflected those of the parent drug following administration of the SUBA® and SPORANOX® formulations in the fed condition.

Adverse Events

Single oral doses of itraconazole, administered as the 50 mg SUBA®-itraconazole and 100 mg SPORANOX® (itraconazole) formulations, were well tolerated by male and female subjects when given in the fed condition. There were no serious adverse events and no severe adverse events reported during the study.

The majority of adverse events reported during the study were not related to treatment with the study drug. The incidence of drug-related adverse events (the number of subjects reporting adverse events) was slightly lower following 50 mg SUBA®-itraconazole. The number of drug-related adverse events was slightly higher following 50 mg SUBA®-itraconazole compared to 100 mg SPORANOX®. The majority of drug-related adverse events were mild in severity and resolved without treatment.

Discussion

This study investigated the bioequivalence of itraconazole when administered as 50 mg SUBA®-itraconazole and 100 mg SPORANOX® (itraconazole) capsule formulations in the fed condition. The present study was conducted using a replicate design, which is justified given the highly variable pharmacokinetics of itraconazole.

The administration of itraconazole as the 50 mg SUBA® formulation compared to the clinically used 100 mg SPORANOX® formulation in the fasted condition was found to provide 20% to 24% lower systemic exposure (AUC0-72 h, 536 ng·h/mL and 692 ng·h/mL; AUC0-tlast, 479 ng·h/mL and 602 ng·h/mL; and AUC0-∞, 611 ng·h/mL and 800 ng·h/mL, respectively) and 21% lower maximum plasma concentrations (41.3 ng/mL and 52.6 ng·h/mL, respectively). Statistical analysis of the systemic exposure results (based on AUC and Cmax) showed that the 50 mg SUBA® capsule formulation was not bioequivalent with the 100 mg SPORANOX® capsule. This result is in contrast to a previous bioavailability study (Example 10) which demonstrated that SUBA®-itraconazole 50 mg capsules under fed conditions compared to SPORANOX® 100 mg capsules under fed conditions met the bioequivalence criteria for highly variable drugs. However, the results of the study demonstrated that the SUBA® formulation was less variable in pharmacokinetic profile than the SPORANOX®.

Although between-subject variability was high for all measures of systemic exposure to itraconazole with both formulations of the study drug, the SUBA® formulation demonstrated consistently lower between-subject variability than the SPORANOX®. Between-subject variability in Cmax was similar for the SUBA® and the SPORANOX® formulations.

Statistical analysis showed that the systemic exposure with the SUBA® formulation was also less variable between dosing occurrences. Ratios of geometric LS means (Occurrence 1: Occurrence 2) for the SUBA® formulation were close to unity (range of 0.902 to 0.987); whereas the ratios for the SPORANOX® were considerably lower (range from 0.771 to 0.792).

The increase in exposure and between-subject variability following dosing with 100 mg SPORANOX® can be partially explained by 2 subjects with outlying pharmacokinetic data. Subject 27 and Subject 42 displayed significant increases in exposure in Occurrence 2 compared to Occurrence 1. For Subject 27, AUC measures increased by approximately double and Cmax increased 1.6-fold. Subject 42 showed particularly high variability, AUC measures increased approximately 5.5-fold and Cmax increased 4-fold between Occurrence 1 and Occurrence 2. No reasons could be found for this increased exposure following dosing with the 100 mg SPORANOX® capsules.

Within-subject variability in total exposure was considerably lower (approximately 50%) for the SUBA® formulation than for the SPORANOX®. Analysis of the confidence intervals obtained for AUC0-72 h, AUC0-tlast and AUC0-∞ for the two formulations showed no overlap of the ranges. On this basis, it was concluded that the lower within-subject variability observed for the SUBA® formulation was statistically significant at the 90% level compared to the SPORANOX®. Within-subject variability in Cmax was similar for the SUBA® and the Sporanox® formulations.

Single oral doses of itraconazole as 50 mg SUBA® and 100 mg SPORANOX® formulations were safe and well tolerated by healthy male and female subjects in this study. The majority of adverse events reported during the study were not related to treatment with the study drug. There were no serious adverse events, no severe adverse events reported during the study and the majority of drug-related adverse events were mild in severity and resolved without treatment. Headache was the most frequently reported drug-related adverse event. A total of 17 episodes were reported by 12 subjects, with 4 of these subjects reporting headache in at least 2 treatment periods. Overall, the incidence and frequency of headaches were similar for both treatments.

There were no clinically significant findings in clinical laboratory evaluations, vital signs, ECGs and physical examination findings during the study.

The systemic exposure to itraconazole, based upon AUC and Cmax, was 20% to 24% lower when administered as the SUBA® itraconazole formulation compared to the SPORANOX® formulation in the fed condition (AUC0-72 h, 536 ng·h/mL and 692 ng·h/mL; AUC0-tlast, 479 ng·h/mL and 602 ng·h/mL; AUC0-00, 611 ng·h/mL and 800 ng·h/mL; and Cmax, 41.3 ng/mL and 52.6 ng·h/mL, respectively).

Between-subject variability was noted for itraconazole AUC and Cmax for both formulations. However, between-subject variability in total exposure was consistently lower for the SUBA® formulation compared to the SPORANOX® formulation.

Systemic exposure for the SUBA® formulation was considerably less variable between dosing occurrences than that of the 100 mg SPORANOX®.

Within-subject variability in total exposure to itraconazole was statistically significantly lower for the SUBA® formulation compared to the SPORANOX® at the 90% level. Within-subject variability in Cmax was similar for both formulations.

The pharmacokinetics of hydroxyitraconazole reflected those of the parent drug following administration of the SUBA® and SPORANOX® formulations in the fed condition.

There were no clinically significant findings in clinical laboratory evaluations, vital signs, ECGs and physical examination findings during the study.

Single oral doses of itraconazole administered as the 50 mg SUBA® and 100 mg SPORANOX® formulations were considered to be safe and well tolerated when administered to healthy male and female subjects in the fed condition in this study.

Re-Analysis of this Study's Dataset

Although not pre-defined in the study protocol, Applicants conducted re-analysis of the dataset in order to better understand the results obtained. Specifically, Applicants explored two issues:
1. Applicants noted that the European Medicines Agency guidelines outline different statistical methodologies that can be used to analyze data from replicate-design pharmacokinetic studies.
2. Noting that subject 27 and 42 displayed significant increases in exposure following administration of the Reference in Occurrence 2 compared to Occurrence 1 but not after administration of the Test, Applicants investigated the affect on the bioequivalence comparisons if these subjects were removed from the analysis.

There are three possible methods by which to analyze the data from this study:
1) "Approach compatible with CHMP guideline (Method A)", which is the same analysis method as is used for 2×2 trials.
2) "Slight modification to approach compatible with CHMP guideline (Method B)"
3) An alternative method outlined in FDA guidance (Method C).

Initially, Applicants were of the view that the FDA method, Method C, was the optimal approach and it was used when analyzing the results from this study. Post-completion of this study however, Applicants' interpretation is that Method A is a preferred method when the sources of variation are thought to be fixed rather than random effects, and that Method C is acceptable when the sources of variation are thought to be random rather than fixed effects but tends to provide wider confidence intervals than Method A.

Given the results of this study used Method C, Applicants commissioned analysis of the data using Method A.

As subject 42 demonstrated the greatest increase in exposure following Reference Occurrence 2, it was decided to investigate the effect of removing this subject from the bioequivalence analyses.

Below are qualitative summaries of the bioequivalence ratios and confidence intervals derived using the existing SAP (Method C) (Table 66), and Method A (Table 67); a "yes" value indicates that the acceptance criteria are met, a "no" value indicates that the acceptance criteria have not been met. Table 68, Table 69 and Table 70 provide quantitative summaries.

A review of the qualitative summary under the current SAP, Method C, presented in (Table 66) indicates that there are several permutations for which the ratio for either Cmax or AUC0-72 meets the acceptance criteria. Overall, there is no observable trend or pattern. However, none of the permutations yielded an acceptable confidence interval (i.e., 0.80-1.25). As the reference formulation is considered to be a highly variable drug product, the 90% CI bioequivalence acceptance range for Cmax can be widened. The extent of widening is based on the calculated within-subject variability (CV %) for Cmax. The qualitative summaries presented in (Table 66) and (Table 67) present the within-subject variability that would have to observed in order for the Cmax ratio to be acceptable. Aside from the basic analysis, where both occurrences are pooled for both the Test and Reference, the within subject variability criteria are not met.

A review of the qualitative summary under Method A (Table 67) indicates that there are several permutations for which the ratio for either Cmax or AUC0-72 meets the acceptance criteria. Overall, there is no observable trend or pattern. However, none of the permutations yielded an acceptable confidence interval (i.e., 0.80-1.25). Further, the within subject variability criteria are not met.

Hence the conclusions from this re-analysis of this study's dataset are:
1. Using generally accepted statistical methods, 90% confidence intervals were widened based on Reference within subject variability.
2. In all cases, itraconazole Cmax and AUC values failed on the lower boundary of the widened 90% confidence intervals.
3. In a few cases, the T/R ratios for Cmax and AUC were within the 80-125% criteria.
4. The deletion of data from one subject (subject #42) did not significantly change the results.

TABLE 66

Qualitative Summary of the Ratios and Confidence Intervals for the Comparisons Performed, using the Current SAP Approach (Method C)

| BIOEQUIVALENCE | | $AUC_{0-72}$ | | $C_{max}$ | | CV% |
|---|---|---|---|---|---|---|
| Test | Reference | Ratio | CI | Ratio | CI | Target |
| SUBACAP both Occurances Pooled | Sporanox both Occurances Pooled | NO | NO | NO | NO | 35% |
| SUBACAP both Occurances Pooled | Sporanox Occurance 1 only | YES | NO | YES | NO | 40% |

TABLE 66-continued

Qualitative Summary of the Ratios and Confidence Intervals for the Comparisons Performed, using the Current SAP Approach (Method C)

| Test | Reference | | | | | |
|---|---|---|---|---|---|---|
| SUBACAP Occurance 1 | Sporanox Occurance 1 only | YES | NO | YES | NO | 45% |
| SUBACAP both Occurances Pooled | Sporanox both Occurances Pooled Minus Subject 42 | YES | NO | YES | NO | 50% |
| SUBACAP both Occurances Pooled | Sporanox Occurance 1 only- Minus Subject 42 | NO | NO | NO | NO | 40% |
| SUBACAP Occurance 1 | Sporanox Occurance 1 only- Minus Subject 42 | YES | NO | NO | NO | 50% |

| DRUG PERFORMANCE | | AUC$_{0-72}$ | | C$_{max}$ | | CV% |
|---|---|---|---|---|---|---|
| Test | Reference | Ratio | CI | Ratio | CI | Target |
| Difference in Absorption for Sporanox Occurance 1 | Difference in Absorption for Sporanox Occurance 2 | YES | NO | NO | NO | 50% |
| Difference in Absorption for Sporanox Occurance 1- Minus Subject 42 | Difference in Absorption for Sporanox Occurance 2- Minus Subject 42 | YES | NO | YES | NO | 50% |
| Difference in Absorption for SUBACAP Occurance 1 | Difference in Absorption for SUBACAP Occurance 2 | YES | YES | YES | NO | 35% |
| Difference in Absorption for SUBACAP Occurance 1- Minus Subject 42 | Difference in Absorption for SUBACAP Occurance 2- Minus Subject 42 | YES | YES | YES | NO | 35% |

TABLE 67

Qualitative Summary of the Ratios and Confidence Intervals for the Comparisons Performed, using the EMA Approach, Method A

| BIOEQUIVALENCE | | AUC$_{0-72}$ | | C$_{max}$ | | CV % |
|---|---|---|---|---|---|---|
| Test | Reference | Ratio | CI | Ratio | CI | Target |
| SUBACAP both Occurances Pooled | Sporanox both Occurances Pooled | NO | NO | NO | NO | 50% |
| SUBACAP both Occurances Pooled | Sporanox Occurance 1 only | YES | NO | YES | NO | 40% |
| SUBACAP Occurance 1 | Sporanox Occurance 1 | YES | NO | YES | NO | 40% |
| SUBACAP both Occurances Pooled- Minus Subject 42 | Sporanox both Occurances Pooled- Minus Subject 42 | NO | NO | NO | NO | 35% |
| SUBACAP both Occurances Pooled- Minus Subject 42 | Sporanox Occurances 1 only- Minus Subject 42 | YES | NO | YES | NO | 40% |
| SUBACAP Occurance 1- Minus Subject 42 | Sporanox Occurance 1- Minus Subject 42 | YES | NO | YES | NO | 45% |

TABLE 68

Quantitative Summary of the Geometric LS Means for the Comparisons Performed using the Current SAP Approach (Method C)

| | Geometric LS Mean | | | | | | | |
|---|---|---|---|---|---|---|---|---|
| | AUC (0-72) | | AUC (last) | | AUC (inf) | | Cmax | |
| | 50 mg SUBA Capsule Fed | 100 mg Sporanox Capsule Fed | 50 mg SUBA Capsule Fed | 100 mg Sporanox Capsule Fed | 50 mg SUBA Capsule Fed | 100 mg Sporanox Capsule Fed | 50 mg SUBA Capsule Fed | 100 mg Sporanox Capsule Fed |
| Original Analyses EXISTING SAP | 536 | 692 | 479 | 602 | 611 | 800 | 41.3 | 52.6 |
| SUBACAP both Occurances Pooled vs Sporanox both Occurances Pooled | 537 | 690 | 492 | 599 | 607 | 800 | 41.4 | 52.4 |
| SUBACAP both Occurances Pooled vs Sporanox Occurance 1 only | 538 | 617 | 492 | 561 | 611 | 716 | 41.4 | 49 |
| SUBACAP Occurance 1 vs Sporanox Occurance 1 | 534 | 616 | 466 | 530 | 593 | 697 | 39.3 | 46.7 |
| SUBACAP both Occurances Pooled vs Sporanox both Occurances Pooled- Minus Subject 42 | 527 | 673 | 480 | 585 | 594 | 779 | 40.6 | 51.4 |
| SUBACAP both Occurances Pooled vs Sporanox Occurance 1 only- Minus Subject 42 | 526 | 614 | 480 | 556 | 603 | 714 | 40.3 | 48.9 |
| SUBACAP Occurance 1 vs Sporanox Occurance 1- Minus Subject 42 | 521 | 612 | 455 | 526 | 577 | 693 | 38.4 | 46.3 |
| Difference in Absorption for Sporanox Occurance 1 vs Occurance 2 | 637 | 794 | 733 | 919 | 535 | 683 | 46.9 | 59.3 |

TABLE 68-continued

Quantitative Summary of the Geometric LS Means for the Comparisons
Performed using the Current SAP Approach (Method C)

| | Geometric LS Mean | | | | | | | |
|---|---|---|---|---|---|---|---|---|
| | AUC (0-72) | | AUC (last) | | AUC (inf) | | Cmax | |
| | 50 mg SUBA Capsule Fed | 100 mg Sporanox Capsule Fed | 50 mg SUBA Capsule Fed | 100 mg Sporanox Capsule Fed | 50 mg SUBA Capsule Fed | 100 mg Sporanox Capsule Fed | 50 mg SUBA Capsule Fed | 100 mg Sporanox Capsule Fed |
| Difference in Absorption for Sporanox Occurance 1 vs Occurance 2- Minus Subject 42 | 630 | 757 | 528 | 652 | 724 | 873 | 46.4 | 57.1 |
| Difference in Absorption for SUBACAP Occurance 1 vs Occurance 2 | 547 | 556 | 464 | 519 | 608 | 624 | 39.3 | 43.6 |
| Difference in Absorption for SUBACAP Occurance 1 vs Occurance 2- Minus Subject 42 | 534 | 543 | 452 | 507 | 589 | 606 | 38.3 | 42.9 |

TABLE 69

Quantitative Summary of the Geometric LS Means for the Comparisons
Performed, using the EMEA Approach, Method A

| | Geometric LS Mean | | | | | | | |
|---|---|---|---|---|---|---|---|---|
| | AUC (0-72) | | AUC (last) | | AUC (inf) | | Cmax | |
| | 50 mg SUBA Capsule Fed | 100 mg Sporanox Capsule Fed | 50 mg SUBA Capsule Fed | 100 mg Sporanox Capsule Fed | 50 mg SUBA Capsule Fed | 100 mg Sporanox Capsule Fed | 50 mg SUBA Capsule Fed | 100 mg Sporanox Capsule Fed |
| Original Analyses METHOD FROM EMEA GUIDANCE | 536 | 692 | 479 | 602 | 611 | 800 | 41.3 | 52.6 |
| SUBACAP both Occurances Pooled vs Sporanox both Occurances Pooled | 537 | 690 | 492 | 600 | 612 | 799 | 41.4 | 52.5 |
| SUBACAP both Occurances Pooled vs Sporanox Occurance 1 only | 526 | 618 | 481 | 556 | 603 | 714 | 40.6 | 48.9 |
| SUBACAP Occurance 1 vs Sporanox Occurance 1 | 534 | 616 | 466 | 530 | 593 | 697 | 39.3 | 46.6 |
| SUBACAP both Occurances Pooled vs Sporanox both Occurances Pooled- Minus Subject 42 | 527 | 673 | 481 | 584 | 599 | 778 | 40.6 | 51.4 |
| SUBACAP both Occurances Pooled vs Sporanox Occurance 1 only- Minus Subject 42 | 526 | 614 | 480 | 566 | 603 | 714 | 40.3 | 48.9 |
| SUBACAP Occurance 1 vs Sporanox Occurance 1- Minus Subject 42 | 521 | 612 | 454 | 526 | 577 | 693 | 38.4 | 46.3 |

TABLE 70

Quantitative Summary of the Ratios and Confidence Intervals for the Comparisons Performed, Current SAP Approach (Method C)

| | Ratio (50 mg SUBA: 100 mg Sporanox) | | | | | | | | | | | |
|---|---|---|---|---|---|---|---|---|---|---|---|---|
| | AUC (0-72) | | | AUC (last) | | | AUC (int) | | | Cmax | | |
| | Ratio | Lower 90% CI | Upper 90% CI | Ratio | Lower 90% CI | Upper 90% CI | Ratio | Lower 90% CI | Upper 90% CI | Ratio | Lower 90% CI | Upper 90% CI |
| Original Analysis Existing SAP | 0.774 | 0.696 | 0.861 | 0.797 | 0.704 | 0.901 | 0.763 | 0.678 | 0.859 | 0.785 | 0.695 | 0.888 |
| SUBACAP both Occurances Pooled vs Sporanox both Occurances Pooled | 0.778 | 0.700 | 0.865 | 0.821 | 0.723 | 0.932 | 0.760 | 0.676 | 0.855 | 0.789 | 0.700 | 0.865 |
| SUBACAP both Occurances Pooled vs.Sporanox Occurance 1 only | 0.872 | 0.786 | 0.966 | 0.878 | 0.773 | 0.997 | 0.854 | 0.763 | 0.954 | 0.843 | 0.757 | 0.938 |
| SUBACAP Occurance 1 vs SporanoxOccurance1 | 0.867 | 0.760 | 0.989 | 0.897 | 0.762 | 1.010 | 0.850 | 0.737 | 0.981 | 0.843 | 0.730 | 0.973 |
| SUBACAP both Occurances Pooled vs. Sporanox both Occurances Pooled-Minus Subject 42 | 0.783 | 0.702 | 0.873 | 0.822 | 0.721 | 0.936 | 0.762 | 0.676 | 0.868 | 0.791 | 0.698 | 0.896 |
| SUBACAP both Occurances Pooled vs Sporanox Occurance 1 only-Minus Subject 42 | 0.857 | 0.783 | 0.938 | 0.864 | 0.767 | 0.974 | 0.844 | 0.761 | 0.937 | 0.831 | 0.751 | 0.920 |
| SUBACAP Occurance 1 vs Sporanox Occurance 1-Minus Subject 42 | 0.852 | 0.748 | 0.970 | 0.864 | 0.749 | 0.997 | 0.832 | 0.724 | 0.958 | 0.831 | 0.719 | 0.960 |
| Difference in Absorption for Sporanox Occurance 1 vs Occurance 2 | 0.802 | 0.654 | 0.984 | 0.797 | 0.632 | 0.101 | 0.784 | 0.611 | 0.101 | 0.792 | 0.648 | 0.969 |
| Difference in Absorption for Sporanox Occurance 1 vs. Occurance 2-Minus Subject 42 | 0.832 | 0.717 | 0.967 | 0.81 | 0.671 | 0.978 | 0.829 | 0.699 | 0.984 | 0.812 | 0.698 | 0.944 |
| Difference in Absorption for SUBACAP Occurrance 1 vs. Occurance 2 | 0.985 | 0.811 | 1.11 | 0.895 | 0.767 | 1.04 | 0.974 | 0.834 | 1.14 | 0.901 | 0.778 | 1.04 |
| Difference in Absorption for SUBACAP Occurrance 1 vs. Occurance 2-Minus Subject 42 | 0.983 | 0.88 | 1.1 | 0.892 | 0.768 | 1.04 | 0.971 | 0.836 | 1.13 | 0.849 | 0.773 | 1.03 |

Example 13—a Comparison and Analysis Across Bioavailability Studies

Table 71 presents an overview of the biopharmaceutical studies, and Table 71 presents a comparison of the results. A summary of the key observations across the studies is presented below. Rate of Exposure The rate of exposure to itraconazole after single doses of Test (1×50 mg) and of the European Reference (1×100 mg) formulations in the fed and the fasted states were comparable:

In the study described in Example 10 the tmax was 6 hours for the Test and 5 hours for the Reference in the fed state and 2.5 hours for both formulations in the fasted state.

In the study described in Example 12 the tmax was 6.5 hours for the Test and 5.5 hours for the Reference.

Extent of Exposure
Single Dose Studies

The extent of exposure after single doses of Test (1×50 mg) and of the European Reference (1×100 mg) formulations was investigated in two bioequivalence studies: (i) a four-way crossover-design in both the fed and fasted states (Example 10) and (ii) a replicate-designed study in the fed state (Example 12).

In both studies, 50 mg of the Test itraconazole had an overall exposure that was comparable to, but lower than the Reference in both the fed and the fasted states:

1) In Example 10 in the fed state, the Test met exhibited 90% confidence intervals and test/reference (T/R) ratios for the AUC0-t value. In relation to Cmax, the T/R ratio was 0.93, however, the lower boundary of the 90% confidence internal was 0.76 and therefore did not meet the BE criteria.

2) In Example 10 in the fasted state, the T/R ratios were 0.61 and 0.99 for the AUC0-t and Cmax.

3) In Example 12 in the fed state, the T/R ratios were 0.80 and 0.79 for the AUC0-t and Cmax, with the lower boundary of the 90% confidence internal below 0.80 for both parameters.

In Example 10, the exposure to itraconazole was higher for both the Test and the Reference in the fasted compared to the fed state, although the food effect was less pronounced for the Test than the Reference:

a) Fasted/fed Ratio of Test: 1.26 and 1.90 for AUC0-t and Cmax, respectively;

b) Fasted/fed Ratio of Reference: 2.05 and 1.76 for AUC0-t and Cmax, respectively.

In the Single Dose studies with US-sourced Reference the following observations can be made:

a) Dose-proportional bioavailability of the Test at doses of 50 mg, 60 mg and 70 mg for both AUC and Cmax;

b) The bioavailability of Itraconazole from a single 100 mg dose of the Reference is comparable to the bioavailability of Itraconazole from the 50 mg dose of the Test;

c) A single 110 mg dose of the Test is comparable to the bioavailability of Itraconazole from a 200 mg dose of the Reference.

Multiple Dose Studies

Consistent with the Single dose studies described above, Multiple dose studies conducted with US Reference demonstrated that the Test exhibited an AUC and Cmax that were 20-30% lower for the Test compared to the Reference:

1) Example 6: the overall steady state bioavailability of itraconazole as measured by AUC and Cmax of a multiple dose of the Test (2×50 mg capsules) given for 15 consecutive days is approximately 20% lower than that of a multiple dose of the Reference (2×100 mg capsules) given for 15 consecutive days under fed conditions.

2) Example 7: the overall steady state bioavailability of itraconazole as measured by AUC and Cmax of a twice daily dose of the Test (2×50 mg capsules) given for 14.5 consecutive days is approximately 30% lower than that of a twice daily dose of the Reference (2×100 mg capsules) given for 14.5 consecutive days under fed conditions.

Variation in Exposure

Single Dose Studies

In both Single dose studies involving European-Reference drug, in the fed state the Test formulation demonstrated less variation in exposure than the Reference, particularly for AUC0-tlast:

1) Example 12: the Test demonstrated less intra-subject variation than the Reference, with % CV of 27.8% versus 51.2% for AUC0-tlast 2) Example 10: the Test demonstrated less inter-subject variation than the Reference, with % CV of 65 versus 102 for AUC0-tlast and 66 versus 88 for Cmax.

Taking into account the results from Study Example 12, the higher variation in exposure from the Reference is at least partially explained by a minority of subjects who absorb up to 5-fold higher than the mean.

Multiple Dose Studies—US Sourced Reference

Following twice/day dosing with food, SUBACAP™ 50 mg Hard Capsules (2×50 mg) demonstrated less fluctuations at steady state (on day 15) than US-sourced SPORANOX® (2×100 mg) (0.1213 vs. 0.2667 and 0.118 vs. 0.29) as determined by both [(Cmax on Day 15—Cmin on Day 15)/Cave on Day 15] and [(Cmax on Day 15—Cmin on Day 15)/Cmin on Day 15].

In addition, standard deviation values for AUC, Cmax, and Cmin were significantly lower following dosing with SUBACAP™ 50 mg Hard Capsules compared with SPORANOX® indicating that the Test product showed less variance compared to the Reference product.

However, the results of the once/day dosing in Example 6, showed that the fluctuations at steady state (on day 15) for SUBACAP™ 50 mg Hard Capsules and SPORANOX® (2×100 mg) were essentially similar using both methods of calculation (0.9668 vs. 0.8518 and 1.41 vs. 1.31), with SUBACAP™ 50 mg Hard Capsules actually a little higher. In addition, although the standard deviation values for AUC0-72 h, Cmax, and Cmin, were lower following dosing with SUBA®-Itraconazole compared with SPORANOX®, the difference was not so marked as following the twice/day dosing regimen.

TABLE 71

Overview of SUBACAP ™ 50 mg Capsule Study PK Program

| Study Number | n | Dates | Dose (SUBACAP ™) | Dose (Sporanox ®) | Fed/Fasted |
|---|---|---|---|---|---|
| HGN008 | 48 | November 2010 | 1 × 50 mg | 1 × 100 mg | Fed |
| HGN007 | 36 | March 2010 | 1 × 50 mg | 1 × 100 mg | Fed and fasting |
| 10850702 | 24 | October 2008 | 1 × 50 mg, 2 × 50 mg | 1 × 100 mg, 2 × 100 mg | Fasted |
| 10850706 | 24 | August 2008 | 4 × 50 mg | 4 × 100 mg | Fed |
| 10850705 | 24 | August 2008 | 2 × 50 mg | 2 × 100 mg | Fed |
| 10850703 | 36 | July 2008 | 1 × 50 mg | 1 × 100 mg | Fed and fasting |
| CM3007 | 12 | September 2007 | 1 × 50 mg + 1 × 60 mg | 2 × 100 mg | Fed and fasting |
| CM2907 | 12 | June 2007 | 50 mg, 60 mg, 70 mg | 1 × 100 mg | Fed |

TABLE 72-1

Comparison of PK Parameter Results post-IND Studies

| | Fasted Dose Ranging 10850702 (N = 24) | | | |
|---|---|---|---|---|
| Parameter | 1 × SUBA ® | 1 × Sporanox ® | Ratio | 90% C.I. |
| $AUC_{0-t}$ | 635.81 | 744.98 | 0.8535 | 0.7035-1.0354 |
| $AUC_{0-\infty}$ | 683.56 | 805.34 | 0.8488 | 0.7007-1.0282 |
| $C_{max}$ | 70.72 | 59.45 | 1.1894 | 0.9517-1.4865 |

| | Fasted Dose Ranging 10850702 (N = 24) | | | |
|---|---|---|---|---|
| Parameter | 2 × SUBA ® | 2 × Sporanox ® | Ratio | 90% C.I. |
| $AUC_{0-t}$ | 1674.84 | 1570.63 | 1.0664 | 0.8813-1.2903 |
| $AUC_{0-\infty}$ | 1814.68 | 1722.77 | 1.0534 | 0.8718-1.2727 |
| $C_{max}$ | 156.50 | 122.01 | 1.2827 | 1.0295-1.5982 |

| | Fed Fasted 10850703 (N = 36) | | | |
|---|---|---|---|---|
| Parameter | SUBA ® Fasted | Sporanox ® Fasted | Ratio | 90% C.I. |
| $AUC_{0-t}$ | 676.00 | 927.60 | 0.7288 | 0.6299-0.8432 |
| $AUC_{0-\infty}$ | 735.77 | 1011.63 | 0.7273 | 0.6268-0.8440 |
| $C_{max}$ | 69.92 | 71.26 | 0.9813 | 0.8113-1.1870 |

TABLE 72-1-continued

Comparison of PK Parameter Results post-IND Studies

Fed Fasted 10850703 (N = 36)

| Parameter | SUBA ®-Fed | Sporanox ® Fed | Ratio | 90% C.I. |
|---|---|---|---|---|
| $AUC_{0-t}$ | 533.30 | 692.62 | 0.7700 | 0.6639-0.8930 |
| $AUC_{0-\infty}$ | 588.76 | 762.64 | 0.7720 | 0.6656-0.8954 |
| $C_{max}$ | 32.76 | 50.11 | 0.6538 | 0.5388-0.7934 |

Fed Fasted 10850703 (N = 36)

| Parameter | SUBA ® Fasted | Sporanox ® Fed | Ratio | 90% C.I. |
|---|---|---|---|---|
| $AUC_{0-t}$ | 676.00 | 692.62 | 0.9760 | 0.8434-1.1294 |
| $AUC_{0-\infty}$ | 735.77 | 762.64 | 0.9648 | 0.8337-1.1164 |
| $C_{max}$ | 69.92 | 50.11 | 1.3954 | 1.1533-1.6882 |

Fed Multiple dose, low dose 10850705 (N = 24)

| Parameter | 2 × SUBA ® | 2 × Sporanox ® | Ratio | 90% C.I. |
|---|---|---|---|---|
| $AUC_{0-t}$ | 12212 | 14649 | 0.8336 | 0.7535-0.9222 |
| $AUC_{0-\infty}$ | 17438 | 21695 | 0.8038 | 0.6832-0.9456 |
| $C_{max}$ | 402 | 496 | 0.8107 | 0.7334-08962 |

Fed Multiple dose, high dose 10850706 (N = 24)

| Parameter | 4 × SUBA ® | 4 × Sporanox ® | Ratio | 90% C.I. |
|---|---|---|---|---|
| $AUC_{0-72}$ | 44400.50 | 67186.24 | 0.6609 | 0.5974-0.7310 |
| $AUC_{0-\infty}$* | — | — | — | — |
| $C_{max}$ | 1042.83 | 1540.24 | 0.6771 | 0.6186-0.7410 |

TABLE 72-2

Comparison of PK Parameter Results post-IND Studies Continued

| Parameter | 1 × SUBA ® | 1× Sporanox ® | Ratio | 90% C.I. |
|---|---|---|---|---|
| Study HGN007—Fed State (n = 35) | | | | |
| AUC0-t | 359 | 358 | 1.00 | 0.827, 1.22 |
| $AUC_{0-\infty}$ | 521 | 591 | 0.883 | 0.774, 1.05 |
| $C_{max}$ | 33.6 | 36.2 | 0.927 | 0.763, 1.12 |
| Study HGN007—Fasted State (n = 35) | | | | |
| $AUC_{0-t}$ | 448 | 733 | 0.611 | 0.557, 0.670 |
| $AUC_{0-\infty}$ | 591 | 866 | 0.682 | 0.629, 0.740 |
| $C_{max}$ | 63.4 | 63.8 | 0.993 | 0.859, 1.15 |
| Study HGN008—Fed State, Replicate Design (n = 48) | | | | |
| $AUC_{0-tlast}$ | 479 | 602 | 0.797 | 0.704, 0.901 |
| $AUC_{0-\infty}$ | 611 | 800 | 0.763 | 0.678, 0.859 |
| $C_{max}$ | 41.3 | 52.6 | 0.785 | 0.695, 0.888 |

Example 4

The results of this study show a dose-proportional bioavailability relationship for the bioavailability of SUBA®-Itraconazole at doses of 50 mg, 60 mg and 70 mg for both AUC and Cmax. The bioavailability of Itraconazole from a single 100 mg dose of SPORANOX® was comparable to the bioavailability of Itraconazole from the 50 mg dose of SUBA®-Itraconazole.

Efficacy Study

Example 14—a Randomized, Double Blind, Multiple-Site, Placebo-Controlled Study, Comparing the Efficacy and Safety of SUBA™-Itraconazole Capsules Compared to SPORANOX® (Itraconazole) Capsules in the Treatment of Onychomycosis of the Toenail Study Rationale This study compared the relative efficacy and safety of SUBA™-Itraconazole 50 mg Capsules to an already marketed oral formulation of itraconazole, SPORANOX® (itraconazole) 100 mg capsules, in the treatment of onychomycosis of the toenail. Both the test and the reference formulations were also compared to a placebo formulation to test for superiority.

Study Design

This study was a randomized, double-blind, multiple-site, placebo-controlled study comparing SUBA™-Itraconazole 50 mg capsules to the currently marketed reference product SPORANOX® (itraconazole) 100 mg capsules.

Patients with a confirmed diagnosis of moderate to severe onychomycosis of the toenail were randomized to one of three treatment groups as follows:

Test Group: SUBA™-Itraconazole 2×50 mg capsules (100 mg dose) once a day approximately 30 minutes prior to breakfast for 12 weeks;

Reference Group: SPORANOX® (itraconazole) 2×100 mg capsules (200 mg dose) taken once a day with breakfast for 12 weeks; or Placebo Group: 2× placebo capsules taken once a day approximately 30 minutes prior to breakfast for 12 weeks.

One hundred seventy-five (175) patients were enrolled in the study. Seventy-six (76) patients were enrolled in the Test group, 75 in the Reference group and 24 in the Placebo group. The three primary efficacy endpoints in the study were the proportion of patients considered a Therapeutic Cure, Clinical Cure and Mycological Cure, 24 weeks after starting treatment. Safety was evaluated by comparing adverse events, monitoring vital signs, EKG parameters, audiology and changes in clinical laboratory results obtained throughout the study.

Eligible patients were randomly assigned in a 3:3:1 ratio to the Test formulation 100 mg (2×50 mg capsules) once a day, Reference formulation 200 mg (2×100 mg capsules) once a day, or Placebo (2× capsules) once a day for 12 weeks of treatment.

Non-inferiority was determined by evaluating the difference between the proportion of patients in the Test and Reference groups who were considered:

1) a Therapeutic Cure at the End of Study Visit (Week 24);
2) a Clinical Cure at the End of Study Visit (Week 24); or
3) a Mycological Cure at the End of Study Visit (Week 24).

The intent to treat population (ITT) was used for the primary analysis of non-inferiority.

The superiority of the test and reference formulations against the Placebo was tested using the same 3 dichotomous endpoints. The ITT was used for all analysis of superiority.

There were 4 secondary endpoints:

1) The proportion of patients in each treatment group who were considered a Therapeutic Cure at the End of Treatment (Week 12);

2) The proportion of patients in each treatment group who were considered a Clinical Cure at the End of Treatment (Week 12);
3) The proportion of patients in each treatment group who were considered a Mycological Cure at the End of Treatment (Week 12);
4) The proportion of patients in each treatment group who showed a relapse during the study. Relapse was defined as being a Mycological Cure at Week 12 but being re-infected at Week 24

All secondary endpoints were tested for superiority against Placebo. The ITT was used for all secondary analysis of non-inferiority and superiority.

Statistical Methods

All statistical analysis was conducted using SAS®, Version 9.1.3.

Baseline comparability of all treatment groups was compared using appropriate statistical tests (e.g., one way analysis of variance, Cochran-Mantel-Haenszel Test). The groups were compared for basic demographics (age, gender, ethnicity, race), number of previous onychomycosis infections of the toenails, estimated duration of current infection, number of toes infected, % of toe infected, infecting organism (presence or absence of *T. rubrum* and presence or absence of *T. mentagrophytes*), presence or absence of concurrent tinea pedis infection and total NIRS score.

The primary measure of non-inferiority of the Test group to the Reference group was evaluated using those patients eligible for inclusion in the ITT. The three primary endpoints of the study were; the proportion of patients who were considered a Therapeutic Cure, Clinical Cure and Mycological Cure at the End of Study Visit (Week 24).

To demonstrate non-inferiority an upper bound 95% confidence interval approach comparing the difference between the cure rate in the Test and the Reference groups was used. If the lower bound 95% confidence interval of the difference between the proportion of patients in the Test group compared to the Reference group considered a Therapeutic Cure, Clinical Cure and Mycological Cure as appropriate, at Week 24 was greater than −20 then non-inferiority was considered to have been demonstrated. Secondary measures of non-inferiority also used the ITT.

For each of the four dichotomous secondary endpoints, the same statistical analysis as used for the primary endpoint was used. Specifically if the lower bound 95% confidence interval of the difference between the proportion of patients in the Test group compared to the Reference group considered a cure at the visit being analyzed was greater than −20 then non-inferiority was considered to have been demonstrated. All primary and secondary endpoints were tested for superiority against Placebo. The ITT was used for all superiority testing.

For the three primary endpoints and all four dichotomous secondary endpoints, if the difference between the proportion of patients considered a cure in the Test or Reference group was statistically greater (p<0.05) than the proportion of patients considered a cure in the Placebo group, then superiority of that treatment over placebo was considered to have been demonstrated. A one-sided continuity corrected Z-test was used for superiority testing.

Safety analysis included all patients who were randomized and used study medication on at least one occasion. For the analysis of clinical laboratory testing descriptive analyses (mean, standard deviation, median, maximum and minimum) of each laboratory parameter were calculated at each time point by treatment group. Shift analysis using the categories; below, above and within the laboratory normal range was performed to identify any specific laboratory parameter that showed a trend to show potentially clinically significant changes.

Comparative Efficacy Analysis

The primary measure of non-inferiority of the Test group to the Reference group was evaluated using those patients eligible for inclusion in the ITT. The three primary endpoints of the study were the proportion of patients in each treatment group who were considered a Therapeutic Cure, Clinical Cure and Mycological Cure at the End of Study Visit (week 24). A patient was considered a Therapeutic Cure if they were both a Clinical Cure (NIRS of 0) and a Mycological Cure (negative KOH and mycological culture). Any patient who was discontinued from the study prior to Visit 7 because of lack of efficacy was automatically considered a Clinical Failure and thus a Therapeutic Failure. If the lower bound 95% confidence interval of the difference between the proportion of patients in the Test group compared to the Reference group considered a Therapeutic Cure, Clinical Cure or Mycological Cure as appropriate at Visit 7 was greater than −20, then non-inferiority was considered to have been demonstrated.

All primary and secondary endpoints were tested for superiority against Placebo. The ITT was used for all secondary analysis of non-inferiority and superiority. Any patient who was discontinued from the study prior to Visit 7 because of lack of efficacy was considered a Clinical Failure. If a sample for KOH and/or mycological culture was obtained, the result was carried forward for later visits.

For each of the four secondary endpoints, the same statistical analysis as used for the primary endpoint was performed. Specifically, if the lower bound 95% confidence interval of the difference between the proportion of patients in the test group compared to the reference group considered a cure at the visit being analyzed was greater than −20 then non-inferiority was considered to have been demonstrated.

Superiority to Placebo Analysis

The ITT was used for all superiority testing. For the three primary endpoints and all four secondary endpoints, if the difference between the proportion of patients considered a cure was statistically greater (p<0.05) than the proportion of patients considered a cure in the Placebo group, then superiority was considered to have been demonstrated. A one-sided continuity corrected Z-test was used for superiority testing.

A summary of the results from this study is shown in Tables 73-78 which show that SUBA™-Itraconazole is superior to placebo for mycological cure.

TABLE 73

Summary of Results: Non-Inferiority (Primary Analysis)
Primary Analysis - Non Inferiority Intent-to-Treat Population (ITT)

| Therapeutic Cure at Visit 7 (Week 24) | | | | |
|---|---|---|---|---|
| | N | Therapeutic Cure | Difference | Lower 95% CI |
| Test | 76 | 8 (10.53%) | 6.47 | −1.77 |
| Ref | 74 | 3 (4.05%) | | |

| Clinical Cure at Visit 7 (Week 24) | | | | |
|---|---|---|---|---|
| | N | Clinical Cure | Difference | Lower 95% CI |
| Test | 76 | 12 (15.79%) | 10.38 | 0.92 |
| Ref | 74 | 4 (5.41%) | | |

TABLE 73-continued

Summary of Results: Non-Inferiority (Primary Analysis)
Primary Analysis - Non Inferiority Intent-to-Treat Population (ITT)

Mycological Cure at Visit 7 (Week 24)

|  | N | Mycological Cure | Difference | Lower 95% CI |
|---|---|---|---|---|
| Test | 76 | 25 (32.89%) | 3.17 | −10.62 |
| Ref | 74 | 22 (29.73%) | | |

TABLE 74

Summary of Results: Non-Inferiority (Secondary Analysis)
Secondary Analysis - Non inferiority (ITT)

Therapeutic Cure at Visit 6 (Week 12)

|  | N | Therapeutic Cure |
|---|---|---|
| Test | 76 | 0 (0.00%) |
| Ref | 74 | 0 (0.00%) |

Clinical Cure at Visit 6 (Week 12)

|  | N | Clinical Cure | Difference | Lower 95% CI |
|---|---|---|---|---|
| Test | 76 | 1 (1.32%) | 1.32 | −2.17 |
| Ref | 74 | 0 (0.00%) | | |

Mycological Cure at Visit 6 (Week 12)

|  | N | Mycological Cure | Difference | Lower 95% CI |
|---|---|---|---|---|
| Test | 76 | 16 (21.05%) | −0.57 | −12.91 |
| Ref | 74 | 16 (21.62%) | | |

Mycological Relapse Between Treatment Groups (Visit 6 to Visit 7)

|  | N | Relapse | Difference | Lower 95% CI |
|---|---|---|---|---|
| Test | 16 | 3 (18.75%) | −6.25 | −36.47 |
| Ref | 16 | 4 (25.00%) | | |

TABLE 75

Summary of Results: Superiority (Primary Analysis)
Primary Analysis - Superiority (ITT)

Therapeutic Cure at Visit 7 (Week 24)

|  | N | Therapeutic Cure | Comparison | One sided p-value |
|---|---|---|---|---|
| Test | 76 | 8 (10.53%) | Test v. Placebo | p = 0.0135* |
| Ref | 74 | 3 (4.05%) | Ref v. Placebo | p = 0.2861 |
| Placebo | 24 | 0 (0.00%) | | |

Clinical Cure at Visit 7 (Week 24)

|  | N | Clinical Cure | Comparison | One sided p-value |
|---|---|---|---|---|
| Test | 76 | 12 (15.79%) | Test v. Placebo | p = 0.0009* |
| Ref | 74 | 4 (5.41%) | Ref v. Placebo | p = 0.1570 |
| Placebo | 24 | 0 (0.00%) | | |

Mycological Cure at Visit 7 (Week 24)

|  | N | Mycological Cure | Comparison | One sided p-value |
|---|---|---|---|---|
| Test | 76 | 25 (32.89%) | Test v. Placebo | p = 0.0001* |
| Ref | 74 | 22 (29.73%) | Ref v. Placebo | p = 0.0003* |
| Placebo | 24 | 1 (4.17%) | | |

*Statistically significant if p < 0.05

TABLE 76

Summary of Results: Superiority (Secondary Analysis)
Secondary Analysis - Superiority (ITT)

Therapeutic Cure at Visit 6 (Week 12)

|  | N | Therapeutic Cure |
|---|---|---|
| Test | 76 | 0 (0.00%) |
| Ref | 74 | 0 (0.00%) |
| Placebo | 24 | 0 (0.00%) |

Clinical Cure at Visit 6 (Week 12)

|  | N | Clinical Cure | Comparison | One sided p-value |
|---|---|---|---|---|
| Test | 76 | 1 (1.32%) | Test v. Placebo | p = 0.1377 |
| Ref | 74 | 0 (0.00%) | | |
| Placebo | 24 | 0 (0.00%) | | |

Mycological Cure at Visit 6 Week 12)

|  | N | Mycological Cure | Comparison | One sided p-value |
|---|---|---|---|---|
| Test | 76 | 16 (21.05%) | Test v. Placebo | p = 0.2396 |
| Ref | 74 | 16 (21.62%) | Ref v. Placebo | p = 0.2210 |
| Placebo | 24 | 3 (12.50%) | | |

Mycological Relapse Between Treatment Groups (Visit 6 to Visit 7)

|  | N | Relapse | Comparison | One sided p-value |
|---|---|---|---|---|
| Test | 16 | 3 (18.75%) | Test v. Placebo | p = 0.0096* |
| Ref | 16 | 4 (25.00%) | Ref v. Placebo | p = 0.0179* |
| Placebo | 3 | 2 (66.67%) | | |

*Statistically significant if p < 0.05

TABLE 77

Interim Visit Efficacy Analysis - Non-Inferiority
Interim Visit Efficacy Analysis - Non Inferiority (ITT)

Therapeutic Cure at Visit 4 (Week 6)

|  | N | Therapeutic Cure |
|---|---|---|
| Test | 76 | 0 (0.00%) |
| Ref | 74 | 0 (0.00%) |

Clinical Cure at Visit 4 (Week 6)

|  | N | Clinical Cure |
|---|---|---|
| Test | 76 | 0 (0.00%) |
| Ref | 74 | 0 (0.00%) |

Mycological Cure at Visit 4 (Week 6)

|  | N | Mycological Cure | Difference | Lower 95% CI |
|---|---|---|---|---|
| Test | 76 | 11 (14.47%) | 7.72 | −1.81 |
| Ref | 74 | 5 (6.76%) | | |

TABLE 78

Interim Visit Analysis - Superiority
Interim Visit Superiority Analysis (ITT)

Therapeutic Cure at Visit 4 (Week 6)

|  | N | Therapeutic Cure |
|---|---|---|
| Test | 76 | 0 (0.00%) |
| Ref | 74 | 0 (0.00%) |
| Placebo | 24 | 0 (0.00%) |

TABLE 78-continued

Interim Visit Analysis - Superiority
Interim Visit Superiority Analysis (ITT)

Clinical Cure at Visit 4 (Week 6)

|  | N | Clinical Cure |
|---|---|---|
| Test | 76 | 0 (0.00%) |
| Ref | 74 | 0 (0.00%) |
| Placebo | 24 | 0 (0.00%) |

Mycological Cure at Visit 4 (Week 6)

|  | N | Mycological Cure | Comparison | One sided p-value |
|---|---|---|---|---|
| Test | 76 | 11 (14.47%) | Test v. Placebo | p = 0.0018* |
| Ref | 74 | 5 (6.76%) | Ref v. Placebo | p = 0.0853 |
| Placebo | 24 | 0 (0.00%) |  |  |

*Statistically significant if p < 0.05

Figure 58:
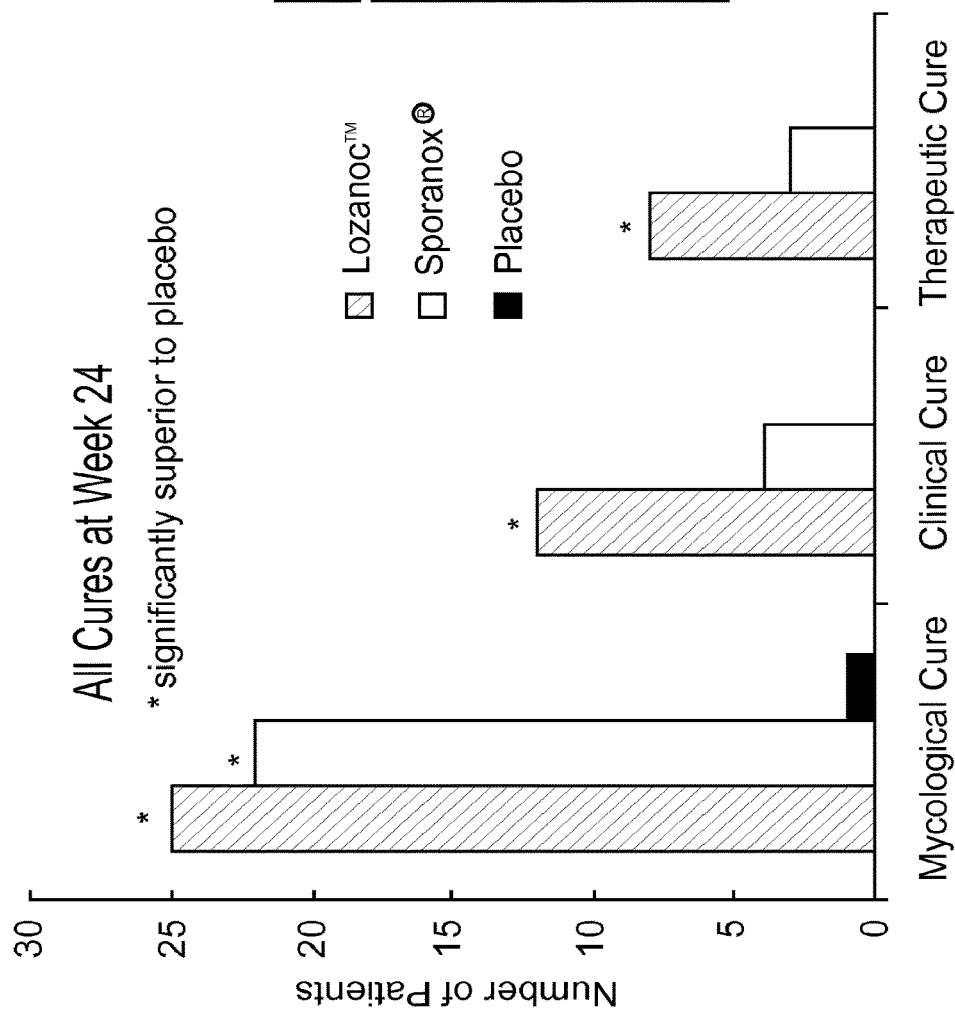
FIG. 58 is a graph which shows that SUBA™-Itraconazole was significantly superior to placebo for both efficacy endpoints, whereas SPORANOX® (itraconazole) was not significantly different to placebo. A comparison of mycological, clinical, and therapeutic cure at Week 24. Mycological Cure was measured by negative stain and culture; clinical cure was measured as a nail rating score of zero; therapeutic cure required both mycological cure and clinical cure. The Nail Rating Score was determined to be 0 if less than 10% of the nail is missing, and there is no thickening or discloration.

As shown in FIG. 58, SUBA™-Itraconazole was significantly superior to placebo for both efficacy endpoints, whereas SPORANOX® (itraconazole) was not significantly different to placebo.

The more reliable extent of exposure following administration of SUBA'-Itraconazole compared with SPORANOX® (itraconazole) may result in faster accumulation of itraconazole in the nail bed, clearing the infection more quickly and allowing a faster clinical cure.

Figure 59:
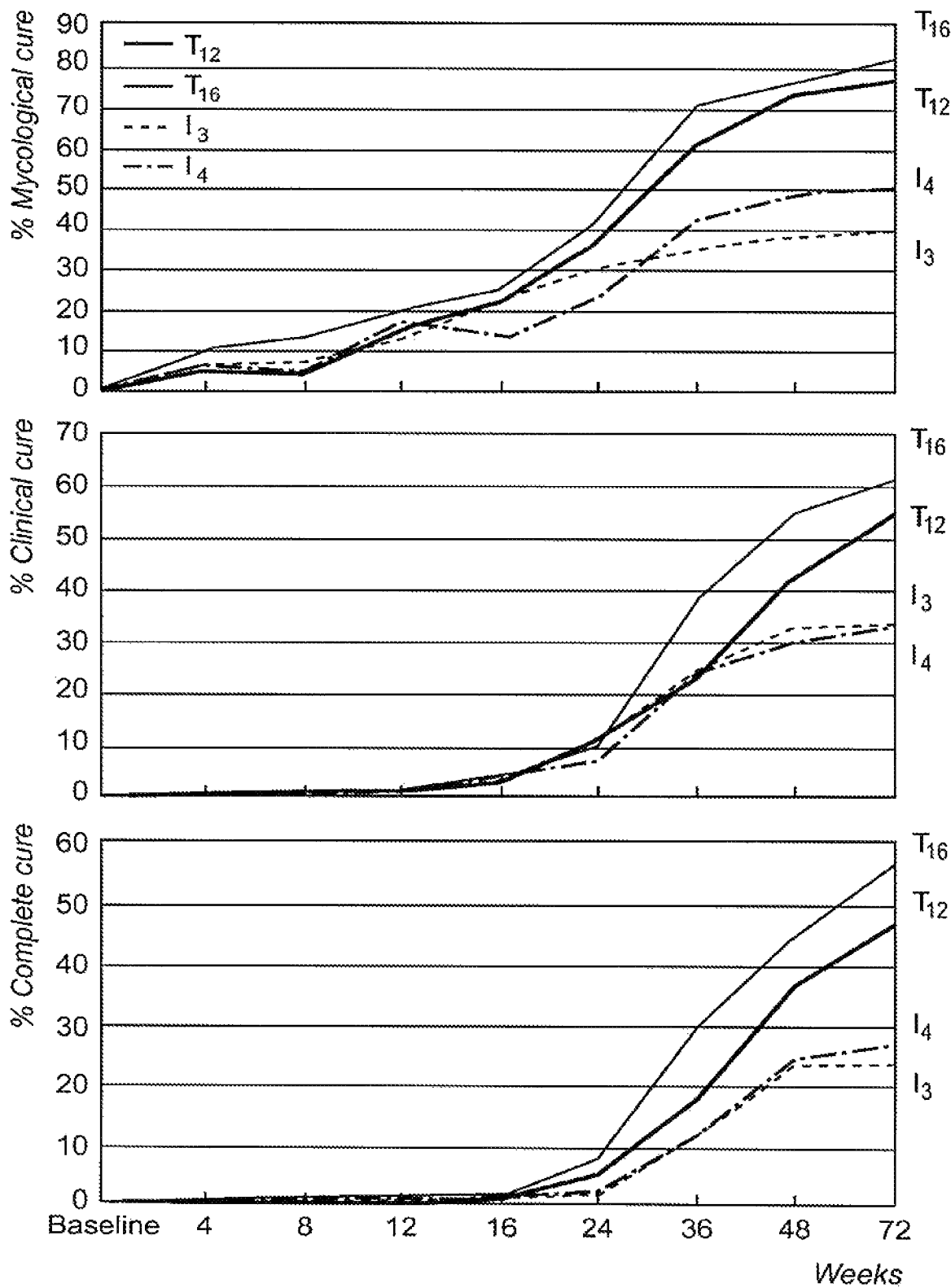
FIG. 59 is a graph illustrating illustrates the rates (%) of mycological cure, clinical cure, and complete cure for LOZANOC. The cure rates for LOZANOC at week 24 are comparable to terbinafine pulse therapy and are higher than would be expected for conventional itraconazole. For all comparisons, p<0.0001 except for clinical cure $T_{12}$ v $I_3$ where p<0.0015; $T_{12}$ v $I_4$ p=0.0022; and for complete cure $T_{12}$ v $I_3$ p=0.0007 and $T_{12}$ v $I_4$ p=0.0044.

Moreover, the results of this study are clinically significant. As shown in FIG. 59, which illustrates the cure rates for this study with the LION Study (Evans et al. 1999), the cure rates for LOZANOC at week 24 are comparable to terbinafine pulse therapy and are higher than would be expected for conventional itraconazole. For all comparisons, p<0.0001 except for clinical cure $T_{12}$ v $I_3$ where p<0.0015; $T_{12}$ v $I_4$ p=0.0022; and for complete cure $T_{12}$ v $I_3$ p=0.0007 and $T_{12}$ v $I_4$ p=0.0044.

SUBA™-Itraconazole Capsule dosed at 100 mg once a day has been shown to be non-inferior to SPORANOX® (itraconazole) capsule dosed at 200 mg once a day in the treatment of onychomycosis of the toenail, as measured using the primary endpoints of Therapeutic Cure, Clinical Cure and Mycological Cure at Week 24.

The Test formulation was shown to be superior to Placebo for each of the three endpoints at Week 24. The Reference product was shown to be superior to Placebo for Mycological Cure, but not Clinical Cure or Therapeutic Cure at Week 24.

For the secondary endpoints of Clinical Cure and Mycological Cure at Week 12, the Test formulation was shown to be non-inferior to the Reference product. Because of the small sample size neither treatment was superior to Placebo for these secondary endpoints. There were no Therapeutic Cure's in any group at Week 12.

Mycological relapse rate was lower (18.75%) in the Test group than the Reference group (25.00%) but the small sample size (N=16 in each group) did not allow for statistical non-inferiority. Both Test and Reference formulations were superior to Placebo (66.67%) in relapse rate.

SUBA™-Itraconazole Capsule dosed at 100 mg once a day was demonstrated to have a similar safety profile to SPORANOX® (itraconazole) capsule dosed at 200 mg once a day.

Analysis of Adverse Events

All 175 patients enrolled in the study were included in the adverse event analysis. Ninety (90) patients reported a total of 219 adverse events during the study. Fisher's exact test analysis was performed for adverse events reported at least once in two or more treatment groups. There were no significant differences in the frequency of adverse events between the treatment groups. There were no significant differences between the Test and the Reference groups with respect to type, frequency or severity or adverse events reported or observed during the study. The safety profile of SUBA'-Itraconazole Capsule dosed at 100 mg once a day is consistent with the known safety profile to SPORANOX® (itraconazole) capsule dosed at 200 mg once a day. No significantly new or unexpected adverse events attributable to itraconazole were observed in this study.

Example 15—Comparison of AUC/MIC Ratios and Relationship to Clinical Efficacy

Itraconazole has been used to treat a wide variety of fungal infections since its first introduction into clinical practice. For instance, with both the 100 mg capsule (SPORANOX®) form of itraconazole and the oral solution, there are data in oropharyngeal candidosis to establish a relationship between minimum inhibitory concentration (MIC) value, serum level, and clinical response (Cross, Bagg et al. 2000). In aspergillosis, it has been more difficult to establish a relationship between MIC values and clinical responses given that many infections also occur in teh context of severe immunosuppression leading to greater unpredictability. However, in a muring model of aspergillosis, a similar positive predictive value of MIC determination and clinical response was seen (Denning, Radford et al. 1997). Notably, some strains of *Aspergillus fumigatus* show MIC values at the upper range. However, resistance to trazole antifungals occurs in fewer than 2% of strains and there is evidence that there is cross resistance between itraconazole, posaconazole, and voriconazole (Pfaller, Boyken et al. 2011).

There is limited evidence for a relationship between MIC level and clinical breakpoints for other systemic infections, such as histoplasmosis, However the relationship between the low MICs for *Histoplasma capsulatum* and its clinical efficacy are sufficiently consistent to continue to reccommend this drug as primary treatment of histoplasmosis.

Given that: i) oral itraconazole has been sucessfully used for decades to treat a wide range of superficial and systemic fungal infections; and ii) LOZANOC 50 mg hard capsules and SPORANOX® 100 mg Capsules contain the same drug substance, the goal of a comparison of AUC/MIC ratios for the two formulations is not to predict the clinical efficacy of itraconazole. Rather, it is to assess: 1) the probability that a LOZANOC 50 mg hard capsule patient will achieve a lower exposure than is necessary for therapeutic effect compared to tghe corresponding probability with SPORANOX® 100 mg Capsules; and 2) the probability that a LOZANOC 50 mg hard capsule patient will achieve a much greater exposure than is necessary compared to the corresponding probability with SPORANOX® 100 mg Capsules.

Tables 79A and 79B list the typical infecting organisms for specific superficial and systemic mycoses and their corresponding MIC ranges.

TABLE 79A

| INDICATIONS | | INFECTING ORGANISM<br>Superficial mycoses | MIC RANGE |
|---|---|---|---|
| Dermatomycoses | tinea corporis | Trichophyton sp. (rubrum, tonsurans interdigitale, mentagrophytes, concentricim, violaceum et al.) | 0.01-8<br>$MIC_{90} = 0.25$-$0.5$ |
| | | Microsporum sp. (canis, gypseum, et al.) | 0.01-4<br>$MIC_{90} = 0.25$-$0.5$ |
| | | Epidermophyton floccosum | 0.01-8<br>$MIC_{90} = 0.125$ |
| | tinea cruris | Trichophyton sp. (rubrum, tonsurans interdigitale, mentagrophytes, et al.) | 0.01-8<br>$MIC_{90} = 0.25$-$0.5$ |
| | | Microsporum sp. (canis, et al.) | 0.01-4<br>$MIC_{90} = 0.25$-$0.5$ |
| | | Epidermophyton floccosum | 0.01-8<br>$MIC_{90} = 0.125$ |
| | tinea pedis | Trichophyton sp. (rubrum, tonsurans interdigitale, mentagrophytes, et al.) | 0.01-8<br>$MIC_{90} = 0.25$-$0.5$ |
| | | Microsporum sp. (canis, gypseum, et al.) | 0.01-4<br>$MIC_{90} = 0.25$-$0.5$ |
| | | Epidermophyton floccosum | 0.01-8<br>$MIC_{90} = 0.125$ |
| | tinea manuum | Trichophyton sp. (rubrum, interdigitale, mentagrophytes.) | 0.01-8<br>$MIC_{90} = 0.25$-$0.5$ |
| | | Epidermophyton floccosum | 0.01-8<br>$MIC_{90} = 0.125$ |
| | tinea unguium | Trichophyton sp. (rubrum, tonsurans interdigitale, mentagrophytes, et al.) | 0.01-8<br>$MIC_{90} = 0.25$-$0.5$ |
| | | Microsporum sp. (canis, et al.) | 0.01-4<br>$MIC_{90} = 0.25$-$0.5$ |
| | | Epidermophyton floccosum | 0.01-8<br>$MIC_{90} = 0.125$ |
| | tinea capitis | Trichophyton sp. (tonsurans violaceum, soudanese, schoenleinii, mentagrophytes, verrucossum, et al.) | 0.01-8<br>$MIC_{90} = 0.25$-$0.5$ |
| | | Microsporum sp. (audounti, canis, gypseum, ferrugineum et al. | 0.01-4<br>$MIC_{90} = 0.25$-$0.5$ |
| Pityriasis versicolor | | Malassezia sp. (florfur, globosa, obtuse, sympodialis etc). | 0.3-16<br>$MIC_{90} = 0.125$ |

TABLE 79B

| INDICATIONS | INFECTING ORGANISM<br>Systemic mycoses | MIC RANGE |
|---|---|---|
| Candidiasis | C. albicans | 0.008-8<br>$MIC_{90} = 0.125$ |
| | C. parapsilosis | 0.016-2<br>$MIC_{90} = 0.25$ |
| | C. glabrata | 0.008-16<br>$MIC_{90} = 16$ |
| | C. kruset | 0.008-8<br>$MIC_{90} = 0.5$ |
| | C. tropicalis | 0.03-8<br>$MIC_{90} = 0.5$ |
| Aspergillosis | A. fumigatus complex | 0.03-16<br>$MIC_{90} = 0.5$ |
| | A. flavus complex | 0.03-8<br>$MIC_{90} = 0.5$ |
| | A. terreus complex | 0.03-1<br>$MIC_{90} = 0.25$ |
| | A. nidulans complex | 0.03-8<br>$MIC_{90} = 0.25$ |
| | A. niger complex | 0.03-8<br>$MIC_{90} = 0.5$ |
| Histoplasmosis | H. capsulatum | 0.03-8<br>$MIC_{90} = 0.06$ |

When reviewing Table 79, the following should be noted:

All dermatophytes have the ability to cause infection of keratinaceous substrates like skin, hair, and nails. Species listed in this table are the most common for the clinical entity described (Rippon 1988; Elewski 1998).

In general, dermatophytes are generally considered to be fully susceptible to itraconazole, resistant strains are very uncommon. However the MIC data presented is a composite of reports that may use different methodology; standardised CLSI methodology for testing antifungal susceptibility to dermatophytes only became available in 2008 (CLSI document M38-A2) (Fernandez-Tones, Carrillo et al. 2001; Sabatelli, Patel et al. 2006; Santos and Hamdan 2006).

With regards to pityriasis veriscolor, seven species of Malassezia have now been recognised as causative agents. Antifungal susceptibility testing is difficult because they do not grow readily on the usual media. However, all are considered susceptible to itraconazole (Gueho, Midgley et al. 1996; Nakamura, Kano et al. 2000; Velegraki, Alexopoulos et al. 2004; Miranda, de Araujo et al. 2007).

Several species of Candida may be aetiological agents, most commonly C. albicans (~48%), followed by C. parapsilosis (~19%), C. glabrata (~18%), C. krusei (~5%) and C. tropicalis (~5%). However, a number of other species may also be isolated (~5% eg C. dubliensis, C. guilliermondii, C. lustianiae, C. kefry etc). All are ubiquitous and occur naturally on humans. CLSI and EUCAST antifungal susceptibility methodology is available. Resistance to itraconazole (MIC >1 µg/ml) has been detected in most species; however, it occurs predominantly in isolates of C. glabrata (Espinel-Ingroff 2001; Pfaller, Messer et al. 2002; Hajjeh, Sofair et al. 2004; Richter, Galask et al. 2005; Chen, Slavin et al. 2006; Cuenca-Estrella, Gomez-Lopez et al. 2006; Pfaller and Diekema 2007; Ellis and Handke 2010).

Overall, itraconazole resistance in Aspergillus remains low. The emergence of invasive infection due to triazole-resistant, including cross-resistant, A. fumigatus isolates is of increasing concern in Europe, where 3-6% of isolates have been reported resistant at different centres. However, to date, a similar emergence of triazole- and/or cross-resistant A. fumigatus has not been observed in the Australian setting. A recent surveillance study of all A. fumigatus isolates at The Alfred Hospital, Melbourne, identified no triazole-resistant A. fumigatus isolates over a one year period (May 2009-April 2010) (Espinel-Ingroff 2001; Espinel-Ingroff, Boyle et al. 2001; Pfaller, Messer et al. 2002; Cuenca-Estrella, Gomez-Lopez et al. 2006; Sabatelli, Patel et al. 2006; Verweij, Mellado et al. 2007; Kidd, Handke et al. 2011) (S. Kidd, unpublished data).

Itraconazole is an important antifungal for the management of histoplasmosis (Espinel-Ingroff 2001; Gonzalez, Fothergill et al. 2005; Sabatelli, Patel et al. 2006; Wheat, Freifeld et al. 2007)

If one assigns a clinical breakpoint and a target AUC/MIC ratio for optimal therapeutic effect then the minimum AUC required can be calculated. As highlighted in Table 79, these breakpoints and AUC/MIC ratios vary according to the infecting organism so it is instructive to consider multiple scenarios. For illustrative purposes, Table 80, lists three scenarios selected based on the following rationale:

A MIC90 of <1 mcg/ml is appropriate for treating the majority of susceptible superficial and systemic infections within the proposed indications for this application A MIC90 of >4 mcg/ml would normally be considered resistant but in some cases itraconazole is used to treat specific mycoses considered to be due to an organism resistant at this level if clinically indicated A MIC90 of 16 mcg/ml is the maximum point on the standard 0.0008-16 mcg/ml testing range employed in mycology laboratories.

A target AUC/MIC ratio of greater than 25 has been designated in Table 80, as it has been determined to be the ratio at which optimal efficacy rates are achieved for the triazole class (Andes 2003).

highly variable Sporanox for MIC90 >4 mcg/ml and also for the majority when MIC >16 mcg/ml.

A key question is whether Lozanoc 50 mg hard capsules should be taken in the fed or the fasted state, or whether it can be taken regardless of food. The study described in Example 10 indicated that Lozanoc 50 mg Hard Capsules taken in the fed state performed better than in the fasted state. However, three observations suggest that Lozanoc 50 mg hard capsules can be taken regardless of food:

1. In the study described in Example 10, the variance in AUC(0-inf) for Lozanoc 50 mg hard capsules is significantly lower than Sporanox® 100 mg Capsules when the fed and fasted data are pooled, which in part is due to the variance being significantly less when Lozanoc 50 mg hard capsules are taken in the fasted state versus Sporanox® 100 mg Capsules in the fed state.

Figure 63:
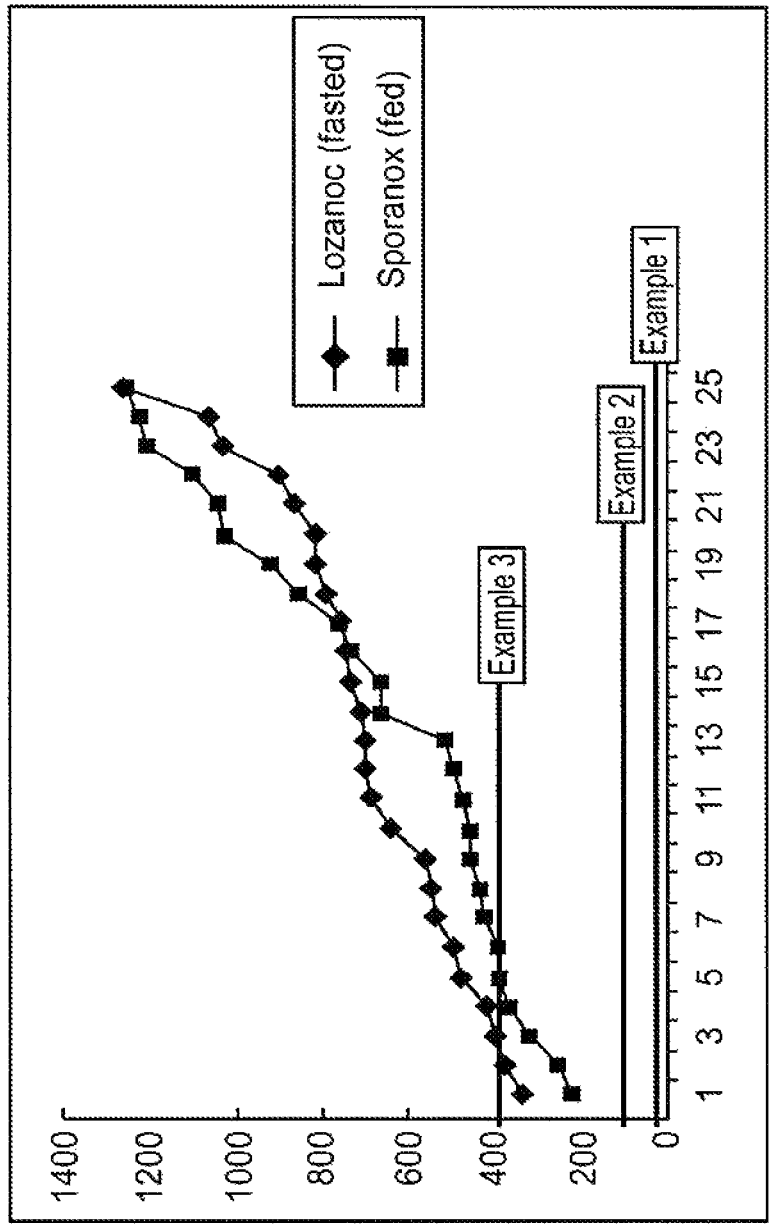
FIG. 63 shows the comparison of the individual AUC/MIC ratios for subjects in the study described in Example 10 who received Lozanoc 50 mg hard capsules in the fasted state versus Sporanox® 100 mg Capsules in the fed state.
Figure 64:
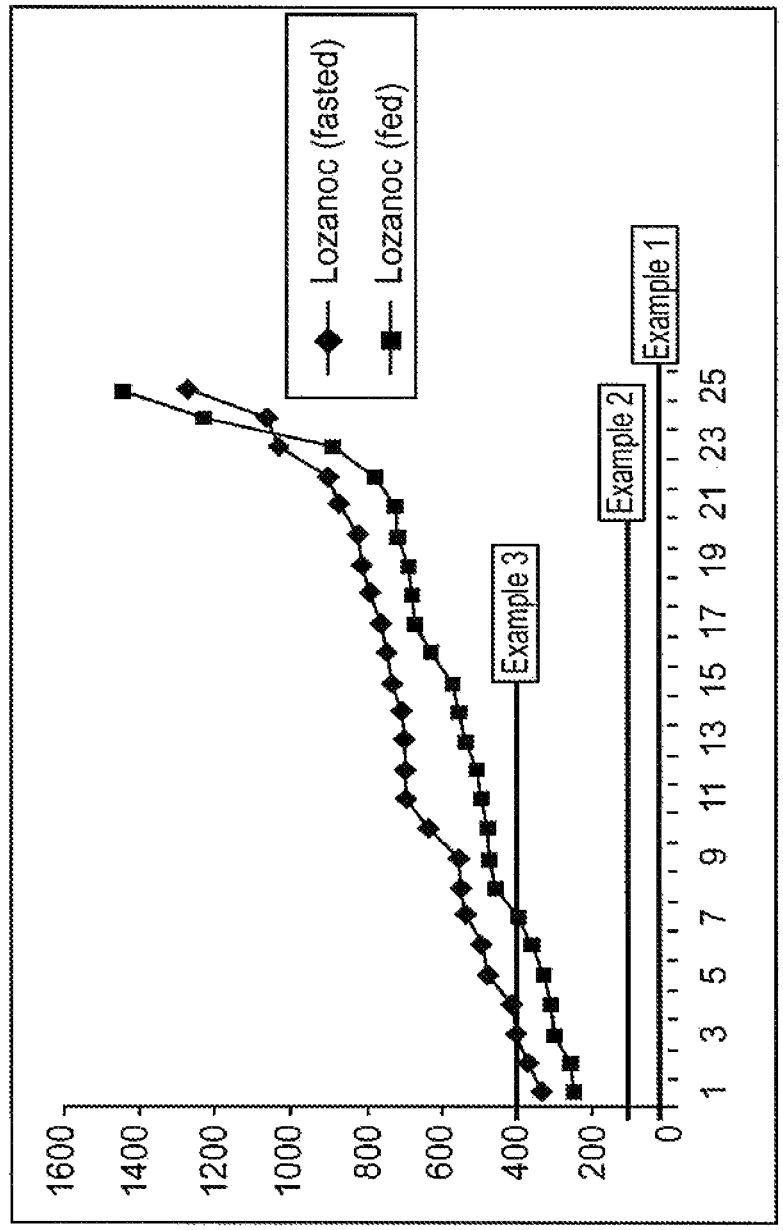
FIG. 64 shows the comparison of the individual AUC/MIC ratios for subjects in the study described in Example 10 who received Lozanoc 50 mg Hard Capsules in the fasted state versus the fed state.

2. When one then compares the individual AUC/MIC ratios for subjects in the study described in Example 10: (i) taking Lozanoc 50 mg hard capsules in the fasted state versus Sporanox® 100 mg Capsules in the fed state (FIG. 63) and (ii) Lozanoc 50 mg Hard Capsules in the fasted state versus the fed state (FIG. 64), it is apparent that the performance of Lozanoc 50 mg hard capsules is comparable regardless of food.

3. In the onychomycosis efficacy study described in Example 14, Lozanoc 50 mg hard capsules was dosed in the fasted state (30 minutes prior to breakfast) and at week 24 demonstrated superior efficacy rates to placebo.

The most important PK-PD parameter for itraconazole is the AUC/MIC ratio which should be greater than 25 for optimal efficacy. The above data demonstrate that 50 mg of

TABLE 80

Calculations of minimum AUC required for optimal therapeutic effect

| Scenario number | Clinical breakpoint (mcg/ml) | Target AUC/MIC ratio | Minimum AUC required[1] (ng · hr/ml) |
|---|---|---|---|
| 1 | 1 | 25 | 25 |
| 2 | 4 | 25 | 100 |
| 3 | 16 | 25 | 400 |

[1]Obtained by multiplying column 2 × column 3

Figure 60:
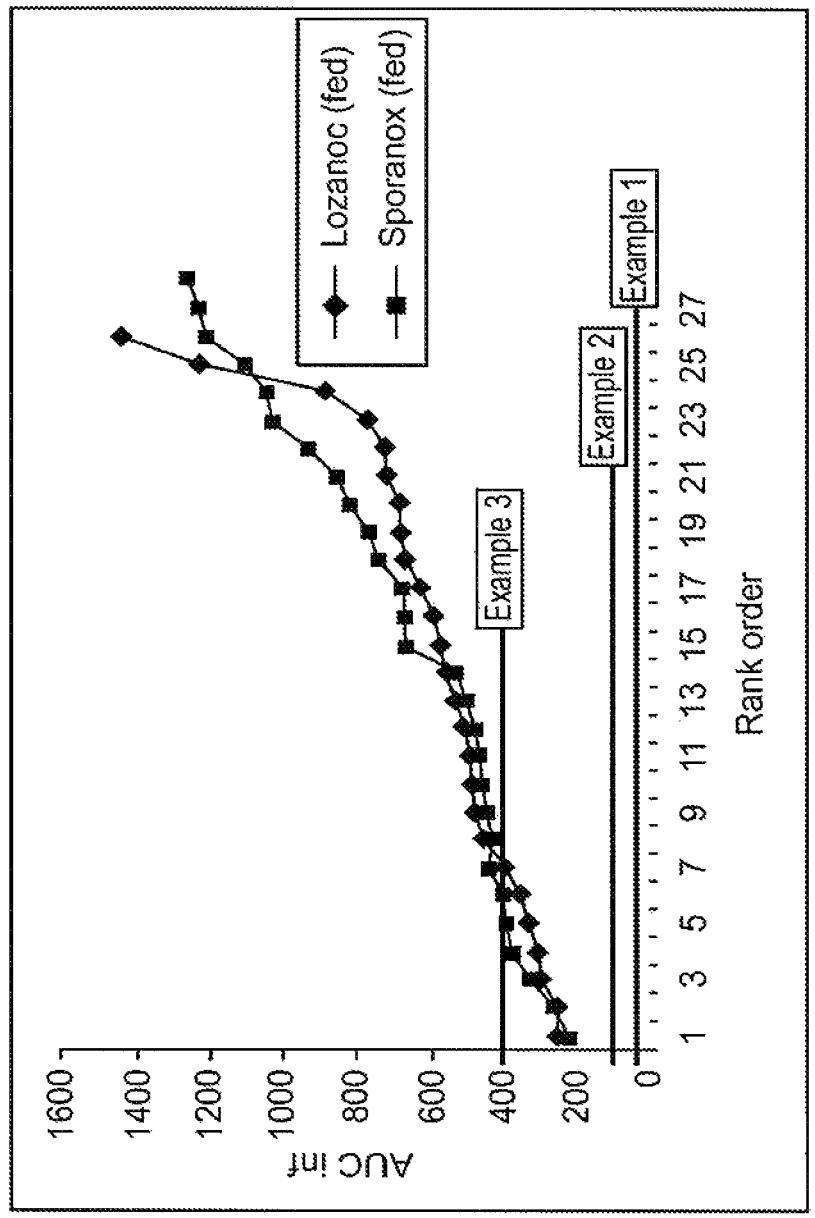
FIG. 60 is a graph showing individual subject $AUC_{inf}$ results ranked in order of lowest to highest for both test and reference, with the minimum AUC thresholds arrived at in Table 80 superimposed. This illustrates the actual AUCs required for optimal therapeutic effect and compares the relative performance of Lozanoc 50 mg hard capsules and Sporanox® 100 mg Capsules in Example 10.

In FIG. 60 the individual subject $AUC_{inf}$ results were ranked in order of lowest to highest for both test and reference, with the minimum AUC thresholds arrived at in Table 80 superimposed. This illustrates actual AUCs required for optimal therapeutic effect and compares the relative performance of Lozanoc 50 mg hard capsules and Sporanox® 100 mg Capsules in Example 10 (see pharmacokinetics section).

Figure 61:
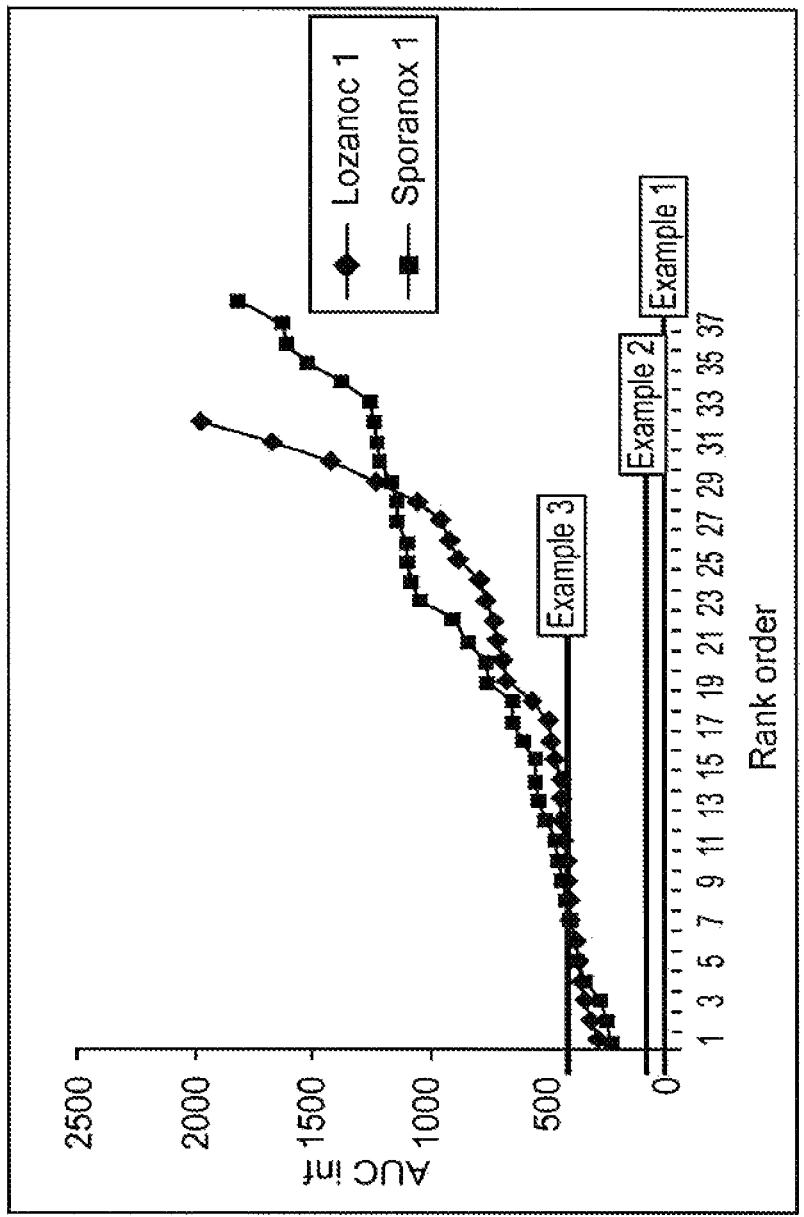
FIG. 61 is a graph showing individual subject $AUC_{inf}$ results ranked in order of lowest to highest for both test and reference, with the minimum AUC thresholds arrived at in Table 80 superimposed. This illustrates the actual AUCs required for optimal therapeutic effect and compares the relative performance of Lozanoc 50 mg hard capsules and Sporanox® 100 mg Capsules in the first administration of Lozanoc described in Example 12 (see pharmacokinetics section).
Figure 62:
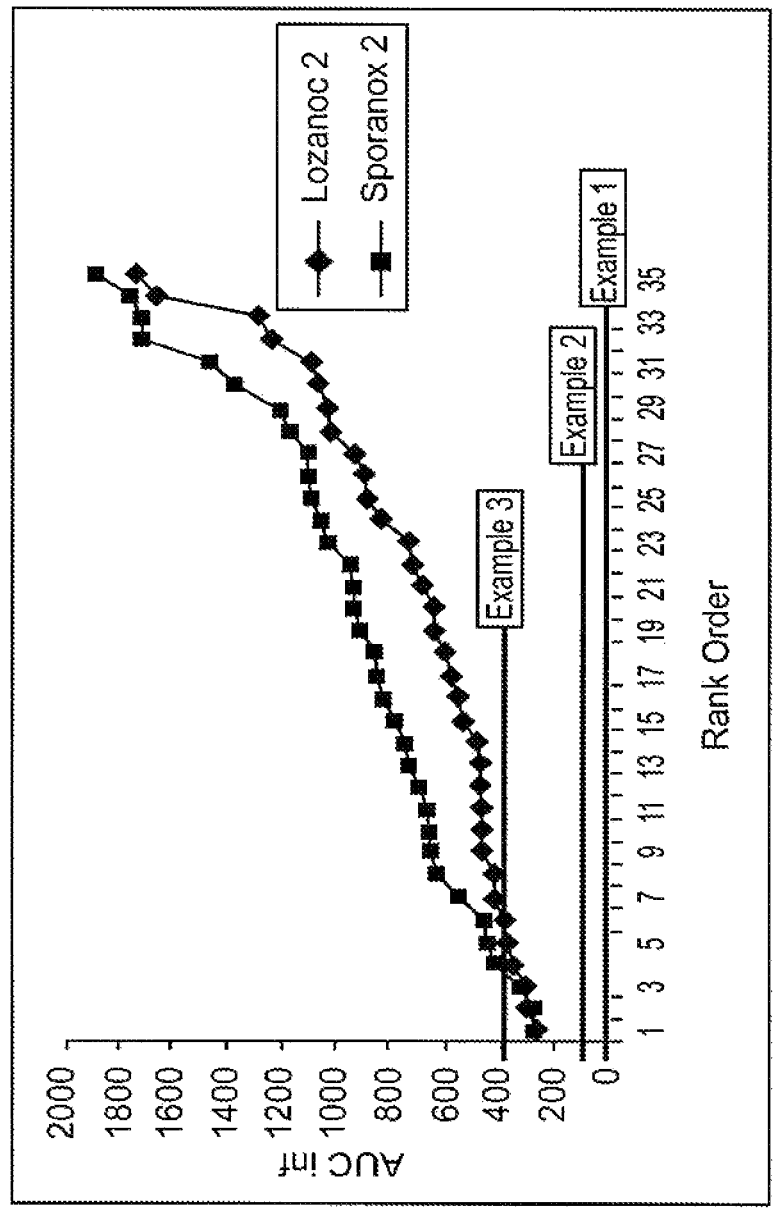
FIG. 62 is a graph showing individual subject $AUC_{inf}$ results ranked in order of lowest to highest for both test and reference, with the minimum AUC thresholds arrived at in Table 80 superimposed. This illustrates the actual AUCs required for optimal therapeutic effect and compares the relative performance of Lozanoc 50 mg hard capsules and Sporanox® 100 mg Capsules in the second administration of Lozanoc described in Example 12 (see pharmacokinetics section).

FIG. 61 and FIG. 62 apply the same principles for each occurrence in the study described in Example 12.

Review of FIG. 61 and FIG. 62 highlights that regardless of the formulation, all subjects in the study described in Examples 10 and 12 achieved an exposure sufficient to achieve above the desired AUC/MIC ratio for Scenarios 1 and 2. As one might expect for oral itraconazole, the majority but not all subjects achieved an exposure sufficient to achieve above the desired AUC/MIC ratio for Scenario 3, with no apparent difference between the formulations.

The most important pharmacokinetic-pharmacodynamic (PK-PD) parameter for itraconazole is the AUC/MIC ratio which should be greater than 25 for optimal efficacy. The above data demonstrate that 50 mg of the test product, taken in the fed state, achieves this comfortably for the above listed organisms and with more certainty compared to the test product, taken in fasted state, achieves this comfortably for the above listed organisms and with more certainty compared to the highly variable Sporanox for MIC90 >4 mcg/ml and also for the majority when MIC >16 mcg/ml.

Sporanox is an established antifungal agent for the treatment of a wide variety of superficial and systemic fungal infections. It is widely used despite the known problems of high inter- and intra-individual variation. To get the "right" dose, frequent drug level monitoring may be required.

Lozanoc 50 mg hard capsules has demonstrated advantages over the reference, such as lower inter and intra-individual variability, less pronounced food effect and therefore more predictability of dosing. In addition, the PK-PD parameter demonstrates that Lozanoc 50 mg hard capsules achieves the AUC/MIC ratio which should be greater than 25 for optimal efficacy in both the fed and fasted state for a number of organisms.

The clinical study in onychomycosis demonstrated superiority of Lozanoc 50 mg hard capsules compared to placebo. However Lozanoc 50 mg hard capsules can be considered a therapeutic alternative to Sporanox in the treatment of certain superficial and systemic mycoses.

Example 16—Study of 65 mg Dose LOZANOC

Study Rationale

This study will evaluate the relative bioavailability of a new strength of SUBA®-itraconazole capsules with 65 mg itraconazole ("test capsules") compared to SPORANOX® 100 mg itraconazole capsules when administered to healthy adult subjects as single oral doses under fasted and fed conditions.

Study Design

The study will be a randomized, single-dose, four treatment, four period, crossover, open-label, analytically blinded study for comparing single oral doses of the Test SUBA®-itraconazole 65 mg capsules to single oral doses of the Reference SPORANOX® (itraconazole) 100 mg capsules under fasted and fed conditions. In each of four study periods, a single oral dose of itraconazole will be administered to all subjects either as (1×65 mg) SUBA®-itraconazole capsule or (1×100 mg) SPORANOX® (itraconazole) capsule.

In two of the study periods, subjects will be dosed with either Test or Reference Products following an overnight fast of at least 10 hours. After dosing, all subjects will continue to fast for an additional 4 hours post-dose. In the other two study periods, subjects will be dosed with either Test or Reference Product following the FDA standardized high fat, high calorie breakfast, preceded by an overnight fast of at least 10 hours. Subjects following the standardized high fat breakfast regimen will be administered their study treatment (dose) 30 minutes after starting their meal. Each study treatment/dose will be administered with 240 mL of ambient temperature water and any other fluids (other than the milk given with the 'fed' breakfast) will be restricted from one hour pre-dosing until one hour post-dose. Water will be encouraged ad lib at other times.

Study Population

Fifty two (52) healthy, non-tobacco using, adult male and non-pregnant female subjects, who satisfy all entry criteria, will be enrolled in the study. Enrolled subjects will be aged from 18 to 65 years and with a body mass index (BMI) between 18.0 and 30.0 kg/m2, inclusive.

Study Treatments

Test (A): 1× SUBA®-itraconazole 65 mg capsule following an overnight fast of at least 10 hours.

Test (B): 1× SUBA®-itraconazole 65 mg capsule following a standardized high fat breakfast, preceded by an overnight fast of at least 10 hours.

Reference (C): 1× SPORANOX® (itraconazole) 100 mg capsule following an overnight fast of at least 10 hours.

Reference (D): 1× SPORANOX® (itraconazole) 100 mg capsule following a standardized high fat breakfast, preceded by an overnight fast of at least 10 hours.

The subjects will receive the Test Product (SUBA®-itraconazole 65 mg capsule) in two periods (once fasted and once fed) and the Reference Product (SPORANOX® itraconazole 100 mg capsule) in the other two periods (once fasted and once fed); with the order of administration in accordance with the 4 sequence dosing randomization schedule.

Single dosages will be administered in each study treatment period, and there will be at least a 14-day washout interval between the four dose/treatment administrations.

In each study period, blood samples for pharmacokinetic analysis will be collected pre-dose (0.0 h) and at 1.0, 1.5, 2.0, 2.5, 3.0, 3.5, 4.0, 4.5, 5.0, 5.5, 6.0, 6.5, 7.0, 8.0, 9.0, 10.0, 11.0, 12.0, 16, 24.0, 36.0, 48.0, 72.0*, 96.0* and 120* hours post-dose administration. The * indicates return samples Pharmacokinetic Analysis The following pharmacokinetic information will be calculated for itraconazole and hydroxyitraconazole, the latter for informational purposes:

Plasma concentrations and time points
Subject, period, sequence, treatment
AUC0-t, AUC0-inf, Cmax, Tmax, Kel, and T1/2
Inter-subject, intra-subject, and/or total variability, if available.

The statistical information provided for AUC0-t, AUC0-inf, Cmax will be the geometric mean, the arithmetic mean, the ratio of means and confidence intervals (CI), with log transformation provided for measures used to demonstrate bioequivalence. Equivalence will have been demonstrated if the 90% CI for the Test/Reference ratio for AUC0-t, AUC0-inf, and Cmax for itraconazole falls within the range 80.00-125.00%. Equivalence will be tested under fasting conditions (Test A v Reference C), and fed conditions (Test B v Reference D). The reference range will be expanded for AUC0-t, AUC0-inf, and Cmax as appropriate for a highly variable drug based on the within-subject variability as assessed by ANOVA. Intersubject variability in AUC will be assessed to test the hypothesis that SUBA®-itraconazole 65 mg capsule produce less variable itraconazole exposure than SPORANOX® itraconazole 100 mg capsules.

The median, range and inter-quartile range (IQR) of AUC0-t and AUC0-inf will be compared between Test A and Reference C (fasted) and between Test B and Reference D (fed). Variability in AUC0-t and AUC0-inf will be compared graphically using Box-plots, and differences in variance between the Test and Reference formulations assessed via the Bartlett's test.

Statistical Analysis

The pharmacokinetic and statistical analyses will be performed in accordance with the relevant FDA Guidances for Industry.

Bioequivalence will be based on itraconazole pharmacokinetic parameters, although full pharmacokinetics and statistical analyses will be performed on the hydroxyitraconazole data.

Subjects who complete at least two periods of the study will be included in the final data set.

The Statistical Analysis System (SAS) will be used for all pharmacokinetic and statistical calculations. Linear and semi-logarithmic graphs of the concentration-time profiles for each subject will be provided, using the actual times of sample collections. Graphical presentations of mean results will use the scheduled times of sample collections. A complete listing of the deviations from the actual sampling times will be provided. Concentration values reported for each collected sample will be provided.

Data from subjects with missing concentration values (missed blood draws, lost samples, samples unable to be quantified) may be used if pharmacokinetic parameters can be estimated using remaining data points, otherwise data from these subjects will be excluded from final analysis.

For all treatments, the following pharmacokinetic information will be calculated for itraconazole and hydroxyitraconazole, the latter for informational purposes:

Cmax will be the observed maximum plasma concentration.

Tmax will be the collection time at which Cmax is first observed.

AUC0-t, the area under the plasma concentration versus time curve from time 0 to the last measurable concentration, will be calculated by the linear trapezoidal method;

AUC0-inf, the area under the plasma concentration versus time curve from time 0 to infinity will be calculated as the sum of AUC0-t plus the ratio of the last measurable plasma concentration (Ct) to the elimination rate constant (Kel).

Kel, the apparent first-order terminal rate constant will be calculated from a semi-log plot of the plasma concentration versus time curve. The parameter will be calculated by linear least-squares regression analysis using the maximum number of points in the terminal log-linear phase (e.g., three or more non-zero plasma concentrations).

T1/2, the apparent first-order terminal half-life will be calculated as ln(2)/Kel.

No concentration estimates will be provided for missing sample values. Any sample with a missing value will be treated as if the sample had not been scheduled for collection.

Individual and mean results for all derived parameters and for the concentrations at each scheduled collection time will be presented in summary tabulations. If a subject has a pre-dose (0 hour sample) plasma level for an analyte that is greater than 5% of their measured Cmax value, the subject will be dropped from all BE study evaluations. If measurable plasma levels are equal to or less than 5% of their measured Cmax, the subject's data will be included in all pharmacokinetic measurements without adjustment.

Data from subjects who experience emesis during the first 10 hours post-dosing (based on approximately 2× the Tmax of approximately 5 hours) will be dropped from that period of the study and their samples from that period not analyzed.

To determine relative bioavailability and food effects, Analyses of Variance will be performed using the MIXED procedure of SAS with hypothesis testing for treatment effects at α=0.05. The itraconazole treatments will be tested separately under fed and fasted conditions and will be repeated for hydroxyitraconazole for informational purposes. As the variance for all pharmacokinetic parameters increases as the mean increases, the parameters will be log-transformed (base e) prior to analysis. Using bioavailability as an example, the residual variance from the mixed model will be used to calculate 90% CI for the difference between the test and reference investigational products. These values will be back-transformed to give geometric LS means, a point estimate and 90% CI for the ratio of the test investigational product relative to the reference investigational product. This procedure is equivalent to Schuirmann's two one-sided tests at the 0.05 level of significance. Equivalence will have been demonstrated if the 90% confidence interval for the Test/Reference ratio for AUC0-t, AUC0-inf, and Cmax for itraconazole falls within the standard reference range 80.00-125.00%. Residual plots will be produced to assess the adequacy of the model.

Bioequivalence will be tested under fasting conditions (Test A v Reference C), and fed conditions (Test B v Reference D) 7-9. The effect of food on each formulation will be based on the log-transformed data for itraconazole by comparing Test A v Test B and Reference C v Reference D. If the 90% confidence interval for the Test/Reference ratio for AUC0-t, AUC0-inf and Cmax for itraconazole all fall in the range 80.00-125.00% in the fed state compared to the fasted state, then food will be considered not to have any effect on the bioavailability of that formulation. The relative bioavailability of a single 65 mg capsule dose of the Test formulation under fasted conditions compared to a single 100 mg capsule dose of the Reference formulation under fed conditions (A v D) will be presented for informational purposes. The reference range for the 90% confidence interval will be expanded for AUC0-t, AUC0-inf, and Cmax based on within-subject variability using the limits described in Karalis et al. for highly variable drugs.13

The parameter tmax will be analysed nonparametrically using the Wilcoxon signed-rank test.

An additional data analysis will conducted to compare the inter-subject variability in itraconazole exposure. The distributions of log-transformed and untransformed AUC0-t, AUC0-inf and Cmax will be compared graphically between Test and Reference in Fasted and Fed conditions using boxplots. The hypothesis that the two formulations differ in the variability of exposure will be examined using Bartlett's tests (significance level p=0.05).

Predicted Results

It is predicted that the 65 mg SUBA® formulation will be bioequivalent to the 100 mg SPORANOX® formulation. It is also predicted that the 65 mg SUBA® formulation will give AUC values that are between those of the 60 mg formulation and 70 mg formulation (Example 4). Thus, the principle pharmacokinetic parameters may be those shown in Table 5.

Specific Embodiments of the Invention

1. An oral pharmaceutical composition comprising about 50 mg of itraconazole, wherein the composition exhibits an $AUC_{0-t}$ which is 80% to 125% of about 440 h*ng/ml to about 740 h*ng/ml following administration of the composition to a subject under fed conditions.

2. The oral pharmaceutical composition of embodiment 1, wherein the composition exhibits a C which is 80% to 125% of about 60 ng/ml to about 75 ng/ml following administration of the composition to a subject under fed conditions.

3. The oral pharmaceutical composition of embodiment 1 or 2, wherein the composition exhibits reduced food effect as compared to a reference composition of itraconazole.

4. The oral pharmaceutical composition of any one of embodiments 1 to 3, which under fed conditions is therapeutically similar to a reference composition under fed conditions.

5. The oral pharmaceutical composition of embodiment 4, which under fed conditions is bioequivalent to the reference composition under fed conditions.

6. The oral pharmaceutical composition of any one of embodiment 1 to 3, which under fasting conditions is therapeutically similar to a reference composition under fed conditions.

7. The oral pharmaceutical composition of embodiment 6, which under fasting conditions is bioequivalent to the reference composition under fed conditions.

8. The oral pharmaceutical composition of any one of embodiments 1 to 7, wherein the composition under fed conditions is substantially similar to the same composition under fasting conditions.

9. The oral pharmaceutical composition of embodiment 8, which exhibits a difference of less than about 35% between a $AUC_{0-t}$ under fasting conditions and a $AUC_{0-t}$ under fed conditions.

10. The oral pharmaceutical composition of any one of embodiments 1 to 9, which exhibits reduced intra-subject variability as compared to a reference composition of itraconazole.

11. The oral pharmaceutical composition of embodiment 10, which exhibits a reduced variability in the AUC0-t as compared to the reference composition.

12. The oral pharmaceutical composition of any one of embodiments 1 to 11, which exhibits reduced inter-subject variability as compared to a reference composition of itraconazole.

13. The oral pharmaceutical composition of embodiment 12, which exhibits a reduced variability in the AUC0-t as compared to the reference composition.

14. The oral pharmaceutical composition of any one of embodiments 1 to 11, which exhibits a ratio in the range from about 0.70 to about 1.43 for AUC0-t between the oral pharmaceutical composition and a reference composition with the 90% confidence interval.

15. The oral pharmaceutical composition of any one of embodiments 1 to 14, which, upon administration under fed conditions, exhibits a relative bioavailability ($F_{rel}$) of greater than about 150% relative to a reference composition under fed conditions.

16. The oral pharmaceutical composition of any one of embodiments 1 to 15, which exhibits a minimum inhibitory concentration (MIC) value of less than about 16 mcg/ml.

17. The oral pharmaceutical composition of any one of embodiments 1 to 16, which exhibits an AUC/MIC ratio of about 25 or greater.

18. An oral pharmaceutical composition comprising about 50 mg of itraconazole, wherein the composition exhibits an $AUC_{0-t}$ which is 80% to 125% of about 350 h*ng/ml to about 620 h*ng/ml following administration of the composition to a subject under fasting conditions.

19. The oral pharmaceutical composition of embodiment 18, wherein the composition exhibits a $C_{max}$ which is 80% to 125% of about 30 ng/ml to about 60 ng/ml following administration of the composition to a subject under fasting conditions.

20. The oral pharmaceutical composition of embodiment 18 or 19, wherein the composition exhibits reduced food effect as compared to a reference composition of itraconazole.

21. The oral pharmaceutical composition of any one of embodiments 18 to 20, which under fed conditions is therapeutically similar to a reference composition under fed conditions.

22. The oral pharmaceutical composition of embodiment 21, which under fed conditions is bioequivalent to the reference composition under fed conditions.

23. The oral pharmaceutical composition of any one of embodiments 18 to 20, which under fasting conditions is therapeutically similar to a reference composition under fed conditions.

24. The oral pharmaceutical composition of embodiment 23, which under fasting conditions is bioequivalent to the reference composition under fed conditions.

25. The oral pharmaceutical composition of any one of embodiments 18 to 24, wherein the composition under fed conditions is substantially similar to the same composition under fasting conditions as to food effect.

26. The oral pharmaceutical composition of embodiment 25, which exhibits a difference of less than about 35% between a $AUC_{0-t}$ under fasting conditions and a $AUC_{0-t}$ under fed conditions.

27. The oral pharmaceutical composition of any one of embodiments 18 to 26, which exhibits reduced intra-subject variability as compared to a reference composition of itraconazole.

28. The oral pharmaceutical composition of embodiment 27, which exhibits a reduced variability in the $AUC_{0-t}$ as compared to the reference composition.

29. The oral pharmaceutical composition of any one of embodiments 18 to 28, which exhibits reduced inter-subject variability as compared to a reference composition of itraconazole.

30. The oral pharmaceutical composition of embodiment 29, which exhibits a reduced variability in the $AUC_{0-t}$ as compared to the reference composition.

31. The oral pharmaceutical composition of any one of embodiments 18 to 30, which exhibits a ratio in the range from about 0.70 to about 1.43 for $AUC_{0-t}$ between the oral pharmaceutical composition and a reference composition with the 90% confidence interval.

32. The oral pharmaceutical composition of any one of embodiments 18 to 31, which exhibits a minimum inhibitory concentration (MIC) value of less than about 16 mcg/ml.

33. The oral pharmaceutical composition of any one of embodiments 18 to 32, which exhibits an AUC/MIC ratio of about 25 or greater.

34. The oral pharmaceutical composition of any one of embodiments 18 to 33, which, upon administration under fed conditions, exhibits a relative bioavailability ($F_{rel}$) of greater than about 150% relative to a reference composition under fed conditions.

35. The oral pharmaceutical composition of any one of embodiments 18 to 34, which exhibits an AUC which is 80% to 125% of about 440 h*ng/ml to about 740 h*ng/ml following administration of the composition to a subject under fed conditions.

36. The oral pharmaceutical composition of embodiment 35, wherein the composition exhibits a $C_{max}$ which is 80% to 125% of about 60 ng/ml to about 75 ng/ml following administration of the composition to a subject under fed conditions.

37. The oral pharmaceutical composition of any one of embodiments 18 to 36, which is therapeutically equivalent to a reference composition.

38. An oral pharmaceutical composition comprising about 65 mg of itraconazole, wherein the composition exhibits an $AUC_{0-t}$ which is 80% to 125% of about 650 h*ng/ml to about 1200 h*ng/ml following administration of the composition to a subject under fed conditions.

39. The oral pharmaceutical composition of embodiment 38, wherein the composition exhibits a $C_{max}$ which is 80% to 125% of about 65 ng/ml to about 100 ng/ml following administration of the composition to a subject under fed conditions.

40. The oral pharmaceutical composition of embodiments 38 or 39, wherein the composition exhibits reduced food effect as compared to a reference composition of itraconazole.

41. The oral pharmaceutical composition of any one of embodiments 38 to 40, which under fed conditions is therapeutically similar to a reference composition under fed conditions.

42. The oral pharmaceutical composition of cembodiment 41, which under fed conditions is bioequivalent to the reference composition under fed conditions.

43. The oral pharmaceutical composition of any one of embodiments 38 to 40, which under fasting conditions is therapeutically similar to a reference composition under fed conditions.

44. The oral pharmaceutical composition of embodiment 43, which under fasting conditions is bioequivalent to the reference composition under fed conditions.

45. The oral pharmaceutical composition of any one of embodiments 38 to 44, wherein the composition under fed conditions is substantially similar to the same composition under fasting conditions as to food effect.

46. The oral pharmaceutical composition of embodiment 45, which exhibits a difference of less than about 35% between a $AUC_{0-t}$ under fasting conditions and a $AUC_{0-t}$ under fed conditions.

47. The oral pharmaceutical composition of any one of embodiments 38 to 46, which exhibits reduced intra-subject variability as compared to a reference composition of itraconazole.

48. The oral pharmaceutical composition of embodiment 47, which exhibits a reduced variability in the $AUC_{0-t}$ as compared to the reference composition.

49. The oral pharmaceutical composition of any one of embodiments 38 to 48, which exhibits reduced inter-subject variability as compared to a reference composition of itraconazole.

50. The oral pharmaceutical composition of embodiment 49, which exhibits a reduced variability in the $AUC_{0-t}$ as compared to the reference composition.

51. The oral pharmaceutical composition of any one of embodiments 38 to 48, which exhibits a ratio in the range from about 0.70 to about 1.43 for $AUC_{0-t}$ between the oral pharmaceutical composition and a reference composition with the 90% confidence interval.

52. The oral pharmaceutical composition of any one of embodiments 38 to 51, which, upon administration under fed conditions, exhibits a relative bioavailability ($Fr_e i$) of greater than about 150% relative to a reference composition under fed conditions.

53. The oral pharmaceutical composition of any one of embodiments 38 to 52, which exhibits a minimum inhibitory concentration (MIC) value of less than about 16 mcg/ml.

54. The oral pharmaceutical composition of embodiment 53, which exhibits an AUC/MIC ratio of about 25 or greater.

55. An oral pharmaceutical composition comprising about 65 mg of itraconazole, wherein the composition exhibits an $AUC_{0-t}$ which is 80% to 125% of about 450 h*ng/ml to about 900 h*ng/ml following administration of the composition to a subject under fasting conditions.

56. The oral pharmaceutical composition of embodiment 55, wherein the composition exhibits a $C_{max}$ which is 80% to 125% of about 36 ng/ml to about 70 ng/ml following administration of the composition to a subject under fasting conditions.

57. The oral pharmaceutical composition of embodiment 55 or 56, wherein the composition exhibits reduced food effect as compared to a reference composition of itraconazole.

58. The oral pharmaceutical composition of any one of embodiments 55 to 57, which under fed conditions is therapeutically similar to a reference composition under fed conditions.

59. The oral pharmaceutical composition of embodiment 58, which under fed conditions is bioequivalent to the reference composition under fed conditions.

60. The oral pharmaceutical composition of any one of embodiments 55 to 59, which under fasting conditions is therapeutically similar to a reference composition under fed conditions.

61. The oral pharmaceutical composition of embodiment 60, which under fasting conditions is bioequivalent to the reference composition under fed conditions.

62. The oral pharmaceutical composition of any one of embodiments 55 to 61, wherein the composition under fed conditions is substantially similar to the same composition under fasting conditions.

63. The oral pharmaceutical composition of embodiment 62, which exhibits a difference of less than about 35% between a $AUC_{0-t}$ under fasting conditions and a $AUC_{0-t}$ under fed conditions.

64. The oral pharmaceutical composition of any one of embodiments 55 to 63, which exhibits reduced intra-subject variability as compared to a reference composition of itraconazole.

65. The oral pharmaceutical composition of embodiment 64, which exhibits a reduced variability in the $AUC_{0-t}$ as compared to the reference composition.

66. The oral pharmaceutical composition of any one of embodiments 55 to 65, which exhibits reduced inter-subject variability as compared to a reference composition of itraconazole.

67. The oral pharmaceutical composition of embodiment 66, which exhibits a reduced variability in the $AUC_{0-t}$ as compared to the reference composition.

68. The oral pharmaceutical composition of any one of embodiments 55 to 67, which exhibits a ratio in the range from about 0.70 to about 1.43 for $AUC_{0-t}$ between the oral pharmaceutical composition and a reference composition with the 90% confidence interval.

69. The oral pharmaceutical composition of any one of embodiments 55 to 68, which, upon administration under fed conditions, exhibits a relative bioavailability ($F_{rel}$) of greater than about 150% relative to a reference composition under fed conditions.

70. The oral pharmaceutical composition of any one of embodiments 55 to 69, which exhibits an $AUC_{0-t}$ which is 80% to 125% of about 650 h*ng/ml to about 1200 h*ng/ml following administration of the composition to a subject under fed conditions.

71. The oral pharmaceutical composition of embodiment 70, wherein the composition exhibits a $C_{max}$ which is 80% to 125% of about 65 ng/ml to about 100 ng/ml following administration of the composition to a subject under fed conditions.

72. The oral pharmaceutical composition of embodiment 71, which is therapeutically equivalent to a reference composition.

73. The oral pharmaceutical composition of any one of embodiments 55 to 72, which exhibits a minimum inhibitory concentration (MIC) value of less than about 16 mcg/ml.

The oral pharmaceutical composition of embodiment 73, which exhibits an AUC/MIC ratio of about 25 or greater.

75. An oral pharmaceutical composition comprising itraconazole, wherein the composition exhibits an $AUC_{0-t}$ which is 80% to 125% of about 8.8 h*ng/ml to about 14.8 h*ng/ml per milligram of itraconazole following administration of the composition to a subject under fed conditions.

76. The oral pharmaceutical composition of embodiment 75, wherein the composition exhibits a $C_{max}$ which is 80% to 125% of about 1.2 ng/ml to about 1.5 ng/ml per milligram of itraconazole following administration of the composition to a subject under fed conditions.

77. The oral pharmaceutical composition of embodiment 75 or 76, wherein the composition exhibits reduced food effect as compared to a reference composition of itraconazole.

78. The oral pharmaceutical composition of any one of embodiments 75 to 77, which under fasting conditions is therapeutically similar to a reference composition under fed conditions.

79. The oral pharmaceutical composition of any one of embodiments 75 to 78, wherein the composition under fed conditions is substantially similar to the same composition under fasting conditions.

80. The oral pharmaceutical composition form of any one of embodiments 75 to 79, which exhibits an intra-subject coefficient of variation under fed conditions for the $AUC_{0-t}$ of less than about 35%.

81. The oral pharmaceutical composition of any one of embodiments 75 to 79, which exhibits an inter-subject coefficient of variation under fed conditions for the $AUC_{0-t}$ of less than about 35%.

82. The oral pharmaceutical composition of any one of embodiments 75 to 81, which exhibits a ratio in the range from about 0.70 to about 1.43 for $AUC_{0-t}$ between the oral pharmaceutical composition and a reference composition with the 90% confidence interval.

83. The oral pharmaceutical composition of any one of embodiments 75 to 81, which, upon administration under fed conditions, exhibits a relative bioavailability ($Fr_e i$) of greater than about 150% relative to a reference composition under fed conditions.

84. The oral pharmaceutical composition of any one of embodiments 75 to 83, which exhibits a minimum inhibitory concentration (MIC) value of less than about 16 mcg/ml.

85. The oral pharmaceutical composition of embodiment 84, which exhibits an AUC/MIC ratio of about 25 or greater.

86. An oral pharmaceutical composition comprising itraconazole, wherein the composition exhibits an $AUC_{0-t}$ which is 80% to 125% of about 7.0 h*ng/ml to about 12.4 h*ng/ml per milligram of itraconazole following administration of the composition to a subject under fasting conditions.

87. The oral pharmaceutical composition of embodiment 86, wherein the composition exhibits a $C_{max}$ which is 80% to 125% of about 1.2 ng/ml to about 1.5 ng/ml per milligram of itraconazole following administration of the composition to a subject under fasting conditions.

88. The oral pharmaceutical composition of embodiment 86 or 87, wherein the composition exhibits reduced food effect as compared to a reference composition of itraconazole.

89. The oral pharmaceutical composition of any one of embodiments 86 to 88, which under fasting conditions is therapeutically similar to a reference composition under fed conditions.

90. The oral pharmaceutical composition of any one of embodiments 86 to 89, wherein under fed conditions the composition is substantially similar to the same composition under fasting conditions.

91. The oral pharmaceutical composition form of any one of embodiments 86 to 90, which exhibits an intra-subject coefficient of variation under fed conditions for the $AUC_{0-t}$ of less than about 35%.

92. The oral pharmaceutical composition of any one of embodiments 86 to 90, which exhibits an inter-subject coefficient of variation under fed conditions for the $AUC_{0-t}$ of less than about 35%.

93. The oral pharmaceutical composition of any one of embodiments 86 to 92, which exhibits a ratio in the range from about 0.70 to about 1.43 for $AUC_{0-t}$ between the oral pharmaceutical composition and a reference composition with the 90% confidence interval.

94. The oral pharmaceutical composition of any one of embodiments 86 to 93, which, upon administration under fed conditions, exhibits a relative bioavailability ($F_{rel}$) of greater than about 150% relative to a reference composition under fed conditions.

95. The oral pharmaceutical composition of any one of embodiments 86 to 94, which exhibits a minimum inhibitory concentration (MIC) value of less than about 16 mcg/ml.

96. The oral pharmaceutical composition of embodiment 95, which exhibits an AUC/MIC ratio of about 25 or greater.

97. An oral pharmaceutical composition comprising itraconazole, which exhibits an intra-subject coefficient of variation under fed conditions for the $AUC_{0-t}$ of less than about 35%.

98. The oral pharmaceutical composition of embodiment 97, which exhibits an intra-subject coefficient of variation under fed conditions for the $AUC_{0-\infty}$ of less than about 35%.

99. The oral pharmaceutical composition of embodiments 97 or 98, wherein the amount of itraconazole in the composition is about 50% to about 65% by weight of the amount of itraconazole in a reference composition.

100. An oral pharmaceutical composition comprising itraconazole, which exhibits an inter-subject coefficient of variation under fed conditions for the $AUC_{0-t}$ of less than about 35%.

101. The oral pharmaceutical composition of embodiments 100, which exhibits an inter-subject coefficient of variation under fed conditions for the $AUC_{0-\infty}$ of less than about 35%.

102. The oral pharmaceutical composition of embodiment 100 or 101, wherein the amount of itraconazole in the composition is about 50% to about 65% by weight of the amount of itraconazole in a reference composition.

103. The oral pharmaceutical composition of embodiment 97 or 100, wherein the amount of itraconazole in the composition is about 50 mg.

104. The oral pharmaceutical composition of embodiment 97 or 100, wherein the amount of itraconazole in the composition is about 65 mg.

105. The oral pharmaceutical composition of any one of embodiments 97 to 104, which exhibits a minimum inhibitory concentration (MIC) value of less than about 16 mcg/ml.

106. The oral pharmaceutical composition of embodiment 105, which exhibits an AUC/MIC ratio of about 25 or greater.

107. An oral pharmaceutical composition comprising itraconazole, wherein the composition under fed conditions is substantially similar to the same composition under fasting conditions.

108. The oral pharmaceutical composition of embodiment 107, wherein the amount of itraconazole in the composition is about 50% to about 65% by weight of the amount of itraconazole in a reference composition.

109. The oral pharmaceutical composition of embodiment 107 or 108, which exhibits a difference of less than about 35% between a $AUC_{0-t}$ under fasting conditions and a $AUC_{0-t}$ under fed conditions.

110. The oral pharmaceutical composition of any one of embodiments 107 to 109, which under fasting conditions is therapeutically similar to a reference composition under fed conditions.

111. The oral pharmaceutical composition of any one of embodiments 107 to 110, wherein the composition exhibits an $AUC_{0-t}$ which is 80% to 125% of about 8.8 h*ng/ml to about 14.8 h*ng/ml per milligram of itraconazole following administration of the composition to a subject under fed conditions.

112. The oral pharmaceutical composition of any one of embodiments 107 to 111, wherein the composition exhibits an $AUC_{0-t}$ which is 80% to 125% of about 7.0 h*ng/ml to about 12.4 h*ng/ml per milligram of itraconazole following administration of the composition to a subject under fasting conditions.

113. The oral pharmaceutical composition of any one of embodiments 107 to 112, wherein the amount of itraconazole in the composition is about 50 mg.

114. The oral pharmaceutical composition of any one of embodiments 107 to 112, wherein the amount of itraconazole in the composition is about 65 mg.

115. The oral pharmaceutical composition of any one of embodiments 107 to 114, which exhibits a minimum inhibitory concentration (MIC) value of less than about 16 mcg/ml.

116. The oral pharmaceutical composition of embodiment 115, which exhibits an AUC/MIC ratio of about 25 or greater.

117. A method of reducing food effect of itraconazole in a subject comprising administering to the subject an oral pharmaceutical composition comprising about 50 mg of itraconazole, and the composition provides an $AUC_{0-t}$ which is 80% to 125% of about 440 h*ng/ml to about 740 h*ng/ml following administration of the composition to a subject under fed conditions.

118. The method of embodiment 117, wherein the composition exhibits an $AUC_{0-t}$ which is 80% to 125% of about 350 h*ng/ml to about 620 h*ng/ml following administration of the composition to a subject under fasting conditions.

119. A method of reducing food effect of itraconazole in a subject comprising administering to the subject an oral pharmaceutical composition comprising about 65 mg of itraconazole, and the composition provides an $AUC_{0-t}$ which is 80% to 125% of about 650 h*ng/ml to about 1200 h*ng/ml following administration of the composition to a subject under fed conditions.

120. The method of embodiment 119, wherein the composition exhibits an $AUC_{0-t}$ which is 80% to 125% of about 450 h*ng/ml to about 900 h*ng/ml following administration of the composition to a subject under fasting conditions.

121. A method of reducing food effect of itraconazole in a subject comprising administering to the subject an oral pharmaceutical composition comprising of itraconazole, and the composition provides an $AUC_{0-t}$ which is 80% to 125% of about 8.8 h*ng/ml to about 14.8 h*ng/ml per milligram of itraconazole following administration of the composition to a subject under fed conditions.

122. The method of embodiment 121, wherein the composition provides an $AUC_{0-t}$ which is 80% to 125% of about 7.0 h*ng/ml to about 12.4 h*ng/ml per milligram of itraconazole following administration of the composition to a subject under fasting conditions.

123. A method of reducing intra-subject variability of itraconazole comprising administering to a subject an oral pharmaceutical composition comprising itraconazole, and the composition exhibits an intra-subject coefficient of variation under fed conditions for the $AUC_{0-t}$ of less than about 35%.

124. A method of reducing inter-subject variability of itraconazole comprising administering to subjects an oral pharmaceutical composition comprising itraconazole, and the composition exhibits an inter-subject coefficient of variation under fed conditions for the $AUC_{0-t}$ of less than about 35%.

125. A method of treating onychomycosis comprising administering to a subject an oral pharmaceutical composition comprising itraconazole, wherein the amount of itraconazole in the composition is about 50% to about 65% by weight of the amount of itraconazole in a reference composition and the composition is therapeutically equivalent to the reference composition.

126. A method of treating onychomycosis comprising administering to a subject an oral pharmaceutical composition comprising itraconazole, wherein the amount of itraconazole in the composition is about 50% to about 65% by weight of the amount of itraconazole in a reference composition and the method provides an effective cure with faster onset efficacy as compared to the reference composition.

127. The method of 126, wherein the method exhibits efficacy end points at a time when the reference composition does not exhibits efficacy end points.

128. The method of 127, wherein the efficacy end points is at week five, six, seven, eight, or nine.

129. A method of treating a disease or condition comprising co-administering to a subject
an oral pharmaceutical composition comprising itraconazole; and
a gastric acid suppressor or neutralizer.

130. A method of treating cancer comprising administering to a subject an oral pharmaceutical composition of any one of embodiments 1 to 100.

131. The method of 130, wherein the cancer is prostate cancer, skin cancer, or lung cancer.

The detailed description herein describes various aspects and embodiments of the invention, however, unless otherwise specified, none of those are intended to be limiting. Indeed, a person of skill in the art, having read this disclosure, will envision variations, alterations, and adjustments that can be made without departing from the scope and spirit of the invention, all of which should be considered to be part of the invention unless otherwise specified. Applicants thus envision that the invention described herein will be limited only by the appended claims.

The invention claimed is:
1. A method of treating cancer in a subject, comprising administering to the subject in need thereof an oral pharmaceutical composition comprising 65 mg of itraconazole in each unit dosage form and wherein the composition exhibits an $AUC_{0-t}$ which is 80% to 125% of 650 h*ng/ml to 1200 h*ng/ml following administration of the composition to the subject under fed conditions.

2. The method of claim 1, wherein the composition under fed conditions is therapeutically similar to a composition containing 100 mg of itraconazole, sugar spheres, hydroxypropyl methyl cellulose, and polyethylene glycol in a capsule shell, under fed conditions.

3. The method of claim 1, wherein the composition exhibits an $AUC_{0-t}$ which is 80% to 125% of 650 h*ng/ml to 1200 h*ng/ml following administration of the composition to a subject under fed conditions.

4. The method of claim 1, wherein the composition exhibits a $C_{max}$ which is 80% to 125% of 65 ng/ml to 100 ng/ml following administration of the composition to the subject under fed conditions.

5. The method of claim 1, wherein the composition exhibits a $C_{max}$ which is 80% to 125% of 36 ng/ml to 70 ng/ml following administration of the composition to a subject under fasting conditions.

6. The method of claim 1, wherein the composition exhibits an $AUC_{0-t}$ which is 80% to 125% of 450 h*ng/ml to 900 h*ng/ml following administration of the composition to the subject under fasting conditions.

7. The method of claim 1, wherein the composition under fasting conditions is therapeutically similar to a composition containing 100 mg of itraconazole, sugar spheres, hydroxypropyl methyl cellulose, and polyethylene glycol in a capsule shell, under fed conditions.

8. The method of claim 1, wherein the composition exhibits a ratio in the range from 0.70 to 1.43 for $AUC_{0-t}$ between the oral pharmaceutical composition and a composition containing 100 mg of itraconazole, sugar spheres, hydroxypropyl methyl cellulose, and polyethylene glycol in a capsule shell, with the 90% confidence interval.

9. The method of claim 1, wherein the oral pharmaceutical composition is in solid dosage form.

10. The method of claim 1, wherein the oral pharmaceutical composition comprises one or more unit dosage forms.

11. The method of claim 1, wherein the cancer is prostate cancer, skin cancer, or lung cancer.

12. The method of claim 1, wherein the oral pharmaceutical composition comprises a pharmaceutically acceptable polymer.

13. The method of claim 12, wherein the pharmaceutically acceptable polymer is an enteric polymer or an acid-resistant polymer.

14. The method of claim 1, wherein the amount of itraconazole per dose for treating cancer is 100 mg or higher.

15. The method of claim 1, wherein the amount of itraconazole per dose for treating cancer is 400 mg or higher.

* * * * *